United States Patent
Igawa et al.

(10) Patent No.: US 10,011,858 B2
(45) Date of Patent: Jul. 3, 2018

(54) METHODS FOR PRODUCING POLYPEPTIDES BY REGULATING POLYPEPTIDE ASSOCIATION

(75) Inventors: Tomoyuki Igawa, Shizuoka (JP); Hiroyuki Tsunoda, Shizuoka (JP)

(73) Assignee: Chugai Seiyaku Kabushiki Kaisha, Tokyo (JP)

(*) Notice: Subject to any disclaimer, the term of this patent is extended or adjusted under 35 U.S.C. 154(b) by 1183 days.

(21) Appl. No.: 11/910,128

(22) PCT Filed: Mar. 31, 2006

(86) PCT No.: PCT/JP2006/306803
§ 371 (c)(1),
(2), (4) Date: Oct. 7, 2008

(87) PCT Pub. No.: WO2006/106905
PCT Pub. Date: Oct. 12, 2006

(65) Prior Publication Data
US 2010/0015133 A1  Jan. 21, 2010

(30) Foreign Application Priority Data

Mar. 31, 2005 (JP) .................. 2005-101105
Dec. 28, 2005 (JP) .................. 2005-378266

(51) Int. Cl.
*A61K 39/00* (2006.01)
*C12P 21/02* (2006.01)
*C07K 16/18* (2006.01)

(52) U.S. Cl.
CPC .............. *C12P 21/02* (2013.01); *C07K 16/18* (2013.01); *A61K 2039/505* (2013.01); *C07K 2317/31* (2013.01)

(58) Field of Classification Search
CPC ............................................... A61K 2039/505
USPC .......................................... 530/350; 536/23.5
See application file for complete search history.

(56) References Cited

U.S. PATENT DOCUMENTS

| | | | |
|---|---|---|---|
| 4,208,479 A | 6/1980 | Zuk et al. | |
| 4,444,878 A | 4/1984 | Paulus | |
| 4,474,893 A | 10/1984 | Reading | |
| 5,126,250 A | 6/1992 | McDonough et al. | |
| 5,322,678 A | 6/1994 | Morgan et al. | |
| 5,496,549 A | 3/1996 | Yamazaki et al. | |
| 5,591,828 A | 1/1997 | Bosslet et al. | |
| 5,639,641 A | 6/1997 | Pedersen et al. | |
| 5,670,373 A | 9/1997 | Kishimoto | |
| 5,744,446 A | 4/1998 | Lollar et al. | |
| 5,795,965 A | 8/1998 | Tsuchiya et al. | |
| 5,837,821 A | 11/1998 | Wu | |
| 5,859,205 A | 1/1999 | Adair et al. | |
| 5,877,291 A | 3/1999 | Mezes et al. | |
| 5,945,311 A | 8/1999 | Lindhofer et al. | |
| 5,990,286 A | 11/1999 | Khawli et al. | |
| 6,005,091 A | 12/1999 | Blackburn et al. | |
| 6,010,902 A | 1/2000 | Ledbetter et al. | |
| 6,126,980 A | 10/2000 | Smith et al. | |
| 6,132,992 A | 10/2000 | Ledbetter et al. | |
| 6,183,744 B1 | 2/2001 | Goldenberg | |
| 6,323,000 B2 | 11/2001 | Briggs et al. | |
| 6,329,511 B1 | 12/2001 | Vasquez et al. | |
| 6,342,220 B1 | 1/2002 | Adams et al. | |
| 6,368,596 B1 | 4/2002 | Ghetie et al. | |
| 6,485,943 B2* | 11/2002 | Stevens ................ | C07K 16/00 435/69.6 |
| 6,677,436 B1 | 1/2004 | Sato et al. | |
| 6,683,157 B2 | 1/2004 | Briggs et al. | |
| 6,699,686 B1 | 3/2004 | Brocard et al. | |
| 6,723,319 B1 | 4/2004 | Ito et al. | |
| 6,884,879 B1 | 4/2005 | Baca et al. | |
| 6,913,747 B1 | 7/2005 | Co et al. | |
| 7,018,632 B2 | 3/2006 | Lindhofer et al. | |
| 7,033,590 B1 | 4/2006 | Scheiflinger et al. | |
| 7,052,873 B2 | 5/2006 | Tsuchiya | |
| 7,122,637 B2 | 10/2006 | Presta | |
| 7,217,797 B2 | 5/2007 | Hinton et al. | |
| 7,276,585 B2 | 10/2007 | Lazar et al. | |
| 7,538,196 B2 | 5/2009 | Jung | |
| 7,615,213 B2 | 11/2009 | Kasaian et al. | |
| 7,732,149 B2 | 6/2010 | Kojima et al. | |
| 8,062,635 B2 | 11/2011 | Hattori et al. | |
| 8,217,147 B2 | 7/2012 | Stavenhagen et al. | |

(Continued)

FOREIGN PATENT DOCUMENTS

| AU | 755822 | 3/1999 |
|---|---|---|
| AU | 2009290162 | 4/2010 |

(Continued)

OTHER PUBLICATIONS

Kurfis et al. (Biochem. Biophys. Res. Commun. Oct. 5, 1999; 263 (3): 816-9).*
Merchant et al. (Nat. Biotechnol. Jul. 1998; 16 (7): 677-81).*
Raffen et al. (Protein Eng. Apr. 1998; 11 (4): 303-9).*
Marti et al. (Biochemistry. Oct. 5, 2004; 43 (39): 12436-47).*
Ridgway et al. (Protein Eng. Jul. 1996; 9 (7): 617-21).*
Marvin et al. (Biochemistry. Jun. 17, 2003; 42 (23): 7077-83).*
Gunasekaran et al. (J. Biol. Chem. Jun. 18, 2010; 285 (25): 19637-46).*
Asian et al. (J. Biotechnol. Feb. 1, 2007; 128 (2): 213-25).*
Atwell et al. (J. Mol. Biol. Jul. 4, 1997; 270 (1): 26-35).*
. Carter (J. Immunol. Methods. Feb. 1, 2001; 248 (1-2): 7-15).*
Baerga-Ortiz et al. (Protein Sci. Jan. 2004; 13 (1): 166-76).*
Raffen et al. (Protein Eng. 1998; 11 (4): 303-9).*
Marvin et al. (Acta Pharmacol Sin. Jun. 2005; 26 (6): 649-58).*
O'Shea et al. (Curr. Biol. 1993: 3 (10): 658-67).*
Igawa et al. (Protein Eng. Des. Sel. Aug. 2010; 23 (8): 667-77).*
Klein et al. (MAbs. Nov.-Dec. 2012; 4 (6):653-63).*
Choi et al. (PLoS One. Dec. 16, 2015; 10 (12): e0145349; pp. 1-20).*

(Continued)

*Primary Examiner* — Stephen Rawlings
(74) *Attorney, Agent, or Firm* — Fish & Richardson P.C.

(57) ABSTRACT

In the course of the present invention, it was discovered that one could regulate association between polypeptides by modifying amino acid residues that form the interface during the association to amino acids carrying the same type of charge. In this context, the present invention enables efficient formation of heterologous molecules. For example, the present invention can be suitably applied to the preparation of bispecific antibodies.

54 Claims, 32 Drawing Sheets

(56) References Cited

U.S. PATENT DOCUMENTS

| | | | |
|---|---|---|---|
| 8,592,562 B2* | 11/2013 | Kannan | C07K 16/468 530/387.3 |
| 8,597,911 B2 | 12/2013 | Miyazaki et al. | |
| 8,637,641 B2 | 1/2014 | Dahiyat et al. | |
| 9,096,651 B2 | 8/2015 | Igawa et al. | |
| 9,228,017 B2 | 1/2016 | Igawa et al. | |
| 9,334,331 B2 | 5/2016 | Igawa et al. | |
| 9,670,269 B2 | 6/2017 | Igawa et al. | |
| 9,688,762 B2 | 6/2017 | Igawa et al. | |
| 2001/0001663 A1 | 5/2001 | Kishimoto et al. | |
| 2001/0006796 A1 | 7/2001 | Briggs et al. | |
| 2002/0028178 A1 | 3/2002 | Hanna et al. | |
| 2002/0062010 A1 | 5/2002 | Arathoon et al. | |
| 2002/0142374 A1 | 10/2002 | Gallo et al. | |
| 2002/0147326 A1 | 10/2002 | Chaiklin et al. | |
| 2002/0155537 A1 | 10/2002 | Carter et al. | |
| 2002/0164339 A1 | 11/2002 | Do et al. | |
| 2002/0164668 A1 | 11/2002 | Durham et al. | |
| 2002/0187150 A1 | 12/2002 | Mihara et al. | |
| 2002/0193571 A1 | 12/2002 | Carter et al. | |
| 2002/0197706 A1 | 12/2002 | Snodgrass et al. | |
| 2003/0073161 A1 | 4/2003 | Briggs et al. | |
| 2003/0082612 A1 | 5/2003 | Nadkarni et al. | |
| 2003/0148409 A1 | 8/2003 | Rossi et al. | |
| 2003/0190311 A1 | 10/2003 | Dall'Aqua et al. | |
| 2003/0207346 A1 | 11/2003 | Arathoon et al. | |
| 2003/0219441 A1 | 11/2003 | Thorpe et al. | |
| 2003/0224397 A1* | 12/2003 | Lowman et al. | 435/6 |
| 2004/0071706 A1 | 4/2004 | Ito et al. | |
| 2004/0081651 A1 | 4/2004 | Karpusas et al. | |
| 2004/0091475 A1 | 5/2004 | Tsuchiya et al. | |
| 2004/0219643 A1 | 11/2004 | Winter et al. | |
| 2004/0236080 A1 | 11/2004 | Aburatani et al. | |
| 2004/0242847 A1 | 12/2004 | Fukushima et al. | |
| 2005/0095243 A1 | 5/2005 | Chan et al. | |
| 2005/0130224 A1 | 6/2005 | Saito et al. | |
| 2005/0142133 A1 | 6/2005 | Lazar et al. | |
| 2005/0142635 A1 | 6/2005 | Tsuchiya et al. | |
| 2005/0191293 A1 | 9/2005 | Deshpande et al. | |
| 2005/0244403 A1 | 11/2005 | Lazar et al. | |
| 2005/0261229 A1 | 11/2005 | Gillies et al. | |
| 2005/0266425 A1 | 12/2005 | Zauderer et al. | |
| 2006/0019342 A1 | 1/2006 | Dall Acqua et al. | |
| 2006/0024298 A1 | 2/2006 | Lazar et al. | |
| 2006/0058511 A1 | 3/2006 | Tanikawa et al. | |
| 2006/0063228 A1 | 3/2006 | Kasaian et al. | |
| 2006/0134709 A1 | 6/2006 | Stavenhagen et al. | |
| 2006/0141456 A1 | 6/2006 | Edwards et al. | |
| 2006/0159673 A1 | 7/2006 | Kojima | |
| 2006/0160184 A1 | 7/2006 | Hoogenboom et al. | |
| 2006/0189794 A1 | 8/2006 | Tsuchiya et al. | |
| 2006/0194280 A1 | 8/2006 | Dillon et al. | |
| 2006/0204493 A1 | 9/2006 | Huang et al. | |
| 2006/0222643 A1 | 10/2006 | Tsunoda et al. | |
| 2006/0269989 A1 | 11/2006 | Miyazaki et al. | |
| 2006/0275282 A1 | 12/2006 | Moore et al. | |
| 2006/0275301 A1 | 12/2006 | Ozaki et al. | |
| 2006/0292147 A1 | 12/2006 | Yoshizaki et al. | |
| 2007/0003556 A1 | 1/2007 | Tsuchiya et al. | |
| 2007/0036785 A1 | 2/2007 | Kishimoto et al. | |
| 2007/0041978 A1 | 2/2007 | Hattori et al. | |
| 2007/0054354 A1 | 3/2007 | Humphreys et al. | |
| 2007/0059312 A1 | 3/2007 | Baca et al. | |
| 2007/0087381 A1 | 4/2007 | Kojima | |
| 2007/0110757 A1 | 5/2007 | Wei et al. | |
| 2007/0134234 A1 | 6/2007 | Smith et al. | |
| 2007/0148163 A1 | 6/2007 | Takahashi et al. | |
| 2007/0148164 A1 | 6/2007 | Farrington et al. | |
| 2007/0281327 A1 | 12/2007 | Nakano et al. | |
| 2008/0009038 A1 | 1/2008 | Ohtomo et al. | |
| 2008/0063635 A1 | 3/2008 | Takahashi et al. | |
| 2008/0075712 A1 | 3/2008 | Hattori et al. | |
| 2008/0166756 A1 | 7/2008 | Tsuchiya et al. | |
| 2008/0206229 A1 | 8/2008 | Ono et al. | |
| 2009/0028854 A1 | 1/2009 | Igawa et al. | |
| 2009/0117097 A1 | 5/2009 | Igawa et al. | |
| 2009/0208416 A1 | 8/2009 | Moretta et al. | |
| 2009/0214535 A1 | 8/2009 | Igawa et al. | |
| 2009/0221803 A1 | 9/2009 | Dall'Acqua et al. | |
| 2009/0263392 A1 | 10/2009 | Igawa et al. | |
| 2009/0297501 A1 | 12/2009 | Igawa et al. | |
| 2009/0324589 A1 | 12/2009 | Igawa et al. | |
| 2010/0003254 A1 | 1/2010 | Hattori et al. | |
| 2010/0004429 A1 | 1/2010 | Kai et al. | |
| 2010/0008907 A1 | 1/2010 | Nishimoto et al. | |
| 2010/0055092 A1 | 3/2010 | Hasegawa et al. | |
| 2010/0239577 A1 | 9/2010 | Igawa et al. | |
| 2010/0291072 A1* | 11/2010 | Lowman et al. | 424/133.1 |
| 2010/0298542 A1 | 11/2010 | Igawa et al. | |
| 2011/0076275 A1 | 3/2011 | Igawa et al. | |
| 2011/0111406 A1 | 5/2011 | Igawa et al. | |
| 2011/0129459 A1 | 6/2011 | Kuramochi et al. | |
| 2011/0236374 A1 | 9/2011 | Shitara et al. | |
| 2011/0245473 A1 | 10/2011 | Igawa et al. | |
| 2012/0028304 A1 | 2/2012 | Dahiyat et al. | |
| 2012/0065379 A1 | 3/2012 | Igawa et al. | |
| 2012/0071634 A1 | 3/2012 | Igawa et al. | |
| 2012/0237517 A1 | 9/2012 | Hattori et al. | |
| 2012/0238729 A1 | 9/2012 | Kuramochi et al. | |
| 2013/0011866 A1 | 1/2013 | Igawa et al. | |
| 2013/0018174 A1 | 1/2013 | Igawa et al. | |
| 2013/0030156 A1 | 1/2013 | Apostolou et al. | |
| 2013/0052196 A1 | 2/2013 | Apostolou et al. | |
| 2013/0101581 A1 | 4/2013 | Kuramochi et al. | |
| 2013/0195849 A1 | 8/2013 | Spreter et al. | |
| 2013/0330345 A1 | 12/2013 | Igawa et al. | |
| 2014/0037632 A1 | 2/2014 | Igawa et al. | |
| 2014/0112883 A1 | 4/2014 | Ponath et al. | |
| 2014/0112914 A1 | 4/2014 | Nezu et al. | |
| 2014/0370018 A1 | 12/2014 | Igawa et al. | |
| 2014/0370020 A1 | 12/2014 | Kuramochi et al. | |
| 2014/0377253 A1 | 12/2014 | Harding et al. | |
| 2015/0118184 A1 | 4/2015 | Kawai | |
| 2015/0274809 A1 | 10/2015 | Igawa et al. | |
| 2015/0284465 A1 | 10/2015 | Igawa et al. | |
| 2015/0315278 A1 | 11/2015 | Igawa et al. | |
| 2016/0159915 A1 | 6/2016 | Igawa et al. | |
| 2016/0168259 A1 | 6/2016 | Igawa et al. | |
| 2016/0222129 A1 | 8/2016 | Igawa et al. | |
| 2016/0229915 A1 | 8/2016 | Igawa et al. | |
| 2017/0022293 A1 | 1/2017 | Igawa et al. | |

FOREIGN PATENT DOCUMENTS

| | | |
|---|---|---|
| CA | 2 203 182 | 5/1996 |
| CA | 2 331 641 | 11/1999 |
| CA | 2 019 559 | 1/2002 |
| CA | 2 443 294 | 10/2002 |
| CA | 2 523 577 | 11/2004 |
| CA | 2 531 482 | 1/2005 |
| CA | 2 549 467 | 7/2005 |
| CA | 2 560 953 | 9/2005 |
| CA | 2 603 264 | 10/2006 |
| CA | 2 625 773 | 4/2007 |
| CA | 2 626 688 | 4/2007 |
| CA | 2 647 846 | 10/2007 |
| CA | 2 700 986 | 4/2009 |
| CA | 2 819 530 | 6/2012 |
| CN | 101198698 | 6/2008 |
| CN | 102471378 | 5/2012 |
| CN | 103833852 | 6/2014 |
| DE | 198 19 846 | 11/1999 |
| EP | 0 369 566 | 5/1990 |
| EP | 437 622 | 7/1991 |
| EP | 0 637 593 | 2/1995 |
| EP | 0 404 097 | 9/1996 |
| EP | 0 774 511 | 5/1997 |
| EP | 0 783 893 | 7/1997 |
| EP | 811691 B1 | 12/1997 |
| EP | 1 069 185 | 1/2001 |
| EP | 1 220 923 | 7/2002 |
| EP | 1 327 681 | 7/2003 |
| EP | 1510943 | 3/2005 |
| EP | 0 979 281 | 7/2005 |

(56) References Cited

FOREIGN PATENT DOCUMENTS

| | | |
|---|---|---|
| EP | 1 605 058 | 12/2005 |
| EP | 1 693 448 | 8/2006 |
| EP | 1 701 979 | 9/2006 |
| EP | 1 773 391 | 4/2007 |
| EP | 1 847 602 | 10/2007 |
| EP | 1870458 A1 | 12/2007 |
| EP | 1870459 | 12/2007 |
| EP | 1 876 236 | 1/2008 |
| EP | 1900814 A1 | 3/2008 |
| EP | 2 006 381 | 12/2008 |
| EP | 2 009 101 | 12/2008 |
| EP | 2031064 | 3/2009 |
| EP | 1 505 148 | 4/2009 |
| EP | 2 107 115 | 10/2009 |
| EP | 2 194 066 | 6/2010 |
| EP | 2 196 541 | 6/2010 |
| EP | 2 202 245 | 6/2010 |
| EP | 2 206 775 | 7/2010 |
| EP | 2 275 443 | 1/2011 |
| EP | 1 688 488 | 8/2011 |
| EP | 2 409 991 | 1/2012 |
| EP | 2 522 724 | 11/2012 |
| EP | 2 543 727 | 1/2013 |
| EP | 2 647 707 | 10/2013 |
| EP | 2 905 290 | 8/2015 |
| EP | 2914634 A1 * | 9/2015 |
| JP | S63-52890 | 3/1988 |
| JP | 2-028200 | 1/1990 |
| JP | H02-145187 | 6/1990 |
| JP | H05-184383 | 7/1993 |
| JP | H05-199894 | 8/1993 |
| JP | H05-203652 | 8/1993 |
| JP | H05-213775 | 8/1993 |
| JP | H05-304992 | 11/1993 |
| JP | 07-67688 | 3/1995 |
| JP | 7-503622 | 4/1995 |
| JP | 8-500979 | 2/1996 |
| JP | 8-510555 | 11/1996 |
| JP | 09506001 | 6/1997 |
| JP | 10-505231 | 5/1998 |
| JP | 10-165184 | 6/1998 |
| JP | 10-511085 | 10/1998 |
| JP | 11-500915 | 1/1999 |
| JP | 11-500916 | 1/1999 |
| JP | 11-71288 | 3/1999 |
| JP | 11-506310 | 6/1999 |
| JP | 3032287 | 4/2000 |
| JP | 2001-506135 | 5/2001 |
| JP | 2001-513999 | 9/2001 |
| JP | 2001-518930 | 10/2001 |
| JP | 2001-523971 | 11/2001 |
| JP | 2002-514406 | 5/2002 |
| JP | 2002-518041 | 6/2002 |
| JP | 2002-543822 | 12/2002 |
| JP | 2002-544173 | 12/2002 |
| JP | 2003-055398 | 2/2003 |
| JP | 2003-509049 | 3/2003 |
| JP | 2003-515323 | 5/2003 |
| JP | 2004-086682 | 3/2004 |
| JP | 2004-86862 | 3/2004 |
| JP | 2004-511426 | 4/2004 |
| JP | 2005-535341 | 11/2005 |
| JP | 2005/537009 | 12/2005 |
| JP | 2008-512995 | 5/2008 |
| JP | 2008-538920 | 11/2008 |
| JP | 2009-500458 | 1/2009 |
| JP | 2012-510281 | 6/2010 |
| JP | 2010-522701 | 7/2010 |
| JP | 2011-508604 | 3/2011 |
| JP | 2012-522527 | 9/2012 |
| JP | 2012-531439 | 12/2012 |
| JP | 5144499 | 2/2013 |
| JP | 2013-515509 | 5/2013 |
| JP | 2013-529084 | 7/2013 |
| JP | 2013-529190 | 7/2013 |
| JP | 2013-165716 | 8/2013 |
| JP | 5334319 | 11/2013 |
| JP | 5484060 | 5/2014 |
| JP | 5717624 | 5/2015 |
| JP | 2015-130883 | 7/2015 |
| JP | 5787446 | 9/2015 |
| JP | 5912436 | 4/2016 |
| KR | 2009/0107091 | 10/2009 |
| KR | 2010/0056467 | 5/2010 |
| KR | 2010/0074221 | 7/2010 |
| KR | 2013/0130765 | 12/2013 |
| MX | 9905856 A | 7/2000 |
| RU | 94028282 | 7/1996 |
| RU | 2232773 | 7/2004 |
| RU | 2266298 | 12/2005 |
| RU | 2339696 | 11/2008 |
| TW | 2007/14313 | 4/2007 |
| TW | 2012/49872 | 12/2012 |
| TW | I452135 | 9/2014 |
| TW | I452136 | 9/2014 |
| WO | WO 91/01335 | 2/1991 |
| WO | WO 91/08770 | 6/1991 |
| WO | WO 92/19759 | 11/1992 |
| WO | WO 93/11161 | 6/1993 |
| WO | WO 94/05690 | 3/1994 |
| WO | WO 94/13804 | 6/1994 |
| WO | WO 95/01571 | 1/1995 |
| WO | WO 95/14710 | 6/1995 |
| WO | WO9533844 | 12/1995 |
| WO | WO9601653 | 1/1996 |
| WO | WO 96/04925 | 2/1996 |
| WO | WO 96/07754 | 3/1996 |
| WO | WO 96/11020 | 4/1996 |
| WO | WO 96/12503 | 5/1996 |
| WO | WO 96/16673 | 6/1996 |
| WO | WO 96/26964 | 9/1996 |
| WO | WO 96/27011 | 9/1996 |
| WO | WO 96/34892 | 11/1996 |
| WO | WO 97/09351 | 3/1997 |
| WO | WO 97/10354 | 3/1997 |
| WO | WO 97/31108 | 8/1997 |
| WO | WO9803546 | 1/1998 |
| WO | WO 98/28331 | 7/1998 |
| WO | WO 98/41641 | 9/1998 |
| WO | WO 98/42378 | 10/1998 |
| WO | WO 98/50431 | 11/1998 |
| WO | WO 99/02567 | 1/1999 |
| WO | WO 99/03495 | 1/1999 |
| WO | WO 99/10494 | 3/1999 |
| WO | WO 99/18212 | 4/1999 |
| WO | WO 99/51743 | 10/1999 |
| WO | WO 99/58572 | 11/1999 |
| WO | WO 99/67359 | 12/1999 |
| WO | WO 00/44788 | 8/2000 |
| WO | WO 00/67795 | 11/2000 |
| WO | WO 00/69462 | 11/2000 |
| WO | WO 01/19992 | 3/2001 |
| WO | WO 01/30854 | 5/2001 |
| WO | WO 01/36486 | 5/2001 |
| WO | WO 01/44282 | 6/2001 |
| WO | WO 01/64713 | 9/2001 |
| WO | WO 01/66737 | 9/2001 |
| WO | WO 01/70775 | 9/2001 |
| WO | WO 01/74388 | 10/2001 |
| WO | WO 01/79494 | 10/2001 |
| WO | WO 01/82899 | 11/2001 |
| WO | WO 01/90192 | 11/2001 |
| WO | WO 01/97858 | 12/2001 |
| WO | WO 02/04021 | 1/2002 |
| WO | WO 02/06838 | 1/2002 |
| WO | WO 02/22212 | 3/2002 |
| WO | WO 02/33072 | 4/2002 |
| WO | WO 02/33073 | 4/2002 |
| WO | WO 02/072605 | 9/2002 |
| WO | WO 02/078612 | 10/2002 |
| WO | WO 03/000883 | 1/2003 |
| WO | WO 03/020949 | 3/2003 |
| WO | WO 03/033654 | 4/2003 |
| WO | WO 03/035835 | 5/2003 |

(56) References Cited

FOREIGN PATENT DOCUMENTS

| | | |
|---|---|---|
| WO | WO 03/042231 | 5/2003 |
| WO | WO 03/087163 | 10/2003 |
| WO | WO 03/091424 | 11/2003 |
| WO | WO 03/104425 | 12/2003 |
| WO | WO 03/105757 | 12/2003 |
| WO | WO 2004/009618 | 1/2004 |
| WO | WO 2004/016740 | 2/2004 |
| WO | WO 2004/019966 | 3/2004 |
| WO | WO 2004/020579 | 3/2004 |
| WO | WO 2004/033499 | 4/2004 |
| WO | WO 2004/060919 | 7/2004 |
| WO | WO 2004/065611 | 8/2004 |
| WO | WO 2004/068931 | 8/2004 |
| WO | WO 2004/081048 | 9/2004 |
| WO | WO 2004/087763 | 10/2004 |
| WO | WO 2004/096273 | 11/2004 |
| WO | WO 2004/097041 | 11/2004 |
| WO | WO 2004/111233 | 12/2004 |
| WO | WO2004113387 | 12/2004 |
| WO | WO 2005/005604 | 1/2005 |
| WO | WO 2005/025615 | 3/2005 |
| WO | WO 2005/035753 | 4/2005 |
| WO | WO 2005/035754 | 4/2005 |
| WO | WO 2005/035756 | 4/2005 |
| WO | WO 2005/047327 | 5/2005 |
| WO | WO 2005/056604 | 6/2005 |
| WO | WO 2005/056606 | 6/2005 |
| WO | WO 2005/059106 | 6/2005 |
| WO | WO 2005/062916 | 7/2005 |
| WO | WO 2005/067620 | 7/2005 |
| WO | WO 2005/107784 | 11/2005 |
| WO | WO 2005/112564 | 12/2005 |
| WO | WO 2005/123126 | 12/2005 |
| WO | WO 2006/004663 | 1/2006 |
| WO | WO 2006/019447 | 2/2006 |
| WO | WO 2006/029879 | 3/2006 |
| WO | WO 2006/030200 | 3/2006 |
| WO | WO 2006/030220 | 3/2006 |
| WO | WO 2006/033386 | 3/2006 |
| WO | WO 2006/047350 | 5/2006 |
| WO | WO 2006/050491 | 5/2006 |
| WO | WO 2006/067913 | 6/2006 |
| WO | WO 2006/071877 | 7/2006 |
| WO | WO 2006/075668 | 7/2006 |
| WO | WO 2006/106905 | 10/2006 |
| WO | WO 2006/109592 | 10/2006 |
| WO | WO 2006/113767 | 10/2006 |
| WO | WO2006106903 | 10/2006 |
| WO | WO2006106905 | 10/2006 |
| WO | WO2006106905 A1 * | 10/2006 |
| WO | WO 2006/116260 | 11/2006 |
| WO | WO 2006/121852 | 11/2006 |
| WO | WO 2007/009065 | 1/2007 |
| WO | WO 2007/060411 | 5/2007 |
| WO | WO 2007/108559 | 9/2007 |
| WO | WO 2007/110205 | 10/2007 |
| WO | WO 2007/114319 | 10/2007 |
| WO | WO 2007/114325 | 10/2007 |
| WO | WO 2007/142325 | 12/2007 |
| WO | WO 2007/147901 | 12/2007 |
| WO | WO 2008/043822 | 4/2008 |
| WO | WO 2008/090960 | 7/2008 |
| WO | WO 2008/092117 | 7/2008 |
| WO | WO 2008/118970 | 10/2008 |
| WO | WO 2008/119353 | 10/2008 |
| WO | WO 2008/145141 | 12/2008 |
| WO | WO 2009/012394 | 1/2009 |
| WO | WO 2009/041062 | 4/2009 |
| WO | WO 2009/041613 | 4/2009 |
| WO | WO 2009/041621 | 4/2009 |
| WO | WO 2009/041643 | 4/2009 |
| WO | WO 2009/041734 | 4/2009 |
| WO | WO 2009/052439 | 4/2009 |
| WO | WO 2009/053368 | 4/2009 |
| WO | WO 2009/072604 | 6/2009 |
| WO | WO 2009/079649 | 6/2009 |
| WO | WO 2009/089004 | 7/2009 |
| WO | WO 2009/100309 | 8/2009 |
| WO | WO 2009/125825 | 10/2009 |
| WO | WO 2009/139822 | 11/2009 |
| WO | WO 2010/035769 | 4/2010 |
| WO | WO 2010/063746 | 6/2010 |
| WO | WO 2010/064090 | 6/2010 |
| WO | WO 2010/107109 | 9/2010 |
| WO | WO 2010/107110 | 9/2010 |
| WO | WO 2010/115589 | 10/2010 |
| WO | WO 2010/129304 | 11/2010 |
| WO | WO 2010/151792 | 12/2010 |
| WO | WO 2011/037158 | 3/2011 |
| WO | WO 2011/078332 | 6/2011 |
| WO | WO 2011/090754 | 7/2011 |
| WO | WO 2011/090762 | 7/2011 |
| WO | WO 2011/091177 | 7/2011 |
| WO | WO 2011/091181 | 7/2011 |
| WO | WO 2011/108502 | 9/2011 |
| WO | WO 2011/108714 | 9/2011 |
| WO | WO 2011/111007 | 9/2011 |
| WO | WO 2011/131746 | 10/2011 |
| WO | WO 2011/133886 | 10/2011 |
| WO | WO 2011/143545 | 11/2011 |
| WO | WO 2012/067176 | 5/2012 |
| WO | WO 2010/073985 | 6/2012 |
| WO | WO 2012/073985 | 6/2012 |
| WO | WO 2012/145238 | 10/2012 |
| WO | WO 2013/060867 | 5/2013 |
| WO | WO 2013/065708 | 5/2013 |
| WO | WO 2013/181543 | 12/2013 |
| WO | WO 2014/028354 | 2/2014 |
| WO | WO 2014/051433 | 4/2014 |
| WO | WO 2014/054804 | 4/2014 |
| WO | WO 2015/046467 | 4/2015 |
| WO | WO 2015/046554 | 4/2015 |
| WO | WO 2015/156268 | 10/2015 |
| WO | WO 2015/174439 | 11/2015 |
| WO | WO 2016/047722 | 3/2016 |
| WO | WO 2016/159213 | 10/2016 |
| WO | WO 2017/159287 | 9/2017 |

OTHER PUBLICATIONS

U.S. Examiner Ilia I. Ouspenski, USPTO Final Office Action in U.S. Appl. No. 10/575,905, dated Feb. 24, 2011, 7 pages.
U.S. Examiner Lynn Anne Bristol, USPTO Restriction Requirement in U.S. Appl. No. 12/295,075, dated Feb. 22, 2011, 9 pages.
International Preliminary Report on Patentability for U.S. Appl. No. PCT/JP2009/057309, dated Nov. 30, 2010, 7 pages.
U.S. Examiner Anne Gussow, USPTO Restriction Requirement in U.S. Appl. No. 11/910,117, dated May 3, 2010, 9 pages.
Abe et al., "Surrogate thrombopoietin," *Immunology Letters*, 61:73-78 (1998).
Andris-Widhopf et al., "Methods for the generation of chicken monoclonal antibody fragments by phage display," *Journal of Immunological Methods*, 242:159-181 (2000).
Arndt et al., "Generation of a highly stable, internalizing anti-DC22 single-chain Fv fragment for targeting non-Hodgkin's lymphoma," *Int. J. Cancer*, 107(5):822-829 (2003).
Bowie et al., "Deciphering the Message in Protein Sequences: Tolerance to Amino Acid Substitutions," *Science*, 247:1306-1310 (1990).
Carter, "Bispecific human IgG by design," *J. Immunol. Methods*, 248:7-15 (2001).
Casset et al., "A peptide mimetic of an anti-CD4 monoclonal antibody by rational design," *Biochemical and Biophysical Research Communications*, 307:198-205 (2003).
Cekaite et al., "Protein Arrays: A versatile toolbox for target identification and monitoring of patient immune responses," *Methods Mol. Biol.*, 360:335-348 (2007).
Chen et al., "Selection and analysis of an optimized anti-VEGF antibody: crystal structure of an affinity-matured Fab in complex with antigen," *Journal of Molecular Biology*, 293:865-881 (1999).
Clackson et al., "Making antibody fragments using phage display libraries," *Nature*, 352:624-628 (1991).

(56) References Cited

OTHER PUBLICATIONS

Cochlovius et al., "Treatment of human B cell lymphoma xenografts with a CD3 x CD19 diabody and T cells," *The Journal of Immunology*, 165:888-895 (2000).

Creighton, T., "Protein folding," *Biochem. J.*, 270(1):1-16 (1990).

Dejonge et al., "In vivo retargeting of T cell effector function by recombinant bispecific single chain Fv (anti-DC3 x anti-idiottype) induces long term survival of the murine BCL1 lymphoma model," *J. Immunol.*, 161(3):1454-1461 (1998).

De Jonge et al., "Production and Characterization of Bispecific Single-Chain Antibody Fragments," *Mol. Immunol.*, 32:1405-1412 (1995).

Desplancq et al., "Multimerization behaviour of single chain Fv variants for the tumour-binding antibody B72.3," *Protein Engineering*, 7(8):1027-1033 (1994).

Eijsink et al., "Rational engineering of enzyme stability," *Journal of Biotechnology*, 113:105-120 (2004).

Ewert et al., "Biophysical properties of human antibody variable domains," *J. Mol. Biol.*, 325:531-553 (2003).

Ewert et al., "Stability improvement of antibodies for extracellular and intracellular applications: CDR grafting to stable frameworks and structure-based framework engineering," *Methods*, 34:184-199 ( 2004).

Ewert et al., "Structure-based improvement of the biophysical properties of immunoglobulin $V_H$ domains with a generalizable approach," *Biochemistry*, 42:1517-1528 (2003).

Goding, "Monoclonal Antibodies: Principles and Practice," *Academic Press*, second Ed., 125:129 (1986).

Goldstein et al., "Cytolytic and Cytostatic Properties of an Anti-Human FcγRI (CD64) x Epidermal Growth Factor Bispecific Fusion Protein," *J. Immunol.*, 158:872-879 (1997).

Gruber et al., "Efficient tumor cell lysis mediated by a bispecific single chain antibody expressed in *Escherichia coli*," *Journal of Immunology*, 152:5368-5374 (1994).

Hoogenboom et al., "Multi-subunit proteins on the surface of filamentous phage: methodologies for displaying antibody (Fab) heavy and light chains," *Nucleic Acids Res.*, 19:4133-4137 (1991).

Hozumi and Tonegawa, "Evidence for somatic rearrangement of immunoglobulin genes coding for variable and constant regions," *Proc. Natl. Acad. Sci. USA*, 73(10):3628-3632 (1976).

Jäger et al., "Folding and assembly of an antibody Fv fragment, a heterodimer stabilized by antigen," *Journal of Molecular Biology*, 285:2005-2019 (1999).

Kipriyanov and Little, "Generation of Recombinant Antibodies," *Molecular Biotechnology*, 12:173-201 (1999).

Kipriyanov et al., "Bispecific tandem diabody for tumor therapy with imprived antigen binding and pharmacokinetics," *Journal of Molecular Biology*, 293:41-56 (1999).

Kipriyanov et al., "Bispecific CD3 x CD19 diabody for T cell-mediated lysis of malignant human B cells," *In. J. Cancer*, 77:763-772 (1998).

Kontermann, R., "Recombinant bispecific antibodies for cancer therapy," *Acta Pharmacol. Sin.*, 26(1):1-9 (2005).

Korn et al., "Recombinant bispecific antibodies for the targeting of adenoviruses to CEA-expressing tumour cells: a comparative analysis of bacterially expressed single-chain diabody and tandem scFv," *The Journal of Gene Medicine*, 6:642-651 (2004).

Krebber et al., "Reliable cloning of functional antibody variable domains from hybridomas and spleen cell repertoires employing a reengineered phage display system," *J. Immunol. Methods*, 201:35-55 (1997).

Kriangkum et al., "Bispecific and bifunctional single chain recombinant antibodies," *Biomol. Eng.*, 18(2):31-40 (2001).

Kumar et al., "Molecular cloning and expression of the fabs of human autoantibodies in *Escherichia coli*," *The Journal of Biological Chemistry*, 275(41):35129-35136 (2000).

Kurucz et al., "Retargeting of CTL by an efficiently refolded bispecific single-chain Fv dimer produced in bacteria," *The Journal of Immunology*, 154:4576-4582 (1995).

Le Gall et al., "Effect of linker sequences between the antibody variable domains on the formation, stability and biological activity of a bispecific tandem diabody," *Protein Engineering Design & Selection*, 17(4):357-366 (2004).

Little et al., "Of mice and men: hybridoma and recombinant antibodies," *Immunol. Today*, 21:364-370 (2000).

Mack et al., "A small bispecific antibody construct expressed as a functional single-chain molecule with high tumor cell cytotoxicity," *Proc. Natl. Acad. Sci. USA*, 92(15):7021-7025 (1995).

Mallender et al., "Construction, expression and activity of a bivalent bispecific single-chain antibody," *J. Biol. Chem.*, 269(1):199-206 (1994).

McGuinness et al., "Phage diabody repertoires for selection of large number of bispecific antibody fragments," *Nature Biotechnology*, 14(9):1149-1154 (1996).

Meng et al., "The evaluation of recombinant, chimeric, tetravalent antihuman CD22 antibodies," *Clinical Cancer Research*, 10:1274-1281 (2004).

Ngo et al., "Computational Complexity, Protein Structure Prediction, and the Levinthal Paradox ," *The Protein Folding Problem and Tertiary Structure Prediction*, Merz, Jr. et al. Editors, Birkhauser Boston, 433-506 (1994).

Nieba et al., "Disrupting the hydrophobic patches at the antibody variable/constant domain interface: improved *in vivo* folding and physical characterization of an engineered scFv fragment," *Protein Engineering*, 10(4):435-444 (1997).

Palacios et al., "IL-3-dependent mouse clones that express B-220 surface antigen, contain Ig genes in germ-line configuration, and generate B lymphocutes in vivo," *Cell*, 41:727-734 (1985).

Peipp et al., "Bispecific antibodies targeting cancer cells," *Biochem. Soc. Trans.*, 30:507-511 (2002).

Rajagopal et al., "A form of anti-Tac (Fv) which is both single-chain and disulfide stabilized: comparison with its single-chain and disulfide-stabilized homologs," *Protein Engineering*, 10(12):1453-1459 (1997).

Rousch et al., "Somatostatin displayed on filamentous phage as a receptor-specific agonist," *Br. J. Pharmacol.*, 125:5-16 (1998).

Shalaby et al., "Development of Humanized Bispecific Antibodies Reactive with Cytotoxic Lymphocytes and Tumor Cells Overexpressing the HER2 Protooncogene," *J. Exp. Med.*, 175:217-225 (1992).

Shimba et al., "Comparative thermodynamic analyses of the Fv, Fab and Fab fragments of anti-dansyl mouse monoclonal antibody," *FEBS Letters*, 360:247-250 (1995).

Shire et al., "Challenges in the development of high protein concentration formulations," *Journal of Pharmaceutical Sciences*, 93(6):1390-1402 (2004).

Skerra, "Use of the tetracycline promoter for the tightly regulated production of a murine antibody fragment in *Escherichia coli*," *Gene*, 151:131-135 (1994).

Smith-Gill et al., "Contributions of immunoglobulin heavy and light chains to antibody specificity for lysozyme and two haptens," *The Journal of Immunology*, 139:4135-4144 (1987).

Song et al., "Light chain of natural antibody plays a dominant role in protein antigen binding," *Biochemical and Biophysical Research Communications*, 268:390-394, (2000).

Souyri, M., "Mpl: from an acute myeloproliferative virus to the isolation of the long sought thrombopoietin," *Seminars in Hematology*, 35(3):222-231 (1998).

Tang et al., "Selection of linkers for a catalytic single-chain antibody using phage display technology", *The Journal of Biological Chemistry*, 271(26):15682-15686 (1996).

Turner et al., "Importance of the linker in expression of single-chain Fv antibody fragments: optimization of peptide sequence using phage display technology," *Journal of Immunological Methods*, 205:43-54 (1997).

Van Den Burg et al., "Selection of mutations for increased protein stability," *Curr. Opin. Biotechnol.*, 13(4):333-337 (2002).

Vieille et al., "Hyperthermophilic enzymes: sources, uses, and molecular mechanisms for thermostability," *Microbiology and Molecular Biology Reviews*, 65(1):1-43 (2001).

(56) References Cited

OTHER PUBLICATIONS

Volkel et al., "Optimized linker sequences for the expression of monomeric and dimeric bispecific single-chain diabodies," *Protein Engineering*, 14(10):815-823 (2001).
Wells, "Perspectives in Biochemistry," *Biochemistry*, 29(37):8509-8517 (1990).
Whitlow et al., "An improved linker for single-chain Fv with reduced aggregation and enhanced proteolytic stability," *Protein Engineering*, 6(8):989-995 (1993).
Worn et al., "Stability engineering of antibody single-chain Fv fragments," *J. Mol. Biol.*, 305:989-1010 (2001).
Zhu et al., "An efficient route to the production of an IgG-like bispecific antibody", Protein Eng., 13:361-367 (2000).
U.S. Examiner Lorraine Spector, USPTO Restriction Requirement in U.S. Appl. No. 10/551,504, dated Jun. 27, 2008, 6 pages.
Fish & Richardson P.C., Response to Restriction Requirement dated Jun. 27, 2008 in U.S. Appl. No. 10/551,504, dated Sep. 29, 2008, 13 pages.
U.S. Examiner Lorraine Spector, USPTO Restriction Requirement in U.S. Appl. No. 10/551,504, dated Dec. 16, 2008, 5 pages.
Fish & Richardson P.C., Response to Restriction Requirement dated Dec. 16, 2008 in U.S. Appl. No. 10/551,504, dated Dec. 23, 2008, 14 pages.
U.S. Examiner Lorraine Spector, USPTO Non-Final Office Action in U.S. Appl. No. 10/551,504, dated Apr. 15, 2009, 35 pages.
Fish & Richardson P.C., Amendment in Reply to Action dated Apr. 15, 2009 in U.S. Appl. No. 10/551,504, dated Aug. 14, 2009, 19 pages.
Japanese Examiner Yoshiko Kuwahara, International Preliminary Report on Patentability for App. Ser. No. PCT/JP2004/018506, 8 pages.
U.S. Examiner Lynn Anne Bristol, USPTO Restriction Requirement in U.S. Appl. No. 10/560,098, dated Jul. 13, 2007, 9 pages.
Fish & Richardson P.C., Response to Restriction Requirement dated Jul. 13, 2007 in U.S. Appl. No. 10/560,098, filed Aug. 10, 2007, 6 pages.
U.S. Examiner Lynn Anne Bristol, USPTO Non-Final Office Action in U.S. Appl. No. 10/560,098, dated Oct. 23, 2007, 17 pages.
U.S. Examiner Lynn Anne Bristol, USPTO Final Office Action in U.S. Appl. No. 10/560,098, dated Sep. 11, 2008, 20 pages.
U.S. Examiner Lynn Anne Briston, USPTO Interview Summary for U.S. Appl. No. 10/560,098, dated Jun. 5, 2009, 8 pages.
Fish & Richardson P.C., Amendment in Reply to Office Action dated Sep. 11, 2008 in U.S. Appl. No. 10/560,098, filed Jun. 10, 2009, 12 pages.
U.S. Examiner Lynn Anne Bristol, USPTO Office Action in U.S. Appl. No. 10/560,098, dated Aug. 13, 2009, 21 pages.
Japanese Patent Office, International Preliminary Report on Patentability for App. Ser. No. PCT/JP2004/008585, 10 pages.
Japanese Examiner Yoshiko Kuwahara, International Preliminary Report on Patentability for App. Ser. No. PCT/JP2006/306800, dated Oct. 3, 2007, 6 pages.
Japanese Examiner Yoshiko Kuwahara, International Preliminary Report on Patentability for App. Ser. No. PCT/US2006/306803, dated Oct. 3, 2007, 6 pages.
Japanese Examiner Masashi Honda, International Preliminary Report on Patentability for App. Ser. No. PCT/JP2006/311575, dated Dec. 11, 2007, 5 pages.
Japanese Examiner Yoshiko Kuwahara, International Preliminary Report on Patentability for App. Ser. No. PCT/JP2006/31160, dated Dec. 11, 2007, 8 pages.
U.S. Appl. No. 11/373,063, Ozaki et al., filed Mar. 10, 2006.
U.S. Appl. No. 10/582,176, Nakano et al., filed Jun. 9, 2006.
U.S. Appl. No. 10/582,413, Ohtomo et al., filed Oct. 26, 2006.
U.S. Appl. No. 10/582,304, Kimura et al., filed Jun. 9, 2006.
U.S. Appl. No. 11/547,747, Ozaki et al., filed Oct. 5, 2006.
U.S. Appl. No. 11/910,117, Igawa et al., filed Sep. 28, 2007.
Fish & Richardson P.C., Response to Restriction Requirement dated Mar. 18, 2011 in U.S. Appl. No. 11/910,836, filed Sep. 6, 2011, 1 page.
U.S. Examiner Michael Edward Szperka, USPTO Non-Final Office Action in U.S. Appl. No. 11/910,836, dated Sep. 30, 2011, 21 pages.
Sinha et al., "Electrostatics in protein binding and function," Curr. Protein Pept. Sci., 3(6):601-14 (2002).
U.S. Examiner Lynn Anne Bristol, USPTO Non-Final Office Action in U.S. Appl. No. 12/295,075, dated Nov. 4, 2011, 14 pages.
Arndt et al., "Helix-stabilized Fv (hsFv) antibody fragments: substituting the constant domains of a Fab fragment for a heterodimeric coiled-coil domain," J. Mol. Biol., 312:221-228 (2001).
U.S. Examiner Lynn Anne Bristol, USPTO Non-Final Office Action in U.S. Appl. No. 10/560,098, dated Dec. 8, 2011, 11 pages.
Examiner James L. Rogers, USPTO Restriction Requirement in U.S. Appl. No. 12/936,587, dated Dec. 6, 2011, 7 pages.
Sinha et al., "Molecular dynamics simulation of a high-affinity antibody-protein complex: the binding site is a mosaic of locally flexible and preorganized rigid regions," Cell Biochem Biophys., 43:253-273 (2005).
Wu et al., "Development of motavizumab, an ultra-potent antibody for the prevention of respiratory syncytial virus infection in the upper and lower respiratory tract," J. Mol. Biol., 368(3):652-65 (2007).
Yamasaki et al., "Pharmacokinetic analysis of in vivo disposition of succinylated proteins targeted to liver nonparenchymal cells via scavenger receptors: importance of molecular size and negative charge density for in vivo recognition by receptors," J. Pharmacol. Exp. Ther., 301:467-477 (2002).
Yang et al., "Tailoring structure-function and pharmacokinetic properties of single-chain Fv proteins by site-specific PEGylation," Protein Eng., 16:761-770 (2003).
Zuckier et al., "Chimeric human-mouse IgG antibodies with shuffled constant region exons demonstrate that multiple domains contribute to in vivo half-life," Cancer Res., 58:3905-08 (1998).
Japanese Examiner Yoshiko Kuwahara, International Preliminary Report on Patentability for App. Ser. No. PCT/JP2007/057036, dated Oct. 21, 2008, 6 pages.
Japanese Examiner Masashi Honda, International Preliminary Report on Patentability for App. Ser. No. PCT/JP2007/057058, dated Oct. 21, 2008, 11 pages.
International Preliminary Report on Patentability for App. Ser. No. PCT/JP2008/067534, dated Apr. 7, 2010, 7 pages.
Examiner Meera Natarajan, USPTO Restriction Requirement in U.S. Appl. No. 12/295,039, dated Oct. 12, 2010, 9 pages.
Fish & Richardson P.C., Amendment and Response to Restriction Requirement dated Nov. 18, 2009 in U.S. Appl. No. 10/575,905, filed Apr. 16, 2010, 12 pages.
Fish & Richardson P.C., Amendment in Reply to Action dated Jun. 23, 2010 in U.S. Appl. No. 10/575,905, filed Dec. 22, 2010, 10 pages.
Fish & Richardson P.C., Amendment in Reply to Action dated Jun. 23, 2010 in U.S. Appl. No. 10/575,193, filed Dec. 22, 2010, 13 pages.
Ballmaier et al., "c-mpl mutations are the cause of congenital amegakaryocytic thrombocytopenia," Blood, 97:139-146 (2001).
Brinkmann et al., "FTY720: targeting G-protein-coupled receptors for sphingosine 1-phosphate in transplantation and autoimmunity," Curr. Opin. Immunol., 14:569-575 (2002).
Bruenke et al., "A recombinant bispecific single-chain Fv antibody against HLA class II and FcγRIII (CD16) triggers effective lysis of lymphoma cells," Br. J. Haematol., 125:167-179 (2004).
Clark, "CD22, a B Cell-Specific Receptor, Mediates Adhesion and Signal Transduction," J. Immunol., 150:4715-4718 (1993).
Co et al., "A Humanized Antibody Specific for the Platelet Integrin gpIIb/IIIa," J. Immunol., 152:2968-2976 (1994).
Daniel et al., "Induction of Apoptosis in Human Lymphocytes by Human Anti-HLA Class I Antibodies," Transplantation, 75:1380-1386 (2003).
De Felice et al., "Differential regulatory role of monomorphic and polymorphic determinants of histocompatibility leukocyte antigen class I antigens in monoclonal antibody OKT3-induced T cell proliferation," J. Immunol., 139:2683-2689 (1987).

(56) References Cited

OTHER PUBLICATIONS

DeNardo et al., "Anti-HLA-DR/anti-DOTA Diabody Construction in a Modular Gene Design Platform: Bispecific Antibodies for Pretargeted Radioimmunotherapy," *Cancer Biother. Radiopharm.*, 16:525-535 (2001).

Deng et al., "An Agonist Murine Monoclonal Antibody to the Human c-Mpl Receptor Stimulates Megakaryocytopoiesis," *Blood*, 92:1981-1988 (1998).

Ebert et al., "Expression of Metallothionein II in Intestinal Metaplasia, Dysplasia, and Gastric Cancer," *Cancer Res.*, 60:1995-2001 (2000).

Elliott et al., "Activation of the Erythropoietin (EPO) Receptor by Bivalent Anti-EPO Receptor Antibodies," *J. Biol. Chem.*, 271:24691-24697 (1996).

Fayen et al., "Negative signaling by anti-HLA class I antibodies is dependent upon two triggering events," *Int. Immunol.*, 10:1347-1358 (1998).

Funaro et al., "Monoclonal antibodies and therapy of human cancers," *Biotechnol. Adv.*, 18:385-401 (2000).

Genestier et al., "Antibodies to HLA Class 1 α1 Domain Trigger Apoptosis of CD40-Activated Human B Lymphocytes," *Blood*, 90:726-735 (1997).

Genestier et al., "Caspase-dependent Ceramide Production in Fas- and HLA Class I-mediated Peripheral T Cell Apoptosis," *J. Biol. Chem.*, 273:5060-5066 (1998).

Genestier et al., "Fas-Independent Apoptosis of Activated T Cells Induced by Antibodies to the HLA Class I α1 Domain," *Blood*, 90:3629-3639 (1997).

Genestier et al., "T cell sensitivity to HLA class I-mediated apoptosis is dependent on interleukin-2 and interleukin-4," *Eur. J. Immunol.*, 27:495-499 (1997).

Ghetie et al., "Homodimerization of tumor-reactive monoclonal antibodies markedly increases their ability to induce growth arrest or apoptosis of tumor cells," *Proc. Natl. Acad. Sci. USA*, 94:7509-7514 (1997).

Goel et al., "$^{99m}$Tc-Labeled Divalent and Tetravalent CC49 Single-Chain Fv's: Novel Imaging Agents for Rapid in Vivo Localization of Human Colon Carcinoma," *J. Nucl. Med.*, 42:1519-1527 (2001).

Goel et al., "Genetically Engineered Tetravalent Single-Chain Fv of the Pancarcinoma Monoclonal Antibody CC49: Improved Biodistribution and Potential for Therapeutic Application," *Cancer Res.*, 60:6964-6971 (2000).

Goto et al., "A Novel Membrane Antigen Selectively Expressed on Terminally Differentiated Human B Cells," *Blood*, 84:1922-1930 (1994).

Holliger et al., "'Diabodies': Small bivalent and bispecific antibody fragments," *Proc. Natl. Acad. Sci. USA*, 90:6444-6448 (1993).

Hu et al., "Minibody: A Novel Engineered Anti-Carcinoembryonic Antigen Antibody Fragment (Single-Chain Fv-$C_H3$) Which Exhibits Rapid, High-Level Targeting of Xenografts," *Cancer Res.*, 56:3055-3061 (1996).

Hudson et al., "High avidity scFv multimers; diabodies and triabodies," *J. Immunol. Methods*, 231:177-189 (1999).

Kikuchi et al., "A bivalent single-chain Fv fragment against CD47 induces apoptosis for leukemic cells," *Biochem. Biophys. Res. Commun.*, 315:912-918 (2004).

Kimura et al., "2D7 diabody bound to the α2 domain of HLA class I efficiently induces caspase-independent cell death against malignant and activated lymphoid cells," *Biochem. Biophys. Res. Commun.*, 325:1201-1209 (2004).

Kipriyanov et al., "Effect of Domain Order on the Activity of Bacterially Produced Bispecific Single-chain Fv Antibodies," *J. Mol. Biol.*, 330:99-111 (2003).

Kortt et al., "Dimeric and trimeric antibodies: high avidity scFvs for cancer targeting," *Biomol. Eng.*, 18:95-108 (2001).

Kreitman et al., "Cytotoxic Activity of Disulfide-stabilized Recombinant Immunotoxin RFB4(dsFv)-PE38 (BL22) toward Fresh Malignant Cells from Patients with B-Cell Leukemias," *Clin. Cancer Res.*, 6:1476-1487 (2000).

Kulkarni et al., "Construction of a Single-Chain Antibody Derived From 5H7, A Monoclonal Antibody Specific for a Death Signaling Domain of Human Class I Major Histocompatibility Complex," *Transplant. Proc.*, 30:1081 (1998).

Kulkarni et al., "Programmed Cell Death Signaling Via Cell-Surface Expression of a Single-Chain Antibody Transgene," *Transplantation*, 69:1209-1217 (2000).

Lebrun et al., "Antibodies to the Extracellular Receptor Domain Restore the Hormone-insensitive Kinase and Conformation of the Mutant Insulin Receptor Valine 382," *J. Biol. Chem.*, 268:11272-11277 (1993).

Li et al., "The Epitope Specificity and Tissue Reactivity of Four Murine Monoclonal Anti-CD22 Antibodies," *Cell. Immunol.*, 118:85-99 (1989).

Matsuoka et al., "A Monoclonal Antibody to the α2 Domain of Murine Major Histocompatibility Complex Class I that Specifically Kills Activated Lymphocytes and Blocks Liver Damage in the Concanavalin A Hepatitis Model," *J. Exp. Med.*, 198:497-503 (2003).

Matsuoka et al., "A Novel Type of Cell Death of Lymphocytes Induced by a Monoclonal Antibody without Participation of Complement," *J. Exp. Med.*, 181:2007-2015 (1995).

Nishii, "CD22 antibody therapy," *Current Therapy*, 20:47-50 (2001) (English translation included).

Ohtomo et al., "Molecular Cloning and Characterization of a Surface Antigen Preferentially Overexpressed on Multiple Myeloma Cells," *Biochem. Biophys. Res. Commun.*, 258:583-591 (1999).

Oka, "Development of Novel Immunotoxin Using Recombinant Alpha-Sarcin and Its Application Treatment of Hematopoietic Tumor," *Sankyo Seimei Kagaku Kenkyu Shinko Zaidan Kenkyu Hokokushu*, 12:46-56 (1998) (concise English explanation included).

Ono et al., "The humanized anti-HM1.24 antibody effectively kills multiple myeloma cells by human effector cell-mediated cytotoxicity," *Mol. Immunol.*, 36:387-395 (1999).

Orita et al., "A novel therapeutic approach for thrombocytopenia by minibody agonist of the thrombopoietin receptor," *Blood*, 105:562-566 (2005).

Ozaki et al., "A Recombinant HLA Class I-Specific Single Chain Fv Diabody Induces Cell Death in Human Lymphoid Malignancies," *Blood*, 102:933a, Abstract No. 3474 (2003).

Ozaki et al., "Humanized Anti-HM1.24 Antibody Mediates Myeloma Cell Cytotoxicity That is Enhanced by Cytokine Stimulation of Effector Cells," *Blood*, 93:3922-3930 (1999).

Ozaki et al., "Immunotherapy of Multiple Myeloma With a Monoclonal Antibody Directed Against a Plasma Cell-Specific Antigen, HM1.24," *Blood*, 90:3179-3186 (1997).

Pettersen et al., "The TCR-Binding Region of the HLA Class I $α_2$ Domain Signals Rapid Fas-Independent Cell Death: A Direct Pathway for T Cell-Mediated Killing of Target Cells?" *J. Immunol.*, 160:4343-4352 (1998).

Piétri-Rouxel et al., "The biochemical effect of the naturally occurring Trp64→Arg mutation on human β3-adrenoceptor activity," *Eur. J. Biochem.*, 247:1174-1179 (1997).

Plückthun et al., "New protein engineering approaches to multivalent and bispecific antibody fragments," *Immunotechnology*, 3:83-105 (1997).

Rossi et al., "Development of New Multivalent-bispecific Agents for Pretargeting Tumor Localization and Therapy," *Clin. Cancer Res.*, 9:3886s-3896s (2003).

Sato et al., "CD22 is Both a Positive and Negative Regulator of B Lymphocyte Antigen Receptor Signal Transduction: Altered Signaling in CD22-Deficient Mice," *Immunity*, 5:551-562 (1996).

Scheurle et al., "Cancer Gene Discovery Using Digital Differential Display," *Cancer Res.*, 60:4037-4043 (2000).

Smith et al., "Inhibition of T Cell Activation by a Monoclonal Antibody Reactive Against the α3 Domain of Human MHC Class I Molecules," *J. Immunol.*, 153:1054-1067 (1994).

Tahtis et al., "Biodistribution Properties of $^{111}$Indium-labeled C-Functionalized *trans*-Cyclohexyl Diethylenetriaminepentaacetic

(56) References Cited

OTHER PUBLICATIONS

Acid Humanized 3S193 Diabody and F(ab')₂ Constructs in a Breast Carcinoma Xenograft Model," Clin. Cancer Res., 7:1061-1072 (2001).
Tedder et al., "CD22, a B Lymphocyte-Specific Adhesion Molecule That Regulates Antigen Receptor Signaling," Annu. Rev. Immunol., 15:481-504 (1997).
Thilenius et al., "Agonist antibody and Fas ligand mediate different sensitivity to death in the signaling pathways of Fas and cytoplasmic mutants," Eur. J. Immunol., 27:1108-1114 (1997).
Woodle et al., "Anti-Human Class I α3 Domain-Specific Monoclonal Antibody Induces Programmed Cell Death in Murine Cells Expressing Human Class I MHC Transgenes," Transplant. Proc., 30:1059-1060 (1998).
Woodle et al., "Anti-Human Class I MHC Antibodies Induce Apoptosis by a Pathway That is Distinct from the Fas Antigen-Mediated Pathway," J. Immunol., 158:2156-2164 (1997).
Woodle et al., "Class I MHC Mediates Programmed Cell Death in Human Lymphoid Cells," Transplantation, 64:140-146 (1997).
Wu et al., "Tumor localization of anti-CEA single-chain Fvs: improved targeting by non-covalent dimers," Immunotechnology, 2:21-36 (1996).
Xiong et al., "Efficient inhibition of human B-cell lymphoma xenografts with an anti-CD20 × anti-CD3 bispecific diabody," Cancer Lett., 177:29-39 (2002).
Xu et al., "Insight into hepatocellular carcinogenesis at transcriptome level by comparing gene expression profiles of hepatocellular carcinoma with those of corresponding noncancerous liver," Proc. Natl. Acad. Sci. USA, 98:15089-15094 (2001).
Ledbetter et al., Agonistic Activity of a CD4O-Specific Single-Chain Fv Constructed from the Variable Regions of mAb G28-5, Critical Reviews in Immunology, vol. 17, pp. 427-435 (1997).
Kong et al., "A Single Residue, Aspartic Acid 95, in the δ Opioid Receptor Specifies Selective High Affinity Agonist Binding", The Journal of Biological Chemistry, vol. 268(31), pp. 23056-23058 (1993).
Medline Plus Drug Information: Dexamethasone Oral www.nlm.nih.gov/medlineplus/druginfo/meddmaster/a682792.html, downloaded Jul. 19, 2007; last revised Apr. 1, 2003 (see p. 3) (4 pages).
Dall'Acqua et al., "Antibody humanization by framework shuffling," Methods, 36(1):43-60 (2005).
Tsuchiya, Credit Suisse Seminar, "Therapeutic Antibody," at Fuji-Gotemba Laboratories, p. 21 (2006) (English translation).
Fish & Richardson P.C., Amendment in Reply to Office Action dated Jun. 28, 2011 in U.S. Appl. No. 12/295,039, filed Dec. 27, 2011, 14 pages.
Adams et al., "Humanization of a recombinant monoclonal antibody to produce a therapeutic HER dimerization inhibitor, pertuzumab," Cancer Immunol. Immunother., 55:717-727 (2006).
Comper and Glasgow, "Charge selectivity in kidney ultrafiltration," Kidney Int., 47:1242-51 (1995).
Couto et al., "Anti-BA46 Monoclonal Antibody Mc3: Humanization Using a Novel Positional Consensus and in Vivo and in Vitro Characterization," Cancer Research, 55:1717-1722 (1995).
Deen et al., "Structural determinants of glomerular permeability," Am. J. Physiol. Renal. Physiol., 281:F579-F596 (2001).
Ghetie et al., "Multiple roles for the major histocompatibility complex class I- related receptor FcRn," Annu. Rev. Immunol., 18:739-766 (2000).
Kim et al., "Antibody Engineering for the Development of Therapeutic Antibodies," Mol. Cells, 20:17-29 (2005).
Kobayashi et al., "The pharmacokinetic characteristics of glycolated humanized anti-Tac Fabs are determined by their isoelectric points," Cancer Res., 59:422-430 (1999).
Lund et al., "Expression and characterization of truncated forms of humanized L243 IgG1. Architectural features can influence synthesis of its oligosaccharide chains and affect superoxide production triggered through human Fcgamma receptor I," Eur. J. Biochem., 267(24):7246-57 (2000).

Marvin et al., "Redesigning an antibody fragment for faster association with its antigen," Biochemistry, 42:7077-83 (2003).
Shields et al., "High resolution mapping of the binding site on human IgG1 for Fc gamma RI, Fc gamma RII, Fc gamma RIII, and FcRn and design of IgG1 variants with improved binding to the Fc gamma R," J. Biol. Chem., 276:6591-6604 (2001) (Epub Nov. 28, 2000).
Tarditi et al., "Selective high-performance liquid chromatographic purification of bispecific monoclonal antibodies," J. Chromatogr., 599:13-20 (1992).
Ten Kate et al., "Effect of isoelectric point on biodistribution and inflammation: imaging with indium-111-labelled IgG," Eur. J. Nucl. Med., 17:305-309 (1990).
Gelderman et al., "The inhibitory effect of CD46, CD55, and CD59 on complement activation after immunotherapeutic treatment of cervical carcinoma cells with monoclonal antibodies or bispecific monoclonal antibodies," Lab Invest., 82(4):483-93 (2002).
Algonomics—Tripole® applications [online] Retrieved from the Internet on Feb. 29, 2012: http://web.archive.org/web20090221052902/http://www.algonomics.com/proteinengineering/tripole_applications.php, 2 pages (Feb. 21, 2009).
Almagro et al., "Humanization of antibodies," Front Biosci., 13:1619-33 (2008).
Armour et al., "Recombinant human IgG molecules lacking Fcgamma receptor I binding and monocyte triggering activities," Eur. J. Immunol., 29(8):2613-24 (1999).
Bartelds et al., "Clinical response to adalimumab: relationship to anti-adalimumab antibodies and serum adalimumab concentrations in rheumatoid arthritis," Ann Rheum. Dis., 66:921-926 (2007).
Bender et al., "Immunogenicity, efficacy and adverse events of adalimumab in RA patients," Rheumatol. Int., 27:269-274 (2007).
Chau et al., "HuM291(Nuvion), a humanized Fc receptor-nonbinding antibody against CD3, anergizes peripheral blood T cells as partial agonist of the T cell receptor," Transplantation., 71(7):941-50 (2001).
Chen et al., "Generation and analysis of random point mutations in an antibody CDR2 sequence: many mutated antibodies lose their ability to bind antigen," J. Exp. Med., 176(3):855-66 (1992).
Chen et al., "Defective secretion of an immunoglobulin caused by mutations in the heavy chain complementarity determining region 2," J. Exp. Med., 180(2):577-86 (1994).
Chirino et al., "Minimizing the immunogenicity of protein therapeutics," Drug Discov. Today.,.9:82-90 (2004).
Chu et al., "Accumulation of succinimide in a recombinant monoclonal antibody in mildly acidic buffers under elevated temperatures," Pharm. Res., 24(6):1145-56 (2007).
Cole et al., "Human IgG2 variants of chimeric anti-CD3 are nonmitogenic to T cells," J. Immunol., 159(7):3613-21 (1997).
Cordoba et al., "Non-enzymatic hinge region fragmentation of antibodies in solution," J. Chromatogr. B. Analyt. Technol. Biomed. Life Sci., 818(2):115-21 (2005).
Damschroder et al., "Framework shuffling of antibodies to reduce immunogenicity and manipulate functional and biophysical properties," Mol. Immunol., 44(11):3049-60 (2007).
De Groot et al., "De-immunization of therapeutic proteins by T-cell epitope modification," Dev. Biol. (Basel), 122:171-94 (2005).
Fujii, "Antibody affinity maturation by random mutagenesis," Methods Mol. Biol., 248:345-59 (2004).
Gerstner et al., "Sequence plasticity in the antigen-binding site of a therapeutic anti-HER2 antibody," J. Mol. Biol., 321(5):851-62 (2002).
Gessner et al., "The IgG Fc receptor family," Ann. Hematol., 76:231-248 (1998).
Guyre et al., "Increased potency of Fc-receptor-targeted antigens," Cancer Immunol. Immunother., 45(3-4):146-8 (1997).
Hinton et al., "Engineered human IgG antibodies with longer serum half-lives in primates," J. Biol. Chem., 279(8):6213-6 (2004).
Hwang et al., "Use of human germline genes in a CDR homology-based approach to antibody humanization," Methods, 36:35-42 (2005).

(56) References Cited

OTHER PUBLICATIONS

Johnson et al., "Cation exchange-HPLC and mass spectrometry reveal C-terminal amidation of an IgG1 heavy chain," *Anal. Biochem.*, 360:75-83 (2007).
Jones et al., "Identification and removal of a promiscuous CD4+ T cell epitope from the C1 domain of factor VIII," *Thromb. Haemost.*, 3:991-1000 (2005).
Katayose et al., "MUC1-specific targeting immunotherapy with bispecific antibodies: inhibition of xenografted human bile duct carcinoma growth," *Cancer Res.*, 56(18):4205-12 (1996).
Komissarov et al., "Site-specific mutagenesis of a recombinant anti-single-stranded DNA Fab. Role of heavy chain complementarity-determining region 3 residues in antigen interaction," *J. Biol. Chem.*, 272(43):26864-70 (1997).
Leong et al., "Adapting pharmacokinetic properties of a humanized anti-interleukin-8 antibody for therapeutic applications using site-specific pegylation," *Cytokine*, 16(3):106-19 (2001).
Liu et al., "Heterogeneity of monoclonal antibodies," *J. Pharm. Sci.*, 97(7):2426-47 (2008).
Maini et al., "Double-blind randomized controlled clinical trial of the interleukin-6 receptor antagonist, tocilizumab, in European patients with rheumatoid arthritis who had an incomplete response to methotrexate," *Arthritis Rheum.*, 54:2817-29 (2006).
Nesterova et al., "Glypican-3 as a novel target for an antibody-drug conjugate," AACR Abstract No. 656, Los Angeles, CA (Apr. 4-18, 2007).
Nishimoto et al., "Humanized anti-interleukin-6 receptor antibody treatment of multicentric Castleman disease," *Blood*, 106:2627-32 (2005).
Nishimoto et al., "Interleukin 6: from bench to bedside," *Nat. Clin. Pract. Rheumatol.*, 2:619-626 (2006).
Pardridge et al., "Enhanced endocytosis in cultured human breast carcinoma cells and in vivo biodistribution in rats of a humanized monoclonal antibody after cationization of the protein," *J. Pharmacol. Exp. Ther.*, 286(1):548-54 (1998).
Pons et al., "Energetic analysis of an antigen/antibody interface: alanine scanning mutagenesis and double mutant cycles on the HyHEL-10/lysozyme interaction," *Protein Sci.*, 8(5):958-68 (1999).
Presta, "Engineering of therapeutic antibodies to minimize immunogenicity and optimize function," *Adv. Drug Deliv. Rev.*, 58(5-6):640-56 (2006).
Reddy et al., "Elimination of Fc receptor-dependent effector functions of a modified IgG4 monoclonal antibody to human CD4," *J. Immunol.*, 164(4):1925-33 (2000).
Reichert et al., "Development trends for monoclonal antibody cancer therapeutics," *Nat. Rev. Drug Discov.*, 6(5):349-56 (2007).
Rothe et al., "Ribosome display for improved biotherapeutic molecules," *Expert Opin. Biol. Ther.*, 6:177-187 (2006).
Salfeld et al., "Isotype selection in antibody engineering," *Nat. Biotechnol.*, 25:1369-72 (2007).
Sato et al., "Reshaping a human antibody to inhibit the interleukin 6-dependent tumor cell growth," *Cancer Res.*, 53:851-856 (1993).
Schmitz et al., "Phage display: a molecular tool for the generation of antibodies—a review," *Placenta.*, 21 Suppl A:S106-12 (2000).
Strand et al., "Biologic therapies in rheumatology: lessons learned, future directions," *Nat. Rev. Drug Discov.*, 6:75-92 (2007).
Tan et al., "Engineering the isoelectric point of a renal cell carcinoma targeting antibody greatly enhances scFv solubility," *Immunotechnology*, 4(2):107-114 (1998).
Teeling et al., "The biological activity of human CD20 monoclonal antibodies is linked to unique epitopes on CD20," *J. Immunol.*, 177(1):362-71 (2006).
Vaisitti et al., "Cationization of monoclonal antibodies: another step towards the "magic bullet"?," *J. Biol. Regul. Homeost. Agents.*, 19(3-4):105-12 (2005).
Vajdos et al., "Comprehensive functional maps of the antigen-binding site of an anti-ErbB2 antibody obtained with shotgun scanning mutagenesis," *J. Mol. Biol.*, 320(2):415-28 (2002).
Van Walle et al., "Immunogenicity screening in protein drug development," *Expert Opin. Biol. Ther.*, 7(3):405-18 (2007).
Wiens et al., "Somatic mutation in VH complementarity-determining region 2 and framework region 2: differential effects on antigen binding and Ig secretion," *J. Immunol.*, 159(3):1293-302 (1997).
Wiens et al., "Mutation of a single conserved residue in VH complementarity-determining region 2 results in a severe Ig secretion defect," *J. Immunol.*, 167(4):2179-86 (2001).
Xiang et al., "Study of B72.3 combining sites by molecular modeling and site-directed mutagenesis," *Protein Eng.*, 13(5):339-44 (2000).
Zwick et al., "The long third complementarity-determining region of the heavy chain is important in the activity of the broadly neutralizing anti-human immunodeficiency virus type 1 antibody 2F5," *J. Virol.*, 78(6):3155-61 (2004).
Moore et al., "Kinetics and thermodynamics of dimer formation and dissociation for a recombinant humanized monoclonal antibody to vascular endothelial growth factor," Biochemistry, 38:13960-13967 (1999).
U.S. Examiner Shulamith H. Shafer, USPTO Notice of Allowance in U.S. Appl. No. 10/551,504, dated Jan. 7, 2010, 13 pages.
Fish & Richardson P.C., Amendment in Reply to Office Action dated Aug. 13, 2009 in U.S. Appl. No. 10/560,098, filed Feb. 16, 2010, 14 pages.
U.S. Examiner Shulamith H. Shafer, USPTO Notice of Allowance in U.S. Appl. No. 10/551,504, dated May 26, 2010, 7 pages.
U.S. Examiner Lynn Anne Bristol, USPTO Final Office Action in U.S. Appl. No. 10/560,098, dated Jun. 3, 2010, 16 pages.
U.S. Examiner Misook Yu, USPTO Restriction Requirement in U.S. Appl. No. 11/916,979, dated Jul. 1, 2010, 7 pages.
Fish & Richardson P.C., Amendment in U.S. Appl. No. 10/575,193, filed Jun. 17, 2011, 15 pages.
U.S. Examiner Michael Edward Szperka, USPTO Notice of Allowance in U.S. Appl. No. 10/575,193, dated Jul. 13, 2011, 8 pages.
Examiner Meera Natarajan, USPTO Non-Final Office Action in U.S. Appl. No. 12/295,039, dated Jun. 28, 2011, 9 pages.
Fish & Richardson P.C., Amendment in Reply to Final Office Action dated Jun. 3, 2010 in U.S. Appl. No. 10/560,098, filed Jul. 5, 2011, 17 pages.
Fish & Richardson P.C., Response to Restriction Requirement dated Feb. 22, 2011 in U.S. Appl. No. 12/295,075, filed Aug. 18, 2011, 2 pages.
U.S. Examiner Michael Edward Szperka, USPTO Notice of Allowance in U.S. Appl. No. 10/575,193, dated Mar. 18, 2011, 11 pages.
U.S. Examiner Michael Edward Szperka, USPTO Restriction Requirement in U.S. Appl. No. 11/910,836, dated Mar. 18, 2011, 7 pages.
Calbiochem® Buffers, "A guide for the preparation and use of buffers in biological systems," by Chandra Mohan, Ph.D., Copyright © 2003 EMD Biosciences, Inc., an Affiliate of Merck KGaA, Darmstadt, Germany, 37 pages.
Chamow et al., "A humanized, bispecific immunoadhesin-antibody that retargets CD3+ effectors to kill HIV-1-infected cells," *J. Immunol.*, 153(9):4268-80 (1994).
Panka et al., "Variable region framework differences result in decreased or increased affinity of variant anti-digoxin antibodies," *Proc. Natl. Acad. Sci. U.S.A.*, 85(9):3080-4 (1988).
Fish & Richardson P.C., Response to Restriction Requirement dated Oct. 12, 2010 in U.S. Appl. No. 12/295,039, filed Apr. 11, 2011, 9 pages.
Kumar et al., "The second PDZ domain of INAD is a type I domain involved in binding to eye protein kinase C", The Journal of Biological Chemistry 276(27):24971-24977, 2001.
Liu et al., "Functional interactions between arginine-133 and aspartate-88 in the human reduced folate carrier: evidence for a charge-pair association", Biochem. J. 358:511-516, 2001.
Maity et al., "Equilibrium unfolding of dimeric and engineered monomeric forms of Cro (F58W) repressor and the effect of added salts: evidence for the formation of folded monomer induced by sodium perchlorate", Archives of Biochemistry and Biophysics 434:93-107, 2005.
Merchant et al., "An effective route to human bispecific IgG", Nature Biotechnology 16:677-681, 1996.
Nohaile et al., "Altering dimerization specificity by changes in surface electrostatics", PNAS 98(6):3109-3114, 2001.

(56) References Cited

OTHER PUBLICATIONS

Ridgway et al., "'Knobs-into-holes' engineering of antibody $C_H3$ domains for heavy chain heterodimerization", Protein Engineering 9(7):617-621, 1996.
Sal-Man et al., "Arginine mutations within a transmembrane domain of Tar, an *Escherichia coli* aspartate receptor, can drive homodimer dissociation and heterodimer association *in vivo*", Biochem. J. 385:29-36, 2005.
Segal et al., "Bispecific antibodies in cancer therapy", Current Opinion in Immunology 11:558-582, 1999.
Tan et al., "Contributions of a highly conserved $V_H/V_L$ hydrogen bonding interaction to scFv folding stability and refolding efficiency", Biophysical Journal 75:1473-1482, 1998.
Zhu et al., "Remodeling domain interfaces to enhance heterodimer formation", Protein Science 6:781-788, 1997.
Arndt et al., "Factors influencing the dimer to monomer transition of an antibody single-chain Fv fragment," Biochemistry, 37(37):12918-26 (1998).
Chatellier et al., "Functional mapping of conserved residues located at the VL and VH domain interface of a Fab," J. Mol. Biol., 264(1):1-6 (1996).
Chowdhury et al., "Engineering scFvs for improved stability," Methods Mol. Biol., 207:237-54 (2003).
Davies et al., "Antibody VH domains as small recognition units," Biotechnology (N.Y.), 13(5):475-9 (1995).
Jung et al., "The importance of framework residues H6, H7 and H10 in antibody heavy chains: experimental evidence for a new structural subclassification of antibody V(H) domains," J. Mol. Biol., 309(3):701-16 (2001).
Khalifa et al., "Effects on interaction kinetics of mutations at the VH-VL interface of Fabs depend on the structural context," J. Mol. Recognit., 13(3):127-39 (2000).
Vargas-Madrazo et al., "An improved model of association for VH-VL immunoglobulin domains: asymmetries between VH and VL in the packing of some interface residues," J. Mol. Recognit., 16(3):113-20 (2003).
Wu et al., "Multimerization of a chimeric anti-CD20 single-chain Fv-Fc fusion protein is mediated through variable domain exchange," Protein Eng., 14(12):1025-33 (2001).
U.S. Examiner Meera Natarajan, USPTO Restriction Requirement in U.S. Appl. No. 11/916,351, dated Sep. 3, 2010, 8 pages.
Abe et al., "Purification of monoclonal antibodies with light-chain heterogeneity produced by mouse hybridomas raised with NS-1 myelomas: application of hydrophobic interaction high-performance liquid chromatography," J. Biochem. Biophys. Methods, 27:215-227 (1993).
Amersham Biosciences, "Affinity Chromatography: Principles and Methods," Edition AD, pp. 16-18, 137 (2002).
Amersham Biosciences, "Protein Purification Handbook," Edition AC, 98 pages (2001).
Kranenborg et al., "Development and characterization of anti-renal cell carcinoma x antichelate bispecific monoclonal antibodies for two-phase targeting of renal cell carcinoma," Cancer Res., 55:5864s-5867s (1995).
Lansdorp et al., "Purification and analysis of bispecific tetrameric antibody complexes," Mol. Immunol., 27:659-666 (1990).
Morimoto et al., "Single-step purification of F(ab')2 fragments of mouse monoclonal antibodies (immunoglobulins G1) by hydrophobic interaction high performance liquid chromatography using TSKgel Phenyl-5PW," J. Biochem. Biophys. Methods, 24:107-117 (1992).
Presta et al., "Molecular engineering and design of therapeutic antibodies," Curr. Opin. Immunol., 20(4):460-70. doi: 10.1016/j.coi.2008.06.012 (2008).
Suresh et al., "Bispecific monoclonal antibodies from hybrid hybridomas," Methods Enzymol., 121:210-228 (1986).
Warnaar et al., "Purification of bispecific F(ab')2 from murine trinoma OC/TR with specificity for CD3 and ovarian cancer," Hybridoma, 13:519-526 (1994).
Zhu et al., "MHC class I-related neonatal Fc receptor for IgG is functionally expressed in monocytes, intestinal macrophages, and dendritic cells," J. Immunol., 166(5):3266-76 (2001).
Fish & Richardson P.C., Response to Restriction Requirement dated Jul. 27, 2012 and Preliminary Amendment in U.S. Appl. No. 13/434,643, filed Jan. 24, 2013, 12 pages.
U.S. Examiner Michael Edward Szperka, USPTO Non-Final Office Action in U.S. Appl. No. 13/434,643, dated Feb. 12, 2013, 17 pages.
Examiner Bradley Duffy, USPTO Non-Final Office Action U.S. Appl. No. 12/680,082, dated Feb. 14, 2013, 12 pages.
Fish & Richardson P.C., Amendment in Reply to Action dated Jul. 19, 2012 in U.S. Appl. No. 12/295,075, filed Jan. 17, 2013, 113 pages.
Fish & Richardson P.C., Amendment in Reply to Office Action dated Feb. 12, 2013 in U.S. Appl. No. 13/434,643, filed May 13, 2013, 18 pages.
Manz et al., Bioanalytical Chemistry, World Scientific Publishing Co. (2003).
Smans et al., "Bispecific antibody-mediated lysis of primary cultures of ovarian carcinoma cells using multiple target antigens," Int. J. Cancer, 83:270-277 (1999).
U.S. Examiner Nelson B. Moseley II, USPTO Non-Final Office Action in U.S. Appl. No. 12/295,075, dated Jun. 7, 2013, 17 pages.
Angal et al., "A single amino acid substitution abolishes the heterogeneity of chimeric mouse/human (IgG4) antibody," Mol. Immunol., 30:105-108 (1993).
Atwell et al., "Stable heterodimers from remodeling the domain interface of a homodimer using a phage display library," J. Mol. Biol., 270:26-35 (1997).
Burges et al., "Effective relief of malignant ascites in patients with advanced ovarian cancer by a trifunctional anti-EpCAM x anti-CD3 antibody: a phase I/II study," Clin. Cancer Res., 13(13):3899-905 (2007).
Dall'Acqua et al., "Modulation of the effector functions of a human IgG1 through engineering of its hinge region," J. Immunol., 177(2):1129-38 (2006).
Igawa et al., "Engineering the variable region of therapeutic IgG antibodies," MAbs, 3(3):243-52 (2011).
Igawa et al., "Reduced elimination of IgG antibodies by engineering the variable region," Protein Eng. Des. Sel., 23(5):385-92 (2010).
Igawa et al., "Antibody recycling by engineered pH-dependent antigen binding improves the duration of antigen neutralization," Nat. Biotechnol., 28(11):1203-7 (2010).
Kai et al., "Switching constant domains enhances agonist activities of antibodies to a thrombopoietin receptor," Nat. Biotechnol., 26(2):209-11 (2008).
Kim et al., "Mapping the site on human IgG for binding of the MHC class I-related receptor, FcRn," Eur. J. Immunol., 29(9):2819-25 (1999).
Kobayashi et al., "A monoclonal antibody specific for a distinct region of hen egg-white lysozyme," Mol. Immunol., 19:619-30 (1982).
Life Technologies (Invitrogen: "ecdysone analogue" and pIND plasmid), Aug. 10, 2012, 2 pages.
Maeda et al., "pH-dependent receptor/ligand dissociation as a determining factor for intracellular sorting of ligands for epidermal growth factor receptors in rat hepatocytes," J. Control Release, 82(1):71-82 (2002).
Martinez et al., "Disulfide connectivity of human immunoglobulin G2 structural isoforms," Biochemistry, 47(28):7496-7508 (2008).
Maxfield et al., "Endocytic recycling," Nat. Rev. Mol. Cell Biol., 5(2):121-32 (2004).
Morell et al., "Metabolic properties of IgG subclasses in man," J. Clin. Invest., 49(4):673-80 (1970).
Murtaugh et al., "A combinatorial histidine scanning library approach to engineer highly pH-dependent protein switches," Protein Sci., 20(9):1619-31 doi:10.1002/pro 696 (2011).
Ozhegov et al., Tolkovyi Slovar Russkogo iazyka: 2004, p. 292 (with an English translation of the corresponding part only).
Queen et al., "A humanized antibody that binds to the interleukin 2 receptor," Proc. Natl. Acad. Sci. U.S.A., 86(24):10029-10033 (1989).

(56) References Cited

OTHER PUBLICATIONS

Rudikoff et al., "Single amino acid substitution altering antigen-binding specificity," *Proc. Natl. Acad. Sci. U.S.A.*, 79(6):1979-83 (1982).
Ruf et al., "Pharmacokinetics and in vivo stability of intraperitoneally administered therapeutic antibody catumaxomab," *J. Clin. Oncol.*, 26 (May 20 suppl) (2008), abstr 14006.
Smith, "Creative Expression: Mammalian Expression Vectors and Systems," *The Scientist Magazine*, Feb. 2, 1998, 3 pages.
Wang et al., "Polyethylene Glycol-modified Chimeric Toxin Composed of Transforming Growth Factor alpha and *Pseudomonas* Exotoxin," *Cancer. Res.*, 53:4588-4594 (1993).
Wypych et al., "Human IgG2 antibodies display disulfide-mediated structural isoforms," *J. Biol. Chem.*, 283(23):16194-16205 (2008).
Examiner Meera Natarajan, USPTO Final Office Action in U.S. Appl. No. 12/295,039, filed Apr. 12, 2012, 8 pages.
Fish & Richardson P.C., Amendment in Reply to Action dated Nov. 4, 2011 in U.S. Appl. No. 12/295,075, filed May 3, 2012, 12 pages.
Fish & Richardson P.C., Amendment in Reply to Non-Final Office Action dated Dec. 8, 2011 in U.S. Appl. No. 10/560,098, filed Jun. 5, 2012, 11 pages.
U.S. Examiner Lynn Anne Bristol, USPTO Final Office Action in U.S. Appl. No. 10/560,098, filed Aug. 15, 2012, 10 pages.
Fish & Richardson P.C., Amendment in Reply to Final Office Action dated Aug. 15, 2012 in U.S. Appl. No. 10/560,098, filed Sep. 5, 2012, 8 pages.
Fish & Richardson P.C., Third Preliminary Amendment and Response to Restriction Requirement dated Dec. 6, 2011 in U.S. Appl. No. 12/936,587, filed Jun. 5, 2012, 7 pages.
Examiner Bradley Duffy, USPTO Restriction Requirement in U.S. Appl. No. 12/680,082, filed Jun. 6, 2012, 12 pages.
International Preliminary Report on Patentability for App. Ser. No. PCT/JP2010/066490, dated Apr. 11, 2012, 6 pages.
Examiner James L. Rogers, USPTO Restriction Requirement in U.S. Appl. No. 12/936,587, filed Jun. 25, 2012, 5 pages.
Fish & Richardson P.C., Response to Species Election Requirement dated Jun. 25, 2012 in U.S. Appl. No. 12/936,587, filed Jul. 25, 2012, 1 page.
Fish & Richardson P.C., Fourth Preliminary Amendment and Response to Restriction Requirement dated Jun. 6, 2012 in U.S. Appl. No. 12/680,082, filed Jun. 29, 2012, 13 pages.
U.S. Examiner Lynn Anne Bristol, USPTO Final Office Action in U.S. Appl. No. 12/295,075, filed Jul. 19, 2012, 12 pages.
U.S. Examiner Michael Edward Szperka, USPTO Restriction Requirement in U.S. Appl. No. 13/434,643, filed Jul. 27, 2012, 6 pages.
U.S. Examiner Lynn Anne Bristol, USPTO Interview Summary in U.S. Appl. No. 10/560,098, filed Sep. 7, 2012, 3 pages.
Fish & Richardson P.C., Amendment in Reply to Action dated Apr. 12, 2012 in U.S. Appl. No. 12/295,039, filed Sep. 11, 2012, 12 pages.
Examiner Jessica Hope Roark, USPTO Restriction Requirement in U.S. Appl. No. 12/679,922, filed Oct. 2, 2012, 9 pages.
Bayry et al., "Immuno affinity purification of foot and mouth disease virus type specific antibodies using recombinant protein adsorbed to polystyrene wells," *J. Virol. Methods*, 81:21-30 (1999).
International Preliminary Report on Patentability for App. Ser. No. PCT/JP2010/073361, dated Aug. 14, 2012, 7 pages.
Examiner James L. Rogers, USPTO Non-Final Office Action in U.S. Appl. No. 12/936,587, dated Nov. 7, 2012, 13 pages.
Examiner Bradley Duffy, USPTO Restriction Requirement in U.S. Appl. No. 12/680,082, filed Sep. 14, 2012, 6 pages.
Fish & Richardson P.C., Amendment and Response to Election Requirement dated Sep. 14, 2012 in U.S. Appl. No. 12/680,082, filed Nov. 8, 2012, 14 pages.
Fish & Richardson P.C., Response to Restriction Requirement dated Oct. 2, 2012 in U.S. Appl. No. 12/679,922, filed Nov. 1, 2012, 2 pages.
Examiner James L. Rogers, USPTO Non-Final Office Action in U.S. Appl. No. 13/595,139, filed Nov. 14, 2012, 10 pages.

U.S. Appl. No. 13/518,861, Igawa et al., filed Jun. 22, 2012.
U.S. Appl. No. 13/582,073, Kuramochi et al., filed Aug. 31, 2012.
Brown et al., "Tolerance of single, but not multiple, amino acid replacements in antibody $V_H$ CDR2: a means of minimizing B cell wastage from somatic hypermutation?," *J. Immunol.*, 156(9):3285-91 (1996).
Jefferis et al., "Recognition sites on human IgG for Fc gamma receptors: the role of glycosylation," *Immunol. Lett.*, 44(2-3):111-7 (1995).
MacCallum et al., "Antibody-antigen interactions: contact analysis and binding site topography," *J. Mol. Biol.*, 262:732-45 (1996).
Sarmay et al., "Mapping and comparison of the interaction sites on the Fc region of IgG responsible for triggering antibody dependent cellular cytotoxicity (ADCC) through different types of human Fc gamma receptor," *Mol. Immunol.*, 29(5):633-9 (1992).
Sun et al., "Coexpression of Gas6/Ax1 in human ovarian cancers," *Oncology*, 66(6):450-7 (2004).
Examiner Jessica Hope Roark, USPTO Non-Final Office Action in U.S. Appl. No. 12/679,922, filed Jan. 3, 2013, 25 pages.
International Preliminary Report on Patentability for App. Ser. No. PCT/JP2011/055101, dated Oct. 2, 2012, 6 pages.
Examiner Michael D. Allen, USPTO Restriction Requirement in U.S. Appl. No. 13/497,269, filed Dec. 6, 2012, 9 pages.
Allen et al., "Interchain disulfide bonding in human IgG2 antibodies probed by site-directed mutagenesis," *Biochemistry*, 48(17):3755-66 (2009).
U.S. Examiner Nelson B. Moseley II, USPTO Notice of Allowance in U.S. Appl. No. 10/560,098, filed Apr. 25, 2013, 12 pages.
Fish & Richardson P.C., Response to Restriction Requirement dated Dec. 6, 2012 in U.S. Appl. No. 13/497,269, filed May 1, 2013, 2 pages.
Examiner Lynn Anne Bristol, USPTO Restriction Requirement in U.S. Appl. No. 13/257,145, filed Mar. 20, 2013, 11 pages.
Fish & Richardson P.C., Preliminary Amendment and Response to Restriction Requirement dated Mar. 20, 2013 in U.S. Appl. No. 13/257,145, filed Apr. 22, 2013, 7 pages.
Baker et al., "Conversion of a T cell antagonist into an agonist by repairing a defect in the TCR/peptide/MHC interface: implications for TCR signaling," *Immunity*, 13:475-484 (2000).
Burgess, "Possible dissociation of the heparin-binding and mitogenic activities of heparin-binding (acidic fibroblast) growth factor-1 from its receptor-binding activities by site-directed mutagenesis of a single lysine residue," *J. Cell. Biol.*, 111:2129-2138 (1990).
Ju et al., "Conversion of the interleukin 1 receptor antagonist into an agonist by site-specific mutagenesis," *Proc. Natl. Acad. Sci. U.S.A.*, 88:2658-2662 (1991).
Lazar et al., "Transforming growth factor alpha: mutation of aspartic acid 47 and leucine 48 results in different biological activities," *Mol. Cell Biol.*, 8:1247-1252 (1988).
Pakula et al., "Genetic Analysis of Protein Stability and Function," *Annu. Rev. Genet.*, 23:289-310 (1989).
Roitt et al., Immunology, M., Mir, (2000), pp. 110-111 (in Russian, with what is believed to be a published English equivalent of those pages taken from Roitt et al., "Antibody Structure and Function," Immunology, Fifth Ed., (1998), pp. 80-81).
Fish & Richardson P.C., Amendment in Reply to Non-Final Office Action dated Feb. 14, 2013 in U.S. Appl. No. 12/680,082, filed Aug. 12, 2013, 17 pages.
Examiner Jessica Hope Roark, USPTO Final Office Action in U.S. Appl. No. 12/679,922, filed Aug. 2, 2013, 12 pages.
Examiner Michael D. Allen, USPTO Non-Final Office Action in U.S. Appl. No. 13/497,269, filed Aug. 15, 2013, 13 pages.
U.S. Examiner Nelson B. Moseley II, USPTO Notice of Allowance in U.S. Appl. No. 10/560,098, filed Jul. 9, 2013, 6 pages.
U.S. Examiner Michael Edward Szperka, USPTO Final Office Action in U.S. Appl. No. 13/434,643, filed Jul. 11, 2013, 19 pages.
Fish & Richardson P.C., Amendment in Reply to Action dated Jan. 3, 2013 in U.S. Appl. No. 12/679,922, filed Jul. 2, 2013, 18 pages.
Examiner Lynn Anne Bristol, USPTO Non-Final Office Action in U.S. Appl. No. 13/257,145, filed Jul. 2, 2013, 20 pages.
International Preliminary Report on Patentability for App. Ser. No. PCT/JP2011/076486, dated Jun. 12, 2013, 9 pages.

(56) References Cited

OTHER PUBLICATIONS

Figini et al., "In vitro assembly of repertoires of antibody chains on the surface of phage by renaturation," *J Mol Biol.*, May 27, 1994;239(1):68-78.
Vaughan et al., "Human antibodies with sub-nanomolar affinities isolated from a large non-immunized phage display library," *Nat Biotechnol.*, Mar. 1996;14(3):309-14.
Wally et al., "Identification of a novel substitution in the constant region of a gene coding for an amyloidogenic kappal light chain," *Biochim Biophys Acta.*, May 31, 1999;1454(1):49-56.
Dahlback, "Blood coagulation," *Lancet*, 355(9215):1627-32 (2000).
Dumont et al., "Monomeric Fc fusions: impact on pharmacokinetic and biological activity of protein therapeutics," *BioDrugs.*, 20(3):151-60 (2006).
Fay et al., "The size of human factor VIII heterodimers and the effects produced by thrombin," *Biochim Biophys Acta.*, 871(3):268-78 (1986).
Fay et al., "Chapter 2B Nonenzymatic cofactors: factor VIII," *Comprehensive Biochemistry*, 13:35-37 (1986).
Helfrich et al., "A rapid and versatile method for harnessing scFv antibody fragments with various biological effector functions," *J. Immunol. Methods*, 237(1-2):131-45 (2000).
Hombach et al., "A CD16/CD30 bispecific monoclonal antibody induces lysis of Hodgkin's cells by unstimulated natural killer cells in vitro and in vivo," *Int J Cancer*, 55:830-6 (1993).
Hoyer, L.W., "The factor VIII complex: structure and function," *Blood*, 58(1):1-13 (1981).
Hu et al., "Development and characterization of a novel fusion protein composed of a human IgG1 heavy chain constant region and a single-chain fragment variable antibody against Venezuelan equine encephalitis virus," *J Biochem.*, 133(1):59-66 (2003).
Jain et al., "Engineering antibodies for clinical applications," *Trends Biotechnol.*, 25(7):307-16 (2007).
Janeway et al., "Structure of the Antibody Molecule and Immunoglobulin Genes," *Immunobiology, 3rd Edition*, Garland Press, 3:1-3:11 (1997).
Jendeberg et al., "Engineering of Fc(1) and Fc(3) from human immunoglobulin G to analyse subclass specificity for staphylococcal protein A," *J. Immunol. Methods.*, 201(1):25-34 (1997).
Kerschbaumer et al., "An antibody specific for coagulation factor IX enhances the activity of the intrinsic factor X-activating complex," *J. Biol. Chem.*, 279(39):40445-50 (2004).
Kufer et al., "A revival of bispecific antibodies," *Trends Biotechnol.*, 22(5):238-44 (2004).
Miyazaki et al., "Generation of bispecific IgG, which mimics the cofactor function of blood coagulation factor VIII," *Seikagaku*, Poster sessions (2P-B-161) (2006).
Paul, William ed., *Fundamental Immunology, 3rd edition*, p. 242 (1993).
Portolano et al., "Lack of Promiscuity in Autoantigen-Specific H and L Chain Combinations as Revealed by Human H and L Chain "Roulette"," *J. Immunol.*, 150(3):880-887 (1993).
Roguska et al., "Humanization of murine monoclonal antibodies through variable domain resurfacing," *Proc Natl Acad Sci U.S.A.*, 91:969-73 (1994).
Saito et al., "Factor VIII Mimetic Antibody: (1) Establishment and Characterization of Anti-factor IX/anti-factor X Bispecific Antibodies," *2005 International Society of Thrombosis and Haemostasis*, vol. 3, Issue Supplement s1, p. OR160.
Saito et al., "Establishment of Factor VIII Mimetic Antibodies and Their in Vitro Activities in Hemophilia A," *2006 National Hemophilia Foundation Symposia*.
Sampei et al., "Identification and multidimensional optimization of an asymmetric bispecific IgG antibody mimicking the function of factor VIII cofactor activity," *PLoS One*, 2013;8(2):e57479. doi:10.1371/journal.pone.0057479. Epub Feb. 28, 2013.
Shima et al., "Factor VIII Mimetic Antibody: (2) In Vitro Assessment of Cofactor Activity in Hemophilia A," *2005 International Society of Thrombosis and Haemostasis*, vol. 3, Issue Supplement s1, p. P0038.

Shima, M., "Bispecific antibodies to coagulation factors IXa and X mimic the function of factor VIII," *2006 World Federation of Haemophilia* (Haemophilia, 12(Suppl. 2):98 (2006)).
Shirahata, Minna ni yakudatsu ketsuyubyo no kiso to rinsho. Iyaku (Medicine and Drug) Journal Co., Ltd., 280-9 (2009) (including English translation).
Soeda et al., "Factor VIII Taitei Kotai (1) Ko FIXa/FX bispecific Kotai no Sakusei oyobi characterization," Rinsho Ketsueki, 46(8):728 (2005) (including English translation).
Soeda et al., "Phage library-ho ni yori Sakusei shita Ko-FIXa/Ko-FX bispecific Kotai no FVIII Taitei Sayo," *Jpn J Thromb Hemost.*, 16(5):526 (2005) (including English translation).
Staerz et al., "Hybrid hybridoma producing a bispecific monoclonal antibody that can focus effector T-cell activity," *Proc Natl Acad Sci U.S.A.*, 83:1453-7 (1986).
Van Loghem et al., "Staphylococcal protein A and human IgG subclasses and allotypes," *Scand. J. Immunol.*, 15(3):275-8 (1982).
Vehar et al., "Structure of human factor VIII," *Nature*, 312(5992):337-42 (1984).
Wood et al., "Expression of active human factor VIII from recombinant DNA clones," *Nature*, 312(5992):330-7 (1984).
Zuo et al., "An efficient route to the production of an IgG-like bispecific antibody," *Protein Eng.*, 13(5):361-7 (2000).
International Search Report for App. Ser. No. PCT/JP2011/076486, dated Dec. 27, 2011, 4 pages.
Paul, "Structure and function of immunoglobulins," Fundamental Immunology, Third Edition, 292-295 (1993).
U.S. Appl. No. 13/885,421, Igawa et al., filed May 15, 2013.
Medesan et al., "Delineation of the amino acid residues involved in transcytosis and catabolism of mouse IgG1," *J Immunol.*, Mar. 1, 1997;158(5):2211-7.
Pan et al., "Blocking neuropilin-1 function has an additive effect with anti-VEGF to inhibit tumor growth," *Cancer Cell*, Jan. 2007;11(1):53-67.
Singer et al., Genes & Genomes, 1991;67-69.
Singer et al., Genes & Genomes, 1998;1:63-64.
Kabat et al., Sequence of Proteins of Immunological Interest, 5th Edition 1991, p. 690 and p. 693.
Chappel et al., "Identification of a secondary Fc gamma RI binding site within a genetically engineered human IgG antibody," *J Biol Chem.*, Nov. 25, 1993;268(33):25124-31.
Chappel et al., "Identification of the Fc gamma receptor class I binding site in human IgG through the use of recombinant IgG1/IgG2 hybrid and point-mutated antibodies," *Proc Nati Acad Sci U S A.*, Oct. 15, 1991;88(20):9036-40.
Reist et al., "Human IgG2 constant region enhances in vivo stability of anti-tenascin antibody 81C6 compared with its murine parent," *Clin Cancer Res.*, Oct. 1998;4(10):2495-502.
Lindsay, "Chapter 4: Determination of the Kinetics and Mechanism of tg-FIX Activation by Factor XIa," 49-75 (2004).
International Search Report for App. Ser. No. PCT/JP2012/078103, dated Jan. 22, 2013, 6 pages.
International Preliminary Report on Patentability for App. Ser. No. PCT/JP2012/078103, dated May 6, 2014, 6 pages.
Tsubaki et al., "C-terminal modification of monoclonal antibody drugs: amidated species as a general product-related substance," *Int J Biol Macromol.*, 52:139-47. doi:10.1016/j.ijbiomac.2012.09.016. Epub Sep. 25, 2012.
Bowen, Haemophilia A and haemophilia B: molecular insights, Mol Pathol., Feb. 2002;55(1):1-18.
Brandstetter et al., "X-ray structure of clotting factor IXa: active site and module structure related to Xase activity and hemophilia B," Proc Natl Acad Sci U S A, Oct. 10, 1995;92(21):9796-800.
Depascalis et al., "Grafting of "abbreviated" complementarity-determining regions containing specificity-determining residues essential for ligand contact to engineer a less immunogenic humanized monoclonal antibody," J Immunol., Sep. 15, 2002;169(6):3076-84.
Edelman et al., "The covalent structure of an entire gammaG immunoglobulin molecule," Proc Natl Acad Sci U S A., May 1969;63(1):78-85.
Fay, "Activation of factor VIII and mechanisms of cofactor action," Blood Rev., Mar. 2004;18(1):1-15.

(56) References Cited

OTHER PUBLICATIONS

Gonzales et al., "Minimizing the immunogenicity of antibodies for clinical application," Tumour Biol., Jan.-Feb. 2005;26(1):31-43.
Iwahashi et al., "CDR substitutions of a humanized monoclonal antibody (CC49): contributions of individual CDRs to antigen binding and immunogenicity," Mol Immunol., Oct.-Nov. 1999;36(15-16):1079-91.
Jirholt et al., "Exploiting sequence space: shuffling in vivo formed complementarity determining regions into a master framework," Gene., Jul. 30, 1998;215(2):471-6.
Johnson et al., "Kabat database and its applications: 30 years after the first variability plot," Nucleic Acids Res., Jan. 1, 2000;28(1):214-8.
Schmidt et al., "Structure-function relationships in factor IX and factor IXa," Trends Cardiovasc Med., Jan. 2003;13(1):39-45.
Tamura et al., "Structural correlates of an anticarcinoma antibody: identification of specificity-determining residues (SDRs) and development of a minimally immunogenic antibody variant by retention of SDRs only," J Immunol., Feb. 1, 2000;164(3):1432-41.
Notice of Opposition against EP 1 876 236, dated May 20, 2015, in the name of Chugai Seiyaku Kabushiki Kaisha brought by Novo Nordisk A/S, 23 pages.
Notice of Opposition against EP 1 876 236, dated May 22, 2015, in the name of Chugai Seiyaku Kabushiki Kaisha brought by Baxalta Innovations GmbH, 37 pages.
Chugai Seiyaku Kabushiki Kaisha's letter dated Jun. 12, 2013, regarding oral proceedings scheduled on Jun. 26, 2013, in App. Ser. No. EP 06 73 0769.4-1412.
Padlan et al., "Antibody Fab assembly: the interface residues between CH1 and CL," *Mol Immunol.*, 23(9):951-60 (1986).
Rothlisberger et al., "Domain interactions in the Fab fragment: a comparative evaluation of the single-chain Fv and Fab format engineered with variable domains of different stability," *J Mol Biol.*, 347(4):773-89 (2005).
Teerinen et al., "Structure-based stability engineering of the mouse IgG1 Fab fragment by modifying constant domains," *J Mol Biol.*, 361(4):687-97 (2006).
Lin et al., "Preclinical pharmacokinetics, interspecies scaling, and tissue distribution of a humanized monoclonal antibody against vascular endothelial growth factor," *J Pharmacol Exp Ther.*, 288(1):371-8 (1999).
Allard et al., "Antigen binding properties of highly purified bispecific antibodies," *Mol Immunol.*, Oct. 1992;29(10):1219-27.
Haagen et al., "Unprimed CD4+ and CD8+ T cells can be rapidly activated by a CD3 x CD19 bispecific antibody to proliferate and become cytotoxic," *Cancer Immunol Immunother.*, Dec. 1994;39(6):391-6.
IMGT Scientific charts depicting the correspondence between Eu and Kabat numberings for the human IgG constant region, created May 17, 2001 and last updated Aug. 13, 2014.
Lloyd et al., "The production of a bispecific anti-CEA, anti-hapten (4-amino-phthalate) hybrid-hybridoma," *J Natl Med Assoc.*, Oct. 1991;83(10):901-4.
Datta-Mannan et al., "Monoclonal antibody clearance. Impact of modulating the interaction of IgG with the neonatal Fc receptor," *J Biol Chem.*, 282(3):1709-17 (2007).
Jackman et al., "Development of a two-part strategy to identify a therapeutic human bispecific antibody that inhibits IgE receptor signaling," *J Biol Chem.*, Jul. 2, 2010;285(27): 20850-9. doi:10.1074/jbc.M110.113910. Epub May 5, 2010.
Spiess et al., "Bispecific antibodies with natural architecture produced by co-culture of bacteria expressing two distinct half-antibodies," *Nat Biotechnol.*, Aug. 2013; 31(8):753-8. doi:10.1038/nbt.2621. Epub Jul. 7, 2013.
Batra et al., "Pharmacokinetics and biodistribution of genetically engineered antibodies," *Curr Opin Biotechnol.*, Dec. 2002;13(6):603-8.
Borrebaeck et al., "Antibody evolution beyond Nature," *Nat Biotechnol.*, Dec. 2002;20(12):1189-90.

Greenwood et al., "Structural motifs involved in human IgG antibody effector functions," *Eur J Immunol.*, May 1993;23(5):1098-104.
Griffin et al., "Analysis of heavy and light chain sequences of conventional camelid antibodies from *Camelus dromedarius* and *Camelus bactrianus* species," *J Immunol Methods*, Mar. 2014;405:35-46. doi: 10.1016/j.jim.2014.01.003. Epub Jan. 18, 2014.
Hamers-Casterman et al., "Naturally occurring antibodies devoid of light chains," *Nature*, Jun. 3, 1993;363(6428):446-8.
Kenanova et al., "Tailoring the pharmacokinetics and positron emission tomography imaging properties of anti-carcinoembryonic antigen single-chain Fv-Fc antibody fragments," *Cancer Res.*, Jan. 15, 2005;65(2):622-31.
Lebégue et al., "Production and characterization of hybrid monoclonal antibodies with IgG1/IgG3 double isotype," *C R Acad Sci III.*, 1990;310(9):377-82.
Male et al., "Antibodies" *Immunology*, 7th Edition (2006), published by Elsevier Ltd., pp. 59-86.
Michaelsen et al., "A mutant human IgG molecule with only one C1q binding site can activate complement and induce lysis of target cells," *Eur J Immunol.*, Jan. 2006;36(1):129-38.
Roitt et al., *Immunology, M., Mir*, 5th Edition (2000), pp. 97-113.
Smolen et al., "Interleukin-6: a new therapeutic target," *Arthritis Res Ther.*, 2006;8 Suppl 2:S5. Epub Jul. 28, 2006.
Wang et al., "Conserved amino acid networks involved in antibody variable domain interactions," *Proteins*, Jul. 2009;76(1):99-114. doi: 10.1002/prot.22319.
[No Author Listed] "Hemophilia and von Willebrand's disease: 2. Management. Association of Hemophilia Clinic Directors of Canada," CMAJ., 153(2):147-157, Jul. 15, 1995.
Amersdorfer et al., GenPept Accession No. AAC26541, "anti BoNT/A Hc scFv antibody [synthetic construct]," 1 page (Aug. 1, 2001).
Asselta et al., "Factor V Deficiency," Semin. Thromb. Hemost., 35:382-389 (2009).
Bajaj et al., "A Monoclonal Antibody to Factor IX That Inhibits the Factor VIII:Ca Potentiation of Factor X Activation," J. Biol. Chem., Sep. 25, 1985;260(21):11574-11580.
Bebbington et al., "High-Level Expression of a Recombinant Antibody from Myeloma Cells Using a Glutamine Synthetase Gene as an Amplifiable Selectable Marker," Biotechnology (N Y), Feb. 1992;10:169-175.
Bessos et al., "The characterization of a panel of monoclonal antibodies to human coagulation factor IX," Thrombosis Research, Dec. 15, 1985;40:863-867.
Bian et al., "Discovery of promiscuous HLA-II-restricted T cell epitopes with Tepitope," Methods, Dec. 2004;34(4):468-75.
Bolton-Maggs et al., "Haemophilias A and B," The Lancet, May 24, 2003;361:1801-9.
Bos et al., "Enhanced Transfection of a Bacterial Plasmid into Hybridoma Cells by Electroporation: Application for the Selection of Hybrid Hybridoma (Quadroma) Cell Lines," Hybridoma, Feb. 1992;11:41-51.
Brennan et al., "Preparation of Bispecific Antibodies by Chemical Recombination of Monoclonal Immunoglobulin G1 Fragments," Science, Jul. 5, 1985;229:81-3.
Brinkman et al. "Phospholipid-binding domain of factor VIII is involved in endothelial cell-mediated activation of factor X by factor IXa," Arterioscler. Thromb. Vasc. Biol., Mar. 1, 2002;22(3):511-6.
Dall'Acqua et al., "Increasing the affinity of a human IgG1 for the neonatal Fc receptor: biological consequences," J. Immunol., Nov. 1, 2002;169(9):5171-80.
Davie et al., "The coagulation cascade: Initiation, maintenance, and regulation," Biochemistry, Oct. 29, 1991;30(43):10363-70.
Dhiman et al., "Gene expression microarrays: a 21st century tool for directed vaccine design," Vaccine, Oct. 12, 2001;20(1-2):22-30.
Francois et al., "Construction of a Bispecific Antibody Reacting with the α- and β-Chains of the Human IL-2 Receptor," J. Immunol., May 15, 1993;150:4610-9.
Gramer et al., "Production of stable bispecific IgG1 by controlled Fab-arm exchange: scalability from bench to large-scale manufac-

(56) References Cited

OTHER PUBLICATIONS turing by application of standard approaches," MAbs., Nov.-Dec. 2013;5(6):962-73. doi: 10.4161/mabs.26233. Epub Aug. 22, 2013.
Grosse-Hovest et al., "A recombinant bispecific single-chain antibody induces targeted, supra-agonistic CD28-stimulation and tumor cell killing", European Journal of Immunology, May 2003;33(5):1334-40.
Hämmerling et al., "Use of Hybrid Antibody with Anti-γG and Anti-Ferritin Specificities in Locating Cell Surface Antigens by Electron Microscopy," J. Exp. Med., Dec. 1, 1968;128:1461-73.
Hoad et al. "Characterization of monoclonal antibodies to human factor X.Xa: Initial observations with a quantitative ELISA procedure," J. Immunol. Methods, Feb. 15, 1991;136(2):269-78.
Hsia et al., "Treatment of acquired factor X inhibitor by plasma exchange with concomitant intravenous immunoglobulin and corticosteroids," Am. J. Hematol., Apr. 2008;83:318-20.
Huse et al., "Generation of a Large Combinatorial Library of the Immunoglobulin Repertoire in Phage Lambda," Science, Dec. 8, 1989;246:1275-81.
Kabsch et al., "On the use of sequence homologies to predict protein structure: identical pentapeptides can have completely different conformations," Proc Natl Acad Sci U S A., Feb. 1984;81(4):1075-8.
Kang et al., "Linkage of recognition and replication functions by assembling combinatorial antibody Fab libraries along phage surfaces," Proc. Natl. Acad. Sci.USA, May 15, 1991;88:4363-6.
Karpovsky et al., "Production of Target-Specific Effector Cells Using Hetero—Cross-Linked Aggregates Containing Anti-Target Cell and Anti-Fcγ Receptor Antibodies," J. Exp. Med., Dec. 1, 1984;160:1686-701.
Kim et al., "Mammalian type I interferon receptors consists of two subunits: IFNaR1 and IFNaR2," Gene, Sep. 1, 1997;196:279-86.
Klein et al., "Progress in overcoming the chain association issue in bispecific heterodimeric IgG antibodies," MAbs., Nov.-Dec. 2012;4(6):653-63. doi: 10.4161/mabs.21379. Epub Aug. 27, 2012.
Kroesen et al., "Phase I study of intravenously applied bispecific antibody in renal cell cancer patients receiving subcutaneous interleukin 2," Br. J. Cancer, Oct. 1994;70:652-61.
Kurokawa et al., "Enhanced Fibrinolysis by a Bispecific Monoclonal Antibody Reactive to Fibrin and Tissue Plasminogen Activator," Bio/Technology, Nov. 1989;7:1163-7.
Labrijn et al., "Species-specific determinants in the IgG CH3 domain enable Fab-arm exchange by affecting the noncovalent CH3-CH3 interaction strength," J Immunol., Sep. 15, 2011;187(6):3238-46. doi: 10.4049/jimmunol.1003336. Epub Aug. 12, 2011.
Labrijn et al., "Efficient generation of stable bispecific IgG1 by controlled Fab-arm exchange," Pro Natl Acad Sci U S A., Mar. 26, 2013;110(13):5145-50. doi: 10.1073/pnas.1220145110. Epub Mar. 11, 2013.
Lapan et al., "Interaction of the A1 Subunit of Factor VIIIa and the Serine Protease Domain of Factor X Identified by Zero-length Cross-linking," Thromb. Haemost., Sep. 1998;80:418-22.
Le Doussal et al., "Bispecific Monoclonal Antibody-Mediated Targeting of an Indium-111-Labeled DTPA Dimer to Primary Colorectal Tumors: Pharmacokinetics, Biodistribution, Scintigraphy and Immune Response," J. Nucl. Med., Oct. 1993;34:1662-71.
Lenting et al., "The life cycle of coagulation factor VIII in view of its structure and function", Blood, Dec. 1, 1998;92(11):3983-96.
Link et al., "Production and Characterization of a Bispecific IgG Capable of Inducing T-Cell—Mediated Lysis of Malignant B Cells," Blood, Jun. 15, 1993;81:3343-9.
Löfqvist et al., "Haemophilia prophylaxis in young patients—a long-term follow-up," J. Intern. Med., May 1997;241:395-400.
Lu et al., "Fab-scFv fusion protein: an efficient approach to production of bispecific antibody fragments," J. Immunol. Methods, Sep. 15, 2002;267:213-26.
Lu et al., "Di-diabody: a novel tetravalent bispecific antibody molecule by design," J. Immunol. Methods, Aug. 2003;279:219-32.

Massino et al., "Quantitative analysis of the products of IgG chain recombination in hybrid hybridomas based on affinity chromatography and radioimmunoassay," J. Immunol. Methods, Feb. 14, 1997;201:57-66.
McCafferty et al., "Phage antibodies: filamentous phage displaying antibody variable domains," Nature, Dec. 6, 1990;348:552-4.
McPhee et al., "Engineering human immunodeficiency virus 1 protease heterodimers as macromolecular inhibitors of viral maturation," Proc Natl Acad Sci U S A., Oct. 15, 1996;93(21):11477-81.
Menegatti et al., "Factor X Deficiency," Semin. Thromb. Hemost., Jun. 2009;35:407-15.
Mertens et al., "Factor VIII-Factor IX Interactions: Molecular Sites Involved in Enzyme-Cofactor Complex Assembly," Thromb. Haemost., Aug. 1999;82:209-17.
Milstein et al., "Hybrid hybridomas and their use in immunohistochemistry," Nature, Oct. 6-12, 1983;305:537-40.
"National Haemophilia Foundation (NHF) Medical and Scientific Advisory Council (MASAC) Recommendations Concerning Prophylaxis," MedicalBulletin, No. 193, 1 page (1994).
Nilsson et al., "Twenty-five years' experience of prophylactic treatment in severe haemophilia A and B," J. Intern. Med., Jul. 1992;232:25-32.
Nilsson et al., "Induction of split tolerance and clinical cure in high-responding hemophiliacs with factor IX antibodies," Proc. Natl. Acad. Sci. U S A., Dec. 1986;83:9169-73.
Nitta et al., "Preliminary trial of specific targeting therapy against malignant glioma," Lancet, Feb. 17, 1990;335:368-371.
Okubo et al. "The production and characterization of four monoclonal antibodies to human factor X," Nara Med Assoc., 1987;38(1):20-28.
Piper et al., "Interferon therapy in primary care," Primary Care Update for Ob/Gyns, Jul. 2001;8(4):163-69.
Pokkuluri et al., "A domain flip as a result of a single amino-acid substitution," Structure, Aug. 15, 1998;6(8):1067-73.
Price et al., "Tissue factor and tissue factor pathway inhibitor," Anaesthesia, May 2004;59:483-92.
Rispens et al., "Dynamics of inter-heavy chain interactions in human immunoglobulin G (IgG) subclasses studied by kinetic Fab arm exchange," J Biol Chem., Feb. 28, 2014;289(9):6098-109. doi: 10.1074/jbc.M113.541813. Epub Jan. 14, 2014.
Ruef et al., "A bispecific antifibrin-antiplatelet urokinase conjugate (BAAUC) induces enhanced clot lysis and inhibits platelet aggregation," Thromb. Haemost., Jul. 1999;82(1):109-14.
Sato et al., "Properties of Two VEGF Receptors, Flt-1 and KDR, in Signal Transduction," Ann N.Y. Acad. Sci, May 2000;902:201-207, discussion 205-7.
Schaefer et al., "Immunoglobulin domain crossover as a generic approach for the production of bispecific IgG antibodies," Proc Natl Acad Sci U S A., Jul. 5, 2011;108(27):11187-92. doi: 10.1073/pnas.1019002108. Epub Jun. 20, 2011.
Schuurman et al., "Normal human immunoglobulin G4 is bispecific: it has two different antigen-combining sites," Immunology, Aug. 1999;97(4):693-8.
Schuurman et al., "The inter-heavy chain disulfide bonds of IgG4 are in equilibrium with intra-chain disulfide bonds," Mol Immunol., Jan. 2001;38(1):1-8.
Segal et al., "Introduction: bispecific antibodies," J. Immunol. Methods, Feb. 1, 2001;248:1-6.
Shima et al., "Factor VIII Taitei Kotai (2), Ketsuyubyo A Kanja Katsueki ni okeru in vitro Gyoko Kassei no Kento", Rinsho Ketsueki, Aug. 30, 2005;46(8):777 (#WS-36-5) (with English translation).
Stickney et al., "Bifunctional Antibody: A Binary Radiopharmaceutical Delivery System for Imaging Colorectal Carcinoma," Cancer Res., Dec. 15, 1991;51:6650-5.
Suresh et al., "Advantages of bispecific hybridomas in one-step immunocytochemistry and immunoassays," Proc. Natl. Acad. Sci. U S A., Oct. 1986;83:7989-93.
Taki, The Journal of Japanese Society on Thrombosis and Hemostasis, Feb. 2, 2002;13:109-113.
Thies et al., "The alternatively folded state of the antibody C(H)3 domain," J Mol Biol., Jun. 22, 2001;309(5):1077-85.

(56) References Cited

OTHER PUBLICATIONS

Van Der Neut Kolfschoten et al., "Anti-inflammatory activity of human IgG4 antibodies by dynamic Fab arm exchange," Science, Sep. 14, 2007;317(5844):1554-7.
Ward et al., "Effects of engineering complementary charged residues into the hydrophobic subunit interface of tyrosyl-tRNA synthetase. Appendix: Kinetic analysis of dimeric enzymes that reversibly dissociate into inactive subunits," Biochemistry, Jun. 30, 1987;26(13):4131-8.
Weiner et al., "A Human Tumor Xenograft Model of Therapy with a Bispecific Monoclonal Antibody Targeting c-erbB-2 and CD16," Cancer Res., Jan. 1, 1993;53:94-100.
Weiner et al., "The Role of T Cell Activation in Anti-CD3 × Antitumor Bispecific Antibody Therapy," J. Immunol., Mar. 1, 1994;152:2385-92.
Xiang et al., "Production of murine V-human Cr1 chimeric anti-TAG72 antibody using V region cDNA amplified by PCR," Mol Immunol., Aug. 1990;27(8):809-817.
Yasukawa et al., "Structure and expression of human B cell stimulatory factor-2 (BSF-2/IL-6) gene," EMBO J., Oct. 1987;6(10):2939-45.
International Search Report for App. Ser. No. PCT/JP2014/075728, dated Dec. 22, 2014, 4 pages.
International Preliminary Report on Patentability for App. Ser. No. PCT/JP2014/075728, dated Mar. 29, 2016, 15 pages.
U.S. Appl. No. 14/921,590, Hattori et al., filed Oct. 23, 2015.
U.S. Appl. No. 15/172,727, Hattori et al., filed Apr. 3, 2016.
Brenner et al., "Errors in genome annotation," Trends in Genetics, Apr. 1999;15:132-133.
Coloma et al., "Position effects of variable region carbohydrate on the affinity and in vivo behavior of an anti-(1→6) dextran antibody," J Immunol., Feb. 15, 1999;162(4):2162-70.
Diaz et al., "Effects of engineering charged amino acids in the CH3 domains on antibody heavy chain dimerization," Philippine Science Letters. 2011;4(1):48-55.
Ejima et al, "Effects of Acid Exposure on the Conformation, Stability, and Aggregation of Monoclonal Antibodies," Proteins. Mar. 1, 2007;66(4):954-62.
Gen Bank Accession No.AAG00910.2, "recombinant IgG2 heavy chain, partial [Homo sapiens]," May 14, 2001, 1 page.
Hird et al., "Tumour localisation with a radioactively labelled reshaped human monoclonal antibody," Br J Cancer, Nov. 1991;64(5):911-4.
Hong et al., "Enhanced cellular uptake and transport of polyclonal immunoglobulin G and fab after their cationization," J Drug Target., 2000;8(2):67-77.
Ibragimova et al., "Stability of the beta-sheet of the WW domain: A molecular dynamics simulation study," Biophys J., Oct. 1999;77(4):2191-8.
Kabat et al., Sequences of Proteins of Immunological Interest, National Institute of Health, Publ'n No. 91-3242, Vol. 1 p. 647-60 (5th ed. 1991).
Lacroix-Desmazes et al, "Dynamics of factor VIII interactions determine its immunologic fate in hemophilia A," Blood, Jul. 15, 2008;112(2):240-9. doi: 10.1182/blood-2008-02-124941. Epub May 9, 2008.
Li et al., "Construction and characterization of a humanized anti-human CD3 monoclonal antibody 12F6 with effective immunoregulation functions," Immunology, Dec. 2005;116(4):487-98.
Lin et al., "Structure-function relationships in glucagon: properties of highly purified des-His-1-, monoiodo-, and (des-Asn-28, Thr-29)(homoserine lactone-27)-glucagon," Biochemistry, Apr. 22, 1975;14(8):1559-63.
Marshall et al., "Rational design and engineering of therapeutic proteins," Drug Discov Today, Mar. 1, 2003;8(5):212-21.
Morrison, "Two heads are better than one," Nat Biotechnol, Nov. 2007;25(11):1233-4.
Newman et al, "Modification of the Fc Region of a Primatized IgG Antibody to Human CD4 Retains Its Ability to Modulate CD4 Receptors but Does Not Deplete CD4 T Cells in Chimpanzees," Clin Immunol. Feb. 2001;98(2):164-74.
Pardridge et al., "Enhanced cellular uptake and in vivo biodistribution of a monoclonal antibody following cationization," J Pharm Sci., Aug. 1995;84(8):943-8.
Paul et al., "Immunologiya", M.:Mir, 1987-1988, vol. 1, p. 231 (with English translation).
Pritsch et al., "Can Immunoglobulin CH1 Constant Region Domain Modulate Antigen Binding Affinity of Antibodies?," J Clin Invest. Nov. 15, 1996;98(10):2235-43.
Reimann et al., "A humanized form of a CD4-specific monoclonal antibody exhibits decreased antigenicity and prolonged plasma half-life in rhesus monkeys while retaining its unique biological and antiviral properties," AIDS Res Hum Retroviruses, Jul. 20, 1997;13(11):933-43.
Roopenian et al., "FcRn: the neonatal Fc receptor comes of age," Nat Rev Immunol., 7(9):715-25 (Sep. 2007).
Sarkar et al., "Rational cytokine design for increased lifetime and enhanced potency using pH-activated "histidine switching"," Nat Biotechnol., Sep. 2002;20(9):908-13. Epub Aug. 5, 2002.
Schwartz et al., "A superactive insulin: [B10-aspartic acid]insulin(human)," Proc Natl Acad Sci U S A., Sep. 1987;84(18):6408-11.
Sharifi et al., "Improving monoclonal antibody pharmacokinetics via chemical modification," Q J Nucl Med., Dec. 1998;42(4):242-9.
Smith et al., "The challenges of genome sequence annotation or 'the devil is in the details'," Nature Biotechnology, Nov. 1997;15:1222-1223.
Tabrizi et al., "Elimination mechanisms of therapeutic monoclonal antibodies," Drug Discov Today, Jan. 2006;11(1-2):81-8.
Verhoeyen et al., "Construction of a reshaped HMFG1 antibody and comparison of its fine specificity with that of the parent mouse antibody," Immunology, Mar. 1993;78(3):364-70.
Verhoeyen et al., "Monoclonal Antibodies in Clinical Oncology," 1991, Edited by AA Epenetos, Chapter 5, pp. 37-43, Chapman and Hall.
Yang et al., "CDR Walking Mutagenesis for the Affinity Maturation of a Potent Human Anti-HIV-1 Antibody into the Picomolar Range," J Mol. Biol., 254(3):392-403 (Dec. 1995).
U.S. Appl. No. 10/575,905, Hattori et al., filed Apr. 30, 2007.
U.S. Appl. No. 11/910,836, Hattori et al., filed Jan. 12, 2009.
U.S. Appl. No. 13/434,643, Hattori et al., filed Mar. 29, 2012.
U.S. Appl. No. 15/172,727, Hattori et al., filed Jun. 3, 2016.
U.S. Appl. No. 14/019,117, Igawa et al., filed Sep. 5, 2013.
U.S. Appl. No. 14/019,712, Igawa et al., filed Sep. 6, 2013.
U.S. Appl. No. 12/680,082, Igawa et al., filed Jun. 25, 2010.
U.S. Appl. No. 12/295,075, Igawa et al., filed Apr. 20, 2009.
U.S. Appl. No. 13/518,861, Igawa et al., filed Oct. 4, 2012.
U.S. Appl. No. 12/679,922, filed Oct. 1, 2010.
U.S. Appl. No. 13/257,112, filed Nov. 22, 2011.
U.S. Appl. No. 13/885,421, filed Aug. 30, 2013.
U.S. Pat. No. 8,597,911, Miyazaki et al., issued Dec. 3, 2013.
U.S. Pat. No. 9,096,651, Igawa et al., issued Aug. 4, 2015.
U.S. Pat. No. 9,688,762, Igawa et al., issued Jun. 27, 2017.
U.S. Pat. No. 9,228,017, Igawa et al., issued Jan. 5, 2016.
U.S. Pat. No. 9,670,269, Igawa et al., filed Apr. 19, 2017.
U.S. Appl. No. 15/467,654, dated Mar. 23, 2017, Nezu et al.
U.S. Appl. No. 15/490,936, dated Apr. 19, 2017, Igawa et al., filed Apr. 19, 2017.
U.S. Appl. No. 15/614,842, dated Jun. 6, 2017, Igawa et al., filed Jun. 6, 2017.
U.S. Appl. No. 15/617,008, dated Jun. 8, 2017, Igawa et al., filed Jun. 8, 2017.
Bendig M. M., "Humanization of Rodent Monoclonal Antibodies by CDR Grafting," Methods: A Companion to Methods in Enzymology, 1995; 8:83-93.
Chan et al., "Therapeutic antibodies for autoimmunity and inflammation," Nat Rev Immunol. May 2010;10(5):301-16. doi: 10.1038/nri 2761.
Gunawardane et al., "Agonistic Human Antibodies Binding to Lecithin-Cholesterol Acyltransferase Modulate High Density Lipoprotein Metabolism," J Biol Chem. Feb. 5, 2016;291(6)2799-811. doi: 10.1074/jbc.M115.672790. Epub Dec. 7, 2015.

(56) References Cited

OTHER PUBLICATIONS

Hess et al., "Cancer therapy with trifunctional antibodies: linking innate and adaptive immunity," Future Oncol. Jan. 2012: 8(1):73-85. doi: 10.2217/ fon.11.138.
Janeway et al., Immunobiology, 5th edition. 2001:Extract from Chapter 3, pp. 93-122.
Janeway et al., Immunobiology, 5th edition. 2001:Extract from Chapter 4, pp. 123-154.
Jefferis et al., "Interaction sites on human IgG-Fc for FcγR: current models," Immunol Lett. Jun. 3, 2002:82(1-2):57-65.
Jones et al., "Growth factor receptor interplay and resistance in cancer," Endocr Relat Cancer. Dec. 2006:13 Supp 1 1:S45-51.
Kontermann, "Dual targeting strategies with bispecific antibodies," MAbs. Mar.-Apr. 2012;4(2):182-197. doi: 10.4161/mabs.4.2.19000. Epub Mar. 1, 2012.
Murata et al., "Anti-Digoxin Fab Variants Generated by Phage Display," Mol Biotechnol. Jun. 2013:54 (2) :269-77. doi: 10.1007/s12033-012-9564-1.
Nakano et al. "Anti-glypican 3 antibodies cause ADCC against human hepatocellular carcinoma cells," Biochem Biophys Res Conrnun. Jan. 9, 2009:378 (2):279-284. doi: 10.1016/ .bbrc.2008.11.033. Epub Nov. 18, 2008.
Natsume et al., "National Haemophilia Foundation (NHF) Medical and Scientific Advisory Council (MASAC) Recommendations Concerning Prophylaxis," Medical Bulletin, No. 193, 1 page (1994) Improving effector functions of antibodies for cancer treatment: Enhancing ADCC and CDC, Drug Des Devel Ther. Sep. 21, 2009:3:7-16.
Raposo et al., "Epitope-specific antibody response is controlled by immunoglobulin Vh polymorphisms," J Exp Med. Mar. 10, 2014:211(3):405-411.doi:10.1084/jem.20130968. Epub Feb. 17, 2014.
Riechelmann et al., "Adoptive therapy of head and neck squamous cell carcinoma with antibody coated immune cells: a pilot clinical trial," Cancer Immunol Immunother. Sep. 2007:56 (9):1397-406. Epub Feb. 2, 2007.
Rothe et al., Recombinant proteins in rheumatology—recent advances, N. Biotechnol. Sep. 2011;28(5):502-510.doi:10.1016/j.nbt.2011.03.019. Epub Apr. 5. 2011.
Schlereth et al., "T-cell activation and B-cell depletion in chimpanzees treated with a bispecific anti-CD19/anti-CD3 single-chain antibody construct," Cancer Immunol Immunother. May 2006:55(5):503-14. Epub Jul. 20, 2005.
Sebastian et al., "Treatment of non-small cell lung cancer patients with the trifunctional monoclonal antibody catumaxomab (anti-EpCAM x anti-CD3): a phase I study," Cancer Immunol Immunother. Oct. 2007:56 (10) :1637-44. Epub Apr. 5, 2007.
Seimetz et al., "Development and approval of the trifunctional antibody catumaxomab (anti-EpCAM x anti-CD3) as a targeted cancer immunotherapy," Cancer Treat Rev. Oct. 2010:36(6):458-467.doi:10.1016/j.ctrv.2010.03.001 Epub Mar. 27, 2010.
Staerz et al., "Hybrid antibodies can target sites for attack by T cells," Nature. Apr. 18-24, 1985—24:314(6012):628-31.
Ward et al., "Binding activities of a repertoire of single immunoglobulin variable domains secreted from *Escherichia coli*," Nature, 1989;341:544-546.
Wozniak-Knopp et al., "Introducing antigen-binding sites in structural loops of immunoglobulin constant domains: Fc fragments with engineered HER2/neu-binding sites and antibody properties," Protein Eng Des Sel. Apr. 2010; 23(4):289-97.doi:10.1093/protein/gzq005. Epub Feb. 11, 2010.
U.S. Appl. No. 15/614,842, Igawa et al., filed Jun. 6, 2017
U.S. Appl. No. 15/617,008, Igawa et al., filed Jun. 8, 2017
Amann et al., "Therapeutic window of an EpCAM/CD3-specific BiTE antibody in mice is determined by a subpopulation of EpCAM-expressing lymphocytes that is absent in humans," Cancer Immunol Immunother. Jan. 2009:58(1):95-109. Epub Jul. 2, 2008.
Bendig M. M., "Humanization of Rodent Monoclonal Antibodies by CDR Grafting," Methods: A Companion to Methods in Enzymology, 1995;8:83-93.
Campoli et al., "Immunotherapy of Malignant Disease with Tumor Antigen-Specific Monoclonal Antibodies," Clin Cancer Res. Jan. 1, 2010:16 (1): 11-20. doi: 10. 1158/1078-0432. CCR-09-2345. Epub Dec. 22, 2009.
Chan et al. "Therapeutics antibodies for autoimmunity and inflammation," Nat Rev Immunol. May 2010;10(5):301-16. doi: 10.1038/nri 2761.
Gunawardane et al., "Agonistic Human Antibodies Binding to Lecithin-Cholesterol Acyltransferase Modulate High Density Lipoprotein Metabolism," J Biol Chem. Feb. 5, 2016;291(6):2799-811. doi: 10.1074/jbc.M115.672790. Epub Dec. 7, 2015.
Hess et al., "Cancer therapy with trifunctional antibodies: linking innate and adaptive immunity," Future Oncol. Jan. 2012: 8(1):73-85. doi: 10.2217/fon.11.138.
Janeway et al., Immunobiology, 5th edition. 2001: Extract from Chapter 3, pp. 93-122.
Janeway et al., Immunobiology, 5th edition, 2001: Extract from Chapter 4, pp. 123-154.
Jefferis et al., "Interaction sites on human IgC-Fc for FcγR: current models," Immunol Lett. Jun. 3, 2002:82(1-2):57-65.
Jones et al., "Growth factor receptor interplay and resistance in cancer," Endocr Relat Cancer. Dec. 2006: 13 Supp 11: S45-51.
Kontermann, "Dual targeting strategies with bispecific antibodies," MAbs. Mar.-Apr. 2012;4(2):182-97. doi: 10.4161/mabs.4.2.19000. Epub Mar. 1, 2012.
Mezzanzanica et al., "Human Ovarian Carcinoma Lysis by Cytotoxic T Cells Targeted by Bispecific Monoclonal Antibodies: Analysis of the Antibody Components," Int J Cancer. Apr. 15, 1988:41(4):609-15.
Murata et al., "Anti-Digoxin Fab Variants Generated by Phage Display," Mol Biotechnol. Jun. 2013: 54 (2): 269-77. doi: 10.1007/s12033-012-9564-1.
Nakano et al. "Anti-glypican 3 antibodies cause ADCC against human hepatocellular carcinoma cells," Biochem Biophys Res Conrnun, Jan. 9, 2009: 378 (2):279-84. doi: 10.1016/j.bbrc.2008.11.033. Epub Nov. 18, 2008.
Natsume et al., "National Haemophilia Foundation (NHF) Medical and Scientific Advisory Councel (MASAC) Recommendations Concerning Prophylaxis," Medical Bulletin, No. 193, 1 page (1994) Improving effector functions of antibodies for cancer treatment: Enhancing ADCC and CDC, Drug Des Devel Ther. Sep. 21, 2009;3;7-16.
Nimmerjahn et al., "Fcγ receptors as regulators of immune responses," Nat Rev Immunol. Jan. 2008; 8(1):34-47.
Pejchal et al., "A Conformational Switch in Human Immunodeficiency Virus gp41 Revealed by the Structures of Overlapping Epitopes Recognized by Neutralizing Antibodies," J Virol. Sep. 2009;83(17):8451-62. doi:10.1128/JVI.00685-09. Epub Jun. 10, 2009.
Radaev et al., "The Structure of a Human Type III Fcγ Receptor in Complex with Fc," J Biol Chem. May 11, 2001:276 (19):16469-77. Epub Jan. 31, 2001.
Raposo et al., "Epitope-specific antibody response is controlled by immunoglobulin Vh polymorphisms," J Exp Med. Mar. 10, 2014:211(3):405-11.doi:10.1084/jem.20130968. Epub Feb. 17, 2014.
Riechelmann et al., "Adoptive therapy of head and neck squamous cell carcinoma with antibody coated immune cells: a pilot clinical trial," Cancer Immunol Immunother. Sep. 2007:56 (9): 1397-406. Epub Feb. 2, 2007.
Rothe et al., Recombinant proteins in rheumatology—recent advances, N Biotechnol. Sep. 2011;28(5):502-10.doi:10.1016/j.nbt.2011.03.019. Epub Apr. 5, 2011.
Schlereth et al., "T-cell activation and B-cell depletion in chimpanzees treated with bispecific anti-CD19/anti-CD3 single-chain antibody construct," Cancer Immunol Immunother. May 2006:55(5):503-14. Epub Jul. 20, 2005.
Sebastian et al., "Treatment of non-small cell lung cancer patients with the trifunctional monoclonal antibody catumaxomab (anti-EpCAM x anti-CD3): a phase I study," Cancer Immunol Immunother. Oct. 2007: 56 (10): 1637-44. Epub Apr. 5, 2007.
Seimetz et al., "Development and approval of the trifunctional antibody catumaxomab (anti-EpCAM x anti-CD3) as a targeted

(56) References Cited

OTHER PUBLICATIONS cancer immunotherapy," Cancer Treat Rev. Oct. 2010: 36(6):458-67.doi:10.1016/j.ctrv.2010.03.001 Epub Mar. 27, 2010.
Staerz et al., "Hybrid antibodies can target sites for attack by T cells," Nature. Apr. 18, 1985-24:314(6012):628-31.
Unkeless et al., "Structure and Function of Human and Murine Receptors for IgG," Annu Rev Immunol. 1988:6:251-81.
Ward et al., "Binding activities of a repretoire of a single immunoglobulin variable domains secreted from *Escherichia coli*," Nature, 1989;341:544-546.
Wozniak-Knopp et al., "Introducing antigen-binding sites in structural loops of immunoglobulin constant domains: Fc fragments with engineered HER.2/neu-binding sites and antibody properties," Protein Eng Des Sel. Apr. 2010;23(4):289-97.doi:10.1093/protein/gzq005. Epub Feb. 11, 2010.
Zeidler et al., "Simultaneous Activation of T Cells and Accessory Cells by a New Class of Intact Bispecific Antibody Results in Efficient Tumor Cell Killing," J Immuno I. Aug. 1, 1999;163(3):1246-52.
U.S. Appl. No. 14/321,590, Hattori et al., filed Oct. 23, 2015 (abandoned).
U.S. Appl. No. 15/402,580, Hattori et al., filed Jan. 10, 2017.
U.S. Appl. No. 14/019,117, Igawa et al., filed Sep. 5, 2013 (abandoned).
U.S. Appl. No. 13/257,145, Igawa et al., filed Nov. 22, 2011 (abandoned).
U.S. Appl. No. 14/680,250, Igawa et al., filed Apr. 7, 2015.
U.S. Appl. No. 14/962,293, Igawa et al., filed Dec. 8, 2018.
Adams et al., "Humanization of a recombinant monoclonal antibody to producce a therapeutic HER dimerization inhibitor, pertuzumab," Cancer Immunol. Immunother., 55:717-727 (2006).
Binz et al., "Engineering novel binding proteins from nonimmunoglobulin domains," Nat. Biotechnol., 23:1257-68 (2005).
Blazar, "Infusion of Anti-B7.1 (CD80) and Anti-B7.2 (CD86) Monoclonal Antibodies Inhibits Murine Graft-Versus-Host Disease Lethality in Part Via Direct Effects on CD4+ and CD8+ T Cells," J. Immunol., 157:3250-59 (1996).
Branden and Tooze, "Recognition of Foreign Molecules by the Immune System," Introduction to Protein Structure, 2d Ed., Garland Publishing, pp. 299-323 (1999).
Comper and Glosgow, "Charge selectivity in kidney ultrafiltration," Kidney Int., 47:1242-51 (1995).
Couto et al., "Anti-BA46 Monoclonal Antibody Mc3: Humanization Using a Novel Positional Consensus and in Vivo and in Vitro Characterization," Cancer Research, 55: 1717-1722 (1995).
Deen et al., "Structural determinants of giomerular permeability," Am. J. Physiol. Renal. Physiol., 281:F579-F596 (2001).
Del Rio et al., "An Engineered Penicillin Acylase with Altered Surface Charge is More Stable in Alkaline pH," Ann. NY Acad. Sci., 799:61-64 (1996).
Dillon et al., "Structural and functional characterization of disulfide isoforms of the human IgG2 subclass," J. Biol. Chem., 283(23):16206-15 (2008).
Ghetie and Ward, "FcRn: the MHC class I-related receptor that is more than an IgG transporter," Immunol. Today, 18:592-598 (1997).
Ghetie et al., "Increasing the serum persistence of an IgG fragment by random mutagenesis," Nature Biotechnology, 15:637-640 (1997).
Ghetie et al., "Multiple roles for the major histocompatibility complex class I-related receptor FcRn," Annu. Rev. Immunol., 18:739-766 (2000).
Gobburu et al., "Pharmacokinetics/dynamics of 5c8, a monoclonal antibody to CD154 (CD40 ligand) suppression of an immune response in monkeys," J. Pharmacol. Exp. Ther., 286:925-930 (1998).
Goode et al., "The glomerular basement membrane charge-selectivity barrier: an oversimplified concept?," Nephrol. Dial. Transplant., 11:1714-16 (1996).
Graves et al., "Molecular modeling and preclinical evaluation of the humanized NR-LU-13 antibody," Clin. Cancer Res., 5:899-908 (1999).
Gupta et al., "Affinity chromatography and co-chromatography of bispecific monoclonal antibody immunoconjugates," J. Biochem. Biophys. Methods, 51:203-216 (2002).
Hanson et al., "Catalytic antibodies and their applications," Curr. Opin. Biotechnol., 16:631-636 (2005).
He et al., "Humanization and pharmacokinetics of a monoclonal antibody with specificity for both E- and P-selectin," J. Immunol., 160:1029-35 (1998).
Hinton et al., "An engineered human IgG1 antibody with longer serum half-life," J. Immunol., 176:346-356 (2006).
Ito et al., "The His-probe method: effects of histidine residues introduced into the complementarity-determining regions of antibodies on antigen-antibody interactions at different pH values," FEBS Lett., 309:85-88 (1992).
Kashmiri et al., "Generation, characterization, and in vivo studies of humanized anticarcinoma antibody CC49," Hybridoma, 14:461-473 (1995).
Khawli et al., "Improved tumor localization and radioimaging with chemically modified monoclonal antibodies," Cancer Biother. Radiopharm., 11:203-215 (1996).
Kim et al., "Antibody Engineering for the Development of Therapeutic Antibodies," Mol. Cells. 20:17-29 (2005).
Kim et al., "Chemical modification to reduce renal uptake of disulfide-bonded variable region fragment of anti-tac monoclonal antibody labeled with 99mTc," Bioconjugate Chem., 10:447-453 (1999).
Kim et al., "Lowering of pI by acylation improves the renal uptake of 99mTc-labeled anti-Tac dsFv: effect of different acylating reagents," Nucl. Med. Biol., 29:795-801 (2002).
Kobayashi et al., "The pharmacokinectic characteristics of glycolated humanized anti-Tac Fabs are determined by their isoelectric points," Cancer Res., 59:422-430 (1999).
Kreutz et al., "Efficient bispecific monoclonal antibody purification using gradient thiophilic affinity chromatography," J. Chromatogr. B, 714:161-170 (1998).
Lindhofer et al., "Preferential Species-Restricted Heavy/Light Chain Pairing in Rat/Mouse Quadromas," J. Immunol., 155:219-225 (1995).
Lobo et al., "Antibody pharmacokinetics and pharmacodynamics," J. Pharm. Sci., 93:2645-68 (2004).
Lund et al., "Expression and characterization of truncated forms of humanized L243 IgG1. Architectural features can influence synthesis of its oligosaccharide chains and affect superoxide production triggered through human Fcgama receptor I," Eur. J. Biochem., 267(24):7246-57 (2000).
Manzke et al., "Single-step purification of bispecific monoclonal antibodies for immunotherapeutic use by hydrophobic interaction chromatography," J. Immunol. Methods, 208:65-73 (1997).
Martin et al., "Crystal structure at 2.8 A of an FcRn/heterodimeric Fc complex: mechanism of pH-dependent binding," Mol. Cell, 7:867-877 (2001).
Marvin et al., "Recombinant approaches to IgG-like bispecific antibodies," Acta. Pharmacol. Sin., 26:649-658 (2005).
Marvin et al., "Re-designing an antibody fragment for faster association with its antigen," Biochemistry, 42:7077-83 (2003).
Onda et al., "Lowering the Isoelectric Point of the Fv Portion of Recombinant Immunotoxins Leads to Decreased Nonspecific Animal Toxicity without Affecting Antitumor Activity," Cancer Res., 61:5070-77 (2001).
Pavlinkova et al., "Charge-modified single chain antibody constructs of monoclonal antibody CC49: Generation, characterization, pharmacokinetics, and biodistribution analysis," Nucl. Med. Biol., 26:27-34 (1999).
Pavlou et al., "The therapeutic antibodies market to 2008," Eur. J. Pharm. Biopharm., 59:389-396 (2005).
Poduslo et al., "Polyamine modification increases the permeability of proteins at the blood—nerve and blood-brain barriers," J. Neurochem., 66:1599-1609 (1996).

(56) References Cited

OTHER PUBLICATIONS

Rajpal et al., A general method for greatly improving the affinity of antibodies by using combinatorial libraries, Proc. Natl. Acad. Sci. USA, 102:8466-71 (2005).
Rathanaswami et al., "Demonstration of an in vivo generated sub-picomolar affinity fully human monoclonal antibody to interleukin-8," Biochem. Biophys. Res. Commun., 334:1004-13 (2005).
Reichert et al., "Monoclonal antibody successes in the clinic," Nat. Biotechnol., 23:1073-78 (2005).
Sal-Man et al., "Arginine mutations within a transmembrane domain of Tar, an *Escherichia coli* aspartate receptor, can drive homodimer dissociation and heterodimer association in vivo," Biochem. J., 385:29-36 (2005).
Schaeffer et al., "The Rat Glomerular Filtration Barrier Does Not Show Negative Charge Selectivity," Microcirculation, 9:329-342 (2002).
Schmidt et al., Human Physiology, Moscow, 2:431-436 (1996), and English translation: Schmidt et al., "Hemostatis and Coagulation," Human Physiology, R.F. Schmidt, G. Thews (Eds.), Second, Completely Revised Edition, 418-423 [translated by Marguerite A. Biederman-Thorson], Springer-Verlag, 1989.
Schmidt et al., Human Physiology, Moscow, 3:764 (1996), and English translation: Schmidt et al., "Enzymes of the pancreatic juice," Human Physiology, R.F. Schmidt, G. Thews (Eds.), Second, Completely Revised Edition, 716 [translated by Marguerite A. Biederman-Thorson], Springer-Verlag, 1989.
Shaul, "Exploring the charge space of protein-protein association: a proteomic study," Proteins, 60:341-352 (2005).
Shields et al., "High resolution mapping of the binding site on human IgG1 for Fc gamma RI, Fc gamma RII, Fc gamma RIII, and FcRm and design of IgG1 variants with improved binding to the Fc gamma R," J. Biol. Chem., 276:6591-6604 (2001) (Epub Nov. 28, 2000).
Tarditi et al., "Selective high-performace liquid chromatographic purification of bispecific monoclonal antibodies," J. Chromatogr., 599:13-20 (1992).
Ten Kate et al., "Effect of isoelectric point on biodistribution and inflammation: imaging with indium-111-labelled IgC," Eur. J. Nucl. Med., 17:305-309 (1990).
Tsurushita et al., "Design of humanized antibodies: From anti-Tac to Zenapax," Methods, 36:69-83 (2005).
Roitt et al., Immunology, M., Mir, (2000), pp. 110, 150, and 537-9 (in Russian, with what is believed to be a published English equivalent of those pages).
U.S. Appl. No. 15/562,186, Igawa, et al., filed Sep. 27, 2017.
U.S. Appl. No. 15/701,630, Hattori et al., filed Sep. 12, 2017.
U.S. Appl. No. 15/725,692, Igawa et al., filed Oct. 5, 2017.
U.S. Appl. No. 15/782,256, Igawa et al., filed Oct. 12, 2017.
Buque et al., "Trial Watch: Immunomodulatory monoclonal antibodies for oncological indications," Oncoimmunology, Mar. 2, 2015:4(4):e1008814. eCollection 2015.
Hattori, Introduction of ART-Ig and application to hemophilia A treatment, Chugai Seiyaku ni Okeru Dokuji no Kakushinteki Kotai Gijutsu. Dec. 2012; 18: 42-57.
Iwai et al., "Therapeutics Agents for Gastric Cancer," Igan Chiryoyaku, Yakkyoku, Jan. 5, 2016:67(1)138-41 (with English translation).
Kitazawa et al., "A bispecific antibody to factors IXa and X restores factor VIII hemostatic activity in a hemophilia A model," Nat. Med., Oct. 2012;18(10):1570-4. doi:10.1038/nm.2942. Epub Sep. 30, 2012.
Klinger et al., "Harnessing T cells to fight cancer with BiTE((R)) antibody constructs—past developments and future directions," Immunol. Rev., Mar. 2016:270(1):193-208. doi.10.1111/imr.12393.
Labrijn et al., "Controlled Fab-arm exchange for the generation of stable bispecific IgGI," Nat. Protoc., Oct. 2014;9(10): 2450-63. doi:10.1038/nprot.2014.169. Epub Sep. 25, 2014.
Larkin et al., "Combined Nivolumab and Ipilimumab or Monotherapy in Untreated Melanoma," N. Engl. J. Med., Jul. 2, 2015:373(1):23-34. doi:10.1056/NEJMoa1504030. Epub May 31, 2015.
Peters et al., "Engineering an improved IgG4 molecule with reduced disulfide bond heterogeneity and increased Fab domain thermal stability," J. Biol. Chem., Jul. 13, 2012;287(29): 24525-33. doi: 10.1074/jbc.M112.369744. Epub May 18, 2012.
Petkova et al., Enhanced half-life of genetically engineered human 1gG1 antibodies in a humanized FcRn mouse model: potential application in humorally mediated autoimmune disease, Int. Immunol., Dec. 2006; 18(12):1759-69. Epub 2006.
Ruggeri et al., "von Willebrand factor and von Willebrand disease," Blood, Oct. 1987;70(4):895-904.
Vaccaro et al., "Divergent activities of an engineered antibody in murine and human systems have implications for therapeutics antibodies," Proc. Natl. Acad. Sci. U S A., Dec. 5, 2006;103(49):18709-14. Epub Nov. 20, 2006.
U.S. Appl. No. 15/024,063, Igawa et al., filed Mar. 23, 2016.
U.S. Appl. No. 15/562,186, Igawa et al., filed Sep. 27, 2017.
U.S. Appl. No. 10/575,905, Hattori et al., filed Apr. 30, 2007 (abandoned).
U.S. Appl. No. 11/910,836, Hattori et al., filed Jan. 12, 2009 (abandoned).
U.S. Appl. No. 13/434,643, Hattori et al., filed Mar. 29, 2012 (abandoned).
U.S. Appl. No. 14/921,590, Hattori et al., filed Oct. 23, 2015 (abandoned).
U.S. Appl. No. 15/172,727, Hattori et al., filed Jun. 3, 2016 (abandoned).
U.S. Appl. No. 15/402,580, Hattori et al., filed Jan. 10, 2017 (abandoned).
U.S. Appl. No. 14/019,117, Igawa et al., filed Sep. 5, 2013 (abandoned).
U.S. Appl. No. 14/019,712, Igawa et al., filed Sep. 6, 2013 (abandoned).
U.S. Appl. No. 15/132,996, Igawa et al., filed Apr. 19, 2016.
U.S. Appl. No. 15/288,965, Igawa et al., filed Oct. 7, 2016.
U.S. Appl. No. 12/295,039, Igawa et al., filed Jan. 20, 2009.
U.S. Appl. No. 14/741,786, Igawa et al., filed Jun. 17, 2015.
U.S. Appl. No. 15/614,842, Igawa et al., filed Jun. 6, 2017.
U.S. Appl. No. 13/257,145, Igawa et al., filed Nov. 22, 2011.
U.S. Appl. No. 14/680,250, Igawa et al., Apr. 7, 2015.
U.S. Appl. No. 14/962,293, Igawa et al., filed Dec. 8, 2015.
U.S. Appl. No. 13/497,269, Kuramochi et al., filed Jun. 1, 2012.
U.S. Appl. No. 13/582,073, Kuramochi et al., filed Dec. 20, 2012.
U.S. Appl. No. 15/490,936, Igawa et al., filed Apr. 19, 2017.
U.S. Appl. No. 13/518,861, Igawa et al., filed Oct. 4, 2012 (abandoned).
U.S. Appl. No. 15/617,008, Igawa et al., filed Jun. 8, 2017.
U.S. Appl. No. 14/351,654, Kuramochi et al., filed Apr. 14, 2014.
U.S. Appl. No. 15/467,654, Nezu et al.

* cited by examiner

FIG. 1
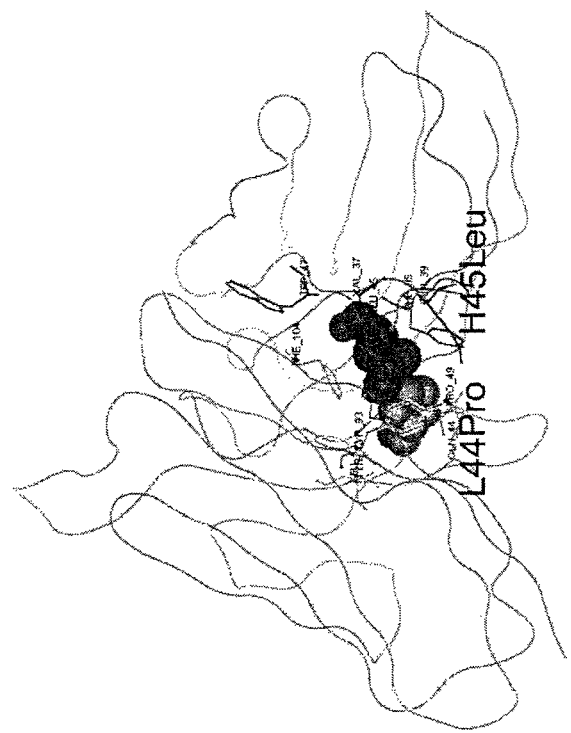
(A)
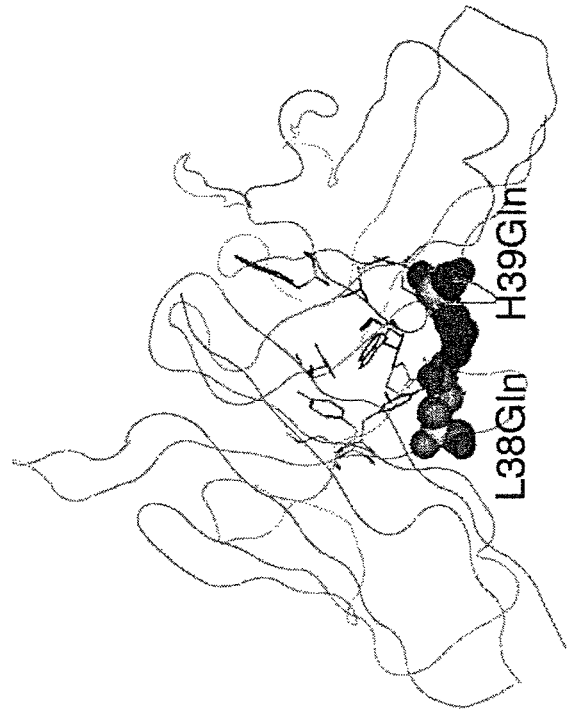
(B)

FIG. 12
(a) 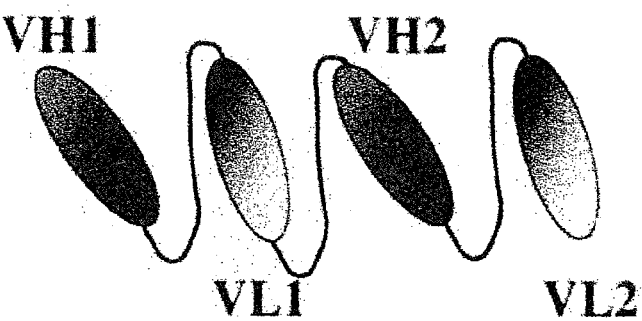
(b) 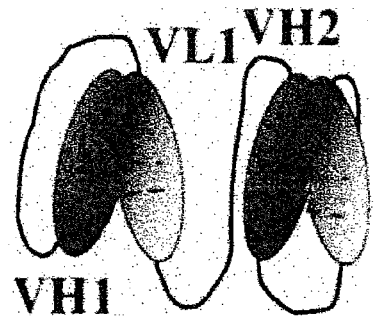
Bivalent scFv-type    Single chain diabody-type

FIG. 18
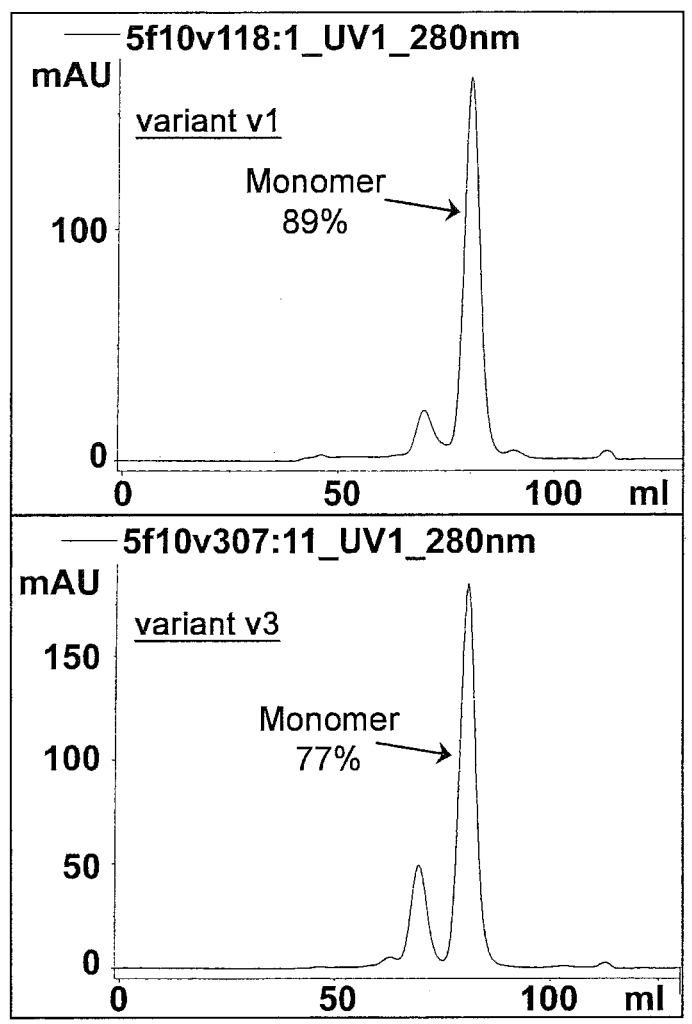
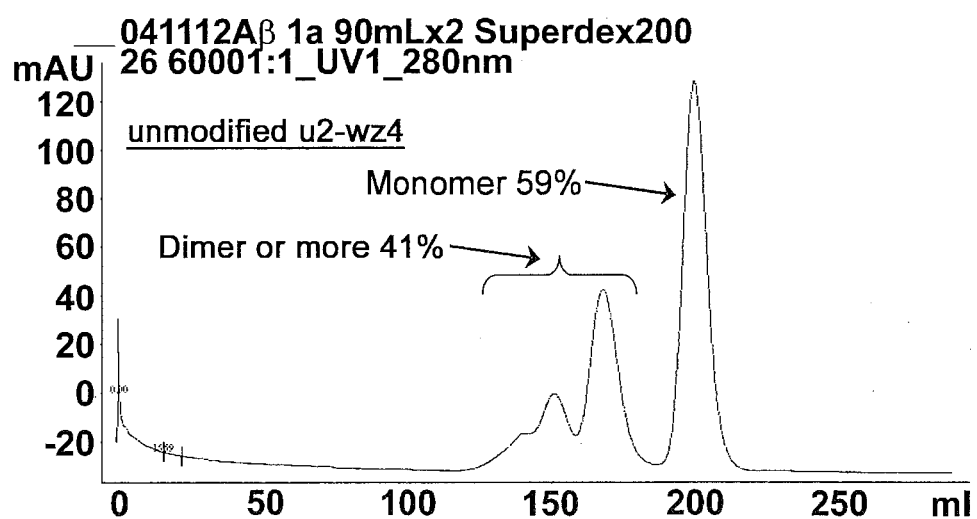

FIG. 22
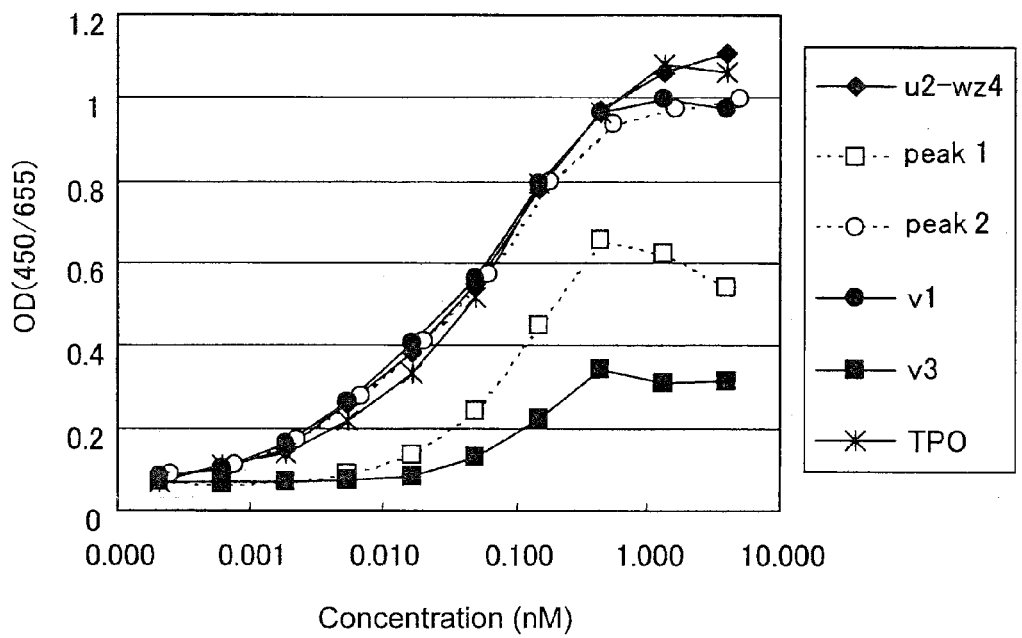
(A) BaF-human Mpl
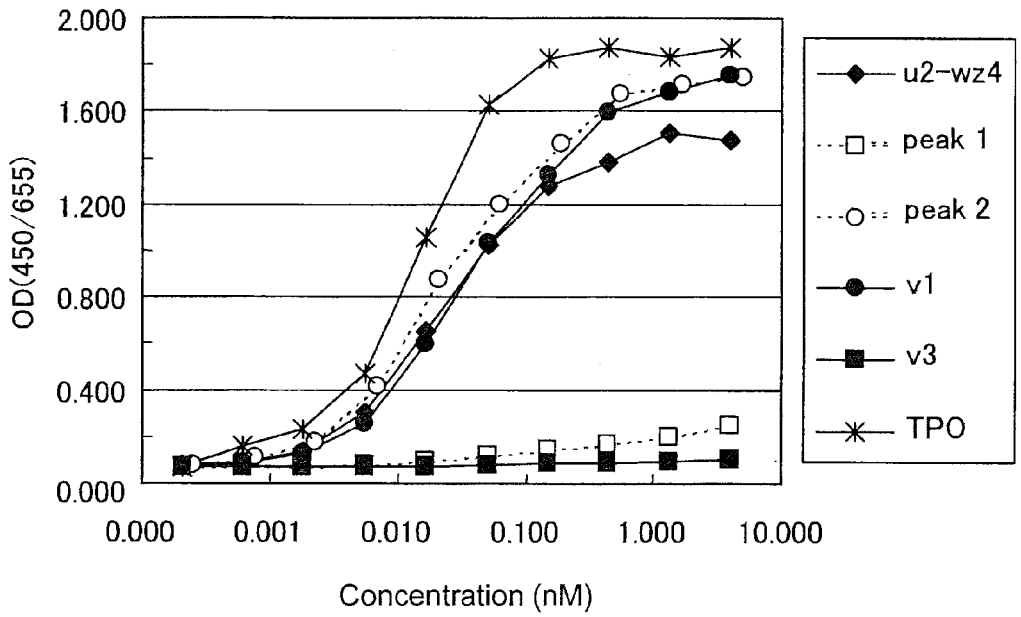
(B) BaF-monkey Mpl

FIG. 23
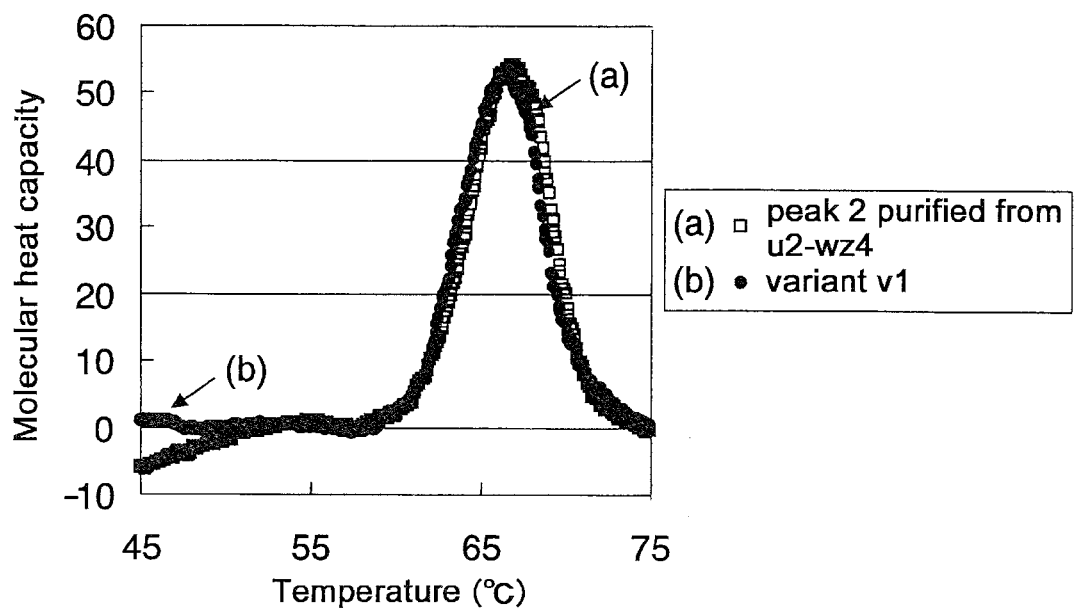
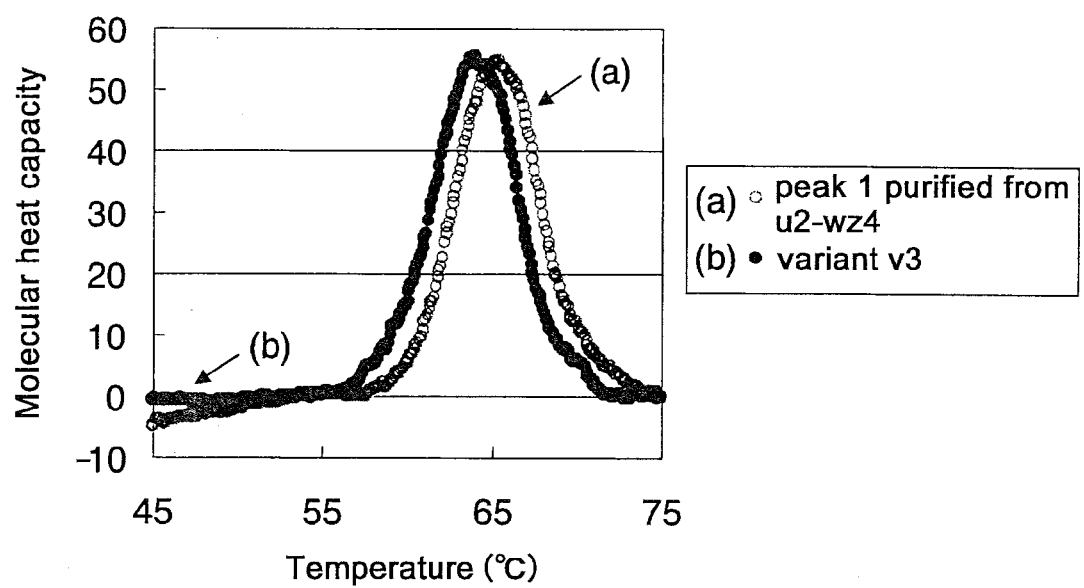

Time (min)

FIG. 29

| Name | A-Homo | BiAb | B-Homo |
|---|---|---|---|
| wild type | 20 | 48 | 32 |
| KiH | 0 | 97 | 3 |
| s1 | 8 | 87 | 5 |
| s2 | 5 | 92 | 3 |
| s3 | 3 | 92 | 6 |
| w1 | 1 | 97 | 2 |
| w2 | 0 | 94 | 6 |
| w3 | 4 | 93 | 3 |

| Name | A-Homo | BiAb | B-Homo |
|---|---|---|---|
| wild type | 21 | 49 | 30 |
| KiH | 0 | 99 | 1 |
| s1C | 5 | 94 | 1 |
| s2C | 11 | 87 | 2 |
| s3C | 3 | 88 | 10 |
| w3C | 3 | 95 | 2 |
| w3C2 | 6 | 93 | 1 |

FIG. 30

| Name | Monomer recovery rate (%) |
|---|---|
| wild type | 66 |
| KiH | 36 |
| s2 | 39 |
| s3 | 72 |
| w3 | 47 |
| s2C | 81 |
| s3C | 79 |
| w3C | 83 |
| w3C2 | 74 |

FIG. 32

| Name | A-Homo | BiAb | B-Homo |
|---|---|---|---|
| wild type | 24 | 50 | 27 |
| KiH | 0 | 99 | 1 |
| w1 | 0 | 98 | 2 |
| w2 | 0 | 98 | 2 |
| w3 | 4 | 94 | 2 |

METHODS FOR PRODUCING POLYPEPTIDES BY REGULATING POLYPEPTIDE ASSOCIATION

CROSS-REFERENCE TO RELATED APPLICATIONS

This application is the National Stage of International Application No. PCT/JP2006/306803, filed on Mar. 31, 2006, which claims the benefit of Japanese Patent Applications Serial No. 2005/101105, filed on Mar. 31, 2005, and Serial No. 2005/378266, filed on Dec. 28, 2005. The contents of all of the foregoing applications are hereby incorporated by reference in their entireties.

TECHNICAL FIELD

The present invention relates to methods for producing polypeptides by regulating the intramolecular or intermolecular association of each molecule, polypeptides whose intramolecular or intermolecular association is regulated, and pharmaceutical compositions and the like containing such polypeptides as an active ingredient.

BACKGROUND ART

Due to their highly stable nature in blood and relatively few side effects, antibodies have been receiving much attention as pharmaceuticals. Of particular note are bispecific antibodies that can simultaneously recognize two types of antigens. MDX-210, which is currently under clinical trial investigation, is an IgG-type bispecific antibody that retargets FcγRI-expressing monocytes and such to HER-2/neu-expressing cancer cells (see Non-Patent Document 1). In general, antibodies are produced using genetic recombination techniques. One specific technique involves the cloning of a DNA encoding an antibody protein from antibody-producing cells, such as hybridomas or sensitized lymphocytes that produce antibodies or a phage library presenting antibody genes, and the insertion of such into a suitable vector, which is then transfected into host cells for antibody production. Production of IgG type bispecific antibodies using genetic recombination techniques involves the introduction of a total of four types of genes into cells, in which these genes of H chains and L chains constitute two types of IgGs of interest, and the secretion of the antibodies by coexpression. In this type of system, expression of the wild type H chains and L chains constituting genes leads to random covalent bonding between two types of H chains and non-covalent bonding between H and L chains, and thus, the proportion of the bispecific antibody of interest becomes very small. More particularly, only one out of ten types produced is the bispecific antibody of interest, rendering the production efficiency quite low. Decreased efficiency in the production of the antibody of interest is not only an obstacle for purifying the antibody of interest, but also increases the nonuniformity, such as the lot-to-lot differences, which, in turn, leads to swelling production costs.

Preferential secretion of IgGs with a heterologous combination of H chains by introducing amino acid substitutions into the IgG H chain CH3 region has been reported as a means to improve the efficiency of bispecific antibody production (see Patent Document 1 and Non-Patent Documents 2 and 3). This method involves induction of promotion of heterologous H chain formation and inhibition of homogeneous H chain formation by substituting an amino acid side chain present in the CH3 region of one of the H chains to a larger side chain (knob), and substituting the amino acid side chain present in the CH3 region of the other H chain to a smaller side chain (hole), such that the knob is placed into the hole. A finding that uses a similar "knob" and "hole" at the interface where the H chain variable region (hereinafter referred to as VH) associates with the L chain variable region (hereinafter referred to as VL) has also been reported (see Non-Patent Document 4). According to the report by Zhe et al., substitution of two types of amino acids present at the VH-VL interface (four types for both chains) promotes the formation of the heterologous molecule 1.28 times more efficiently (wild type: 72%, and modified type: 92%). Meanwhile, substitution of one type of amino acid (two types for both chains) results in the same level of efficiency as the wild type. However, the method of setting a knob and a hole in VH and VL does not sufficiently promote the formation of heterologous molecules.

[Patent Document 1] International publication WO 96/27011
[Non-Patent Document 1] Segal D M et al., Current Opinion in immunology, 1999, Vol. 11, p. 558-562.
[Non-Patent Document 2] Ridgway J B et al., Protein Engineering, 1996, Vol. 9, p. 617-621.
[Non-Patent Document 3] Merchant A M et al., Nature Biotechnology, 1998, Vol. 16, p. 677-681.
[Non-Patent Document 4] Zhe Z et al., Protein Science, 1997, Vol. 6, p. 781-788.

DISCLOSURE OF THE INVENTION

Problems to be Solved by the Present Invention

The present invention was achieved in view of the above circumstances. An objective of the present invention is to provide a method for regulating polypeptide association, polypeptides whose association is regulated, and methods for producing such polypeptides. In one embodiment, it is an objective of the present invention to provide methods for efficiently producing bispecific antibodies by regulating association at the VH-VL interface. Another objective is to provide methods for efficiently producing one of the conformational isomers of sc(Fv)2.

Means for Solving the Problems

The present inventors selected VH and VL of the antibodies as peptides to be subjected for the regulation of association, and carried out dedicated research on methods that allow the association between these VH and VL to be regulated.

As a result, the inventors discovered that the association between VH and VL can be regulated by substituting amino acids present at the VH-VL interface with charged amino acids. This, in turn, leads to a more efficient formation of the heterologous molecules than the above-mentioned methods that utilize the knob and hole techniques.

Surprisingly, according to the methods of the present invention, substitution with only one type of amino acid present at each side of the VH-VL interface (a total of two amino acids for VH and VL) allows for the efficient production of a heterologous molecule. From the viewpoint of antigenicity, fewer amino acid substitutions are preferred. In an embodiment of the present invention, a mere substitution of one amino acid present at the VH-VL interface enables the efficient formation of heterologous molecules.

Accordingly, associations between VH and VL can be regulated by the findings discovered by the present inventors. The present invention can be applied not only to the regulation of association between VH and VL, but can also be applied to the regulation of associations among arbitrary polypeptides.

Furthermore, the present inventors confirmed that function is actually retained in bispecific antibodies obtained by the methods for regulating association of the present invention.

As described above, the present inventors succeeded in developing methods that can regulate the association between arbitrary polypeptides, and thus completed the present invention.

The present invention relates to methods for regulating polypeptide association, polypeptides whose association is regulated, and methods for producing such polypeptides, and more specifically the invention provides:

[1] a method for producing a polypeptide comprising a mutation in an amino acid residue forming a polypeptide interface such that polypeptide association will be regulated, wherein the method comprises:
(a) modifying a nucleic acid encoding an amino acid residue forming the polypeptide interface from the original nucleic acid, such that polypeptide association will be inhibited;
(b) culturing host cells such that said nucleic acid is expressed; and
(c) recovering said polypeptide from the host cell culture;

[2] a method for producing a heteromultimer comprising a mutation in an amino acid residue forming an interface between polypeptides such that heteromultimer association will be regulated, wherein the method comprises:
(a) modifying a nucleic acid encoding an amino acid residue forming the interface between polypeptides from the original nucleic acid, such that the association between polypeptides will be inhibited;
(b) culturing host cells such that said nucleic acid is expressed; and
(c) recovering said heteromultimer from the host cell culture;

[3] the method of [1], wherein a nucleic acid encoding an amino acid residue forming a polypeptide interface is modified from the original nucleic acid, so that the polypeptide association forming one or more types of conformational isomers will be inhibited in a polypeptide that may form two or more types of conformational isomers;

[4] the method of [2], wherein a nucleic acid encoding an amino acid residue forming an interface between polypeptides is modified from the original nucleic acid, so that the association between polypeptides forming one or more types of multimers will be inhibited in a heteromultimer that may form two or more types of multimers;

[5] the method of [1] or [2], wherein the modification of step (a) is modifying the original nucleic acid so that an amino acid residue mutation is introduced to the interface such that two or more amino acid residues forming the interface will carry the same type of charge;

[6] the method of [5], wherein the introduced amino acid residue is glutamic acid (E);

[7] the method of [5], wherein the introduced amino acid residue is aspartic acid (D);

[8] the method of [5], wherein the introduced amino acid residue is lysine (K);

[9] the method of [5], wherein the introduced amino acid residue is arginine (R);

[10] the method of [5], wherein the introduced amino acid residue is histidine (H);

[11] the method of [1] or [2], wherein the modification of step (a) is modifying the original nucleic acid so that an amino acid residue mutation is introduced to the interface such that an amino acid residue forming a hydrophobic core present in the interface will become charged amino acid residues;

[12] the method of [11], wherein the introduced amino acid residue is glutamic acid (E);

[13] the method of [11], wherein the introduced amino acid residue is aspartic acid (D);

[14] the method of [11], wherein the introduced amino acid residue is lysine (K);

[15] the method of [11], wherein the introduced ado acid residue is arginine (R);

[16] the method of [11], wherein the introduced no acid residue is histidine (H);

[17] the method of [1] or [2], wherein the interface of the polypeptide is formed by an antibody heavy chain variable region and light chain variable region;

[18] the method of [1] or [2], wherein the polypeptide interface is formed by two or more types of heavy chain variable regions;

[19] the method of [1] or [2], wherein the polypeptide interface is formed by an antibody heavy chain constant region and light chain constant region;

[20] the method of [1] or [2], wherein the polypeptide interface is formed by two or more types of heavy chain constant regions;

[21] the method of [1] wherein the polypeptide is a single chain polypeptide in which two or more heavy chain variable regions and two or more light chain variable regions are linked by linkers;

[22] the method of [2], wherein the heteromultimer is a multi-specific antibody comprising two or more types of heavy chain variable regions and two or more types of light chain variable regions;

[23] the method of [22], wherein the heteromultimer is a bispecific antibody;

[24] a mutant polypeptide or heteromultimer produced by the method of [1] or [2];

[25] a mutant polypeptide, comprising a modification made to an amino acid residue forming an interface in the original polypeptide such that the association within said polypeptide is inhibited;

[26] a heteromultimer, comprising a modification made to an amino acid residue forming an interface between the original polypeptides such that the association between said polypeptides is inhibited;

[27] the mutant polypeptide of [25], wherein the original polypeptide may form two or more types of conformational isomers;

[28] the heteromultimer of [26], wherein the original polypeptides may form two or more types of multimers;

[29] the mutant polypeptide of [25] or the heteromultimer of [26], wherein said modification of the amino acid residues forming a polypeptide interface is introducing an amino acid residue mutation to the interface such that two or more amino acid residues forming the interface will carry the same type of charge;

[30] the mutant polypeptide or heteromultimer of [29], wherein the introduced amino acid residue is glutamic acid (E);

[31] the mutant polypeptide or heteromultimer of [29], wherein the introduced amino acid residue is aspartic acid (D);

[32] the mutant polypeptide or heteromultimer of [29], wherein the introduced amino acid residue is lysine (K);

[33] the mutant polypeptide or heteromultimer of [29], wherein the introduced amino acid residue is arginine (R);

[34] the mutant polypeptide or heteromultimer of [29], wherein the introduced amino acid residue is histidine (H);

[35] the mutant polypeptide of [25] or the heteromultimer of [26], wherein the modification of amino acid residues forming the polypeptide interface is introducing an amino acid residue mutation to the interface such that an amino acid residue forming a hydrophobic core present in the interface will become charged amino acid residues;

[36] the mutant polypeptide or heteromultimer of [35], wherein the introduced amino acid residue is glutamic acid (E);

[37] the mutant polypeptide or heteromultimer of [35], wherein the introduced amino acid residue is aspartic acid (D);

[38] the mutant polypeptide or heteromultimer of [35], wherein the introduced amino acid residue is lysine (K);

[39] the mutant polypeptide or heteromultimer of [35], wherein the introduced amino acid residue is arginine (R);

[40] the mutant polypeptide or heteromultimer of [35], wherein the introduced amino acid residue is histidine (H);

[41] the mutant polypeptide of [25] or the heteromultimer of [26], wherein the polypeptide interface is formed by an antibody heavy chain variable region and light chain variable region;

[42] the mutant polypeptide of [25] or the heteromultimer of [26], wherein the polypeptide interface is formed by two or more types of heavy chain variable regions;

[43] the mutant polypeptide of [25] or the heteromultimer of [26], wherein the polypeptide interface is formed by an antibody heavy chain constant region and light chain constant region;

[44] the mutant polypeptide of [25] or the heteromultimer of [26], wherein the polypeptide interface is formed by two of more types of heavy chain constant regions;

[45] the mutant polypeptide of [25], wherein the polypeptide is a single chain polypeptide in which two or more heavy chain variable regions and two or more light chain variable regions are linked by linkers;

[46] the heteromultimer of [26], wherein the heteromultimer is a multispecific antibody comprising two or more types of heavy chain variable regions and two or more types of light chain variable regions;

[47] the heteromultimer of [46], wherein the heteromultimer is a bispecific antibody;

[48] a composition comprising the mutant polypeptide of [25] or the heteromultimer of [26], and a pharmaceutically acceptable carrier;

[49] a nucleic aid encoding the mutant polypeptide of [25] or the heteromultimer of [26];

[50] a host cell comprising the nucleic acid of [49];

[51] a method for producing the mutant polypeptide of [25] or the heteromultimer of [26], which comprises the steps of culturing the host cell of [50], and recovering the polypeptide from the cell culture;

[52] a method for regulating polypeptide association, which comprises modifying an amino acid residue forming an interface in the original polypeptide such that the association within the polypeptide is inhibited;

[53] a method for regulating heteromultimer association, which comprises modifying amino acid residues forming an interface between the original polypeptides such that the association between the polypeptides is inhibited;

[54] the method of [52], which comprises modifying an amino acid residue forming an interface in a polypeptide, such that the association of a polypeptide forming one or more types of conformational isomers will be inhibited in a polypeptide that may form two or more types of conformational isomers;

[55] the method of [53], which comprises modifying amino acid residues forming an interface between polypeptides, such that the association between polypeptides that form one or more types of conformational isomers will be inhibited in a heteromultimer that may form two or more types of multimers;

[56] the method of [52] or [53], wherein said modification of an amino acid residue forming a polypeptide interface is introducing an amino acid residue mutation to the interface such that two or more amino acid residues forming the interface will have the same type of charge;

[57] the method of [56], wherein the introduced amino acid residue is glutamic acid (E);

[58] the method of [56], wherein the introduced amino acid residue is aspartic acid (D);

[59] the method of [56], wherein the introduced amino acid residue is lysine (K);

[60] the method of [56], wherein the introduced amino acid residue is arginine (R);

[61] the method of [56], wherein the introduced amino acid residue is histidine (H);

[62] the method of [52] or [53], wherein said modification of amino acid residues forming a polypeptide interface is introducing an amino acid residue mutation to the interface such that an amino acid residue forming a hydrophobic core present in the interface will become charged amino acid residues;

[63] the method of [62], wherein the introduced amino acid residue is glutamic acid (E);

[64] the method of [62], wherein the introduced amino acid residue is aspartic acid (D);

[65] the method of [62], wherein the introduced amino acid residue is lysine (K);

[66] the method of [62], wherein the introduced amino acid residue is arginine (R);

[67] the method of [62], wherein the introduced amino acid residue is histidine (H);

[68] the method of [52] or [53], wherein the polypeptide interface is formed by an antibody heavy chain variable region and light chain variable region;

[69] the method of [52] or [53], wherein the polypeptide interface is formed by two or more types of heavy chain variable regions;

[70] the method of [52] or [53], wherein the polypeptide interface is formed by an antibody heavy chain constant region and light chain constant region;

[71] the method of [52] or [53], wherein the polypeptide interface is formed by two or more types of heavy chain constant regions;

[72] the method of [52], wherein the polypeptide is a single chain polypeptide in which two or more heavy chain variable regions and two or more light chain variable regions are linked by linkers;

[73] the method of [53], wherein the heteromultimer is a multispecific antibody comprising two types or more of heavy chain variable regions and two types or more of light chain variable regions;

[74] the method of [73], wherein the heteromultimer is a bispecific antibody;

[75] an antibody comprising a heavy chain variable region and a light chain variable region, wherein the following amino acid residues of (1) and (2) carry the same type of charge:
(1) an amino acid residue which is included in the heavy chain variable region and corresponds to position 39 (glutamine) in the amino acid sequence of SEQ ID NO: 6; and
(2) an amino acid residue which is included in the light chain variable region and corresponds to position 44 (glutamine) in the amino acid sequence of SEQ ID NO: 8;
[76] an antibody comprising a heavy chain variable region and a light chain variable region, wherein the following amino acid residues of (1) and (2) carry the same type of charge:
(1) an amino acid residue which is included in the heavy chain variable region and corresponds to position 45 (leucine) in the amino acid sequence of SEQ ID NO: 6; and
(2) an amino acid residue which is included in the light chain variable region and corresponds to position 50 proline) in the amino acid sequence of SEQ ID NO: 8;
[77] an antibody comprising a heavy chain variable region and a light chain variable region, wherein either one of the following amino acid residues of (1) or (2) is a charged amino acid residue:
(1) an amino acid residue which is included in the heavy chain variable region and corresponds to position 45 (leucine) in the amino acid sequence of SEQ ID NO: 6; and
(2) an amino acid residue which is included in the light chain variable region and corresponds to position 50 proline) in the amino acid sequence of SEQ ID NO: 8;
[78] the antibody of [75] or [76], wherein amino acid residues carrying the same type of charge are selected from amino acid residues included in the group of either (a) or (b):
(a) glutamic acid (E) and aspartic acid (D); or
(b) lysine (K), arginine (R), and histidine (H);
[79] the antibody of [77], wherein said charged amino acid residue is glutamic acid (E), aspartic acid (D), lysine (K), arginine (R) or histidine (H);
[80] the antibody of any one of [75] to [77], wherein the polypeptide is a single chain polypeptide in which two or more heavy chain variable regions and two or more light chain variable regions are linked by linkers;
[81] the antibody of any one of [75] to [77], wherein the polypeptide is a multispecific antibody comprising two or more types of heavy chain variable regions and two or more types of light chain variable regions;
[82] the antibody of [81], wherein the polypeptide is a bispecific antibody;
[83] a composition comprising the antibody of any one of [75] to [77] and a pharmaceutically acceptable carrier;
[84] a nucleic acid encoding a polypeptide constituting the antibody of any one of [75] to [77];
[85] a host cell comprising the nucleic acid of [84];
[86] the method for producing the antibodies of any one of [75] to [77], which comprises the steps of culturing the host cell of [85] and recovering the polypeptides from the cell culture;
[87] an antibody comprising two or more types of heavy chain CH3 regions, wherein one to three pair(s) of amino acid residues in the first heavy chain CH3 region is/are selected from the pair(s) of amino acid residues indicated in (1) to (3) that car the same type of charge:

(1) amino acid residues included in the heavy chain CH3 region at positions 356 and 439 according to the EU numbering system;
(2) amino acid residues included in the heavy chain CH3 region at positions 357 and 370 according to the EU numbering system; and
(3) amino acid residues included in the heavy chain CH3 region at positions 399 and 409 according to the EU numbering system;
[88] the antibody of [87], in which one to three pairs of the amino acid residues in the second heavy chain CH3 region are (i) selected from the pairs of amino acid residues of (1) to (3) of [87], (ii) corresponds to the pairs of amino acid residues of (1) to (3) of [87], and (iii) carries a charge opposite to the corresponding amino acid residues in the first heavy chain CH3 region;
[89] the antibody of [87], wherein said amino acid residues carrying the same type of charge are selected from the no acid residues included in the group of either (a) or (b):
(a) glutamic acid (E) and aspartic acid (D); or
(b) lysine (K), arginine (R), and histidine (H);
[90] the antibody of [87], wherein said first heavy chain CH3 region and the second heavy chain CH3 region are crosslinked by a disulfide bond;
[91] the antibody of [87], wherein the antibody comprises two or more types of heavy chain constant regions;
[92] the antibody of [87], wherein the multispecific antibody comprises two or more types of heavy chain variable regions and two or more types of light chain variable regions;
[93] the antibody of [92], which is a bispecific antibody;
[94] a composition comprising the antibody of [87] and a pharmaceutically acceptable carrier;
[95] a nucleic acid encoding a polypeptide constituting the antibody of [87];
[96] a host cell comprising the nucleic acid of [95]; and
[97] a method for producing the antibody of [87], which comprises the steps of culturing the host cell of [96], and recovering the polypeptides from the cell culture.

BRIEF DESCRIPTION OF THE DRAWINGS

FIG. 1 depicts models of the Fv region of humanized SB04. Part (A) depicts H39 and L38, which are amino acid residues at the VH-VL interface, and part (B) depicts H45 and L44, which are amino acid residues at the VH-VL interface.

6: R variant: humanized XB12 H chain (R)+humanized XB12 L chain (Q)+humanized SB04 L chain (R); and
7: K variant: humanized XB12 H chain (K)+humanized XB12 L chain (Q)+humanized SB04 L chain (K)

Figure 3:
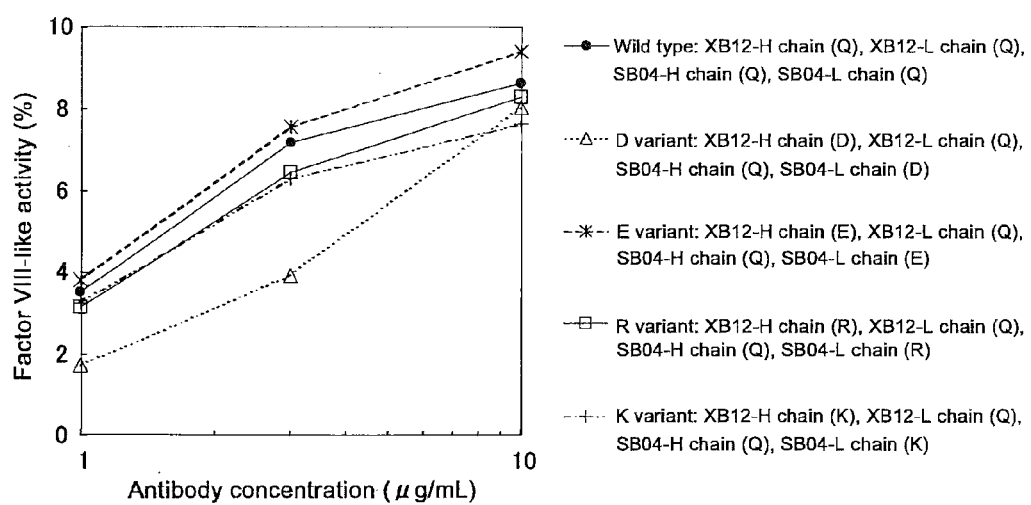

FIG. 3 depicts the results of an assay evaluating coagulation activity in H39 and L38-modified antibodies. The results demonstrate that the bispecific antibody whose XB12 H chain (H39) and SB04 L chain (L38) have been modified to Glu has a coagulation activity equal to or greater than that of the wild-type.

Figure 4:
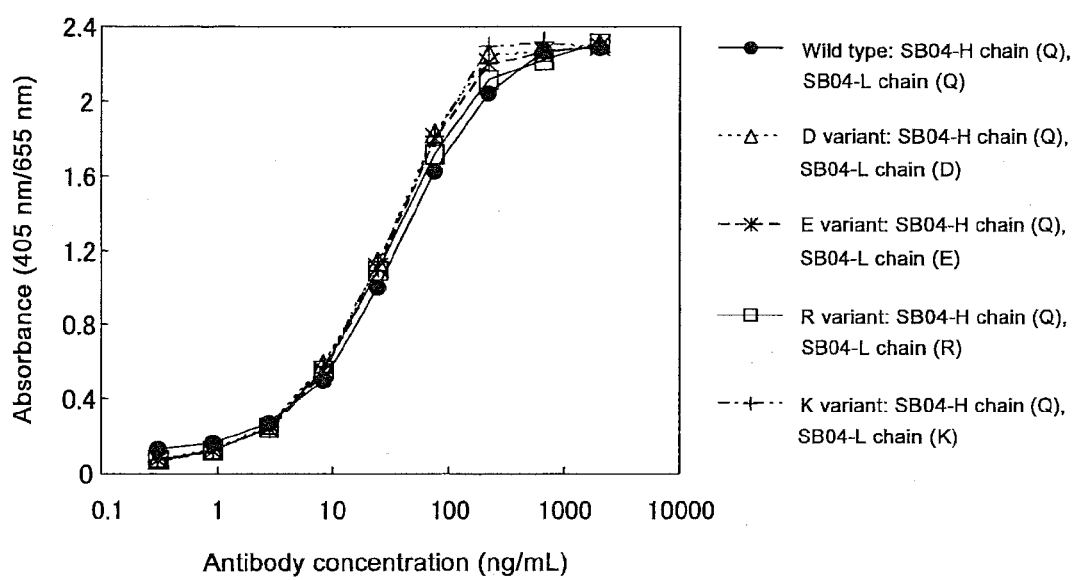

FIG. 4 depicts the results of an assay evaluating Factor IXa binding activity in H39 and L38-modified antibodies. The results demonstrate that all modified antibodies have a binding activity equivalent to that of the wild-type.

Figure 5:
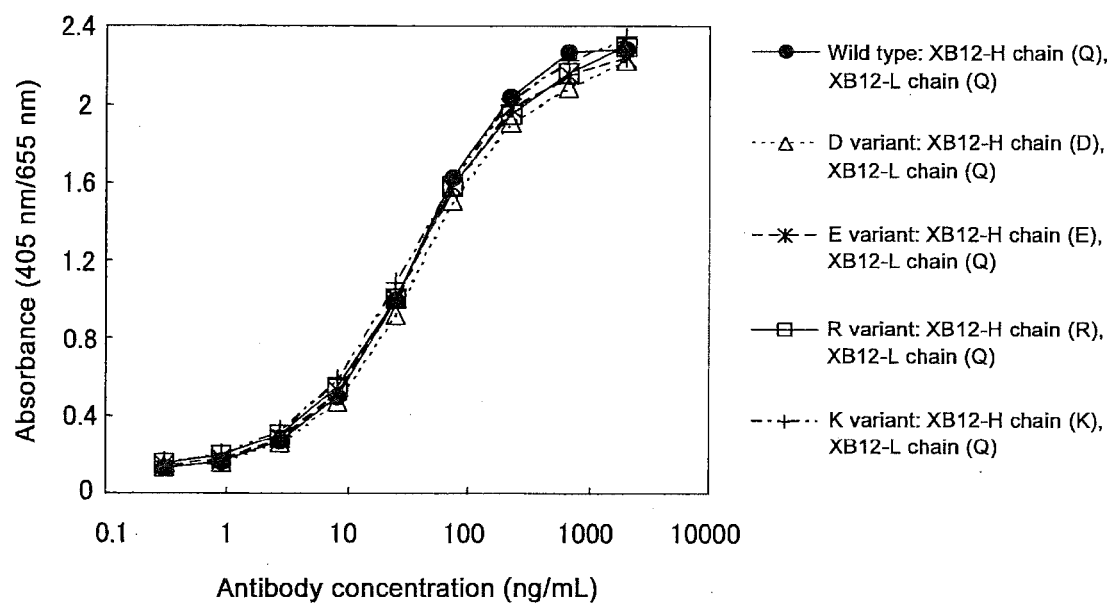

FIG. 5 shows the results of an assay evaluating Factor X binding activity in H39 and L38-modified antibodies. The results show that all modified antibodies have a binding activity equivalent to that of the wild-type.

Figure 6:
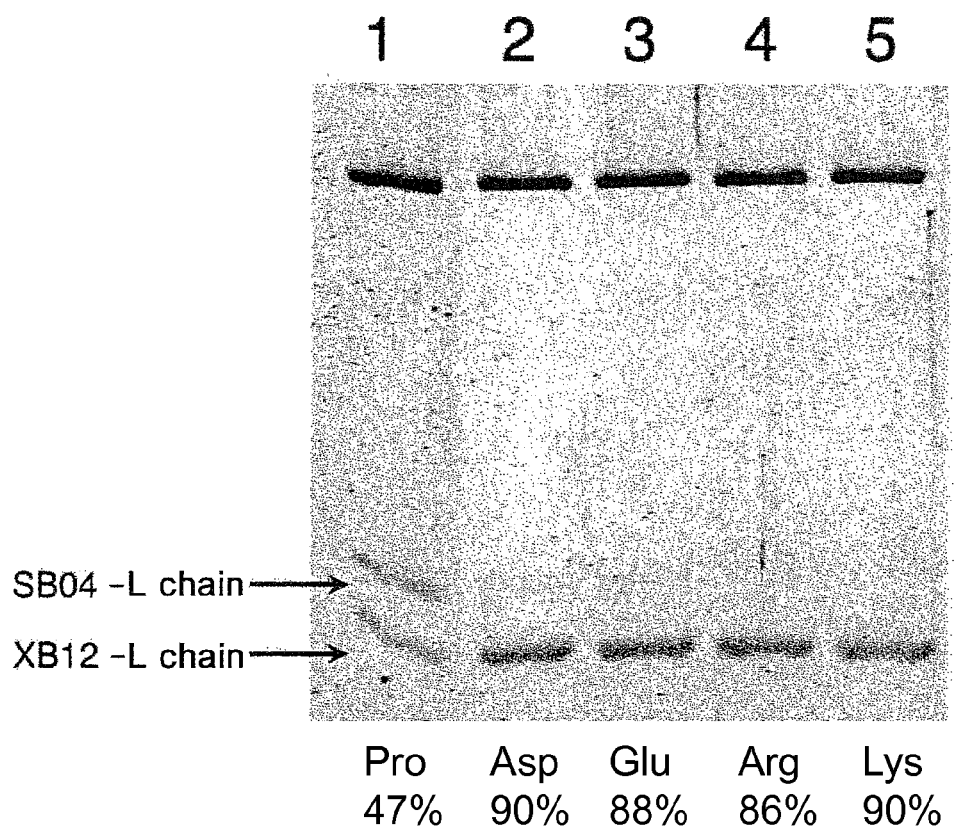

FIG. 6 is a photograph depicting the results of an assay evaluating the association between the H and L chains in the L44-modified antibodies. The results demonstrate that for all modified antibodies, the associated proportion of the antibody of interest is increased when compared to that of the wild type.
Description of the Lanes:
1: wild type: humanized XB12 H chain+humanized XB12 L chain (P)+humanized SB04 L chain (P);
2: D variant: humanized XB12 H chain+humanized XB12 L chain (P)+humanized SB04 L chain (D);
3: E variant: humanized XB12 H chain+humanized XB12 L chain (P)+humanized SB04 L chain (E);
4: R variant: humanized XB12 H chain+humanized XB12 L chain (P)+humanized SB04 L chain (R); and
5: K variant: humanized XB12 H chain+humanized XB12 L chain (P)+humanized SB04 L chain (K)

Figure 7:
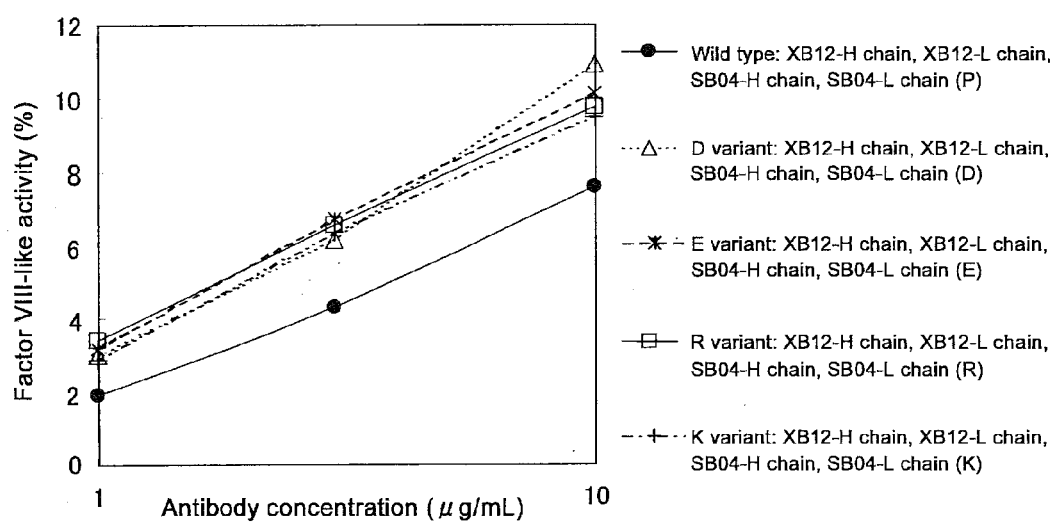

FIG. 7 depicts the results of an assay evaluating coagulation activity in L44-modified antibodies. The results demonstrate that all modified antibodies have coagulation activity greater than that of the wild-type.

Figure 8:
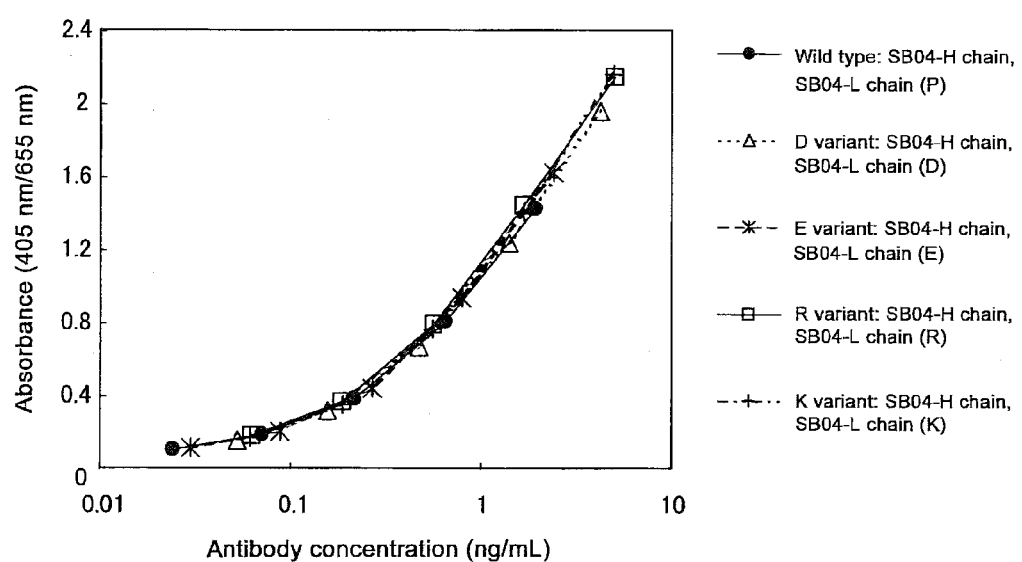

FIG. 8 depicts the results of an assay evaluating Factor X binding activity in L44-modified antibodies. The results demonstrate that all modified antibodies have a binding activity equivalent to that of the wild type.

Figure 9:
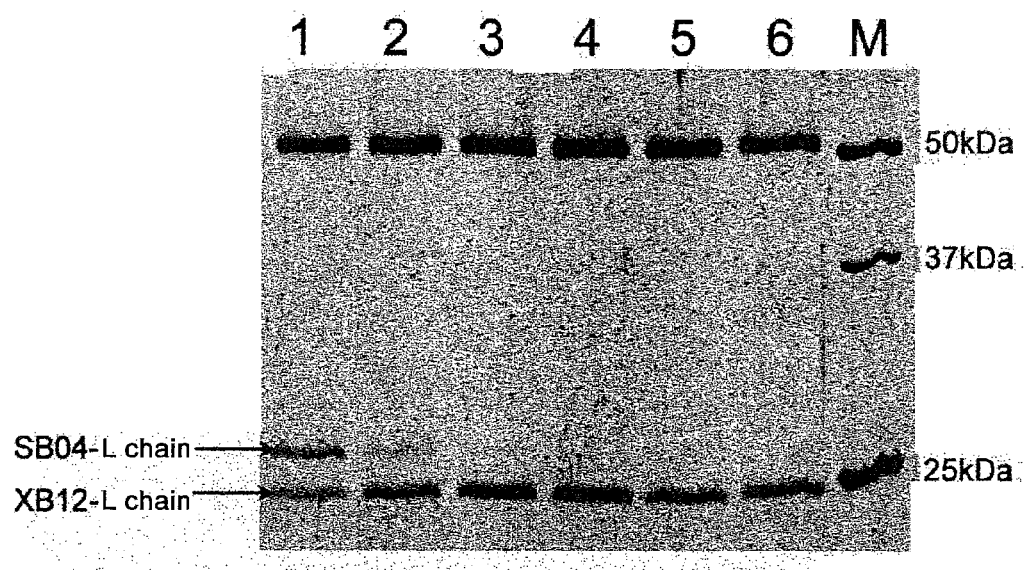
Figure 10:
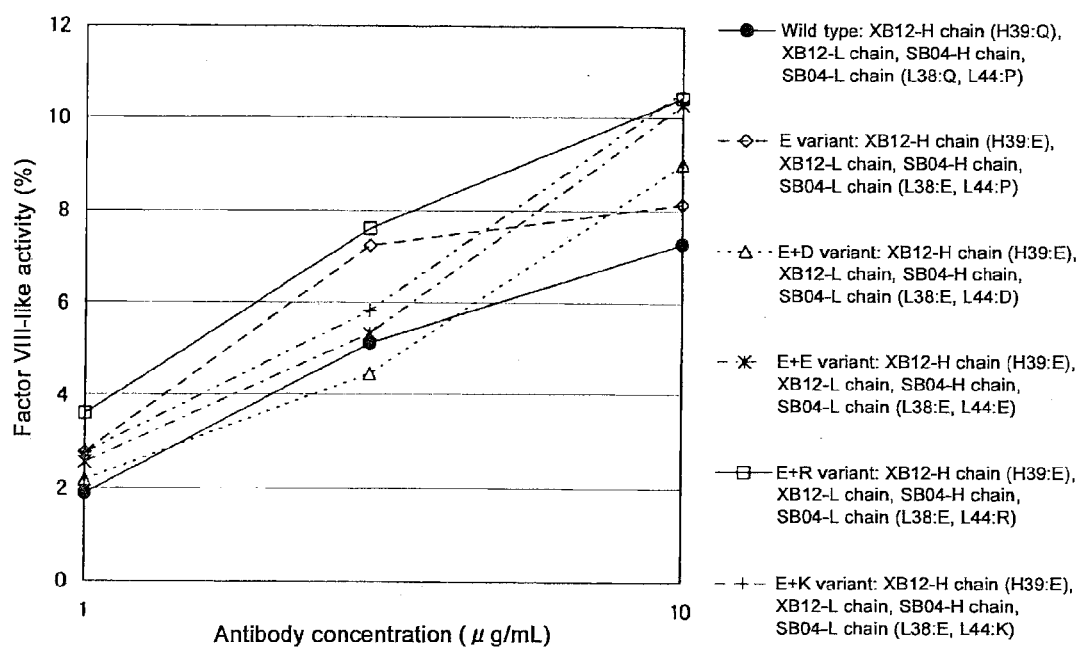

FIG. 9 is a photograph depicting the results of an assay evaluating the association between the H and L chains in H39, L38, and L44-modified antibodies. The results demonstrate that for all modified antibodies, associated proportion of the antibody of interest is increased when compared to that of the wild type.
Description of the Lanes:
1: wild type: humanized XB12 H chain (H39: Q)+humanized XB12 L chain (L38: Q)+humanized SB04 L chain (L38: Q, L44: P);
2: E+D variant: humanized XB12 H chain (H39: E)+humanized XB12 L chain (L38: Q)+humanized SB04 L chain (L38: E, L44: D);
3: E+E variant: humanized XB12 H chain (H39: E)+humanized XB12 L chain (L38: Q)+humanized SB04 L chain (L38: E, L44: E);
4: E+R variant: humanized XB12 H chain (H39: E)+humanized XB12 L chain (L38: Q)+humanized SB04 L chain (L38: E, L44: R);
5: E+K variant: humanized XB12 H chain (H39: E)+humanized XB12 L chain (L38: Q)+humanized SB04 L chain (L38: B, L44: K); and M: molecular marker FIG. 10 depicts the results of an assay evaluating coagulation activity in H39, L38, and L44-modified antibodies. The results demonstrate that bispecific antibodies whose XB12 H chain (H39) and SB04 L chain (L38, L44) have been modified have a coagulation activity equal to or greater than that of the wild type.

Figure 11:
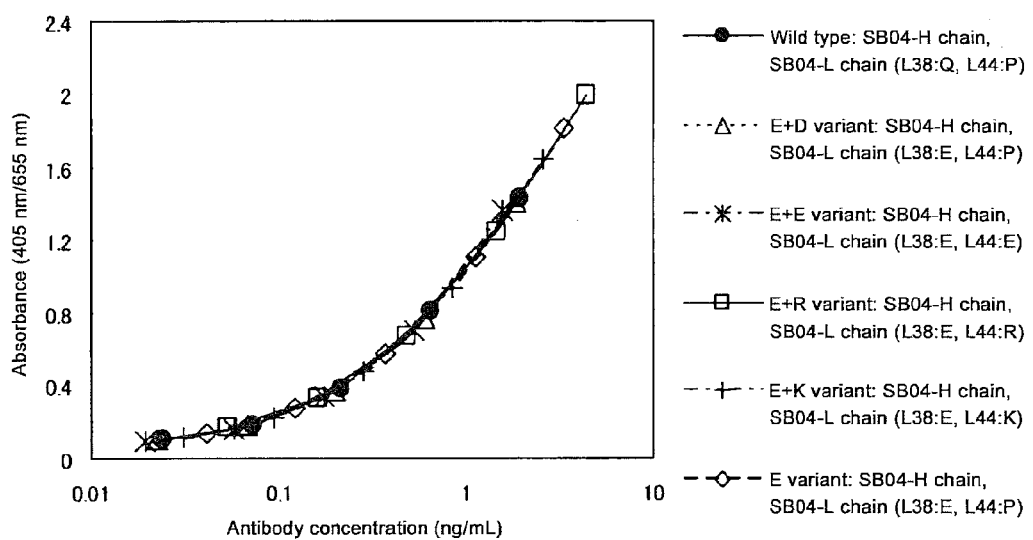

FIG. 11 depicts the results of an assay evaluating Factor IXa binding activity in H39, L38, and L44-modified antibodies. The results demonstrate that all modified antibodies have a binding activity equivalent to that of the wild type.

FIG. 12 presents a schematic diagram of examples of the conformations of an sc(Fv)2 having two types of heavy chain variable regions (VH1 and VH2) and two types of light chain variable regions (VL1 and VL2). An sc(Fv)2 having the structure of (a) is mainly present as two types of conformational isomers shown in (b).

Figure 13:
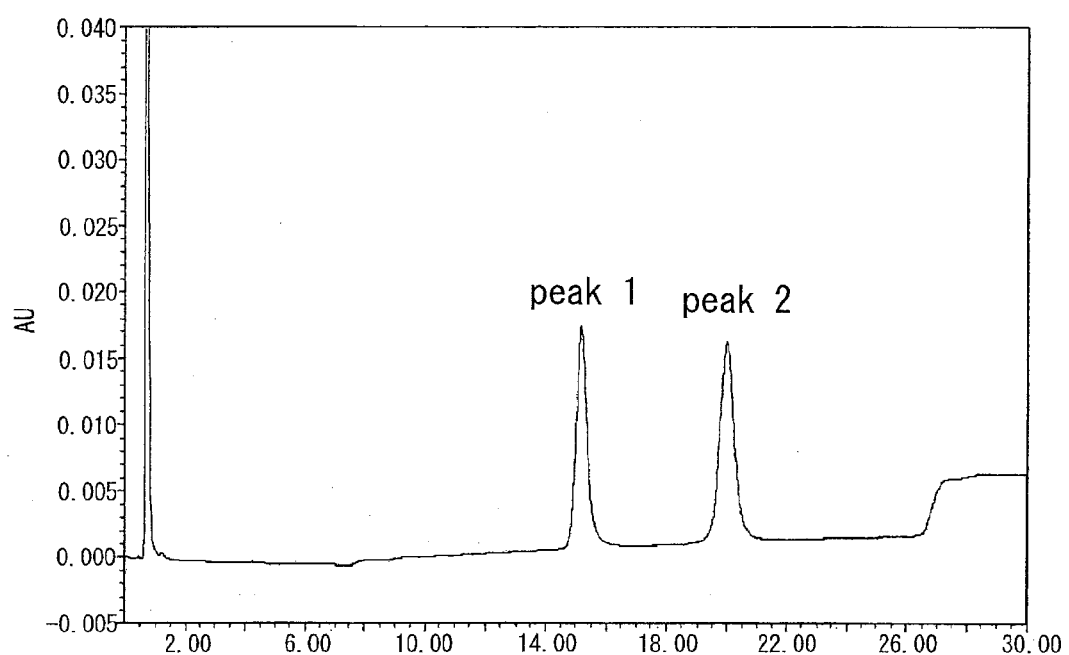

FIG. 13 depicts the results of separating peak 1 and peak 2 corresponding to the conformational isomers of u2-wz4, by cation exchange chromatography.

Figure 14:
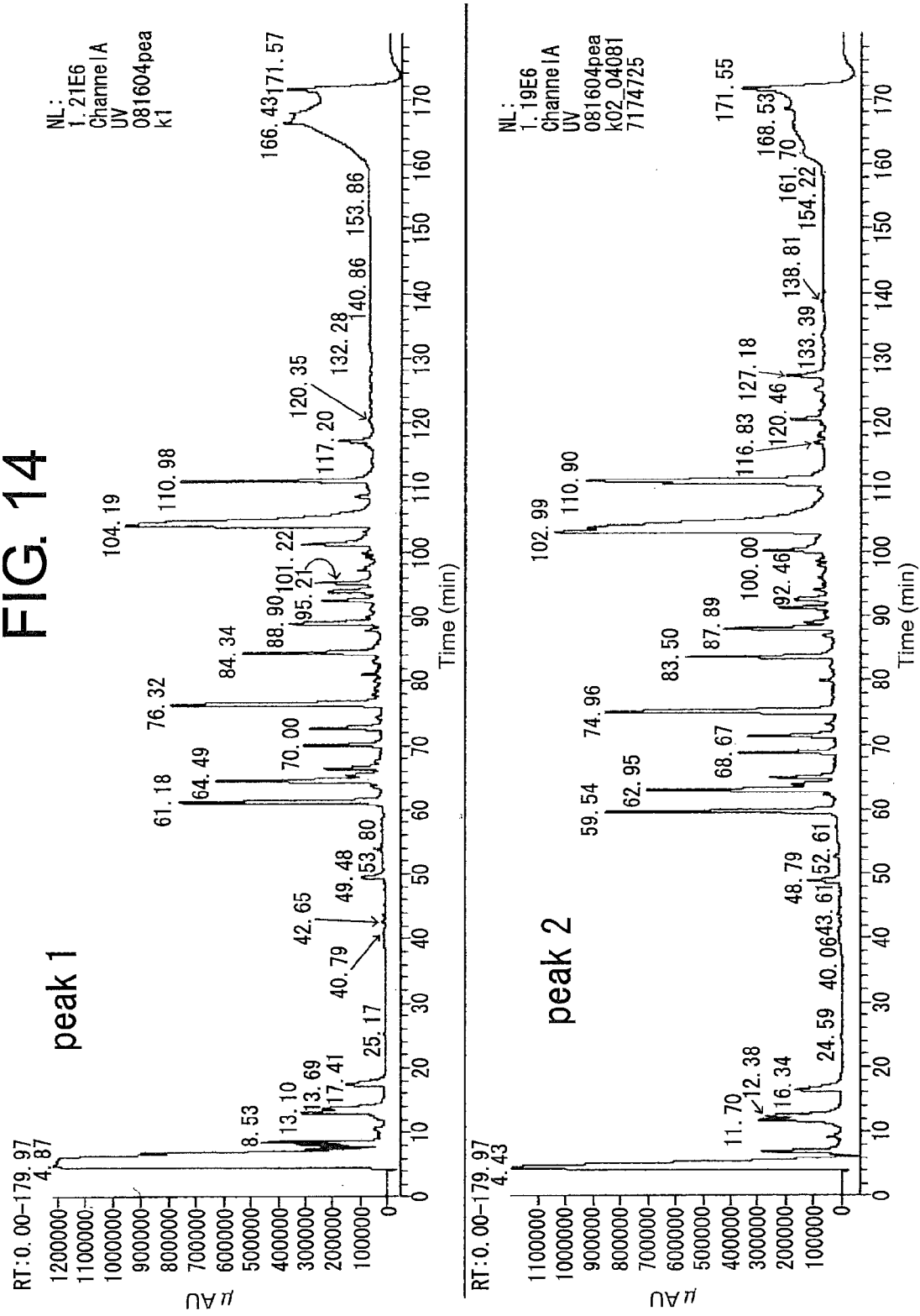

FIG. 14 depicts the results of peptide mapping of peak 1 and peak 2 separated by cation exchange chromatography.

Figure 15:
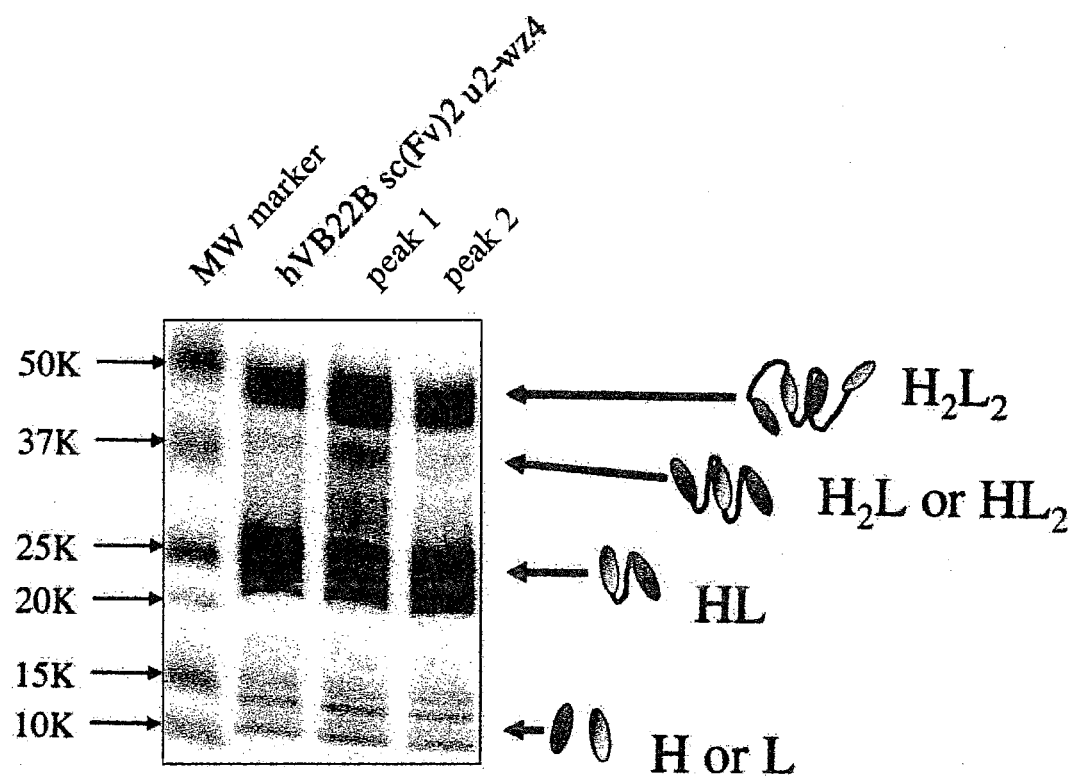

FIG. 15 is a photograph depicting the results of a reduced SDS-PAGE assay performed after subtilisin treatment of u2-wz4 before separation of peak 1 and peak 2, which are conformational isomers of u2-wz4. The conformations corresponding to the obtained bands are shown on the right.

Figure 16:
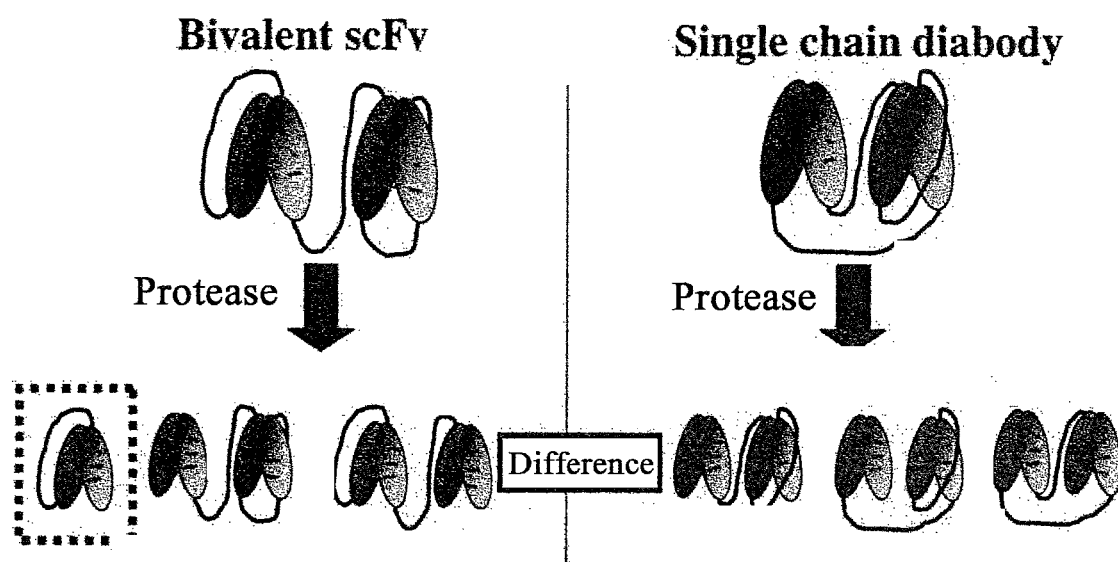

FIG. 16 depicts the difference in degradation patterns after limited proteolysis by subtilisin, which is caused by differences in the conformation of a bivalent scFv and single chain antibody. In the case of the bivalent ScFv structure, the minibody fragment in the dotted frame is formed.

Figure 17:
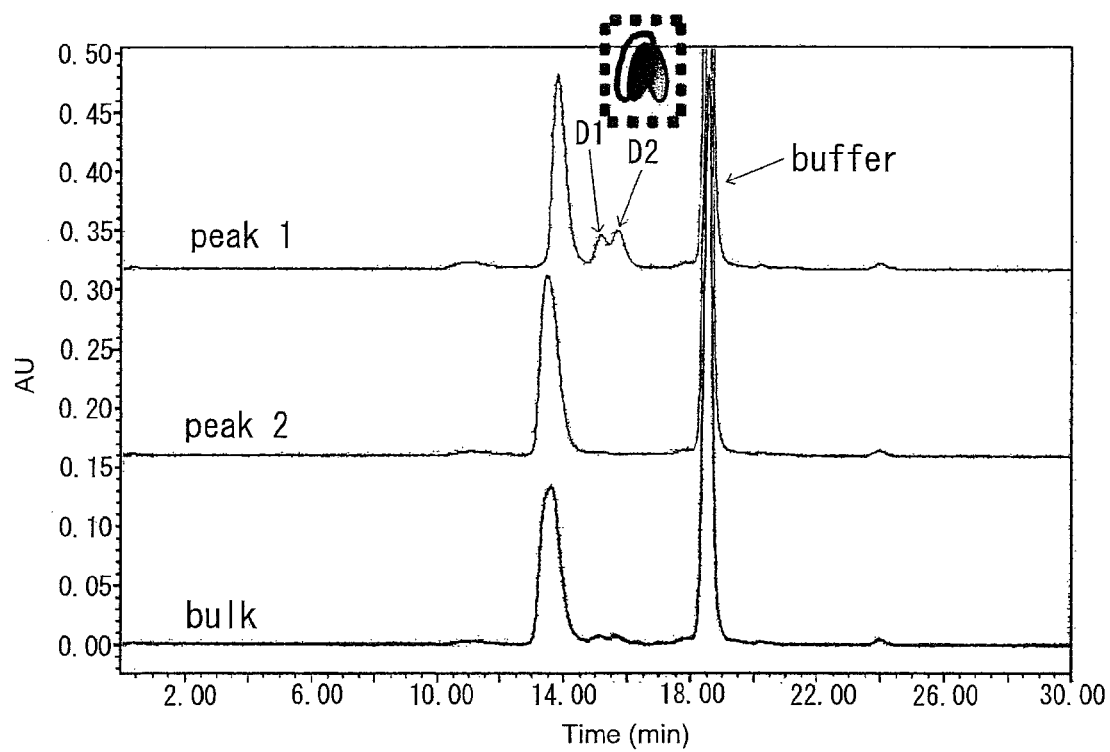

FIG. 17 depicts the results of a gel filtration chromatography assay after limited proteolysis by subtilisin on u2-wz4 before separation and on peak 1 and peak 2, which are conformational isomers of u2-wz4. The elution positions of the minibody peaks are shown by arrows.

FIG. 18 depicts the results of a gel filtration chromatography assay on u2-wz4, variant v1, and variant v3 after purification through an MG10-GST fusion protein-immobilized column.

Figure 19:
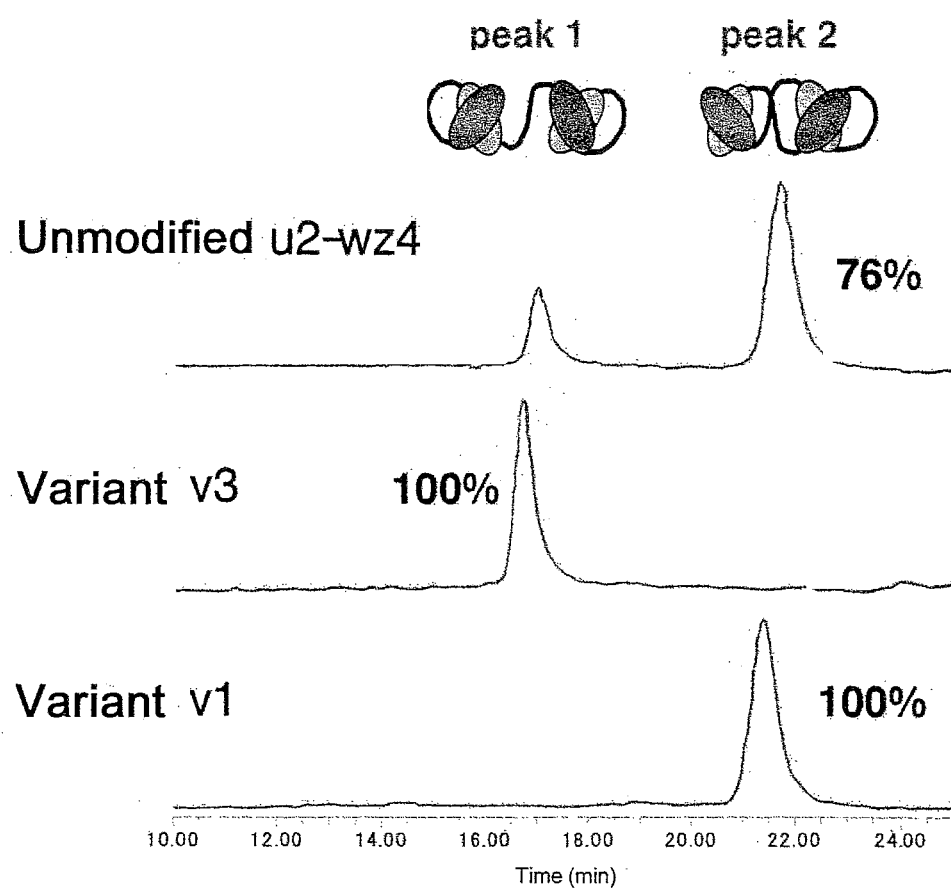

FIG. 19 depicts the results of a cation exchange chromatography assay on u2-wz4, variant v1, and variant v3.

Figure 20:
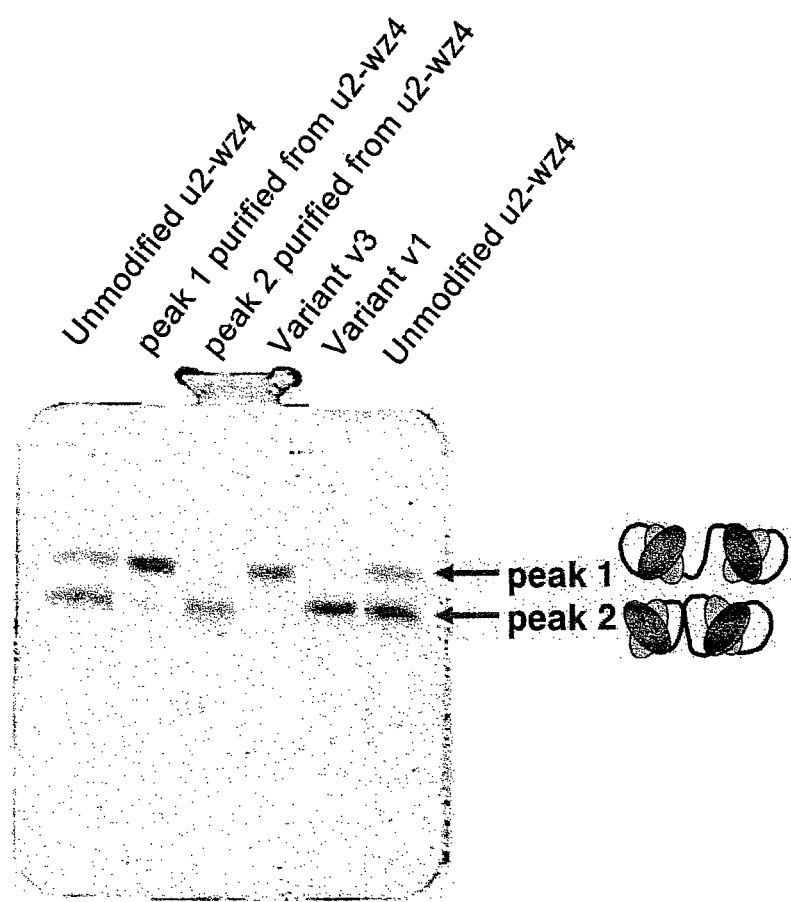

FIG. 20 is a photograph depicting the results of isoelectric focusing of u2-wz4, peak 1 purified from u2-wz4, peak 2 purified from u2-wz4, variant v1, and variant v3.

Figure 21:
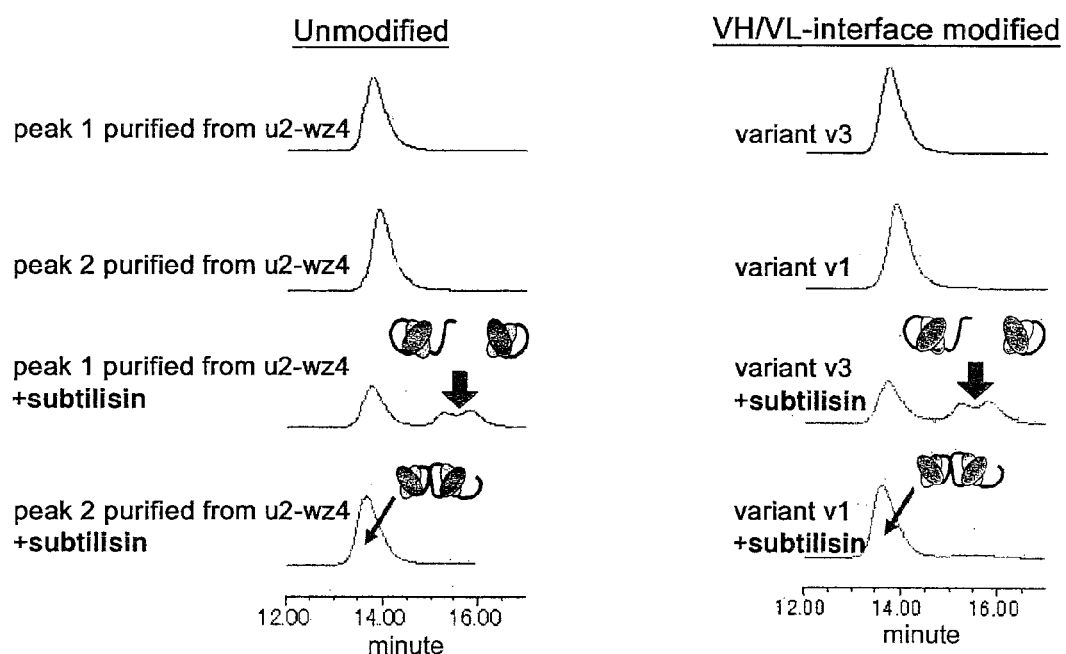

FIG. 21 depicts the results of gel filtration analyses performed after protease-limited proteolysis of peak 1 purified from u2-wz4, peak 2 purified from u2-wz4, variant v1, and variant v3.

FIG. 22 depicts the results of an assay evaluating the TPO-like agonist activity of peak 1 purified from u2-wz4, peak 2 purified from u2-wz4, variant v1, and variant v3.

FIG. 23 depicts the results of DSC analyses of peak 1 purified from u2-wz4, peak 2 purified from u2-wz4, variant v1, and variant v3.

Figure 24:
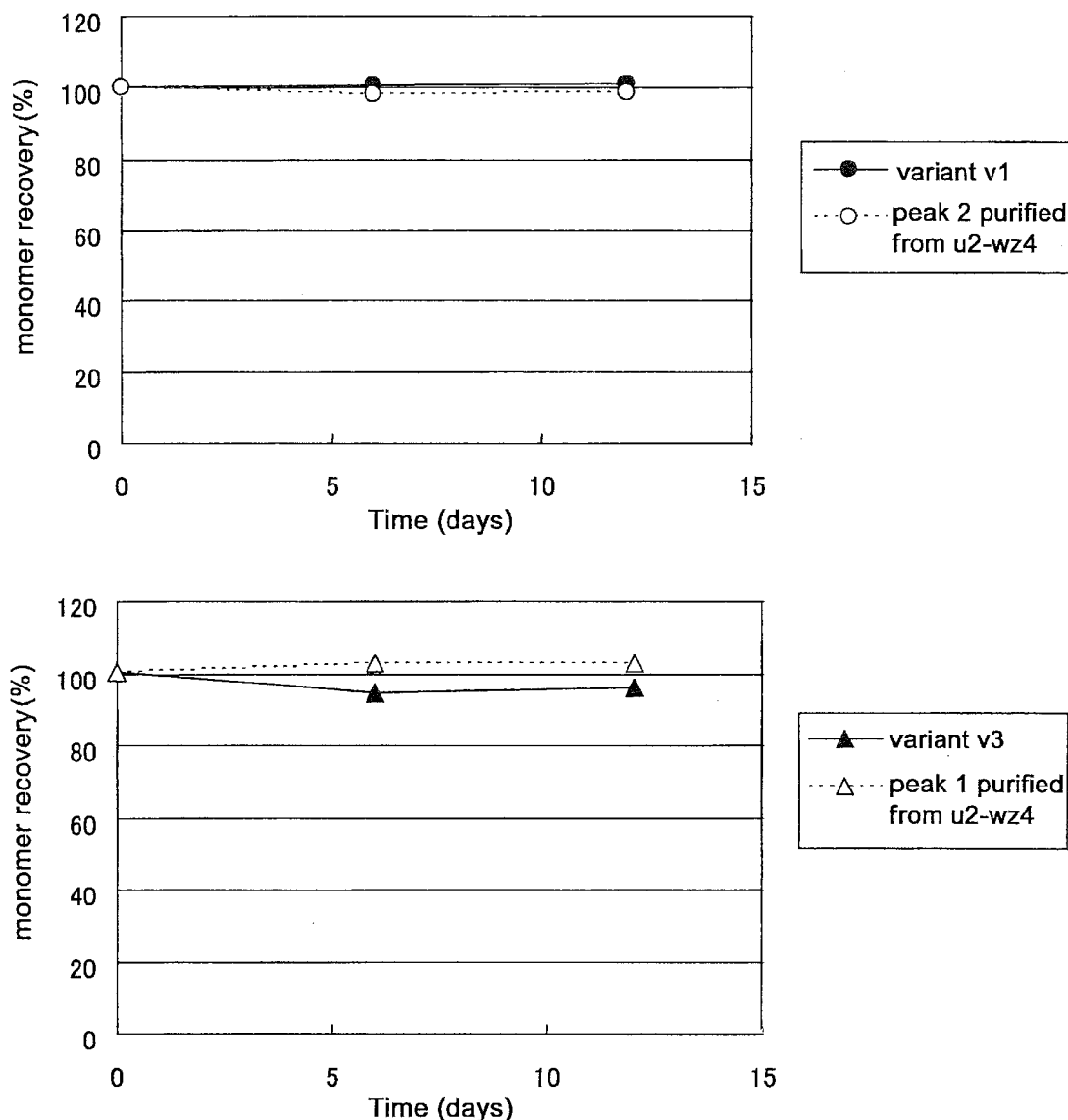

FIG. 24 depicts the percentage of monomers recovered by gel filtration chromatographic analysis in thermal acceleration tests of peak 1 purified from u2-wz4, peak 2 purified from u2-wz4, variant v1, and variant v3.

Figure 25:
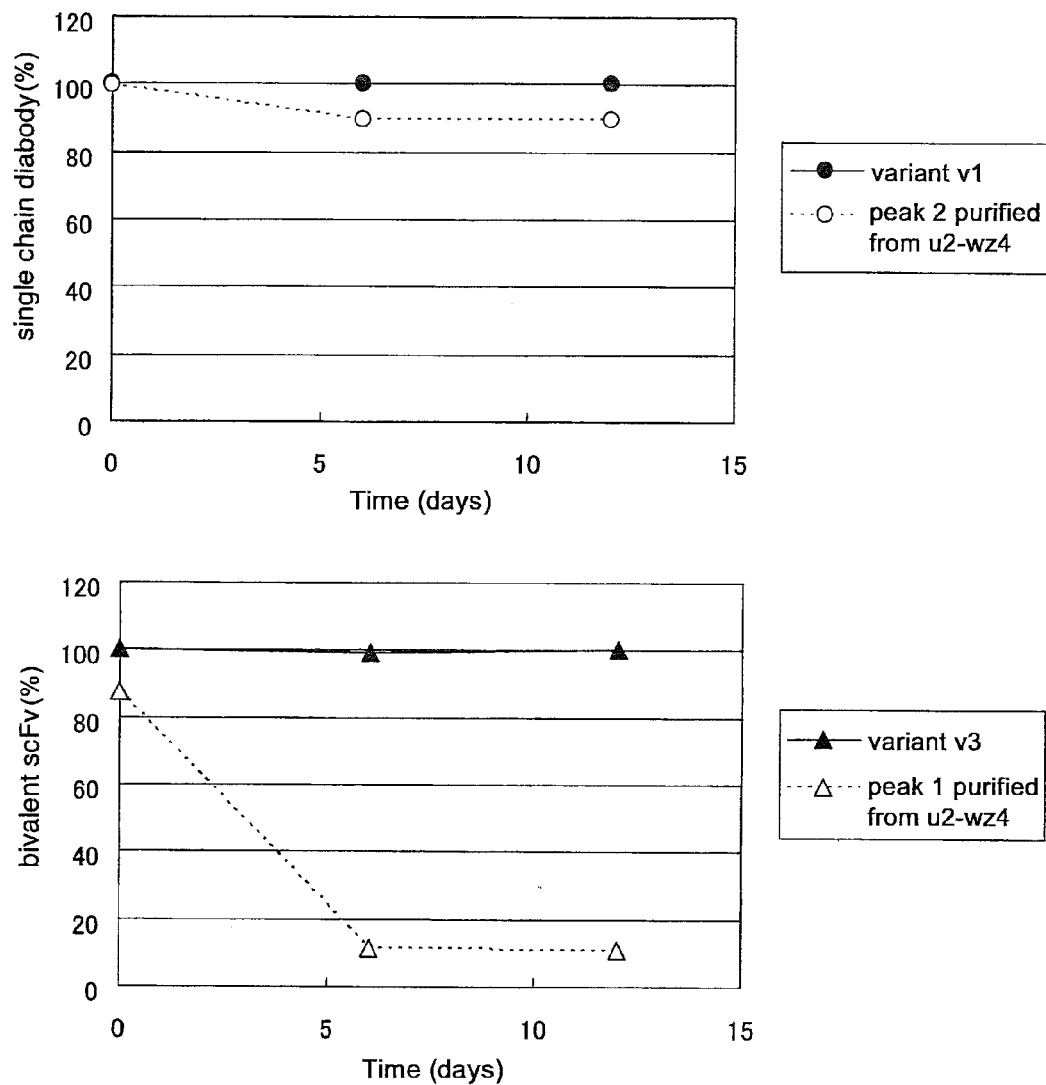

FIG. 25 depicts the conformational isomer content percentage obtained by cation exchange chromatographic analysis in thermal acceleration tests of peak 1 purified from u2-wz4, peak 2 purified from u2-wz4, variant v1, and variant v3.

Figure 26:
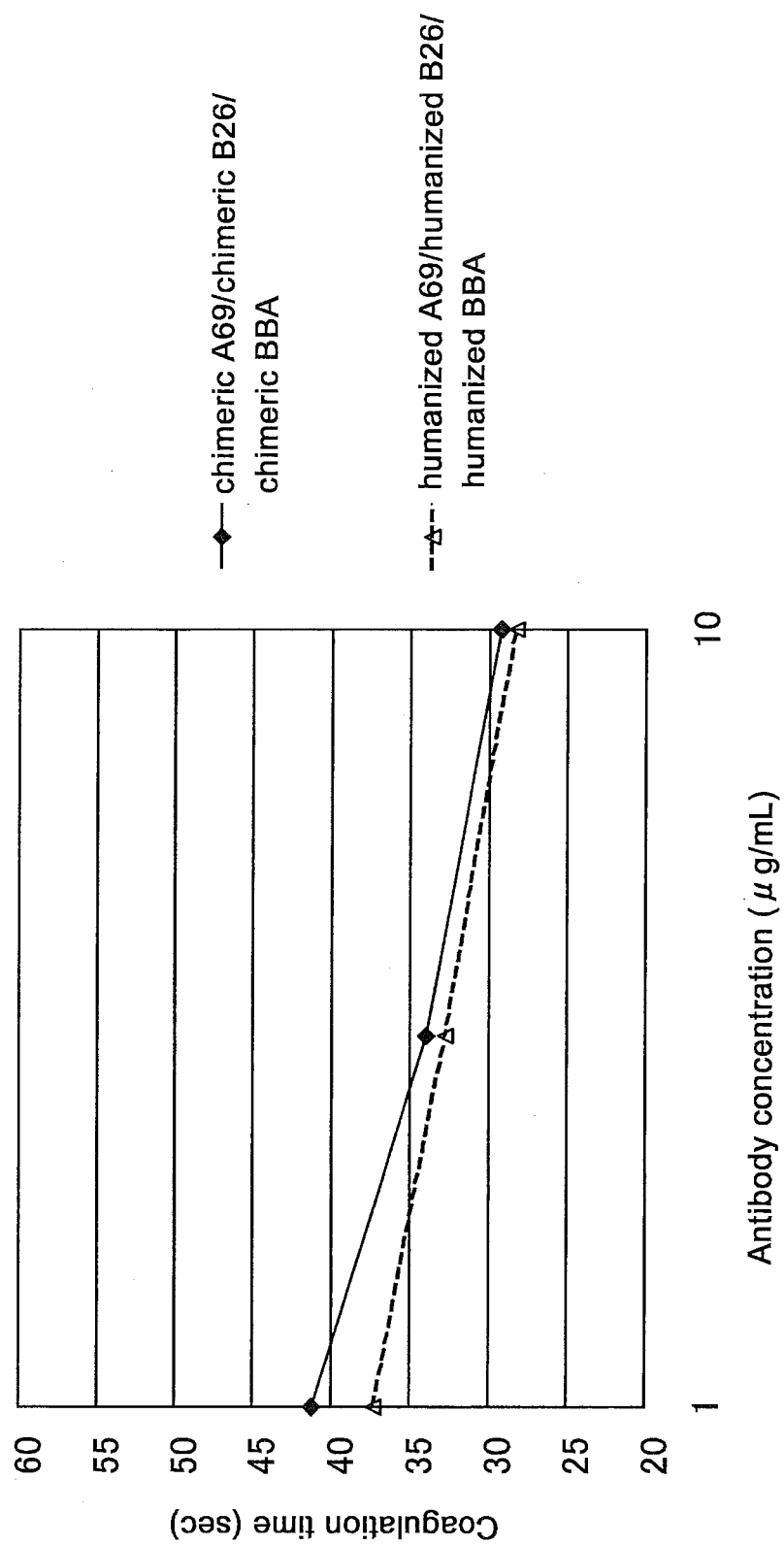

FIG. 26 depicts the results of an assay evaluating the coagulation activities of humanized bispecific antibodies (humanized A69 (hA69-PFL)/humanized B26 (hB26-PF)/ humanized BBA (hAL-AQ)). The results demonstrate that the coagulation activities are equivalent to or greater than those of chimeric bispecific antibodies.

Figure 27:
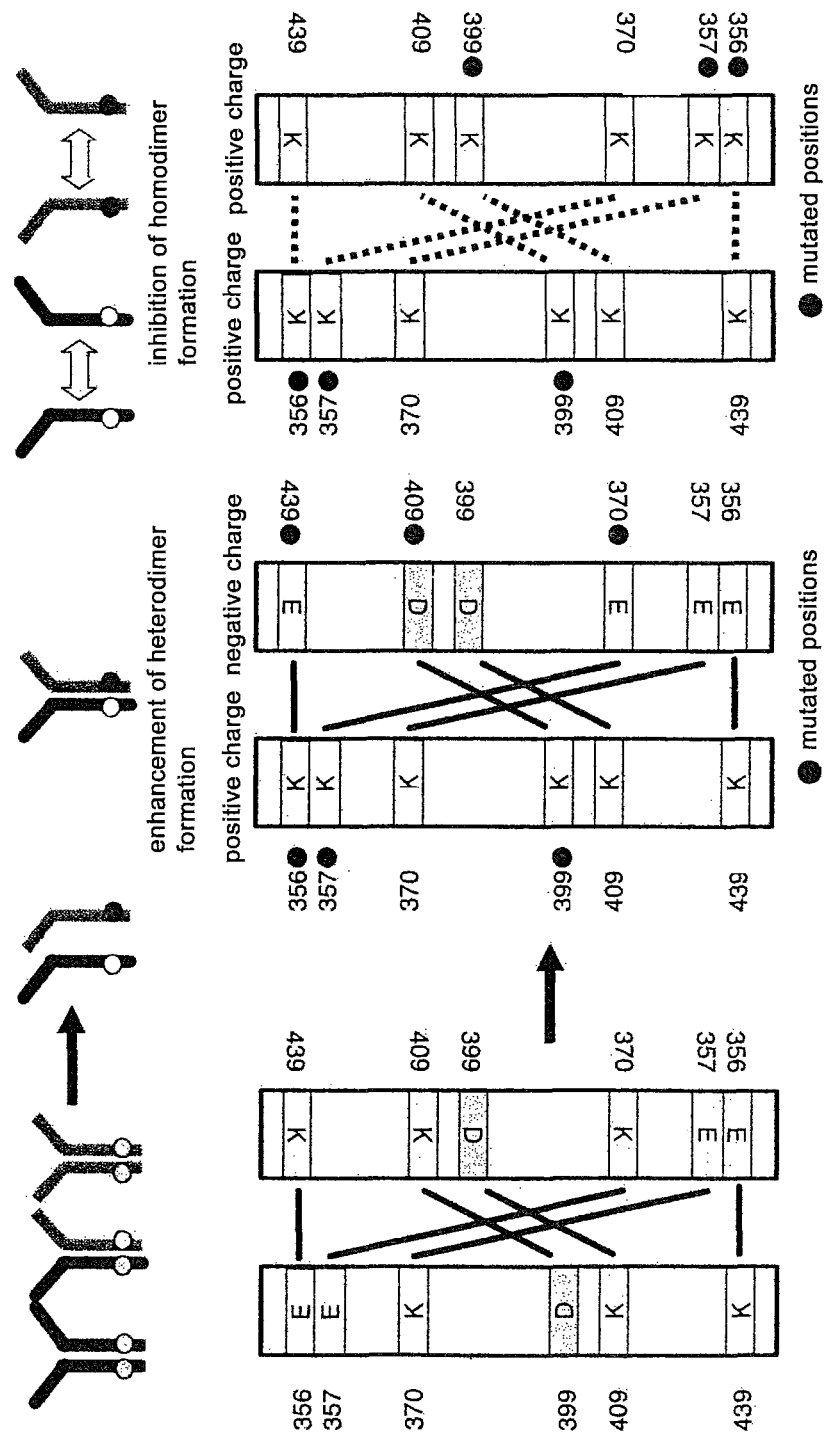

FIG. 27 presents a schematic diagram describing the method for improving the efficiency of the formation of bispecific antibody by modifying the H-chain constant region. The numbers indicating the positions of modification are based on the EU numbering system (Kabat E A et al. 1991. Sequences of Proteins of Immunological Interest. NIH).

Figure 28:
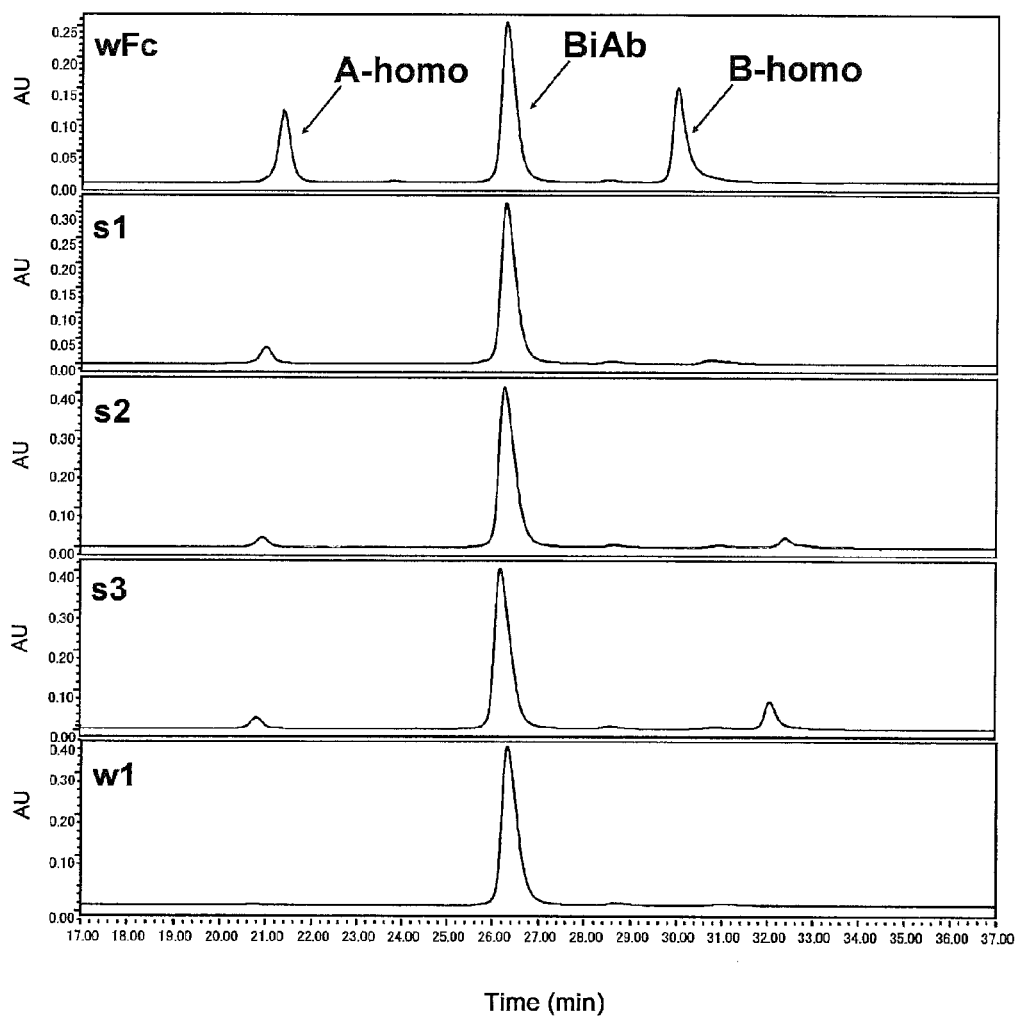

FIG. 28 depicts chromatograms of IEX analysis of humanized bispecific antibodies (IgG4-type) whose CH3 interface has been modified.

FIG. 29 depicts the formation ratio of A-Homo, BiAb, and B-Homo obtained by IEX analysis of humanized bispecific antibodies (IgG4-type) whose CH3 interface has been modified.

FIG. 30 depicts the percentage of monomer recovered after thermal acceleration tests at 60° C.-1 W on BiAb purified from humanized bispecific antibodies (IgG4-type) whose CH3 interface has been modified.

Figure 31:
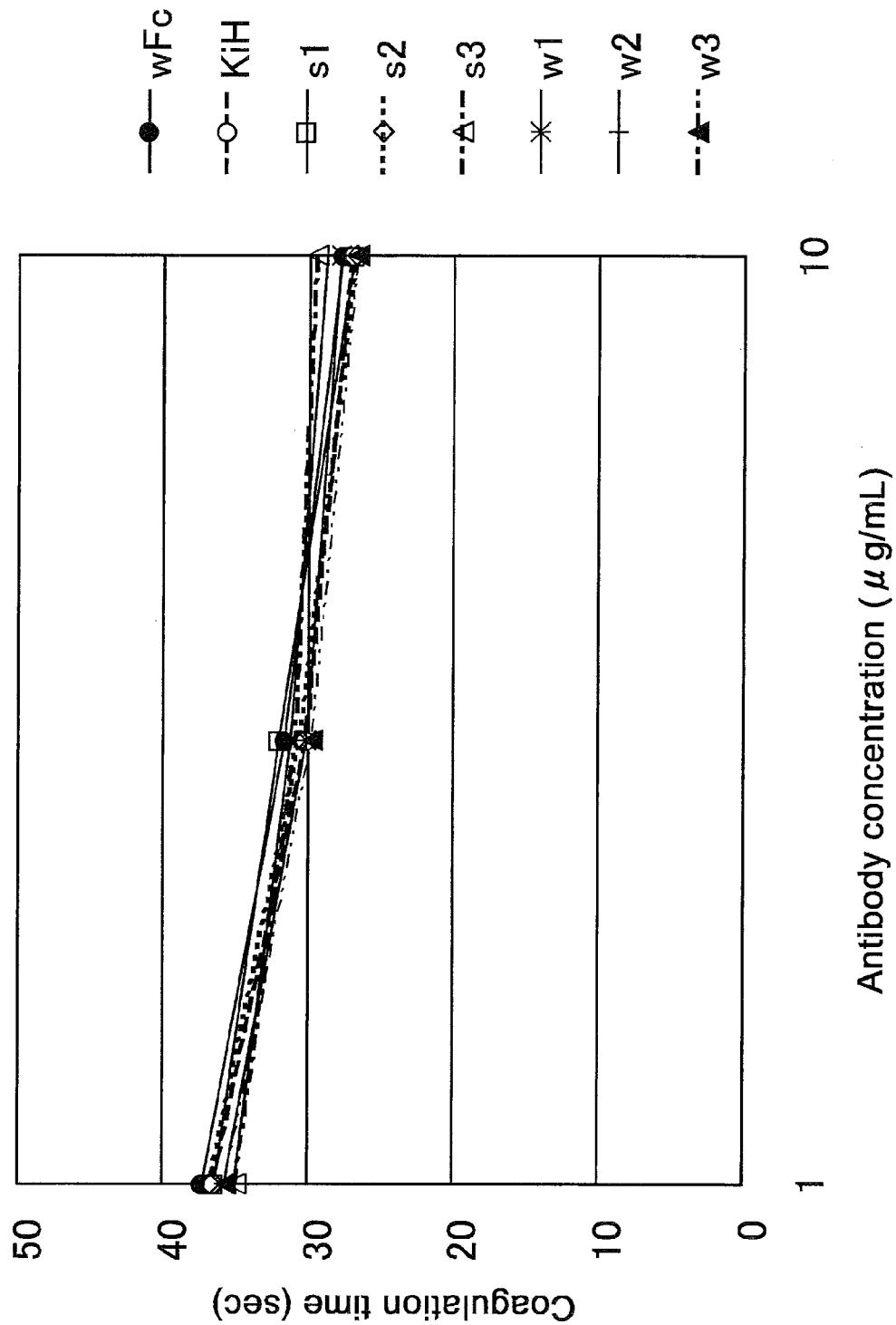

FIG. 31 depicts the results of an assay evaluating coagulation activity of humanized bispecific antibodies (IgG4-type) whose CH3 interface has been modified. The results demonstrate that the coagulation activities are equivalent to that of the unmodified bispecific antibody.

FIG. 32 depicts the formation ratio obtained though IEX analysis for A-Homo, BiAb, and B-Homo, which are humanized bispecific antibodies (IgG1-type) whose CH3 interface has been modified.

BEST MODE FOR CARRYING OUT THE INVENTION

The present invention relates to methods for regulating the association of polypeptides or association of heteromultimers composed of polypeptides.

First, the present invention provides methods for regulating polypeptide association, such methods including the step of modifying amino acid residues in an original peptide forming an interface so as to inhibit the association within the polypeptide.

In the present invention, the term "polypeptides" ordinarily refers to peptides and proteins whose length is about ten amino acids or longer. Polypeptides are ordinarily derived from organisms but are not particularly limited thereto, and for example, they may be composed of an artificially designed sequence. They may also be any of naturally derived polypeptides, synthetic polypeptides, recombinant polypeptides, or such. Additionally, fragments of the above-mentioned polypeptides are also included in the polypeptides of the present invention.

In the present invention, the phrase "polypeptide association" refers to, for example, a condition in which two or more polypeptide regions interact.

In the present invention, the phrase "regulating association" refers to regulating to achieve a desired association condition, and more specifically refers to regulating so that undesirable associations are not formed in the polypeptides.

In the present invention, the term "interface" ordinarily refers to the association surface that results from association (interaction), and amino acid residues that form the interface are ordinarily one or more amino acid residues included in the polypeptide regions which participate in the association, and are more preferably amino acid residues that approach each other during association and are involved in the interaction. More specifically, this interaction includes, for example, instances where the amino acid residues come close during the association to form hydrogen bonds, electrostatic interactions, or salt bridges with each other.

In the present invention, the phrase, "amino acid residues forming an interface" more specifically refers to amino acid residues included in the polypeptide region that constitutes the interface. For example, polypeptide regions constituting the interface refer to polypeptide regions responsible for selective binding within or between molecules such as in antibodies, ligands, receptors, or substrates. More specifically, in antibodies, such examples include heavy chain variable regions and light chain variable regions.

"Modification" of amino acid residues in the methods of the present invention specifically refers to substituting original amino acid residue(s) for other amino acid residue(s), deleting original amino acid residue(s), adding new amino acid residue(s), and such, but preferably refers to substituting one or more original amino acid residues for other amino acid residues.

In the present invention, the term "polypeptides" preferably refers to polypeptides that form two or more types of conformational isomers. Conformational isomers are proteins whose amino acid sequences are identical but their three-dimensional (tertiary) structures are different. Ordinarily, among conformational isomers, at least either one of chemical or physical properties is also different.

A preferred embodiment of the present invention relates to methods for preferentially (efficiently) obtaining desirable conformational isomers from among two or more types of potential conformational isomers. More specifically, an embodiment relates to methods for modifying the one or more amino acid residues that form an interface between the polypeptides so as to inhibit an association between polypeptides forming one or more types of conformational isomers from among those polypeptides that may form two or more types of conformational isomers.

For example, when the first to fourth peptide regions exist in a polypeptide, and any two of these regions can associate, the following cases are conceivable where mainly three types of conformational isomers can exist: (1) the first and second polypeptide regions associate and the third and fourth polypeptide regions associate, (2) the first and third polypeptide regions associate, and the second and fourth polypeptide regions associate, and (3) the first and fourth polypeptide regions associate, and the second and third polypeptide regions associate.

Under the above-mentioned circumstance, when one wishes to preferentially obtain a polypeptide (conformational isomer) associated with the interaction of (1), for example, amino acid residues forming the interfaces present in the first, third, or fourth polypeptide regions are modified so that association of the first polypeptide region with the third and fourth polypeptide regions is inhibited.

The methods of the present invention also relates to methods for regulating heteromultimer association, such methods including the step of modifying amino acid residues that form the interface between the original polypeptides, such that the association between the polypeptides is inhibited.

In the present invention, the term "heteromultimer" refers to a protein multimer composed of more than one type of polypeptide, in which the polypeptides can associate with each other. More specifically, a "heteromultimer" includes at least a first polypeptide and a second polypeptide; in this context, the second polypeptide is a molecule which differs from the first polypeptide by at least one amino acid residue.

Furthermore, without particular limitation, the heteromultimers preferably have binding specificity toward at least two different types of ligands, antigens, receptors, substrates, or such. In addition to a "heterodimer" formed by a first and second polypeptide, another different type of polypeptide may exist in the heteromultimer. More specifically, "heteromultimers" of the present invention are not limited to heterodimers and include for example heterotrimers and heterotetramers.

Preferred embodiments of the above-mentioned methods are methods of modifying amino acid residues that form the interface between polypeptides in heteromultimers that may form two or more types of multimers, such that association between polypeptides forming one or more types of multimers is inhibited.

For example, when any two of the polypeptides can associate in the protein multimers composed of the first to fourth polypeptides, the following multimers can mainly exist: (1) multimers in which the first and second polypeptides are associated and the third and fourth polypeptides are associated, (2) multimers in which the first and third polypeptides are associated and the second and fourth polypeptides are associated, or (3) multimers in which the first and fourth polypeptides are associated and the second and third polypeptides are associated.

Under the above-mentioned circumstance, when one wishes to preferentially obtain multimers associated with the interaction of (1), for example, amino acid residues included in the first, third, or fourth polypeptide can be modified so that association of the first polypeptide with the third and fourth polypeptides is inhibited.

Preferred embodiments of the methods of the present invention for regulating polypeptide association include, for example, methods in which modification of amino acid residues forming the interface of polypeptides include introducing amino acid residue mutations to the interface so that two or more amino acid residues forming an interface will have the same type of charge.

In the methods mentioned above, by modifying two or more amino acid residues involved in an association at the interface such that they carry the same kind of charge, repulsive forces among those charges will inhibit association among these amino acid residues.

Therefore, in the method mentioned above, the amino acid residues that are to be modified are preferably two or more amino acid residues that come close to each other during association in the region between the polypeptide regions that form the interface.

Amino acid residues that come close to each other during association can be identified, for example, by analyzing the three dimensional structures of the polypeptides, and investigating the amino acid sequences of the polypeptide regions forming the interface when these polypeptides associate. Amino acid residues that come close to each other at the interface will be preferred targets for "modifications" in the methods of the present invention.

Some amino acids are known to be charged amino acids. Generally, lysine (K), arginine (R), and histidine (H) are known as positively charged amino acids (cationic amino acids) whereas aspartate (D), glutamate (E), and such are known as negatively charged amino acids (anionic amino acids). Therefore, in the context of the present invention, amino acids carrying the same type of charge preferably refer to amino acids that are either positively charged or negatively charged.

In the methods of the present invention, all of the mutated amino acid residues are preferably modified to have the same type of charges, but the methods are not necessarily limited to such cases. For example, when a number of amino acid residues are introduced by the modification, there may be a few uncharged amino acid residues among these amino acid residues.

The number of amino acid residues that undergo modification in the methods of the present invention is not particularly limited. However, when modifying the variable region(s) of an antibody, it is preferable that only a few amino acid residues are modified so as not to decrease the antigen binding activity or increase the antigenicity of the resulting antibody. The methods of the present invention can regulate association by modifying one or both of the two amino acid residues that come close to each other at the interface, as indicated in the Examples described below. The term "few" as used in the above-mentioned context refers to about one to ten for example, preferably about one to five, more preferably about one to three, and even more preferably about one to two.

In a preferred embodiment, the amino acid residues that are introduced by modification (i.e., subjected to modification) are preferably all selected from among the above-mentioned positively charged amino acids, or, alternatively, are all selected from among the above-mentioned negatively charged amino acids.

Furthermore, in the present invention, preferred amino acid residues to be introduced include glutamic acid (E), aspartic acid (D), lysine (K), arginine (R), or histidine (H).

In another preferred embodiment of the present invention, when an interface-forming amino acid residue (X) in an original polypeptide (before modification) is already charged, it is preferable that the amino acid residue that comes close to and faces this amino acid residue (X) during association is modified to be the same amino acid residue (or an amino acid residue with the same type of charge) as the amino acid residue (X). In this embodiment, it is only necessary to modify one of the amino acid residues that form the interface.

Preferred embodiments of the methods of the present invention for regulating association include methods in which modification of amino acid residues forming the interface of the polypeptides that feature the introduction of amino acid residue mutations to the interface such that the amino acid residues forming a hydrophobic core present at the interface are transformed into charged amino acid residues.

In general, the term "hydrophobic core" refers to a part of a polypeptide that is formed by an assembly of hydrophobic amino acid side chains at the interior of the associated polypeptides. Examples of hydrophobic amino acids include alanine, isoleucine, leucine, methionine, phenylalanine, proline, tryptophan, and valine. Furthermore, amino acid residues other than hydrophobic amino acids (for example tyrosine) may be involved in the formation of a hydrophobic core. This hydrophobic core together with a hydrophilic surface, in which hydrophilic amino acid side chains are exposed to the exterior, becomes a driving force for promoting association of water-soluble polypeptides. When hydrophobic amino acids of two different domains are present on a molecular surface and are exposed to water molecules, the entropy will increase and the free energy will increase. Accordingly, the two domains will associate with each other to decrease the free energy and become stable, and hydrophobic amino acids at the interface will be buried into the interior of the molecule to form a hydrophobic core.

When polypeptide associations take place, modification of hydrophobic amino acids forming the hydrophobic core to charged polar amino acids inhibits the formation of the hydrophobic core, and as a result, inhibits the polypeptide association.

Those skilled in the art can identify the organized sites (regions) and such, as well as the presence of the hydrophobic core, by analyzing the amino acid sequence of the desired polypeptides. Thus, the present invention relates to methods for regulating association that feature the step of modifying amino acid residues involved with the formation of the hydrophobic core at the interface into charged amino acid residues.

Examples of charged amino acid residues suitable for use in the methods described above preferably include glutamic acid (E), aspartic acid (D), lysine (K), arginine (R), and histidine (H).

The methods of the present invention for regulating association can be used as methods for preferentially obtaining (producing) antibodies (polypeptides) of interest and in the production of antibodies, antibody fragments, polypeptides having antibody-like activity, and the like.

Herein, the term "antibody" is used in the broadest sense, and includes monoclonal antibodies, polyclonal antibodies, and mutant antibodies (chimeric antibodies, humanized antibodies, minibodies (including antibody fragments), and multispecific antibodies), so long as they exhibit a desired biological activity. Furthermore, in the context of the present invention, the "antibody" can be a polypeptide or heteromultimer. Preferred antibodies include monoclonal antibodies, chimeric antibodies, humanized antibodies, and minibodies, such as antibody fragments.

In the context of the present invention, the term "multispecific antibody" (used in the present description to have the same meaning as "polyspecific antibody") refers to an antibody that may bind specifically to different types of epitopes. More specifically, multispecific antibodies are antibodies having specificity to at least two different types of epitopes, and, in addition to antibodies recognizing different antigens, antibodies recognizing different epitopes on the same antigen are also included. For example, when the antigens are heterologous receptors, multispecific antibodies can recognize different domains constituting the heterologous receptors; alternatively when the antigens are monomers, multispecific antibodies recognize multiple sites on the monomer antigens. Ordinarily, such molecules bind to two antigens (bispecific antibodies; used in the present description to have the same meaning as "dual-specific antibodies"), but they may even have specificity toward more antigens (for example three types).

In addition to the antibodies described above, the antibodies of the present invention include antibodies whose amino acid sequences have been modified by amino acid substitutions, deletions, additions, and/or insertions, or chimerization, humanization, and such. Such amino acid sequence modifications, such as amino acid substitutions, deletions, additions, and/or insertions, and humanization and chimerization, can be achieved by methods known to those skilled in the art. When the antibodies of the present invention are prepared as recombinant antibodies, likewise, the amino acid sequences of the antibody variable and constant regions may also be modified by amino acid substitutions, deletions, additions, and/or insertions, or chimerization, humanization and the like.

The antibodies of the present invention may be derived from any animal, such as a mouse, human, rat, rabbit, goat, or camel. Furthermore, the antibodies may be modified, for example, chimeric antibodies, and in particular, modified antibodies that include amino acid substitutions in their sequence, such as humanized antibodies. The antibodies may be any type of antibody, such as antibody modification products linked with various molecules, antibody fragments, and minibodies.

"Chimeric antibodies" are antibodies prepared by combining sequences derived from different animals. An example is an antibody having heavy and light chain variable (V) regions from a mouse antibody and heavy and light chain constant (C) regions from a human antibody. Chimeric antibodies can be prepared by known methods. To obtain such chimeric antibodies, for example, a DNA encoding a antibody V region may be ligated with a DNA encoding a human antibody C region; the resulting ligation product can be inserted into an expression vector; and the construct can be introduced into a host to produce the chimeric antibody.

"Humanized antibodies" are also referred to as reshaped human antibodies, and can be obtained by substituting the complementarity determining region (CDR) of a human antibody for the CDR of an antibody derived from a non-human mammal, for example, a mouse. Methods for identifying CDRs are known in the art (Kabat et al., Sequence of Proteins of Immunological Interest (1987), National Institute of Health, Bethesda, Md.; Chothia et al., Nature (1989) 342:877). General genetic recombination techniques suitable for this purpose are also known (see European Patent Application EP 125023; and WO 96/02576). For example, the CDR of a mouse antibody can be determined by known methods, and a DNA can be prepared such that it encodes an antibody in which the CDR is ligated with the framework region (FR) of a human antibody. A humanized antibody can then be produced using a system that uses conventional expression vectors. Such DNAs can be synthesized by PCR, using as primers several oligonucleotides designed to include portions that overlap the ends of both the CDR and FR regions (see the method described in WO 98/13388). Human antibody FRs linked via CDRs are selected such that the CDRs form a suitable antigen binding site. If required, amino acids in the FRs of an antibody variable region may be substituted so that the CDRs of the reshaped human antibody can form a suitable antigen binding site (Sato, K. et al., Cancer Res. (1993) 53:851-856). Modifiable amino acid residues in the FRs include portions that directly bind to an antigen via non-covalent bonds (Amit et al., Science (1986) 233: 747-53), portions that have some impact or effect on the CDR structure (Chothia et al., J. Mol. Biol. (1987) 196: 901-17), and portions involved in the interaction between VH and VL (EP 239400).

When the antibodies of the present invention are chimeric antibodies or humanized antibodies, the C regions of these antibodies are preferably derived from human antibodies. For example, Cγ1, Cγ2, Cγ3, and Cγ4 can be used for the H chain, while Cκ and Cλ can be used for the L chain. Meanwhile, the human antibody C region may be modified as required to improve antibody or production stability. A chimeric antibody of the present invention preferably includes a variable region of an antibody derived from a nonhuman mammal and a constant region of a human antibody. A humanized antibody preferably includes CDRs of an antibody derived from a nonhuman mammal and FRs and C regions of a human antibody. The variable regions are described in detail in (3)-3. The constant regions of the human antibodies include specific amino acid sequences, which vary depending on the isotype of the antibody, for example, IgG (IgG1, IgG2, IgG3, and IgG4), IgM, IgA, IgD, and IgE. The constant regions used to prepare the humanized antibodies of the present invention may be the constant regions of antibodies of any isotype. A constant region of human IgG is preferably used, though the invention is not limited thereto. The FRs derived from a human antibody, which are used to prepare the humanized antibodies, are not particularly limited, and thus may be derived from an antibody of any isotype.

The variable and constant regions of chimeric or humanized antibodies of the present invention may be modified by deletion, substitution, insertion, and/or addition, so long as the antibodies exhibit the same binding specificity as that of the original antibodies.

Since their antigenicity in the human body has been attenuated, chimeric and humanized antibodies using human-derived sequences are expected to find utility when administered to humans for therapeutic purposes or such.

In addition, minibodies are useful as the antibodies because of their in vivo kinetic characteristics and low-cost production using E. coli, plant cells, or such.

Antibody fragments are one type of minibody. The term "minibodies" includes antibodies that include an antibody fragment as a partial structural unit. The minibodies of the present invention are not particularly limited by their structure nor their method of production, so long as they have antigen binding activity. Some minibodies have an activity greater than that of a whole antibody (Orita et al., Blood (2005) 105:562-566). Herein, the "antibody fragments" are not particularly limited, so long as they are a portion of a whole antibody (for example, whole IgG). However, the antibody fragments preferably include a heavy chain variable region (VH) or a light chain variable region (VL). Examples of preferred antibody fragments are: Fab, F(ab')$_2$, Fab', and Fv. The amino acid sequence of a VH or VL in an antibody fragment may be modified by substitution, deletion, addition, and/or insertion. Furthermore, some portions of a VH and VL may be deleted, so long as the resulting fragments retain their antigen binding ability. For example, of the antibody fragments described above, "Fv" is a minimal antibody fragment composed of the complete antigen recognition and binding sites. "Fv" is a dimer (VH-VL dimer) composed of one unit of VH and one unit of VL bound very strongly by non-covalent bonding. An antigen binding site is formed on the surface of the VH-VL dimer by the three complementarity determining regions (CDRs) of each variable region. Six CDRs confer an antigen binding site to the antibody. However, even one variable region (or half of an Fv composed of only three antigen-specific CDRs) has the ability to recognize and bind to an antigen, although its affinity is lower than that of the complete binding site. Thus, molecules smaller than Fv are also included in the context of antibody fragments of the present invention. The variable regions of an antibody fragment may also be chimerized or humanized.

The minibodies preferably include both VH and VL. Examples of suitable minibodies include antibody fragments such as Fab, Fab', F(ab')2, and Fv, and scFv (single-chain Fv), which can be prepared using antibody fragments, (Huston et al., Proc. Natl. Acad. Sci. USA (1988) 85: 5879-83; Plickthun "The Pharmacology of Monoclonal Antibodies" Vol. 113, Resenburg and Moore (eds.), Springer Verlag, New York, pp. 269-315, (1994)); diabodies (Holliger et al., Proc. Natl. Acad. Sci. USA (1993) 90:6444-8; EP 404097; WO93/11161; Johnson et al., Method in Enzymology (1991) 203: 88-98; Holliger et al., Protein Engineering (1996) 9:299-305; Perisic et al., Structure (1994) 2:1217-26; John et al., Protein Engineering (1999) 12(7):597-604; Atwell et al., Mol. Immunol. (1996) 33:1301-12); sc(Fv)2 (Hudson et al., J Immunol. Methods (1999) 231:177-89; Orita et al., Blood (2005) 105:562-566); triabodies (Journal of immunological Methods (1999) 231: 177-89); and tandem diabodies (Cancer Research (2000) 60:4336-41).

An antibody fragment can be prepared by treating an antibody with an enzyme, for example, a protease such as papain or pepsin (see Morimoto et al., J. Biochem. Biophys. Methods (1992) 24: 107-17; Brennan et al., Science (1985) 229:81). Alternatively, antibody fragments can also be produced by genetic recombination based on its amino acid sequence.

A minibody having a structure that results from modification of an antibody fragment can be prepared using antibody fragments obtained by enzyme treatment or genetic recombination. Alternatively, after constructing a gene which encodes a whole minibody, and introducing the construct into an expression vector, the minibody may be expressed in appropriate host cells (see, for example, Co et al., J. Immunol. (1994) 152: 2968-76; Better and Horwitz, Methods Enzymol. (1989) 178: 476-96; Pluckthun and Skerra, Methods Enzymol. (1989) 178: 497-515; Lamoyi, Methods Enzymol. (1986) 121: 652-63; Rousseaux et al., Methods Enzymol. (1986) 121: 663-9; Bird and Walker, Trends Biotechnol. (1991) 9: 132-7).

The above described scFVs are single-chain polypeptides that include two variable regions linked together via a linker or such, as required. The two variable regions in an scFv are typically one VH and one VL, but an scFv may include two VH or two VL. In general, scFv polypeptides include a linker between the VH and VL domains, thereby forming a paired portion of VH and VL required for antigen binding. A peptide linker composed of ten or more amino acids is typically used as the linker between VH and VL when forming an intramolecular paired portion between VH and VL. However, the linkers of the scFv of the present invention are not limited to such peptide linkers, so long as they do not inhibit the formation of an scFv. To review scFv, see Pluckthun "The Pharmacology of Monoclonal Antibody", Vol. 113 (Rosenburg and Moore ed., Springer Verlag, N.Y., pp. 269-315 (1994)).

The term, "diabodies (Db)" refers to bivalent antibody fragments constructed by gene fusion (P. Holliger et al., Proc. Natl. Acad. Sci. USA 90: 6444-6448 (1993); EP 404,097; WO93/11161 and such). Diabodies are dimers composed of two polypeptide chains, wherein each polypeptide chain includes within the same chain a light chain variable region (VL) and a heavy chain variable region (VH) connected with a linker short enough to disable interaction of these two regions, for example a linker of about five amino acid residues. VL and VH encoded on the same polypeptide chain will form a dimer because the linker between VL and VH is too short to form a single chain V region fragment. Therefore, the resulting diabody has two antigen-binding sites. Herein, when VL and VH directed against two different epitopes (a and b) are expressed simultaneously as combinations of VLa-VHb and VLb-VHa connected with a linker of about five residues, they are secreted as bispecific Db. In this case, the two different epitopes may be epitopes at two different sites on the same antigen, or epitopes at two different sites, each on two different antigens.

Since diabodies include two molecules of scFvs, they thus composed of four variable regions, and as a result have two antigen binding sites. When the objective is to form a diabody, unlike as in the case with scFvs that do not form dimers, ordinarily, linkers forming a connection between VH and VL in each scFv molecules are linkers of about five amino acids when used as peptide linkers. However, scFv linkers for diabody formation are not limited to such peptide linkers so long as they do not interfere with scFv expression and diabody formation.

Examples of preferred polypeptides or heteromultimers subjected to the methods of the present invention include polypeptides or heteromultimers composed of antibody heavy chain variable regions and light chain variable regions. More preferably, preferred embodiments of the present invention are methods for regulating association when polypeptides or heteromultimers of the present invention include two or more types of heavy chain variable regions and two or more types of light chain variable regions. Such polypeptides or heteromultimers are preferably those that recognize two or more types of epitopes, and examples include multispecific antibodies.

More preferably, examples of multispecific antibodies in the present invention include bispecific antibodies.

More specifically, preferred embodiments of the present invention relate to, for example, methods for regulating association of bispecific antibodies composed of two types of heavy chain variable regions (first heavy chain and second heavy chain) and two types of light chain variable regions (first light chain and second light chain).

Describing the "bispecific antibodies" of the preferred embodiments of the present invention more precisely, the above-mentioned "first heavy chain" refers to one of the two H chains forming the antibody, and the second H chain refers to the other H chain that is different from the first H chain. That is, of the two H chains, one of them can be arbitrarily defined as the first H chain and the other can be defined as the second H chain. Similarly, the "first light chain" refers to one of the two L chains form the bispecific antibody, and the "second L chain" refers to the other L chain that is different from the first L chain. Of the two L chains, one of them can be arbitrarily defined as the first L chain and the other can be defined as the second L chain. Ordinarily, the first L chain and the first H chain are derived from the same antibody that recognizes a certain antigen (or epitope), and the second L chain and the second H chain are also derived from the same antibody that recognizes a certain antigen (or epitope). Herein, the L chain-H chain pair formed by the first H chain and L chain is called as the first pair, and the L chain-H chain pair formed by the second H chain and L chain is called as the second pair. An antigen (or epitope) used to produce the antibody from which the second pair derives is preferably different from the antigen used to produce the antibody from which the first pair is derives. More specifically, antigens recognized by the first pair and the second pair may be the same but different antigens (or epitopes) are preferred to be recognized. Herein, the H chains and L chains of the first pair and second pair preferably have amino acid sequences that differ from each other. When the first pair and the second pair recognize different epitopes, the first and the second pair may recognize a completely different antigen, or they may recognize different sites (different epitopes) on the same antigen. Furthermore, one of them may recognize an antigen such as a protein, peptide, gene, or sugar, and the other may recognize cytotoxic substances such as radioactive substances, chemotherapeutic agents, or cell-derived toxins. However, when one wishes to produce an antibody having pairs formed by specific combinations of H chains and L chains, those specific H chains and L chains may be arbitrary determined to be the first pair and second pair.

The above-mentioned "bispecific antibodies" are not necessarily limited to antibodies composed of two types of heavy chains and two types of light chains, and for example, they may be antibodies (for example, sc(Fv)2) having a structure in which two types of heavy chain variable regions and two types of light chain variable regions are linked to form a single chain.

As for the genes encoding the H chain or L chain of antibodies before introduction of mutations by methods of the present invention (herein, it may be simply referred to as "an antibody of the present invention"), known sequences can be used, or they can be obtained by methods known to those skilled in the art. For example, they may be obtained from an antibody library, or they may be obtained by cloning genes encoding the antibody from hybridomas producing monoclonal antibodies.

Regarding antibody libraries, many antibody libraries are already well known, and since methods for producing antibody libraries are known, those skilled in the art can appropriately obtain antibody libraries. For example, regarding antibody phage libraries, one can refer to the literature such as Clackson et al., Nature 1991, 253:624-8; Marks et al., J. Mol. Biol. 1991, 222:581-97; Waterhouses et al., Nucleic Acids Res. 1993, 21:2265-6; Griffiths et al., EMBO J. 1994, 13:3245-60; Vaughan et al., Nature Biotechnology 1996, 14:309-14; and Japanese Patent Kohyo Publication No. (JP-A) H10-504970 (unexamined Japanese national phase publication corresponding to a non-Japanese international publication). In addition, known methods, such as methods that use eukaryotic cells as libraries (WO 95/15393) and ribosome display methods, may be used. Furthermore, techniques to obtain human antibodies by panning using human antibody libraries are also known. For example, variable regions of human antibodies can be expressed on the surface of phages as single chain antibodies (scFvs) using phage display methods, and phages that bind to antigens can be selected. Genetic analysis of the selected phages can determine the DNA sequences encoding the variable regions of human antibodies that bind to the antigens. Once the DNA sequences of scFvs that bind to the antigens is revealed, suitable expression vectors can be produced based on these sequences to obtain human antibodies. These methods are already well known, and one can refer to WO92/01047, WO92/20791, WO93/06213, WO93/11236, WO93/19172, WO95/01438, and WO95/15388.

As for methods for obtaining genes encoding antibodies from hybridomas, known techniques may be used, involving the use of desired antigens or cells expressing the desired antigens as sensitizing antigens, using these to perform immunizations according to conventional immunization methods, fusing the immune cells thus obtained with known parent cells by ordinary cell fusion methods, screening monoclonal antibody producing cells (hybridomas) by ordinary screening methods, synthesizing cDNAs of antibody variable regions (V regions) from mRNAs of the obtained hybridomas using reverse transcriptase, and linking them with DNAs encoding the desired antibody constant regions (C regions).

More specifically, without being particular limited to the following examples, sensitizing antigens for obtaining the above-mentioned antibody genes encoding the H chains and L chains include both complete antigens with immunogenicity and incomplete antigens composed of haptens and such that do not show antigenicity. For example, full length proteins and partial peptides of proteins of interest can be used. In addition, it is known that substances composed of polysaccharides, nucleic acids, lipids, and such may become antigens. Thus, there are no particular limitations on antigens of the antibodies of the present invention. Antigens can be prepared by methods known to those skilled in the art, and they can be prepared, for example, by the following methods using baculoviruses (for example, WO98/46777). Hybridomas can be produced, for example, by the following methods of Milstein et al. (G. Kohler and C. Milstein, Methods Enzymol. 1981, 73: 3-46), and such. When the immunogenicity of an antigen is low, it can be linked to a macromolecule that has immunogenicity, such as albumin, and then used for immunization. Furthermore, by linking antigens with other molecules if necessary, they can be converted into soluble antigens. When transmembrane molecules such as receptors are used as antigens, portions of the extracellular regions of the receptors can be used as a fragment, or cells expressing transmembrane molecules on their cell surface may be used as immunogens.

Antibody-producing cells can be obtained by immunizing animals using suitable sensitizing antigens described above. Alternatively, antibody-producing cells can be prepared by in vitro immunization of lymphocytes that can produce antibodies. Various mammals can be used as the animals for immunization, where rodents, lagomorphas and primates are generally used. Examples of such animals include mice, rats, and hamsters for rodents, rabbits for lagomorphas, and monkeys including the cynomolgus monkey, rhesus monkey, hamadryas, and chimpanzees for primates. In addition, transgenic animals carrying human antibody gene repertoires are also known, and human antibodies can be obtained by using these animals (see WO96/34096; Mendez et al., Nat. Genet. 1997, 15: 146-56). Instead of using such transgenic animals, for example, desired human antibodies having binding activity against antigens can be obtained by in vitro sensitization of human lymphocytes with desired antigens or cells expressing the desired antigens, and then fusing the sensitized lymphocytes with human myeloma cells such as U266 (see Japanese Patent Application Kokoku Publication No. (JP-B) H1-59878 (examined, approved Japanese patent application published for opposition)). Furthermore, desired human antibodies can be obtained by immunizing transgenic animals carrying a complete repertoire of human antibody genes, with desired antigens (see WO93/12227, WO92/03918, WO94/02602, WO96/34096, and WO96/33735).

Animal immunization can be carried out by appropriately diluting and suspending a sensitizing antigen in Phosphate-Buffered Saline (PBS), physiological saline, or such, and forming an emulsion by mixing an adjuvant if necessary, followed by an intraperitoneal or subcutaneous injection into animals. After that, the sensitizing antigen mixed with Freund's incomplete adjuvant is preferably administered several times every four to 21 days. Antibody production can be confirmed by measuring the target antibody titer in animal sera using conventional methods.

Antibody-producing cells obtained from lymphocytes or animals immunized with a desired antigen can be fused with myeloma cells to generate hybridomas using conventional fusing agents (for example, polyethylene glycol) (Goding, Monoclonal Antibodies: Principles and Practice, Academic Press, 1986, 59-103). When required, hybridoma cells can be cultured and grown, and the binding specificity of the antibody produced from these hybridomas can be measured using known analysis methods, such as immunoprecipitation, radioimmunoassay (RIA), and enzyme-linked immunosorbent assay (ELISA). Thereafter, hybridomas that produce antibodies of interest whose specificity, affinity, or activity has been determined can be subcloned by methods such as limiting dilution.

Next, genes encoding the selected antibodies can be cloned from hybridomas or antibody-producing cells (sensitized lymphocytes, and such) using probes that may specifically bind to the antibodies (for example, oligonucleotides complementary to sequences encoding the antibody constant regions). Cloning from mRNA using RT-PCR is also possible. Immunoglobulins are classified into five different classes, IgA, IgD, IgE, IgG, and IgM. These classes are further divided into several subclasses (isotypes) (for example, IgG-1, IgG-2, IgG-3, and IgG-4; IgA-1 and IgA-2; and such). H chains and L chains used in the present invention to produce antibodies are not particularly limited and may derive from antibodies belonging to any of these classes or subclasses; however, IgG is particularly preferred.

Herein, it is possible to modify H-chain-encoding genes and L-chain-encoding genes using genetic engineering techniques. Genetically modified antibodies, such as chimeric antibodies, humanized antibodies that have been artificially modified for the purpose of decreasing heterologous antigenicity and such against humans, can be appropriately produced if necessary for antibodies such as mouse antibodies, rat antibodies, rabbit antibodies, hamster antibodies, sheep antibodies, and camel antibodies. Chimeric antibodies are antibodies composed of a nonhuman mammal antibody H chain and L chain variable regions, such as mouse antibody, and the H chain and L chain constant regions of human antibody. They can be obtained by ligating the DNA encoding a variable region of a mouse antibody to the DNA encoding a constant region of a human antibody, incorporating them into an expression vector, and introducing the vector into a host for production of the antibody. A humanized antibody, which is also called a reshaped human antibody, can be synthesized by PCR from a number of oligonucleotides produced so that they have overlapping portions at the ends of DNA sequences designed to link the complementarity determining regions (CDRs) of an antibody of a nonhuman mammal such as a mouse. The obtained DNA can be ligated to a DNA encoding a human antibody constant region. The ligated DNA can be incorporated into an expression vector, and the vector can be introduced into a host to produce the antibody (see EP239400 and WO96/02576). Human antibody FRs that are ligated via the CDR are selected when the CDR forms a favorable antigen-binding site. If necessary, amino acids in the framework region of an antibody variable region may be substituted such that the CDR of the reshaped human antibody forms an appropriate antigen-binding site (K. Sato et al., Cancer Res. 1993, 53: 851-856).

In addition to the humanization techniques described above, antibodies may be modified to improve their biological properties, for example, antigenic affinity. Such modifications can be carried out using methods such as site-directed mutagenesis (see for example, Kunkel (1985) Proc. Natl. Acad. Sci. USA 82: 488), PCR mutagenesis, and cassette mutagenesis. In general, mutant antibodies whose biological properties have been improved show amino acid sequence homology and/or similarity of 70% or higher, more preferably 80% or higher, and even more preferably 90% or higher (for example, 95% or higher, 97%, 98%, 99%, etc.), when compared to the amino acid sequence of the original antibody variable region. Herein, sequence homology and/or similarity is defined as the ratio of amino acid residues that are homologous (same residue) or similar (amino acid residues classified into the same group based on the general properties of amino acid side chains) to the original antibody residues, after the sequence homology value has been maximized by sequence alignment and gap introduction, if necessary. Generally, naturally-occurring amino acid residues are classified into groups based on the characteristics of their side chains: (1) hydrophobic: alanine, isoleucine, norleucine, valine, methionine, and leucine; (2) neutral hydrophilic: asparagine, glutamine, cysteine, threonine, and serine; (3) acidic: aspartic acid, and glutamic acid; (4) basic: arginine, histidine, and lysine; (5) residues that affect the orientation of the chain: glycine, and proline; and (6) aromatic: tyrosine, tryptophan, and phenylalanine.

Ordinarily, a total of six complementarity determining regions (CDRs; hypervariable regions) present in the H chain and L chain variable regions interact to form the antigen binding site(s) of an antibody. Even one of these variable regions is known to have the ability to recognize and bind to the antigen, although the affinity will be lower than when all binding sites are included. Therefore, antibody genes of the present invention encoding the H chain and L chain only have to encode fragment portions having each of the antigen binding sites of H chain and L chain, and polypeptides encoded by these genes only have to maintain affinity with the desired antigens.

The methods of the present invention for regulating association, allow one to preferentially (efficiently) obtain, for example, the desired bispecific antibodies as described above. More specifically, desired bispecific antibodies which are heteromultimers can be efficiently formed from a mixture of monomers.

Herein below, the case of IgG-type bispecific antibodies composed of two types of heavy chain variable regions (VH1 and VH2) and two types of light chain variable regions (VL1 and VL2) are described in detail; however, the methods of the present invention can be applied similarly to other heteromultimers.

When one wishes to obtain a bispecific antibody that recognizes one of the epitopes with a first heavy chain variable region (VH1) and a first light chain variable region (VL1) and the other epitope with a second heavy chain variable region (VH2) and a second light chain variable region (VL2), expressing each of the four types of chains to produce this antibody may theoretically produce 10 types of antibody molecules.

In this case, the desired antibody molecule can be preferentially obtained if the regulation is carried out in a manner to inhibit the association between polypeptides, for example, VH1 and VL2 and/or VH2 and VL1.

An example includes modifying amino acid residues forming the interfaces between the polypeptide of VH1 and the polypeptide of VL2, and/or the polypeptide of VH2 and the polypeptide of VL1 as described above so as to inhibit the associations between these polypeptides.

Furthermore, associations between the heavy chains (VH1 and VH2) or between the light chain (VL1 and VL2) can also be suppressed using the methods of the present invention for regulating association.

Heavy chain variable regions are ordinarily composed of three CDR regions and FR regions as described above. In a preferred embodiment of the present invention, amino acid residues subjected to "modification" can be appropriately selected from among amino acid residues positioned in the CDR regions or FR regions. Generally, modification of the amino acid residues in the CDR regions can decrease affinity towards antigens. Therefore, in the present invention, amino acid residues subjected to "modification" are not particularly limited but are preferred to be appropriately selected from among amino acid residues positioned in the FR regions.

As for the desired polypeptides whose association is to be regulated by the methods of the present invention, those skilled in the art can appropriately find out the types of amino acid residues that come close to each other at the interface of FRs during association.

Furthermore, sequences that can be used as variable region FRs of the antibodies of organisms, such as humans or mice, can be appropriately obtained by those skilled in the art using public databases. More specifically, amino acid sequence information of the FR regions can be obtained by means described later in the Examples.

Specific examples of amino acid residues that come close to each other at the interface of FRs during association in the bispecific antibodies indicated in the following Examples include glutamine (Q) at position 39 in the heavy chain variable region (FR2 region) (for example, at position 39 in the amino acid sequence of SEQ ID NO: 6), and the opposing (contacting) glutamine (Q) at position 38 on the light chain variable region (FR2 region) (for example, at position 44 in the amino acid sequence of SEQ ID NO: 8). Furthermore, favorable examples include leucine (L) at position 45 in the heavy chain variable region (FR2) (for example, at position 45 in the amino acid sequence of SEQ ID NO: 6), and the opposing proline (P) at position 44 in the light chain variable region (FR2) (for example, at position 50 in the amino acid sequence of SEQ ID NO: 8). These positions are numbered according to the document by Kabat et al. (Kabat E A et al. 1991. Sequence of Proteins of Immunological Interest. NIH).

As indicated in the following Examples, desired antibodies can be preferentially obtained by modifying these amino acid residues and performing the methods of the present invention.

Since these amino acid residues are known to be highly conserved in humans and mice (J. Mol. Recognit. 2003; 16: 113-120), association of antibody variable regions can be regulated for VH-VL association of antibodies other than those indicated in the Examples by modifying amino acid residues corresponding to the above-mentioned amino acid residues.

More specifically, in a preferred embodiment, the present invention provides antibodies (polypeptides (for example, sc(Fv)2), heteromultimers (for example IgG-type antibodies or such) composed of heavy chain variable regions and light chain variable regions, which are antibodies whose amino acid residues of (1) and (2), or (3) and (4) described below carry the same kind of charges:

(1) an amino acid residue which is included in the heavy chain variable region and corresponds to position 39 in the amino acid sequence of SEQ ID NO: 6;
(2) an amino acid residue which is included in the light chain variable region and corresponds to position 44 in the amino acid sequence of SEQ ID NO: 8;
(3) an amino acid residue which is included in the heavy chain variable region and corresponds to position 45 in the amino acid sequence of SEQ ID NO: 6; and
(4) an amino acid residue which is included in the light chain variable region and corresponds to position 50 in the amino acid sequence of SEQ ID NO: 8.

The amino acid sequences of SEQ ID NOs: 6 and 8 are mentioned above to exemplify a more specific example of the positions of the amino acid residues that are subjected to modification in the present invention. Accordingly, the present invention is not limited to cases where the heavy chain variable regions or light chain variable regions have these amino acid sequences.

Each of the amino acid residues of (1) and (2), and (3) and (4) mentioned above come close to each other during association as indicated in FIG. 1 and in the following Examples. Those skilled in the art can identify the positions corresponding to the above-mentioned amino acid residues of (1) to (4) in the desired heavy chain variable regions or light chain variable regions using homology modeling and such, using commercially available softwares. Once identified, the amino acid residues of these positions can be appropriately subjected to modification.

In the antibodies mentioned above, "charged amino acid residues" are preferably selected, for example, from amino acid residues included in either one of the following groups:
(a) glutamic acid (E) and aspartic acid (D); and
(b) lysine (K), arginine (R), and histidine (H).

Furthermore the present invention provides antibodies (polypeptides, heteromultimers, and such) having heavy chain variable regions and light chain variable regions, in which either one of the amino acid residues of the following (3) or (4) is a charged amino acid residue. The side chains of the amino acid residues indicated in (3) and (4) shown below may come close to each other to form a hydrophobic core:
(3) an amino acid residue which is included in the heavy chain variable region and corresponds to position 45 in the amino acid sequence of SEQ ID NO: 6; and
(4) an amino acid residue which is included in the light chain variable region and corresponds to position 50 in the amino acid sequence of SEQ ID NO: 8.

In the above-mentioned antibodies, "charged amino acid residues" are preferably, for example, glutamic acid (E), aspartic acid (D), lysine (K), arginine (R), or histidine (H).

Ordinarily, the above-mentioned amino acid residues of (1) to (4) are (1) glutamine (Q), (2) glutamine (Q), (3) leucine (L), and (4) proline (P), respectively, in humans and mice. Therefore, in preferred embodiments of the present invention, these amino acid residues are subjected to modification (for example, substitution to charged amino acids). The types of the above-mentioned amino acid residues of (1) to (4) are not necessarily limited to the above-mentioned amino acid residues, and may be other amino acids that correspond to these amino acids. For example, in the case of humans, an amino acid on the light chain variable region corresponding to position 44 in the amino acid sequence of SEQ ID NO: 8 may be, for example, histidine (H). Those skilled in the art can find out the type of amino acid residue corresponding to any position on SEQ ID NO: 8 by referring to disclosed publications and such (for example, J. Mol. Recognit. 2003; 16:113-120), and can appropriately modify these amino acid residues (for example, substitution to charged amino acids).

Methods for producing the above-mentioned antibodies, and methods of the present invention for regulating association which feature modifying the amino acid residues of (1) to (4) mentioned above are also preferred embodiments of the present invention.

In another embodiment, the present invention provides methods for suppressing association between heavy chains or between a heavy chain and a light chain by introducing electrostatic repulsion to the interface of the heavy chain or light chain constant region. Examples of amino acid residues contacting each other at the interface of heavy chain constant regions include regions corresponding to positions 377 (356) and 470 (439), positions 378 (357) and 393 (370), and positions 427 (399) and 440 (409) in the CH3 region. Examples of amino acid residues that contact each other at the interface between a heavy chain constant region and a light chain constant region include regions corresponding to position 221 (position 213) of the CH1 region and position 123 of the CL region. Numbering in the antibody constant regions is based on the document by Kabat et al. (Kabat E A et al. 1991. Sequences of Proteins of Immunological Interest. NIH), and the EU numbering is shown in parenthesis for the heavy chain constant regions.

As indicated in the following Examples, association of antibody heavy chains will be regulated and desired antibodies can be preferentially obtained by modifying these amino acid residues and performing the methods of the present invention.

More specifically, in a preferred embodiment the present invention provides antibodies having two or more types of heavy chain CH3 regions and Fc region-binding proteins (for example, IgG-type antibodies, minibodies (Alt M et al. FEBS Letters 1999; 454: 90-94), immunoadhesin (Non-Patent Document 2), and such), in which one to three pairs of amino acid residues in the first heavy chain CH3 region, selected from the pairs of amino acid residues indicated in (1) to (3) below, carry the same type of charge:
(1) amino acid residues included in the heavy chain CH3 region at positions 356 and 439 according to the EU numbering system;
(2) amino acid residues included in the heavy chain CH3 region at positions 357 and 370 according to the EU numbering system; and
(3) amino acid residues included in the heavy chain CH3 region at positions 399 and 409 according to the EU numbering system.

In a more preferred embodiment, the present invention provides an antibody in which one to three pairs of the amino acid residues in the second heavy chain CH3 region are (i) selected from the pairs of amino acid residues of (1) to (3) mentioned above, (ii) corresponds to the pairs of amino acid residues of (1) to (3) mentioned above, and (iii) carries a charge opposite to the corresponding amino acid residues in the first heavy chain CH3 region.

Each of the amino acid residues indicated above in (1) to (3) come close to each other during association, as shown in FIG. 27 and in the Examples described below. Those skilled in the art can find out the positions corresponding to the above-mentioned amino acid residues of (1) to (3) in a desired heavy chain CH3 region or heavy chain constant region by homology modeling and such using commercially available software, and amino acid residues of these positions can be appropriately subjected to modification.

In the antibodies mentioned above, "charged amino acid residues" are preferably selected, for example, from amino acid residues included in either one of the following groups:
(a) glutamic acid (E) and aspartic acid (D); and
(b) lysine (K), arginine (R), and histidine (H).

In the above-mentioned antibodies, the phrase "carrying the same charge" means, for example, that all of the two or more amino acid residues composed of the amino acid residues included in either one of (a) or (b) mentioned above. The phrase "carrying opposite charges" means, for example, that when at least one of the amino acid residues among two or more amino acid residues is composed of amino acid residues included in either one of the above-mentioned groups of (a) or (b), and the remaining amino acid residues are composed of the amino acid residues included in the other group.

In a preferred embodiment, the antibodies mentioned above may have their first heavy chain CH3 region and second heavy chain CH3 region crosslinked by disulfide bonds.

In the present invention, amino acid residues subjected to "modification" are not limited to the above-mentioned amino acid residues of the antibody variable regions or the antibody constant regions. Those skilled in the art can identify the amino acid residues that form the interface in mutant polypeptides or heteromultimers using homology modeling and such, using commercially available software; amino acid residues of these positions can then be subjected to modification so as to regulate the association.

The methods of the present invention, although not mandatory, can be carried out in combination with known techniques. For example, in addition to "modifications" of the present invention to promote association between VH1 and VL1, and/or VH2 and VL2, substitution of an amino acid side chain present in one of the H chain variable regions to a larger side chain (knob) and substitution of the opposing amino acid side chain present in the variable region of the other H chain to a smaller side chain (hole) promotes association between VH1 and VL1, and/or VH2 and VL2 such that the knob is placed into the hole. As a result, the association between polypeptides VH1 and VL2, and/or VH2 and VL1 can be further suppressed.

The methods of the present invention for regulating association can be carried out suitably when preferentially (efficiently) obtaining desired sc(Fv)2s. Hereinafter, the case of sc(Fv)2 composed of two types of heavy chain variable regions (H1 and H2) and two types of light chain variable regions (L1 and L2) will be described more precisely as an example.

Generally, sc(Fv)2 is a single chain polypeptide in which two heavy chain variable regions (VH1 and VH2) and two light chain variable regions (VL1 and VL2) are linked by linkers. More specifically, sc(Fv)2 is a minibody in which four antibody variable regions are linked with a linker and such to produce a single chain. Ordinarily, sc(Fv)2 is an antibody in which four variable regions, two light chain variable regions and two heavy chain variable regions, are linked by linkers to produce a single chain (Hudson et al., J. Immunol. Methods 1999; 231:177-189).

sc(Fv)2 can be produced by methods known to those skilled in the art, for example, by linking scFvs with linkers. scFv includes antibody VH and VL, and these regions are present in a single polypeptide chain (for a review on scFv, see Pluckthun "The Pharmacology of Monoclonal Antibodies" Vol. 113 (Rosenburg and Moore ed. (Springer Verlag, New York) pp. 269-315, 1994).

An antibody in which two VHs and two VLs are arranged in the order of VH, VL, VH, VL ([VH] linker [VL] linker [VH] linker [VL]) starting from the N-terminal side of a single chain polypeptide is preferred.

The order of the two VHs and the two VLs is not particularly limited to the above-mentioned arrangement and may be in any order, including for example, the following arrangements.
[VL] linker [VH] linker [VH] linker [VL]
[VH] linker [VL] linker [VL] linker [VH]
[VH] linker [VH] linker [VL] linker [VL]
[VL] linker [VL] linker [VH] linker [VH]
[VL] linker [VH] linker [VL] linker [VH]

sc(Fv)2 may also include amino acid sequences other than those of the antibody variable regions and linkers.

The variable regions of the above-mentioned antibodies may be full-length variable regions or partial sequences of the variable regions, so long as the affinity to antigens is maintained. Furthermore, the amino acid sequences in the variable regions may contain substitutions, deletions, additions, insertions, or such. For example, they may be converted to chimeric or humanized antibodies to decrease antigenicity.

Arbitrary peptide linkers or synthetic linker compounds that can be introduced by genetic engineering (for example, see disclosed in Protein Engineering, 9(3), 299-305, 1996) can be used as linkers that link the variable regions of an antibody, but peptide linkers are preferred in the present invention. The length of the peptide linkers is not particularly limited, and can be suitably selected according to the purpose by those skilled in the art. The length is preferably twelve amino acids or more (with no particular upper limit, normally 30 amino acids or less, and preferably 20 amino acids or less), and particularly preferably 15 amino acids. When three peptide linkers are included in sc(Fv)2, all of the peptide linkers used may have the same length, or peptide linkers of different lengths may be used.

Examples of peptide linkers include:

```
Ser

Gly·Ser

Gly·Gly·Ser

Ser·Gly·Gly

Gly·Gly·Gly·Ser

Ser·Gly·Gly·Gly

Gly·Gly·Gly·Gly·Ser

Ser·Gly·Gly·Gly·Gly

Gly·Gly·Gly·Gly·Gly·Ser

Ser·Gly·Gly·Gly·Gly·Gly

Gly·Gly·Gly·Gly·Gly·Gly·Ser

Ser·Gly·Gly·Gly·Gly·Gly·Gly (Gly·Gly·Gly·Gly·Ser)n (Ser·Gly·Gly·Gly·Gly)n
```

[where n is all integer of 1 or more]. However, the length and sequence of the peptide linkers can be suitably selected according to the purpose by those skilled in the art.

Preferred embodiments of sc(Fv)2 include for example the following sc(Fv)2: [VH] peptide linker (15 amino acids) [VL] peptide linkers (15 amino acids) [VH] peptide linkers (15 amino acids) [VL].

Synthetic linkers (chemical crosslinking agents) that can be used include crosslinking agents that are routinely used to crosslink peptides, for example, N-hydroxy succinimide (NHS), disuccinimidyl suberate (DSS), bis(succinimidyl) suberate (BS³), dithiobis(succinimidyl propionate) (DSP), dithiobis(succinimidyl propionate) (DTSSP), ethylene glycol bis(succinimidyl succinate) (EGS), ethylene glycol bis (sulfosuccinimidyl succinate) (sulfo-EGS), disuccinimidyl tartrate (DST), disulfosuccinimidyl tartrate (sulfo-DST), bis [2-(succinimidoxycarbonyloxy)ethyl]sulfone (BSOCOES), and bis[2-(succinimidoxycarbonyloxy)ethyl]sulfone (sulfo-BSOCOES). These crosslinking agents are commercially available.

Ordinarily, three linkers are required to link four antibody variable regions together and the linkers to be used may all be of the same type or different types.

Furthermore, for example, single chain diabody-type and bivalent scFv-type exist as conformational isomers of sc(Fv) 2.

When the arrangement in sc(Fv)2 is in the order [variable region 1] (linker 1) [variable region 2] (linker 2) [variable region 3] (linker 3) [variable region 4], bivalent scFv-type in the present invention refers to sc(Fv)2 having a structure in which variable region 1 and variable region 2 are associated, as well as variable region 3 and variable region 4 are associated. In the present invention, single chain diabody-type refers to sc(Fv)2 having a structure in which variable region 1 and variable region 4 are associated, as well as variable region 2 and variable region 3 are associated.

An example of a single chain diabody-type is an sc(Fv)2 having the structure shown on the right in FIG. 12(b), and an example of a bivalent scFv-type is an sc(Fv)2 having the structure shown on the left in FIG. 12(b).

Whether an sc(Fv)2 has a single chain diabody-type structure or a bivalent scFv-type structure can be analyzed, for example, by protease-limited proteolysis. For example, the analysis can be carried out by a method such as the following.

Limited proteolysis of a test sc(Fv)2 is carried out using subtilisin A, a type of protease that can partially and restrictively degrade the linker portions of an sc(Fv)2.

When the sc(Fv)2 is the single chain diabody-type, no matter which linker among the three linkers possessed by the sc(Fv)2 is cleaved, the apparent molecular weight will not change due to interaction between the VH and VL.

On the other hand, when the sc(Fv)2 is a bivalent scFv-type, molecular species having half of the original molecular weight will be produced when the central linker is cleaved.

Therefore, the bivalent scFv-type and single chain diabody-type can be differentiated by analyzing the reaction products.

The reaction products can be analyzed, for example, by gel filtration chromatography. Furthermore, using chromatography, the proportions of bivalent sc(Fv)2 and single chain diabody conformations present in sc(Fv)2 can be evaluated quantitatively based on peak areas.

The methods of the present invention for regulating association can be suitably used for the above-mentioned sc(Fv)2 when one wishes to preferentially obtain the desired form, that is either one the single chain diabody-form or bivalent scFv-form.

More specifically, when sc(Fv)2 has the structure VH1-(linker)-VL1-(linker)-VH2-(linker)-VL2, and one wishes to preferentially obtain bivalent scFv-type sc(Fv)2 using the methods of the present invention for regulating association, it is necessary to only suppress the association, for example, between VH1 and VL2, and/or VH2 and VL1 (For example, mutations are introduced so that amino acid residues forming the interface between VH1 and VL2 will carry the same type of charge).

Alternatively, when one wishes to preferentially obtain single-chain diabody type sc(Fv)2, it is necessary to only inhibit the association, for example, between VH1 and VL1, and/or VH2 and VL2 (For example, mutations are introduced so that amino acid residues forming the interface between VH1 and VL1 will carry the same type of charges).

The present invention can also be carried out similarly when sc(Fv)2 is a monospecific antibody.

In addition to these techniques, each of the VH and VL domains can be cross linked by disulfide bonds (Clin. Cancer Res. 1996 February; 2(2):245-52).

The methods of the present invention for regulating association allow, for example, for the efficient production of antibodies or polypeptides that are active. Examples of such activities include binding activity, neutralizing activity, cytotoxic activity, agonist activity, antagonist activity, and enzyme activity and such. Agonist activity is an activity that induces some kind of changes in physiological activity through binding of an antibody to an antigen, such as a receptor, which causes signal transduction or such in cells.

Examples of the physiological activity include growth activity, survival activity, differentiation activity, transcriptional activity, membrane transport activity, binding activity, proteolytic activity, phosphorylation/dephosphorylation activity, redox activity, transfer activity, nucleolytic activity, dehydration activity, cell death-inducing activity, and apoptosis-inducing activity and such, but are not limited thereto.

Antibodies or polypeptides that recognize the desired antigens or bind to the desired receptors can be produced efficiently by the methods of the present invention.

The antigens are not particularly limited, and any type of antigen can be used. Examples of antigens include receptors or their fragments, cancer antigens, MHC antigens, and differentiation antigens and the like, but are not particularly limited thereto.

Examples of the receptors include receptors belonging to the hematopoietic factor receptor family, cytokine receptor family, tyrosine kinase-type receptor family, serine/threonine kinase-type receptor family, TNF receptor family, G protein-coupled receptor family, GPI-anchored receptor family, tyrosine phosphatase-type receptor family, adhesion factor family, hormone receptor family, and such. Reports on the receptors belonging to these receptor families and their characteristics can be found in various sources of documents, for example, in Cooke B A., King R J B., van der Molen H J. ed. New Comprehensive Biochemistry Vol. 18B "Hormones and their Actions Part II" pp. 1-46 (1988) Elsevier Science Publishers BV., New York, USA; Patthy L. (1990) Cell, 61: 13-14; Ullrich A., et al. (1990) Cell, 61: 203-212; Massagul J. (1992) Cell, 69: 1067-1070; Miyajima A., et al. (1992) Annu. Rev. Immunol., 10: 295-331; Taga T. and Kishimoto T. (1992) FASEB J., 7: 3387-3396; Fantl W I., et al. (1993) Annu. Rev. Biochem., 62: 453-481; Smith C A., et al. (1994) Cell, 76: 959-962; Flower D R. (1999) Biochim. Biophys. Acta, 1422: 207-234; Miyasaka M. ed. Cell Technology, Handbook Series "Handbook for adhesion factors" (1994) Shujunsha, Tokyo, Japan; and such. Examples of specific receptors belonging to the above-mentioned receptor families include human or mouse erythropoietin (EPO) receptor, human or mouse granulocyte-colony stimulating factor (G-CSF) receptor, human or mouse thrombopoietin (TPO) receptor, human or mouse insulin receptor, human or mouse Flt-3 ligand receptor, human or mouse platelet-derived growth factor (PDGF) receptor, human or mouse interferon (IFN)-α or -β receptor, human or mouse leptin receptor, human or mouse growth hormone (GH) receptor, human or mouse interleukin (IL)-10 receptor, human or mouse insulin-like growth factor (IGF)-I receptor, human or mouse leukemia inhibitory factor (LIF) receptor, and human or mouse ciliary neurotrophic factor (CNTF) receptor (hEPOR: Simon, S. et al. (1990) Blood 76, 31-35; mEPOR: D'Andrea, A D, et al. (1989) Cell 57, 277-285; hG-CSFR: Fukunaga, R. et al. (1990) Proc. Natl. Acad. Sci. USA. 87, 8702-8706; mG-CSFR: Fukunaga, R. et al. (1990) Cell 61, 341-350; hTPOR: Vigon, I. et al. (1992) 89, 5640-5644.; mTPOR: Skoda, R C. et al. (1993) 12, 2645-2653; hInsR: Ullrich, A. et al. (1985) Nature 313, 756-761; hFlt-3: Small, D. et al. (1994) Proc. Natl. Acad. Sci. USA. 91, 459-463; hPDGFR: Gronwald, R G K. et al. (1988) Proc. Natl. Acad. Sci. USA. 85, 3435-3439; hIFN α/β R: Uze, G. et al. (1990) Cell 60, 225-234; and Novick, D. et al. (1994) Cell 77, 391-400).

Cancer antigens are antigens that are expressed as cells become malignant, and are also called tumor-specific antigens. Furthermore, abnormal sugar chains that appear on cell surfaces and protein molecules when the cells become cancerous are also cancer antigens and are specifically called as carcinoma associated carbohydrate antigen. Examples of cancer antigens include CA19-9, CA15-3, and sialyl SSEA-1 (SLX).

MHC antigens can be classified broadly into MHC class I antigens and MHC class II antigens: MHC class I antigens include HLA-A, -B, -C, -E, -F, -G; and -H; and MHC class II antigens include HLA-DR, -DQ, and -DP.

Differentiation antigens include CD1, CD2, CD3, CD4, CD5, CD6, CD7, CD8, CD10, CD11a, CD11b, CD11c, CD13, CD14, CD15s, CD16, CD18, CD19, CD20, CD21, CD23, CD25, CD28, CD29, CD30, CD32, CD33, CD34, CD35, CD38, CD40, CD41a, CD41b, CD42a, CD42b, CD43, CD44, CD45, CD45RO, CD48, CD49a, CD49b, CD49c, CD49d, CD49e, CD49f, CD51, CD54, CD55, CD56, CD57, CD58, CD61, CD62E, CD62L, CD62P, CD64, CD69, CD71, CD73, CD95, CD102, CD106, CD122, CD126, and CDw130.

The present invention also provides for mutant polypeptides or heteromultimers whose association is regulated by the methods of the present invention. More specifically, the present invention relates to polypeptides or heteromultimers that are obtained by methods of the present invention for regulating associations.

Preferred embodiments of the present invention provide mutant polypeptides that have modifications made to the amino acid residues that form the interface in the original polypeptides so as to inhibit the association within the polypeptides.

Other embodiments of the present invention provide heteromultimers that have modifications made to amino acid residues forming the interface between the original polypeptides such that the association between the polypeptides is inhibited.

In the present invention, the phrase "original polypeptides" refer to polypeptides in the condition before modification by the methods of the present invention where association is regulated.

An example of the above-mentioned mutant polypeptides of the present invention is a mutant in which the original polypeptide can form two types of conformational isomers. Furthermore, an example of the above-mentioned heteromultimers is a multimer in which the original polypeptide can form two or more types of multimers.

Mutant polypeptides or heteromultimers whose association is regulated by the above-mentioned methods of the present invention for regulating association are also included in the present invention. More specifically, in preferred embodiments of the above-described methods for regulating association, a polypeptide or heteromultimer whose association is regulated is also a preferred embodiment of the present invention.

The present invention also provides methods for producing polypeptides or heteromultimers in which association of polypeptides or heteromultimers is regulated.

Preferred embodiments of the production methods of the present invention provides methods for producing polypeptides having mutations in the amino acid residues forming the interface in the polypeptides so that polypeptide association is regulated, wherein the methods for producing the mutant polypeptides include the steps of:
(a) modifying nucleic acids encoding the amino acid residues that form an interface in the polypeptides from the original nucleic acids, so as to inhibit the association in the polypeptides;
(b) culturing host cells so that these nucleic acids are expressed; and
(c) recovering the polypeptides from the host cell culture.

In other embodiments, the present invention provides methods for producing heteromultimers whose amino acid residues that form the interface between polypeptides have mutations that allow for the regulation of the heteromultimer association, wherein the methods for producing heteromultimers include the steps of:
(a) modifying nucleic acids encoding the amino acid residues forming an interface between polypeptides from the original nucleic acids, so as to inhibit the association between the polypeptides;
(b) culturing host cells so that these nucleic acids are expressed; and
(c) recovering the heteromultimers from the host cell culture.

A method including the step of using the above-described methods of the present invention for regulating association to modify nucleic acids encoding amino acid residues forming the interface in (between) polypeptides from the original nucleic acids so that polypeptide association will be inhibited is also a preferred embodiment of the above-mentioned production methods of the present invention.

The phrase "modify nucleic acids" in the above-mentioned methods of the present invention refers to modifying nucleic acids so that they correspond to amino acid residues introduced by the "modifications" of the present invention. More specifically, it refers to modifying the nucleic acids encoding the original (pre-modified) amino acid residues to the nucleic acids encoding the amino acid residues that are to be introduced by the modification. Ordinarily, it means performing gene manipulations or mutation treatment that would result in at least one nucleotide insertion, deletion, or substitution to the original nucleic acid so that codons encoding amino acid residues of interest is formed. More specifically, codons encoding the original amino acid residues are substituted with codons encoding the amino acid residues that are to be introduced by the modification. Such nucleic acid modification can be performed suitably by those skilled in the art using known techniques such as site-specific mutagenesis and PCR mutagenesis.

Furthermore, nucleic acids of the present invention are ordinarily carried by (inserted into) suitable vectors and then introduced into host cells. These vectors are not particularly limited so long as the inserted nucleic acid is stably maintained. For example, when using E. coli as the host, the cloning vector is preferably a pBluescript vector (Stratagene) and such, but various commercially available vectors may be used. Expression vectors are particularly useful as vectors for producing the polypeptides of the present invention. Expression vectors are not particularly limited so long as they can express polypeptides in test tubes, E. coli, cultured cells, or individual organisms. For example, preferred vectors include pBEST vector (Promega) for expression in test tubes, pET vector (Invitrogen) for E. coli, pME18S-FL3 vector (GenBank Accession No. AB009864) for cultured cells, and pME18S vector (Mol. Cell Biol. 8:466-472(1998)) for individual organisms. Insertion of a DNA of the present invention into vectors can be performed by standard methods such as ligase reactions using restriction enzyme sites (Current protocols in Molecular Biology edit. Ausubel et al. (1987) Publish. John Wiley & Sons. Section 11.4-11.11).

The above-mentioned host cells are not particularly limited, and various host cells can be used, depending on the purpose. Cells used for expressing the polypeptides include bacterial cells (for example, Streptococcus, Staphylococcus, E. coli, Streptomyces, and Bacillus subtilis), fungal cells (for example, yeast and *Aspergillus*), insect cells (for example, *Drosophila* S2 and *Spodoptera* SF9), animal cells (for example, CHO, COS, HeLa, C127, 3T3, BHK, HEK293, Bowes melanoma cell), and plant cells. Vectors can be introduced into host cells using known methods, such as the calcium phosphate precipitation method, electroporation method (Current protocols in Molecular Biology edit. Ausubel et al. (1987) Publish. John Wiley & Sons. Section 9.1-9.9), lipofectamine method (GIBCO-BRL), and microinjection method.

For secreting host cell-expressed polypeptides into the lumen of the endoplasmic reticulum, periplasmic space, or extracellular environment, suitable secretion signals can be incorporated into the polypeptides of interest. These signals may be intrinsic or foreign to the polypeptides of interest.

When the polypeptides of the present invention are secreted into the culture media, the polypeptides produced by the above-mentioned method can be harvested by collecting the media. When the polypeptides of the present invention are produced inside cells, first, the cells are lysed, and then these polypeptides are collected.

The polypeptides of the present invention can be collected and purified from recombinant cell cultures by using known methods, including ammonium sulfate or ethanol precipitation, acidic extraction, anion or cation exchange chromatography, phosphocellulose chromatography, hydrophobic interaction chromatography, affinity chromatography, hydroxyapatite chromatography, and lectin chromatography.

The present invention relates to compositions (pharmaceutical agents) composed of a mutant polypeptide or heteromultimer of the present invention and a pharmaceutically acceptable carrier.

In the present invention, pharmaceutical compositions ordinarily refer to pharmaceutical agents for treating or preventing, or testing and diagnosing diseases.

The pharmaceutical compositions of the present invention can be formulated by methods known to those skilled in the art. For example, such pharmaceutical compositions can be used parenterally, as injections which are sterile solutions or suspensions including an antibody along with water or another pharmaceutically acceptable liquid. For example, such compositions may be formulated as unit doses that meet the requirements for the preparation of pharmaceuticals by appropriately combining the antibody with pharmaceutically acceptable carriers or media, specifically with sterile water, physiological saline, a vegetable oil, emulsifier, suspension, detergent, stabilizer, flavoring agent, excipient, vehicle, preservative, binder, or such. In such preparations, the amount of active ingredient is adjusted such that the dose falls within an appropriately pre-determined range.

Sterile compositions for injection can be formulated using vehicles such as distilled water for injection, according to standard protocols for formulation.

Aqueous solutions for injection include, for example, physiological saline and isotonic solutions containing dextrose or other adjuvants (for example, D-sorbitol, D-mannose, D-mannitol, and sodium chloride). Appropriate solubilizers, for example, alcohols (ethanol and such), polyalcohols (propylene glycol, polyethylene glycol, and such), non-ionic detergents (polysorbate 80™, HCO-50, and such), may be used in combination.

Oils include sesame and soybean oils. Benzyl benzoate and/or benzyl alcohol can be used in combination as solubilizers. Buffers (for example, phosphate buffer and sodium acetate buffer), soothing agents (for example, procaine hydrochloride), stabilizers (for example, benzyl alcohol and phenol), and/or antioxidants can also be combined. Prepared injectables are generally filled into appropriate ampules.

The pharmaceutical compositions of the present invention are preferably administered parenterally. For example, the compositions may be injections, transnasal compositions, transpulmonary compositions or transdermal compositions. For example, such compositions can be administered systemically or locally by intravenous injections intramuscular injection, intraperitoneal injection, subcutaneous injection, or such.

The administration methods can be appropriately selected in consideration of a patient's age and symptoms. The dose of a pharmaceutical composition composed of an antibody or a polynucleotide encoding an antibody may be, for example, from 0.0001 to 1000 mg/kg for each administration. Alternatively, the dose may be, for example, from 0.001 to 100,000 mg per patient. However, the doses are not limited to the ranges described above. The doses and administration methods vary depending on a patient's weight, age, symptoms, and such. Those skilled in the art can select appropriate doses and administration methods in consideration of the factors described above.

The polypeptides or heteromultimers of the present invention can be formulated by combining with other pharmaceutical components as necessary.

The present invention also provides nucleic acids that encode the mutant polypeptides of the present invention or the heteromultimers of the present invention. Further, vectors that carry these nucleic acids are also included in the present invention.

The present invention provides host cells carrying the above described nucleic acids. The host cells are not particularly limited and include, for example, *E. coli* and various animal cells. The host cells may be used, for example, as a production system to produce and express the antibodies or the polypeptides of the present invention. In vitro and in vivo production systems are available for polypeptide production systems. Production systems that use eukaryotic cells or prokaryotic cells are examples of in vitro production systems.

Eukaryotic cells that can be used as a host cell include, for example, animal cells, plant cells, and fungal cells. Animal cells include: mammalian cells, for example, CHO (J. Exp. Med. (1995)108, 945), COS, 3T3, myeloma, BHK (baby hamster kidney), HeLa, and Vero; amphibian cells such as *Xenopus laevis* oocytes (Valle, et al. (1981) Nature 291, 338-340); and insect cells (e.g., Sf9, Sf21, and Tn5). In the expression of the antibodies of the present invention, CHO-DG44, CHO-DX11B, COS7 cells, and BHK cells can be suitably used. Among animal cells, CHO cells are particularly preferable for large-scale expression. Vectors can be introduced into a host cell by, for example, calcium phosphate methods, the DEAE-dextran methods, methods using cationic liposome DOTAP (Boehringer-Mannheim), electroporation methods, or lipofection methods.

Plant cells include, for example, *Nicotiana tabacum*-derived cells known as a protein production system. Calluses can be cultured from these cells to produce the antibodies of the present invention. Known protein production systems are those using fungal cells including yeast cells, for example, cells of genus *Saccharomyces* such as *Saccharomyces cerevisiae* and *Saccharomyces pombe*; and cells of filamentous fungi, for example, genus *Aspergillus* such as *Aspergillus niger*. These cells can be used as a host to produce the antibodies of the present invention.

Bacterial cells can be used in the prokaryotic production systems. Examples of bacterial cells include *Bacillus subtilis* as well as *E. coli* described above. Such cells can be used to produce the antibodies of the present invention.

When producing an antibody using a host cell of the present invention, the polynucleotide encoding an antibody of the present invention may be expressed by culturing the host cells transformed with the expression vector containing the polynucleotide. The culture can be performed using known methods. For example, when using animal cells as a host, DMEM, MEM, RPMI 1640, or IMDM may be used as the culture medium, and may be used with or without serum supplements such as FBS or fetal calf serum (FCS). Serum-free cultures are also acceptable. The preferred pH is about 6 to 8 during the course of culturing. Incubation is carried out typically at a temperature of about 30 to 40° C. for about 15 to 200 hours. Medium is exchanged, aerated, or agitated, as necessary.

On the other hand, production systems using animal or plant hosts may be used as systems for producing polypeptides in vivo. For example, a polynucleotide of interest is introduced into an animal or plant and the polypeptide is produced in the body of the animal or plant and then collected. The "hosts" of the present invention includes such animals and plants.

Animals to be used for the production system include mammals or insects. Mammals such as goats, pigs, sheep, mice, and cattle may be used (Vicki Glaser SPECTRUM Biotechnology Applications (1993)). Alternatively, the mammals may be transgenic animals.

For example, a polynucleotide encoding an antibody of the present invention may be prepared as a fusion gene with a gene encoding a polypeptide specifically produced in milk, such as the goat β-casein gene. Polynucleotide fragments containing the fusion gene are injected into goat embryos, which are then introduced back to female goats. The desired antibody can be obtained from milk produced by the transgenic goats, which are born from the goats that received the embryos, or from their offspring. Appropriate hormones may be administered to increase the volume of milk containing the antibody produced by the transgenic goats (Ebert et al., Bio/Technology 12: 699-702 (1994)).

Insects such as silkworms, may also be used for producing the antibodies of the present invention. Baculoviruses carrying a polynucleotide encoding an antibody of interest can be used to infect silkworms, and the antibody of interest can be obtained from the body fluids (Susumu et al., Nature 315: 592-594 (1985)).

Plants used for producing the antibodies of the present invention include, for example, tobacco. When tobacco is used, a polynucleotide encoding an antibody of interest is inserted into a plant expression vector, for example, pMON 530, and then the vector is introduced into a bacterium, such as *Agrobacterium tumefaciens*. The bacteria are then used to infect tobacco such as *Nicotiana tabacum*, and the desired antibodies can be recovered from the leaves (Ma et al., Eur. J. Immunol. 24: 131-138 (1994)).

The resulting antibody may be isolated from the inside or outside (such as the medium and milk) of host cells, and purified as a substantially pure and homogenous antibody. Methods are not limited to any specific method and any standard method for isolating and purifying antibodies may be used. Antibodies may be isolated and purified, by selecting an appropriate combination of, for example, chromatographic columns, filtration, ultrafiltration, salting out, solvent precipitation, solvent extraction, distillation, immunoprecipitation, SDS-polyacrylamide gel electrophoresis, isoelectric focusing, dialysis, recrystallization, and others.

Chromatographies include, for example, affinity chromatographies, ion exchange chromatographies, hydrophobic chromatographies, gel filtrations, reverse-phase chromatographies, and adsorption chromatographies (Strategies for Protein Purification and Characterization: A Laboratory Course Manual. Ed Daniel R. Marshak et al., Cold Spring Harbor Laboratory Press, 1996). These chromatographies can be carried out using liquid phase chromatographies such as HPLC and FPLC. Examples of the affinity chromatography columns include protein A columns and protein G columns. Examples of the proteins A columns include Hyper D, POROS, and Sepharose F. F. (Pharmacia).

An antibody can be modified freely and peptide portions can be deleted from it by treating the antibody with an appropriate protein modifying enzyme before or after antibody purification, as necessary. Such protein modifying enzymes include, for example, trypsins, chymotrypsins, lysyl endopeptidases, protein kinases, and glucosidases.

In another preferred embodiment, the present invention also includes methods for producing the mutant polypeptides or heteromultimers of the present invention, such methods including the steps of culturing the host cells of the present invention as described above and recovering the polypeptides from such cell culture.

All prior art references cited herein are incorporated by reference into the present specification.

EXAMPLES

Herein below, the present invention will be specifically described with reference to Examples; however, the invention should not be construed as being limited thereto.

[Example 1] Production of Non-Neutralizing Antibodies Against Factor IXa (F.IXa)

1-1. Immunization and Hybridoma Production

Eight BALB/c mice (male, starting immunization at 6 weeks of age, Japan Charles River) and 5 MRL/lpr mice (male, starting immunization at 6 weeks of age, Japan Charles River) were immunized as described below with Factor IXaβ Enzyme Research Laboratories, Inc.). Factor IXaβ emulsified in FCA (Freund's complete adjuvant H37 Ra (Difco laboratories)) was administered subcutaneously at 40 μg/head as primary immunization. Two weeks later, Factor IXaβ emulsified in FIA (Freund's incomplete adjuvant (Difco laboratories)) was administered subcutaneously at 40 μg/head. Thereafter, boosters were given at one week intervals, a total of 3 to 7 times. After the elevation in serum antibody titer against factor IXaβ was confirmed by ELISA (enzyme linked immunosorbent assay) shown in 1-2, factor IXaβ diluted in PBS(−) (phosphate buffered saline that does not contain calcium ions and magnesium ions) was administered intravenously at 40 μg/head. Three days after the final immunization, mouse spleen cells and mouse myeloma cells P3X63Ag8U.1 (referred to as P3U1, ATCC CRL-1597) were fused, following conventional procedures using PEG1500 (Roche Diagnostics). Selective culturing of hybridomas was performed by plating fused cells suspended in RPMI1640 medium (Invitrogen) containing 10% FBS (Invitrogen) (hereinafter referred to as 10% FBS/RPMI1640) onto a 96-well culture plate and substituting the medium with HAT selection medium (10% FBS/RPMI1640/2% HAT 50× concentrate (Dainippon Pharmaceutical)/5% BM-Condimed H1 (Roche Diagnostics)) at 1, 2, 3, and 5 days after fusion. Hybridomas having a binding activity to Factor IXa were selected using the culture supernatant collected on day 8 or day 9 after fusion, and measuring binding activity against Factor IXa by ELISA shown in 1-2. Then hybridomas that did not have neutralizing activity against Factor IXa were selected by measuring the ability of hybridoma to neutralize the enzyme activity of Factor IXa, according to the method shown in 5-3. Hybridomas were cloned with two rounds of limiting dilution by plating cells into a 96-well culture plate at one cell per well to establish hybridoma XB12 that produced anti-Factor IXa antibodies.

1-2. Factor IXa ELISA

Factor IXaβ diluted to 1 μg/mL with coating buffer (100 mM sodium bicarbonate, pH9.6, 0.02% sodium azide) was dispensed into Nunc-Immuno plate (Nunc-Immuno™ 96 MicroWell™ plates MaxiSorp™ (Nalge Nunc International)) at 100 μL/well, and then incubated overnight at 4° C. After three washes with PBS(-) containing Tween® 20, the plate was blocked with diluent buffer (50 mM Tris-HCl, pH8.1, 1% bovine serum albumin, 1 mM $MgCl_2$, 0.15 M NaCl, 0.05% Tween® 20, 0.02% sodium azide) at room temperature for two hours. After buffer removal, mouse anti-serum or hybridoma culture supernatant diluted in the diluent buffer was added to the plate at 100 μL/well and incubated at room temperature for one hour. The plate was washed three times, then alkaline phosphatase-labeled goat anti-mouse IgG (H+L) (Zymed Laboratories) diluted at 1/2000 with the diluent buffer was added at 100 μL/well. This was incubated at room temperature for one hour. The plate was washed six times, chromogenic substrate Blue-Phos™ Phosphate Substrate (Kirkegaard & Perry Laboratories) was added at 100 μL/well, and was then incubated at room temperature for 20 minutes. After adding Blue-Phos™ Stop Solution (Kirkegaard & Perry Laboratories) at 100 μL/well, the absorbance at 595 nm was measured with a Microplate Reader Model 3550 (Bio-Rad Laboratories).

1-3. Factor IXa Neutralizing Activity Measurements

Phospholipid (Sigma-Aldrich) was dissolved in distilled water for injection, and then sonicated to prepare a 400 μg/mL phospholipid solution. 40 μL of tris buffer saline solution containing 0.1% bovine serum alburmin (herein after referred to as TBSB), 10 μL of 30 ng/mL Factor IXaβ (Enzyme Research Laboratories), 5 μL of 400 μg/mL phospholipid solution, 5 μL of TBSB containing 100 mM $CaCl_2$ and 20 mM $MgCl_2$, and 10 μL of hybridoma culture supernatant were mixed in a 96-well plate, and then incubated at room temperature for one hour. 20 μL of 50 mg/mL Factor X (Enzyme Research Laboratories) and 10 μL of 3U/mL Factor VIIIa (American diagnostica) were added to this mixed solution, and then were reacted at room temperature for 30 minutes. 10 μL of 0.5 M EDTA was added to stop the reaction. Fifty μL of S-2222 solution (Chromogenix) was added to the reaction solution, which was then incubated at room temperature for 30 minutes, followed by measuring the absorbance at measurement wavelength of 405 nm and control wavelength of 655 nm on a Microplate Reader Model 3550 (Bio-Rad Laboratories, Inc.).

[Example 2] Preparation of Non-Neutralizing Antibodies Against Factor X (F.X)

2-1. Immunization and Hybridoma Preparation

Eight BALB/c mice (male, staring immunization at 6 weeks of age, Japan Charles River) and 5 MRL/lpr mice (male, starting immunization at 6 weeks of age, Japan Charles River) were immunized with factor X (Enzyme Research Laboratories) as described below. For the initial immunization, factor X emulsified with FCA was subcutaneously administered at 40 μg/head. Two weeks later, factor X emulsified with FIA was subcutaneously administered at 20 or 40 μg/head. Thereafter, a total of 3 to 6 boosters were given at one week intervals. After the elevation of the titer of a serum antibody against Factor X was confirmed by ELISA as described in 2-2, Factor X diluted in PBS(-) was administered intravenously at 20 or 40 μg/head as a final immunization. Three days after the final immunization, mouse spleen cells were fused with mouse myeloma P3U1 cells according to a standard method using PEG1500. Fused cells suspended in 10% FBS/RPMI1640 medium were seeded in a 96-well culture plate, and hybridomas were selectively cultured by replacing the medium with a HAT selection medium at 1, 2, 3, and 5 days after the fusion. Binding activity against Factor X was measured by ELISA described in 2-2, using the culture supernatant collected on the eighth day after fusion. Hybridomas having Factor X-binding activity were selected, and their activities to neutralize Factor Xa enzymatic activity were measured according to the method described in 2-3. Hybridomas that were incapable of neutralizing the enzyme activity of Factor Xa were cloned using two rounds of limiting dilution to establish hybridoma SB04 that produced anti-Factor X antibodies.

2-2. Factor X ELISA

Factor X diluted to 1 μg/mL with a coating buffer was dispensed into Nunc-Immuno plate at 100 μL/well, and then incubated overnight at 4° C. After three washes with PBS(-) containing Tween® 20, the plate was blocked with the diluent buffer at room temperature for 2 hours. After removal of the buffer, mouse antiserum or hybridoma culture supernatant diluted with the diluent buffer was added to the plate, and incubated at room temperature for 1 hour. The plate was washed three times, then alkaline phosphatase-labeled goat anti-mouse IgG (H+L) diluted to 1/2000 with the diluent buffer was added, and incubated at room temperature for 1 hour. The plate was washed six times, after which a colorimetric substrate Blue-Phos™ Phosphate Substrate (Kirkegaard & Perry Laboratories) was added at 100 μL/well. The plate was then incubated at room temperature for 20 minutes. After adding Blue-Phos™ Stop Solution (Kirkegaard & Perry Laboratories) at 100 μL/well, the absorbance at 595 nm was measured on a Microplate Reader Model 3550 (Bio-Rad Laboratories).

2-3. Measurement of Factor Xa Neutralizing Activity

Ten μL of hybridoma culture supernatant diluted to 1/5 with TBSB was mixed with 40 μL of TBCP (TBSB containing 2.78 mM $CaCl_2$, 22.2 μM phospholipids (phosphatidylcholine:phosphatidylserine=75:25, Sigma-Aldrich)) containing 250 pg/mL of Factor Xa (Enzyme Research Laboratories) and incubated at room temperature for 1 hour. To this mixed solution, 50 μL of TBCP containing 20 μg/mL prothrombin Enzyme Research Laboratories) and 100 ng/mL activated coagulation factor V (Factor Va (Haematologic Technologies)) were added, and reacted at room temperature for 10 minutes. The reaction was stopped with the addition of 10 μL of 0.5 M EDTA. To this reaction solution, 50 μL of 1 mM S-2238 solution (Chromogenix) was added, followed by incubation at room temperature for 30 minutes, at which point absorbance was measured at 405 nm on a Microplate Reader Model 3550 (Bio-Rad Laboratories, Inc.).

[Example 3] Construction of Chimeric Bispecific Antibody Expression Vectors 3-1. Preparation of Antibody Variable Region-Encoding DNA Fragments from Hybridomas Total RNA was extracted from hybridoma XB12 that produced anti-F.IXa antibody or hybridoma SB04 that produced anti-F.X antibody using QIAGEN® RNeasy® Mini Kit (QIAGEN) according to the method described in the instruction manual. The total RNA was dissolved in 40 µL of sterile water. Single-stranded cDNA was synthesized by RT-PCR using the SuperScript cDNA synthesis system (Invitrogen) with 1-2 µg of the purified RNA as template according to the method described in the instruction manual.

3-2. PCR Amplification of Antibody H-Chain Variable Region and Sequence Analysis HB primer mixture and HF primer mixture described in the report by Krebber et al. (J. Immunol. Methods 1997; 201:35-55) were prepared as amplification primers for the mouse antibody H chain variable region (VH) cDNA. Using 0.5 µL each of 100 µM HB primer mixture and 100 µM HF primer mixture, 25 µL of the reaction solution (2.5 µL of cDNA solution prepared in 3-1, KOD plus buffer (Toyobo), 0.2 mM dNTPs, 1.5 mM $MgCl_2$, 0.75 units DNA polymerase KOD plus (Toyobo)) was prepared. PCR was performed using a thermal cycler GeneAmp PCR system 9700 (Perkin Elmer) under either with condition A (heating at 98° C. for 3 minutes, followed by 32 cycles of reacting at 98° C. for 20 seconds, 58° C. for 20 seconds, and 72° C. for 30 seconds per cycle) or condition B (heating at 94° C. for 3 minutes, followed by 5 cycles of reacting at 94° C. for 20 seconds, 46° C. for 20 seconds, and 68° C. for 30 seconds per cycle, and 30 cycles of reacting at 94° C. for 20 seconds, 58° C. for 20 seconds, and 72° C. for 30 seconds per cycle), depending on the amplification efficiency of the cDNA fragment. After PCR, the reaction solution was subjected to 1% agarose gel electrophoresis. Amplified fragments having the size of interest (approximately 400 bp) were purified using QIAquick Gel Extraction Kit (QIAGEN) according to the method described in the instruction manual, and eluted with 30 µL of sterile water. The nucleotide sequence of each DNA fragment was determined by a DNA sequencer ABI PRISM 3100 Genetic Analyzer (Applied Biosystems) using a BigDye Terminator Cycle Sequencing Kit (Applied Biosystems) according to the method described in the instruction manual. The group of sequences determined by this method was analyzed comparatively using an analysis software GENETYX-SV/RC Version 6.1 (Genetyx), and those having a different sequence were selected.

3-3. Preparations of Antibody Variable Region DNA Fragments for Cloning

The following procedure was performed to add restriction enzyme Sfi I cleavage sites for cloning to both ends of the fragments of antibody variable region that were amplified.

To amplify the Sfi I cleavage site added to the VH fragments (Sfi I-VH), a primer (primer VH-5' end) in which the (Gly4Ser)2-linker sequence of primer HB was modified to a sequence having Sfi I cleavage sites was prepared. Using 0.5 µL each of the 10 µM sequence-specific primer VH-5' end and 10 µM primer scfor (J. Immunol. Methods 1997; 201: 35-55), a reaction solution (20 µL) (1 µL of purified solution of amplified VH cDNA fragment prepared in 3-2, KOD plus buffer (TOYOBO), 0.2 mM dNTPs, 1.5 mM $MgCl_2$, 0.5 units DNA polymerase KOD plus (TOYOBO)) was prepared. Using a thermal cycler GeneAmp PCR system 9700 (Perkin Elmer), PCR was performed either with condition A (heating at 98° C. for 3 minutes, followed by 32 cycles of reacting at 98° C. for 20 seconds, 58° C. for 20 seconds, and 72° C. for 30 seconds per cycle) or condition B (heating at 94° C. for 3 min followed by 5 cycles of reacting at 94° C. for 20 seconds, 46° C. for 20 seconds, and 68° C. for 30 seconds per cycle; and 30 cycles of reacting at 94° C. for 20 seconds, 58° C. for 20 seconds, and 72° C. for 30 seconds per cycle), depending on the amplification efficiency for the fragments. After PCR, the reaction solution was subjected to 1% agarose gel electrophoresis. Amplified fragments of the desired size (about 400 bp) were purified using QIAquick Gel Extraction Kit (QIAGEN) according to the method described in the instruction manual, and eluted with 30 µL of sterile water.

To amplify the mouse antibody L chain variable region (VL) cDNA fragments, 0.5 µL each of the 100 µM LB primer mixture and 100 µM LF primer mixture described in the report by Krebber et al. (J. Immunol. Methods 1997; 201: 35-55) was used first, and a reaction solution (25 µL) (2.5 µL of cDNA solution prepared in 3-1, KOD plus buffer (TOYOBO), 0.2 mM dNTPs, 1.5 mM $MgCl_2$, 0.75 units DNA polymerase KOD plus (TOYOBO)) was prepared. Using a thermal cycler GeneAmp PCR system 9700 (Perkin Elmer), PCR was performed according to the amplification efficiency of the fragments, under conditions of heating at 94° C. for 3 min followed by 5 cycles of reaction (reacting at 94° C. for 20 seconds, 46° C. for 20 seconds, and 68° C. for 30 seconds per cycle, and 30 cycles of reacting at 94° C. for 20 seconds, 58° C. for 20 seconds, and 72° C. for 30 seconds per cycle. After the PCR, the reaction solution was subjected to 1% agarose gel electrophoresis. Amplified fragments of the desired size (about 400 bp) were purified using the QIAquick Gel Extraction Kit (QIAGEN) according to the method described in the instruction manual, and were eluted with 30 µL of sterile water. The fragments are in a state in which the primer LF-derived (Gly4Ser)3-linker sequence is added to their C termini. In order to add an Sfi I cleavage site to the C termini of the fragments, a primer (primer VL-3' end) where the primer LF (Gly4Ser)3-linker sequence was modified to a sequence having Sfi I cleavage site was prepared. To amplify the Sfi I cleavage site-added VL fragments (Sfi I-VL), 0.5 µL each of the 10 µM VL-3' end primer mixture and 10 µM scback primer was used, and 20 µL of a reaction solution (1 µL of a solution of purified VL cDNA amplification fragment, KOD plus buffer (TOYOBO), 0.2 mM dNTPs, 1.5 mM $MgCl_2$, 0.5 units DNA polymerase KOD plus (TOYOBO)) was prepared. PCR was performed using a thermal cycler GeneAmp PCR system 9700 (Perkin Elmer) under conditions of heating at 94° C. for 3 min followed by 5 cycles of reaction (reacting at 94° C. for 20 seconds, 46° C. for 20 seconds, and 68° C. for 30 seconds per cycle, and 30 cycles of reacting at 94° C. for 20 seconds, 58° C. for 20 seconds, and 72° C. for 30 seconds per cycle. After the PCR, the reaction solution was subjected to 1% agarose gel electrophoresis. Amplified fragments of the desired size (about 400 bp) were purified using the QIAquick Gel Extraction Kit (QIAGEN) according to the method described in the instruction manual, and were eluted with 30 µL of sterile water.

Purified Sfi I-VH and Sfi I-VL fragments were digested with Sfi I (Takara Bio) at 50° C. for overnight in a reaction solution prepared according to the method described in the instruction manual. Subsequently, the reaction solution was purified using a QIAquick PCR Purification Kit (QIAGEN) according to the method described in the instruction manual, and eluted with 30 µL of Buffer EB included in the kit.

3-4. Human IgG4-Mouse Chimeric Bispecific IgG Antibody Expression Plasmid

The knobs-into-holes technique of IgG1 (Non-Patent Document 3) was utilized to produce the bispecific IgG antibody of interest, to allow heteromolecule formation in each H chain, and an amino acid substituent in which the CH3 portion of the IgG4 is substituted was prepared. Type a (IgG4γa) is an IgG4 substituted at Y349C and T366W, and type b (IgG4γb) is an IgG4 substituted at E356C, T366S, L368A, and Y407V. Furthermore, a substitution (-ppcpScp-->-ppcpPcp-) was also introduced at the hinge regions of both substituted IgG4s. Most become heteromolecules using this technique; however, this does not necessarily apply to L chains, and the generation of unnecessary antibody molecules may affect subsequent activity measurements. Therefore, in this method those that are inducible by different pharmaceuticals were used as the expression vectors for each HL molecule to separately express the arms of each antibody molecule (called as HL molecule) which have various specificities, and to efficiently produce the bispecific IgG antibody of interest within cells.

As an expression vector for one arm of the antibody molecule (referred to as right arm HL molecule for convenience), a respective H chain or L chain region incorporated to a tetracycline-induced type vector pcDNA4 (Invitrogen) (pcDNA4-g4H or pcDNA4-g4L) was prepared, i.e. a suitable mouse antibody variable region (VH or VL) and a human IgG4γa constant region (SEQ ID NO: 9) or κ constant region (SEQ ID NO: 10) incorporated into the downstream of the signal sequence (IL3ss) used for animal cells (Proc. Natl. Acad. Sci. USA. 1984; 81: 1075). First, Eco RV and Not I (Takara Bio) were used to digest pcDNA4 at the restriction enzyme cleavage sites that are present in the multi-cloning site. The right arm H chain- or L chain-expression unit (about 1.6 kb or about 1.0 kb respectively) of a chimeric bispecific antibody having suitable antibody variable regions was digested with Xho I (Takara Bio). The antibody was then purified with the QIAquick PCR Purification Kit (QIAGEN) according to the method described in the instruction manual, and reacted with DNA polymerase KOD (TOYOBO) at 72° C. for 10 minutes in a reaction solution composition described in the instruction manual to blunt the ends. The blunt-ended fragments were purified with QIAquick PCR Purification Kit (QIAGEN) according to the method described in the instruction manual, and digested with Not I (Takara Bio). The Not I/blunt ended fragments (about 1.6 kb or 1.0 kb respectively) and the Eco RV/Not I-digested pcDNA4 were subjected to ligation reaction using Ligation High (TOYOBO), according to the method described in the instruction manual. An E. coli DH5α strain (Competent high DH5α (TOYOBO)) was transformed with the above-described reaction solution. >From the ampicillin-resistant clones thus obtained, respective plasmid DNAs were isolated using QIAprep Spin Miniprep Kit (QIAGEN).

According to the above-described method, as for the other arm (referred to herein as left arm HL molecule for convenience) of the antibody molecule, the respective H chain or L chain region incorporated to the ecdysone analogue inducible type vector pIND (Invitrogen) (pIND-g4H or pIND-g4L) was prepared, i.e. a suitable mouse antibody variable region (VH or VL) and a human IgG4γb constant region (SEQ ID NO: 11) or κ constant region incorporated into the downstream of the signal sequence (IL3ss) used for animal cells (EMBO. J. 1987; 6: 2939). Respective plasmid DNAs were then isolated.

3-5. Construction of Bispecific Antibody Expression Vectors

The tetracycline-induced type expression plasmid prepared in 3-4 (pcDNA4-g4H or pcDNA4-g4L) was digested with Sfi I, and the reaction solution was subjected to 1% agarose gel electrophoresis. Fragments (approximately 5 kb) lacking the original antibody variable region part (VH or VL) were purified using the QIAquick Gel Extraction Kit (QIAGEN) according to the method described in the instruction manual, and eluted with 30 μL of sterile water. The fragments, and the corresponding Sfi I-VH or Sfi-VL fragment derived from the Sfi I-digested anti-F.IXa antibody XB12 prepared in 3-3, were subjected to ligation reaction using the Quick Ligation Kit (New England Biolabs) according to the method described in the instruction manual. An E. coli DH5α strain (Competent high DH5α (TOYOBO)) was transformed with the above-described reaction solution. Next, fragments obtained by removing the antibody variable region part (VH or VL), using a technique similar to that described above from the Sfi I-digested ecdysone analogue-induced type expression plasmid (pIND-g4H or pIND-g4L) prepared in 3-4, and the corresponding Sfi I-digested anti-F.X antibody SB04-derived Sfi I-VH or Sfi I-VL fragment prepared in 3-3 were incorporated by a similar method.

Nucleotide sequences for each DNA fragment were determined using a BigDye Terminator Cycle Sequencing Kit (Applied Biosystems) and DNA sequencer ABI PRISM 3100 Genetic Analyzer (Applied Biosystems), according to the method described in the instruction manual. A group of sequences determined by the present method were analyzed using an analysis software, GENETYX-SV/RC Version 6.1 (Genetyx).

From the clones of interest, the respective plasmid DNAs were isolated using a QIAprep Spin Miniprep Kit (QIAGEN), and then dissolved in 100 μL of sterile water. Anti-F.IXa antibody chimeric H chain expression vector, anti-F.IXa antibody chimeric L chain expression vector, anti-F.X antibody chimeric H chain expression vector, and anti-F.X antibody chimeric L chain expression vector were named pcDNA4-g4-XB12H, pcDNA4-g4 XB12L, pIND-g4 SB04H, and pIND-g4 SB04L, respectively.

[Example 4] Production of Chimeric Bispecific Antibodies 4-1. Preparation of DNA Solutions Expression of the right arm antibody HL molecule expression vectors (pcDNA4-g4 XB12H and pcDNA4-g4 XB12L) is induced by tetracycline. In the absence of tetracycline, Tet repressor-encoding plasmid pcDNA6/TR (Invitrogen) is required to completely suppress their expressions. Furthermore, expression of the left arm antibody HL molecule expression vectors (pINE-g4 SB04H and pIND-g4 SB04L) was induced by an insect hormone ecdysone analogue (ponasterone A). Thus, plasmid pVgRXR (Invitrogen), which encodes the ecdysone receptor and retinoid X receptor that react with ponasterone A, was required to induce expression. Therefore, for the transfection of animal cells, a mixture of six types of plasmid DNAs in total was prepared. For 10 mL of cell culture, 3 μg each of pcDNA4-g4 XB12H, pcDNA4-g4 XB12L, pIND-g4 SB04H and pIND-g4 SB04L, as well as 18 μg each of pcDNA6/TR and pVgRXR were used.

4-2. Transfection of Animal Cells

Human fetal renal carcinoma cell-derived HEK293H strain (Invitrogen) was suspended in a DMEM medium (Invitrogen) containing 10% FCS (MOREGATE), and 10 mL of this was seeded at a cell density of $5 \times 10^5$ cells/mL in each dish used for adhesive cells (10-cm diameter, CORNING) and cultured for a day and night in a $CO_2$ incubator (37° C., 5% $CO_2$). The plasmid DNA mixture prepared in 4-1 was added to a mixture of transfection reagents, 75.8 μL of Lipofectaine 2000 (Invitrogen) and 2708 μL of Opti-MEM I medium (Invitrogen), and left to stand at room temperature for 20 minutes. The resulting mixture was added to the cells in each well and incubated for 4 to 5 hours in a $CO_2$ incubator (37° C., 5% $CO_2$).

4-3. Induction of Bispecific IgG Antibody Expression

Culture medium was removed by suction from the transfected cell culture as described above, and then 10 mL of a CHO-S-SFM-II (Invitrogen) medium containing 1 µg/mL tetracycline (Wako Pure Chemical Industries) was added. This mixture was incubated for one day in a $CO_2$ incubator (37° C., 5% $CO_2$) to induce primary expression of the right arm antibody HL molecule. Subsequently, after removing the medium by suction and washing with 10 mL of CHO-S-SFM-II medium, and adding 10 mL of a CHO-S-SFM-II medium containing 5 µM of ponasterone A (Invitrogen), this was incubated in a $CO_2$ incubator (37° C., 5% $CO_2$) for 3 days, and secondary expression of the left arm antibody HL molecule was induced so that the bispecific IgG antibody was secreted into the medium. The culture supernatant was recovered and centrifuged (approximately 2000 g for 5 min at room temperature) to remove the cells, and then sterilized by passing through a 0.22 µm filter MILLEX®-GV (Millipore). The sample was stored at 4° C. until use.

4-4. Antibody Purification

One hundred µL of rProtein A Sepharose™ Fast Flow (Amersham Biosciences) was added to 10 mL of the culture supernatant obtained according to the method described in Example 4-3, and the solution was mixed by overlying at 4° C. for 4 hours. The solution was transferred to an Ultrafree®.-MC 0.22 µm filter cup (Millipore) and after washing 3 times with 500 µL of TBS containing 0.01% Tween® 20, the rProtein A Sepharose™ resin was suspended in 100 µL of 10 mM HCl containing 0.01% Tween® 20 at pH 2.0 and left to stand for 2 minutes. Then, the antibody was eluted, and the eluate was immediately neutralized by adding 5 µL of 1 M Tris-HCl, pH 8.0.

4-5. Quantification of Human IgG Concentration

Goat anti-human IgG (Biosource International) was adjusted to 1 µg/mL with a coating buffer, and immobilized to a Nunc-Immuno plate (Nunc). After blocking with a diluent buffer (D.B.), a sample of the culture supernatant suitably diluted with D.B. was added. Furthermore, as a standard for calculating the antibody concentration, human IgG4 (humanized anti-TF antibody, see WO 99/51743) diluted with D.B. in a three-fold dilution series up to eleven stages starting from 2000 ng/mL was added similarly. After 3 washes, goat anti-human IgG, alkaline phosphatase (Biosource International) was reacted. After 5 washes, the color was developed using Sigma 104® phosphatase substrate (Sigma-Aldrich) as a substrate, and the absorbance at 405 nm was measured on an absorbance reader Model 3550 (Bio-Rad Laboratories) with a reference wavelength of 655 nm. Using the Microplate Manager III (Bio-Rad Laboratories) software, human IgG concentration in the culture supernatant was calculated from the standard curve.

[Example 5] Plasma Coagulation Assay

To elucidate whether a bispecific antibody corrects the coagulation ability of hemophilia A blood, effects of the bispecific antibody on activated partial thromboplastin time (APTT) were examined using Factor VIII-deficient plasma. A mixed solution comprising 50 µL of an antibody solution at various concentrations, 50 µL of Factor VIII-deficient plasma (Biomerieux), and 50 µL of APTT reagent (Dade Behring) was heated at 37° C. for 3 minutes. Coagulation reaction was initiated by adding 50 µL of 20 mM $CaCl_2$ (Dade Behring) to this mixed solution. The time required for coagulation was measured with CR-A (Amelung) connected KC10A (Amelung).

Using a calibration curve produced by defining the coagulation time for Factor VIII-deficient plasma as 0% and the coagulation for normal plasma as 100%, Factor VIII-like activity (%) of a bispecific antibody was calculated from the coagulation time measured when bispecific antibody was added.

[Example 6] Humanization of Bispecific Antibody

Anti-factor IXa antibody XB12 and anti-factor X antibody SB04, which were the most effective in shortening blood coagulation time, were subjected to humanization as follows.

6-1. Homology Search of Human Antibodies

Using a database constructed using amino acid sequence data of human antibodies from publicly disclosed Kabat Database (ftp://ftp.ebi.ac.uk/pub/databases/kabat/) and IMGT Database (http://imgt.cines.fr/), a homology search was carried out separately for the mouse XB12-H chain variable region, mouse XB12-L chain variable region, mouse SB04-H chain variable region, and mouse SB04-L chain variable region. The results confirmed that they have high homologies to the human antibody sequences shown below, and it was thus decided that the framework region (hereinafter abbreviated as FR) of humanized antibodies would be used.

(1) XB12-H chain variable region; KABATID-020619 (Kabat Database) (Mariette et al., Arthritis Rheum. 1993; 36: 1315-1324)

(2) XB12-L chain variable region: EMBL Accession No. X61642 (IMGT Database) (Mark et al., J. Mol. Biol. 1991, 222: 581-597.)

(3) SB04-H chain variable region: KABATID-025255 (Kabat Database) (Demaison et al., Immunogetetics 1995; 42: 342-352)

(4) SB04-L chain variable region: EMBL Accession No. AB064111 (IMGT Database) (Unpublished data)

Humanized antibodies in which complementarity determining regions (hereinafter abbreviated as CDR) of each mouse antibody were grafted into the FRs of human antibodies (1)-(4) were prepared.

Also, the web homology search site publicly disclosed by NCBI (http:/www.ncbi.nln.nih.gov/BLAST/) was used to search for secretory signal sequences of human antibodies that are highly homologous to the human antibodies of (1)-(4). The following secretory signal sequences obtained by the search were used.

(1) XB12-H chain variable region: GenBank Accession No. AF062120

(2) XB12-L chain variable region: GenBank Accession No. M74019

(3) SB04-H chain variable region: GenBank Accession No. BC019337

(4) SB04-L chain variable region: GenBank Accession No. AY204756.

6-2. Construction of Humanized Antibody Gene Expression Vector

Twelve synthetic oligoDNAs of about 50 bases were prepared from a nucleotide sequence encoding the amino acid sequence from the secretory signal sequence to the antibody variable region, such that about 20 bases of their 3'-end anneal with each other. Furthermore, a primer annealing to the 5'-end of an antibody variable region gene and having the XhoI cleavage sequence, and a primer annealing to the 3'-end of an antibody variable region gene and having the SfiI cleavage sequence were prepared.

One μL each of the synthetic oligoDNAs prepared at 2.5 μM were mixed, and 1× TaKaRa Ex Taq Buffer, 0.4 mM dNTPs, and 0.5 units TaKaRa Ex Taq (all from Takara Shuzo) were added to prepare a 48 μL reaction solution. After keeping this at 94° C. for 5 minutes, 2 cycles of reacting at 94° C. for 2 minutes, 55° C. for 2 minutes, and 72° C. for 2 minutes were performed to assemble and elongate each of the synthetic oligoDNAs. Next, 1 μL each of a primer annealing to the 5'-end and a primer annealing to the 3'-end of the antibody gene were added at 10 μM, and the antibody variable region genes were amplified by 35 cycles of reacting at 94° C. for 30 seconds, 55° C. for 30 seconds, and 72° C. for 1 min and then reacting at 72° C. for 5 minutes. After PCR, the entire reaction solution was subjected to 1% agarose gel electrophoresis. Amplified fragments having the size of interest (approximately 400 bp) were purified using QIAquick Gel Extraction Kit (QIAGEN) according to the method described in the instruction manual, and eluted with 30 μL of sterile water. These fragments were cloned using the pGEM-T Easy Vector System (Promega) according to the method described in the instruction manual. Nucleotide sequences for each of the DNA fragments were determined using the BigDye Terminator Cycle Sequencing Kit (Applied Biosystems) and an ABI PRISM 3700 DNA Sequencer (Applied Biosystems) according to the method described in the instruction manual.

A plasmid confirmed to have the correct humanized antibody variable region gene sequence was then digested with EcoRI and SfiI and the reaction solution was subjected to 1% agarose gel electrophoresis. DNA fragments having the size of interest (approximately 400 bp) were purified using QIAquick Gel Extraction Kit (QIAGEN) according to the method described in the instruction manual, and eluted with 30 μL of sterile water. Furthermore, after the EcoRI and SfiI digestion of the tetracycline-induced type expression plasmids (pcDNA4-g4H, pcDNA4-g4L) and the ecdysone analogue induced type expression plasmids (pIND-g4H, pIND-g4L) prepared in Example 3-3, fragments comprising the antibody constant region (approximately 5 kb) were purified using the QIAquick Gel Extraction Kit (QIAGEN) according to the method described in the instruction manual, and eluted with 30 μL of sterile water. The humanized XB12 antibody gene fragment (H chain variable region or L chain variable region) digested with EcoRI and SfiI, and the tetracycline-induced type expression plasmid (pcDNA4-g4H, pcDNA4g4L) digested with EcoRI and SfiI were subjected to ligation reaction using Rapid DNA Ligation Kit (Roche Diagnostics) according to the method described in the instruction manual. In addition, the humanized SB04 antibody gene fragment digested with EcoRI and SfiI (H chain variable region or L chain variable region), and the ecdysone analogue induced type expression plasmid (pIND-g4H, pIND-g4L) digested with EcoRI and SfiI were subjected to ligation reaction using the Rapid DNA Ligation Kit (Roche Diagnostics) according to the method described in the instruction manual. A portion of each of the reaction mixture was used to transform DH5α strain E. coli (TOYOBO).

Furthermore, an expression vector was prepared as follows for expression as an ordinary humanized antibody, but not as a bispecific antibody. Plasmids (pCAG-g4H, pCAG-gκ) with an insert of wild type antibody constant regions to pCAGGS having a chicken β-actin promoter (Niwa et al. 1991 Gene, 103: 193-199) were digested with XhoI and SfiI to prepare expression plasmids that carry humanized XB12 antibody gene fragment (H chain variable region or L chain variable region) or humanized SB04 antibody gene fragment (H chain variable region or L chain variable region) collected after digesting the bispecific antibody expression vector mentioned above with XhoI and SfiI. DNA ligation reaction was performed using the Rapid DNA Ligation Kit (Roche Diagnostics), and E. coli DH5α strain (TOYOBO) was transformed.

6-3. Preparation of Humanized Bispecific Antibody

The genes were transfected and expression was induced in HEK293H according to the methods described in Examples 4-2 and 4-3, using 4 types of humanized bispecific antibody expression vectors as well as pcDNA6/TR and pVgRXR. Further antibody purification and quantification of antibody concentration were conducted according to the methods shown in Examples 4-4 and 4-5.

6-4. Preparation of Humanized Antibodies

Expression of an ordinary humanized antibody, which is not a bispecific antibody, was accomplished by transfecting genes to HEK293H according to the method shown in Example 4-2, using humanized H chain antibody expression vector and humanized L chain antibody expression vector prepared in Example 6-3. After gene transfection, cells were washed by addition and removal of 10 mL of CHO-S-SFM-II medium (Invitrogen), then 10 mL of CHO-S-SFM-II was added, and then the cells were cultured for 3 days in a $CO_2$ incubator (37° C., 5% $CO_2$) for secretion of the humanized antibodies.

6-5. Activity Assessment of Humanized Bispecific Antibody and Modification of Antibody Sequence To assess the plasma coagulation ability of the prepared humanized bispecific antibody and chimeric bispecific antibody XB12/SB04, effects of the antibodies on APTT were examined using F.VIII-deficient plasma according to the method of Example 5. Amino acids of the human antibody FR were modified to increase activities of humanized bispecific antibodies whose blood coagulation capability has been reduced. In addition, the cysteine residues in the CDR3 of XB12 antibody VH, whose possible drop in thermostability is a concern, were modified to alanine. Specifically, mutations were introduced into the humanized antibody variable region using the QuikChange Site-Directed Mutagenesis Kit (Stratagene) according to the method described in the instruction manual. By repeating amino acid modifications to the FR sequence and assessment of blood coagulation ability, a humanized bispecific antibody (humanized XB12 antibody (VH:hXB12f-A, VL:hXBVL)/humanized SB04 antibody (VH:hSB04e, VL:hSBVL-F3f)) having the same activity as XB12/SB04 was obtained. Each antibody variable regions sequences is shown in the following SEQ ID NOs.

(1) humanized XB12 antibody VH (hXB12f-A) SEQ ID NO: 1 (nucleotide sequence), SEQ ID NO: 2 (amino acid sequence)
(2) humanized XB12 antibody VL (hXBVL) SEQ ID NO: 3 (nucleotide sequence), SEQ ID NO: 4 (amino acid sequence)
(3) humanized SB04 antibody VH (hSB04e) SEQ ID NO: 5 (nucleotide sequence), SEQ ID NO: 6 (amino acid sequence)
(4) humanized SB04 antibody VL (hSBVL-F3f) SEQ ID NO: 7 (nucleotide sequence), SEQ ID NO: 8 (amino acid sequence)

[Example 7] Modeling of Humanized Antibody

An antibody Fv region model was prepared by homology modeling using MOE software (Chemical Computing Group Inc.) to confirm the amino acid residues at the VH-VL interface of the humanized SB04 antibody. The amino acids of H39 and L38 at the VH-VL interface are both glutamine (Gln) and formation of hydrogen bonds by the side chains of both residues was confirmed (FIG. 1A). The amino acids of H45 and L44 were leucine (Leu) and proline (Pro), respectively, the side chains of both residues were very close to each other and were found to form a hydrophobic core (FIG. 1B). The amino acid residues at these two positions have been reported to be highly conserved in human antibodies (Vargas-Madrazo E et al. J. Mol. Recognit. 2003, 16: 113-120). Numbering of these antibodies such as H39, L38, H45, and L44 were based on the literature of Kabat et al. (Kabat E A et al. 1991. Sequences of Proteins of Immunological Interest. NIH).

[Example 8] Preparation and Assessment of H39 and L38 Amino Acid-Modified Humanized Antibody 8-1. Construction of an Expression Vector of H39 and L38-Modified Antibody To inhibit the association between humanized XB12 H chain and humanized SB04 L chain, H39 glutamine of humanized XB12H chain and L38 glutamine of humanized SB04 L chain were substituted based on the findings in Example 7. Specifically, to inhibit hydrogen bonding of the glutamine side chains and to allow electrostatic repulsion, both amino acids (H39 and L38) were substituted with lysine (Lys) or arginine (Arg) carrying a positive charge on their side chain, or to glutamic acid (Glu) or aspartic acid (Asp) which carry a negative charge on their side chain. Substitution of the humanized antibody gene was performed using QuickChange Site-Directed Mutagenesis Kit (Stratagene), and mutations were introduced according to the method described in the instruction manual. Each humanized antibody gene fragment carrying amino acid substitutions was inserted into a bispecific antibody expression vector used in Example 6-2 or into an ordinary antibody expression vector.

8-2. Preparation of Antibodies for Association Regulation Assessment and Association Regulation Assessment of the Antibodies To assess the regulation of H chain and L chain association, gene transfection into HEK293H was performed according to the method shown in Example 4-2 using 3 types of prepared antibody expression vectors: humanized XB12H chain (H39-modified), humanized SB04 L chain (L38-modified), and wild-type humanized XB12 L chain. The antibodies were then secreted into the culture supernatant. Next, antibody purification and quantification of antibody concentration were carried out according to the methods of Examples 4-4 and 4-5.

Two-hundred ng of purified antibodies were reduced in a sample buffer (TEFCO), applied to a 14% SDS-PAGE mini gel (TEFCO), and then subjected to electrophoresis. After electrophoresis, the gels were subjected to immobilization treatment by soaking in 7% acetic acid solution containing 10% methanol for 30 minutes, and then stained by soaking in SYPRO® Ruby protein gel stain solution (BIO-RAD) for one day and night. Subsequently, the gels were subjected to decolorization treatment by soaking in 7% acetic acid solution containing 10% methanol for 1 hour and the image was analyzed using a fluorescence imager FluorImager SI (Amersham Biosciences) and the image was obtained. The obtained image was used to calculate the fluorescence intensities of the H chain and L chain bands using ImageQuant ver. 4.2 (Amersham Biosciences).

Figure 2:
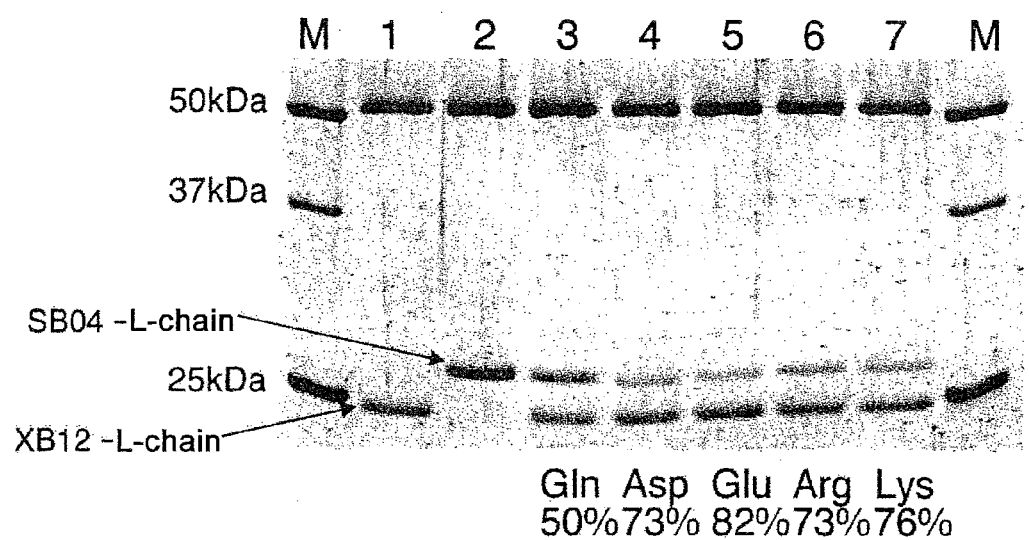
FIG. 2 is a photograph depicting the results of an assay evaluating the associations between H and L chains in H39 and L38-modified antibodies. These results demonstrate that for all modified antibodies, the associated proportion of the antibody of interest is increased when compared to the wild type.
Description of the Lanes:
M: molecular marker;
1: humanized XB12 H chain (Q)+humanized XB12 L chain (Q);
2: humanized XB12 H chain (Q)+humanized SB04 L chain (Q);
3: wild type: humanized XB12 H chain (Q)+humanized XB12 L chain (Q)+humanized SB04 L chain (Q);
4: D variant: humanized XB12 H chain (D)+humanized XB12 L chain (Q)+humanized SB04 L chain (D);
5: E variant: humanized XB12 H chain (E)+humanized XB12 L chain (Q)+humanized SB04 L chain (E)

The results are shown in FIG. 2. The proportion (%) of the XB12-L chain of interest was calculated according to the formula "XB12-L chain/total amount of L chain (XB12-L chain+SB04-L chain)×100" using the calculated fluorescence intensity values. The proportion was 50% when the amino acids of the humanized XB12 H chain (H39) and humaized SB04 L chain (L38) were glutamine (Gln) as in the wild type, whereas the proportion of the humanized XB12L chain increased when H39 and L38 were substituted. In the case of substitution to glutamic acid (Glu), this proportion was found to increase 1.6 times to 82%.

8-3. Preparation of Bispecific Antibodies for Coagulation Activity Assessment and Coagulation Activity Assessment of the Antibodies To assess the coagulation activity, gene transfection into HEK293H and induction of expression were carried out according to the methods described in Examples 4-2 and 4-3, using the prepared humanized XB12 H chain (H39-modified) and humanized SB04 L chain (L38-modified) bispecific antibody expression vector and wild-type humanized XB12 L chain and humanized SB04 H chain bispecific antibody expression vector, pcDNA6/TR and pVgRXR. Furthermore, antibody purification and quantification of antibody concentration were carried out according to the methods of Examples 4-4 and 4-5.

Assessment of coagulation activity was performed according to the method shown in Example 5, and the results are shown in FIG. 3. Glutamic acid (Glu: E)-modified antibody whose proportion increased up to 82% in the association regulation assessment was found to show a coagulation activity greater than or equal to that of the wild type.

8-4. Preparation of Antibodies for Binding Activity Assessment

To assess the binding activity to Factor IXa and Factor X, gene transfection into HEK293H and secretion of antibodies into the culture supernatant was performed according to the method described in Example 4-2, using humanized XB12 H chain (H39-modified) and wild-type humanized XB12L chain antibody expression vector, or wild-type humanized SB04 H chain and humanized SB04 L chain (L38-modified) antibody expression vector. Furthermore, antibody purification and quantification of antibody concentration were carried out according to the methods of Examples 4-4 and 4-5.

Assessment of binding activity against Factor IXa and Factor X were performed according to the methods described in Examples 1-2 and 2-2. The results are shown in FIG. 4 and FIG. 5. It was confirmed that substitution of amino acids at H39 and L38 did not alter the binding activity.

These results suggested that by modifying H39 of XB12 H chain and L38 of SB04 L chain, the proportion of bispecific antibodies of interest could be increased without decreasing biological activities, including binding activity to antigens and coagulation activity that substitute for Factor VIII. So far, including the methods using knob and hole, there are no reported cases where the association was regulated by introducing only a single amino acid mutation in a polypeptide without decreasing the function. Accordingly, the findings of the present invention are considered to be the first of such kind.

[Example 9] Preparation and Assessment of L44 Amino Acid-Modified Humanized Antibody 9-1. Construction of an Expression Vector L44-Modified Antibody To inhibit the association between humanized XB 12 H chain and humanized SB04 L chain, based on the findings in Example 7, L44 proline of humanized SB04 L chain was substituted with an amino acid carrying a charge on its side chain. Specifically, proline present in the hydrophobic core of the VH-VL interface was substituted with lysine (Lys) or arginine (Arg) carrying positive charge on its side chain, or with glutamic acid (Glu) or aspartic acid (Asp) carrying a negative charge on its side chain. Substitution of the humanized antibody gene was performed using QuickChange Site-Directed Mutagenesis Kit (Stratagene), and mutations were introduced according to the method described in the instruction manual. Each humanized antibody gene fragment having amino acid substitutions was inserted into a bispecific antibody expression vector used in Example 6-2 or into an ordinary antibody expression vector.

9-2. Preparation of Antibodies for Association Regulation Assessment and Association Regulation Assessment of the Antibodies To assess the regulation of H chain and L chain association, gene transfection into HEK293H was performed according to the method of Example 4-2, using 3 types of prepared antibody expression vectors, humanized SB04 L chain (L44-modified), wild-type humanized XB12H chain, and wild-type humanized XB12 L chain, and the antibodies were secreted into the culture supernatant. Furthermore, antibody purification and quantification of antibody concentration were carried out according to the methods of Examples 4-4 and 4-5.

Two-hundred ng of purified antibodies were reduced in a sample buffer (TEFCO), applied to a 14% SDS-PAGE mini gel (TEFCO), and then subjected to eectrophoresis. After electrophoresis, the gels were subjected to immobilization treatment by soaking in 7% acetic acid solution containing 10% methanol for 30 minutes, and then stained by soaking in SYPRO® Ruby protein gel stain solution (BIO-RAD) for one day and night. Subsequently, the gels were subjected to decolorization treatment by soaking in 7% acetic acid solution containing 10% methanol for 1 hour and the image was analyzed using a fluorescence imager FluorImager SI (Amersham Biosciences) and the images were obtained. The obtained images were used to calculate the fluorescence intensities of the H chain and L chain bands using ImageQuant ver. 4.2 (Amersham Biosciences).

The results are shown in FIG. 6. The proportion (%) of the XB12-L chain of interest was calculated according to the formula "XB12-L chain/total amount of L chain (XB12-L chain+SB04-L chain)×100" using the calculated fluorescence intensity values. The proportion was 47% when the amino acid of the humanized SB04 L chain (L44) was proline (Pro) as in the wild type, whereas the proportion of the humanized XB12L chain increased when L44 was substituted, and this proportion was found to increase 1.8-1.9 times to 86-90%.

9-3. Preparation of Bispecific Antibodies for Coagulation Activity Assessment and Coagulation Activity Assessment of the Antibodies To assess the coagulation activity, gene transfection into HEK293H and induction of expression were carried out according to the methods described in Examples 4-2 and 4-3, using the prepared humanized SB04 L chain (L44-modified) bispecific antibody expression vector and wild-type humanized XB12 H chain, humanized XB12 L chain, and humanized SB04 H chain bispecific antibody expression vector, pcDNA6/TR and pVgRXR. Furthermore, antibody purification and quantification of antibody concentration were carried out according to the methods of Examples 4-4 and 4-5.

Assessment of coagulation activity was performed according to the method shown in Example 5, and the results are shown in FIG. 7. All modified antibodies whose proportion had increased in the association regulation assessment were found to show a coagulation activity greater than that of the wild type.

9-4. Preparation of Antibodies for Binding Activity Assessment

To assess the binding activity against Factor X, gene transfection into HEK293H and secretion of antibodies into the culture supernatant was performed according to the method described in Example 4-2, using wild-type humanized SB04 H chain and humanized SB04 L chain (L44-modified) antibody expression vector. Furthermore, quantification of antibody concentration in the culture supernatant was carried out according to the method of Example 4-5.

Assessment of binding activity against Factor X was performed using the culture supernatant according to the method described in Example 2-2. The results are shown in FIG. 8. It was confirmed that substitution of amino acid at L44 does not change the binding activity.

These results suggested that by modifying the amino acid at one position, L44, in the SB04 L chain, the proportion of bispecific antibodies of interest could be increased without decreasing biological activities, including binding activity to the antigens and coagulation activity that substitute for Factor VIII. So far, including the methods using knob and hole, there are no reported cases where the association was regulated by introducing only a single amino acid in a polypeptide without decreasing the function. Thus, the findings of the instant invention are considered to be the first of such kind.

[Example 10] Preparation and Assessment of H39 and L38, and L44 Amino Acid-Modified Humanized Antibody 10-1. Construction of an Expression Vector of H39 and L38, and L44-Modified Antibody To inhibit the association between humanized XB12 H chain and humanized SB04 L chain, H39 of humanized XB12 H chain and L38 and L44 of humanized SB04 L chain were substituted with amino acids carrying a charge on their side chain based on the findings of Examples 8 and 9. Specifically both amino acids at H39 of humanized XB12 H chain and L38 of humanized SB04 L chain were substituted with glutamic acid (Glu), which was found to be most effective in Example 8, and proline present at L44 of humanized SB04 L chain was substituted to lysine (Lys) or arginine (Arg) carrying a positive charge in their side chain, or to glutamic acid (Glu) or aspartic acid (Asp) carrying a negative charge in their side chain. Substitution of the humanized antibody gene was performed using QuickChange Site-Directed Mutagenesis Kit (Stratagene), and mutations were introduced according to the method described in the instruction manual. Each humanized antibody gene fragment carrying amino acid substitutions was inserted into the bispecific antibody expression vector used in Example 6-2 or an ordinary antibody expression vector.

10-2. Preparation of Antibodies for Association Regulation Assessment and Association Regulation Assessment of the Antibodies To assess the regulation of H chain and L chain association, gene transfection into HEK293H was performed according to the method of Example 4-2, using 3 types of antibody expression vectors: modified humanized SB04 L chain, modified humanized XB12 H chain, and wild-type humanized XB12 L chain. The antibodies were then secreted into the culture supernatant. Furthermore, antibody purification and quantification of antibody concentration were carried out according to the methods of Examples 4-4 and 4-5.

Two-hundred ng of purified antibodies were reduced in a sample buffer (TEFCO), applied to a 14% SDS-PAGE mini gel (TEFCO), and then subjected to electrophoresis. After electrophoresis, the gels were subjected to immobilization treatment by soaking in 7% acetic acid solution containing 10% menthaol for 30 minutes, and then stained by soaking in SYPRO® Ruby protein gel stain solution (RIO-RAD) for one day and night. Subsequently, the gels were subjected to decolorization treatment by soaking in 7% acetic acid solution containing 10% methanol for one hour and the image was analyzed using a fluorescence imager FluorImager SI (Amersham Biosciences) and the images were obtained. The obtained images were used to calculate the fluorescence intensities of the H chain and L chain bands using ImageQuant ver. 4.2 (Amersham Biosciences).

The results are shown in FIG. 9. The proportion (%) of the XB12-L chain of interest was calculated according to the formula "XB12-L chain/total amount of L chain (XB12-L chain+SB04-L chain)×100" using the calculated fluorescence intensity values. The proportion was 82% when both amino acids of the humanized XB12 H chain (139) and humanized SB04 L chain (L38) was modified to glutamic acid (Glu) and the humanized SB04 L chain (L44) was proline (Pro) as in the wild type, whereas the proportion of the humanized XB12L chain increased to 94-96% when L44 was substituted in addition to the substitution of both amino acids of the humanized XB12 H chain (H39) and humanized SB04 L chain (L38) to glutamic acid (Glu). This increase in proportion was greater tan the 86-90% observed when L44 alone was substituted in Example 9.

10-3. Preparation of Bispecific Antibodies for Coagulation Activity Assessment and Coagulation Activity Assessment of the Antibodies To assess the coagulation activity, gene transfection into HEK293H and induction of expression were carried out according to the methods described in Examples 4-2 and 4-3, using the prepared modified humanized XB12 H chain, humanized XB12 L chain, and humanized SB04 H chain bispecific antibody expression vector and wild-type humanized XB12 H chain, humanized XB12 L chain, and humanized SB04 H chain bispecific antibody expression vector, pcDNA6/TR and pVgRXR. Furthermore, antibody purification and quantification of antibody concentration were carried out according to the methods of Examples 4-4 and 4-5.

Assessment of coagulation activity was performed according to the method shown in Example 5, and the results are shown in FIG. 10. All modified antibodies whose proportion had increased in the association regulation assessment were found to show a coagulation activity equivalent to that of the wild type.

10-4. Preparation of Antibodies for Binding Activity Assessment

To assess the binding activity against Factor X, gene transfection into HEK293H and secretion of antibodies into the culture supernatant was performed according to the method described in Example 4-2 using wild-type humanized SB04 H chain and modified humanized SB04 L chain antibody expression vector. Furthermore, quantification of antibody concentration in the culture supernatant was carried out according to the method of Example 4-5.

Assessment of binding activity against Factor X was performed using the culture supernatant according to the method described in Example 2-2. The results are shown in FIG. 11. It was confirmed that substitution of both amino acids at L38 and L44 did not alter the binding activity.

These results suggested that by modifying the amino acids at H39 of the XB12 H chain and L38 and L44 in the SB04 L chain, the proportion of bispecific antibodies of interest can be increased without decreasing biological activities which are binding activity to antigens and coagulation activity that substitute for Factor VIII. The proportion of the bispecific antibody was found to increase as the number of amino acids modified at the interface increased.

[Example 11] Separation and Structure Determination of Structural Isomers of hVB22B u2-wz4 sc(Fv)2

11-1. Preparation of Humanized Anti-Human MpI Antibody hVB22B u2-wz4 sc(Fv)2

Methods for producing hVB22B u2-wz4 sc(Fv)2 (hereafter referred to as u2-wz4) which is a humanized anti-MpI antibody is described in WO2005/56604. This gene was prepared by PCR using a nucleotide sequence encoding the linker sequence (GlyGlyGlyGlySer) ×3 (SEQ ID NO: 60) so that it will comprise a nucleotide sequence composed of VH-linker sequence-VL-linker sequence-VH-linker sequence-VL (see SEQ ID NO: 12; and SEQ ID NO: 286 of WO2005/56604). After the nucleotide sequence of the gene was confirmed, cell lines with stable expression was prepared by constructing an expression vector by cloning a DNA fragment into expression vector pCXND3, and introducing the gene into CHO-DG44 cells. More specifically, 0.75 mL of a mixture of the expression vector (20 μg) and CHO-DG44 cells (1×10$^7$ cells/mL) suspended in PBS was placed on ice for 10 minutes and transferred to a cuvette, and then a pulse was applied at 1.5 kV and 25 μFD using a Gene Pulser Xcell™ (BioRad). After a recovery period of 10 minutes at room temperature, cells subjected to electroporation treatment were selected by placing them into CHO-S-SFMII medium (Invitrogen) containing 500 μ/mL Geneticin (Invitrogen), and an u2-wz4-producing CHO cell line was established.

Since the humanized antibody, hVB22B u2-wz4 sc(Fv)2, does not have a Flag tag added, the purification from the culture supernatant was carried out using a fusion protein of GST and MG10 (Gln213 to Ala231 in the amino acid sequence of human MpI) which is an epitope recognized by the antibody. The MG10-GST fusion protein was purified using Glutathione Sepharose 4B (Amersham Biosciences) according to the supplier's protocol. Then, the purified MG10-GST fusion protein was immobilized onto HiTrap NHS-activated HP (Amersham Biosciences) to prepare an affinity column, according to the supplier's protocol. The culture supernatant of CHO cells expressing the humanized antibody, hVB22B u2-wz4 sc(Fv)2, was loaded onto the MG10-GST fusion protein-immobilized column, humanized antibody hVB22B u2-wz4 sc(Fv)2 was adsorbed to the column, and then was eluted with 100 mM Glycine-HCl (pH 3.5), 0.01% Tween80. The eluted fractions were immediately neutralized with 1 M Tris-HCl (pH7.4), and the monomer was purified by gel filtration chromatography using HiLoad 16/60 Superdex200pg (Amersham Biosciences). 20 mM citrate buffer (pH7.5) containing 300 mM NaCl and 0.01% Tween 80 was used in the gel filtration chromatography.

11-2. Separation and Purification of Conformational Isomers of hVB22B u2-wz4 sc(Fv)2

Since hVB22B u2-wz4 sc(Fv)2 is an sc(Fv)2 composed of the sequence $VH_1$-linker-$VL_2$-linker-$VH_3$-linker-$VL_4$, as shown in FIG. 12, depending on the combination of Fvs (molecules having non-covalent bonds between VH and VL), 2 kinds of conformational isomers can exist, as in VB22B sc(Fv)2, which are the bivalent scFv-type in which each pairs of $VH_1$ and $VL_2$, and $VH_3$ and $VL_4$ forms a Fv, and the single chain diabody-type in which each pairs of $VH_1$ and $VL_4$, and $VH_2$ and $VL_3$ form a Fv.

Result of examination of the separation of conformational isomers of hVB22 u2-wz4 sc(Fv)2 suggested that each component of hVB22BE u2-wz4 sc(Fv)2 can be separated by cation exchange chromatography using Bio Assist S (TOSOH) under the following elution conditions:

Mobile phase A: 20 mM sodium phosphate, pH7.5
Mobile phase B: 20 mM sodium phosphate, 500 mM NaCl, pH 7.5
Flow rate: 0.8 mL/min
Gradient: B 0% to B 35% (30 minutes)

Under the above-mentioned conditions, hVB22B u2-wz4 sc(Fv)2 was separated into two peaks. The chromatogram shown in FIG. 13 was obtained, and starting from the shorter retention time, the peaks were named peak 1 and peak 2.

The molecular weight of peak 1 and peak 2 were measured using a Q-TOF-type mass spectrometer (Q T of Ultima, Micro Mass). Sample solutions were infused into Q-TOF, and deconvolution of the obtained polyvalent ion spectra (+) using the included software (MassLynx) gave results showing that the molecular weight of peak 1 and peak 2 are 53768 Da and 53769 Da, respectively. This showed that peak 1 and peak 2 have the same molecular weight.

Peptide mapping was performed on peak 1 and peak 2. After reductive denaturation and carboxymethylation, peptide fragments were obtained by digestion using trypsin, and peptide maps were obtained by reverse-phase chromatography (YMC-Pack-ODS). Comparing the peptide maps of peak 1 and peak 2, the mapping patterns of peak 1 and peak 2 were the same as shown in FIG. 14, therefore, the amino acid primary structure was found to be the same.

Since hVB22B u2-wz4 sc(Fv)2 is not glycosylated, peak 1 and peak 2 have the same molecular weight according to TOF-MASS measurements, and peak 1 and peak 2 have the same mapping patterns, peak 1 and peak 2 were found to be conformational isomers having different three dimensional structures.

Since hVB22B u2-wz4 sc(Fv)2 is an sc(Fv)2 comprising the sequence, $VH_1$-linker-$VL_2$-linker-$VH_3$-linker-$VL_4$, as shown in FIG. 12, depending on the combination of Fvs (molecules comprising non-covalent bonds between VH and VL), 2 kinds of conformational isomers can exist. Namely, the isomers are the bivalent scFv-type in which each pairs of $VH_1$ and $VL_2$, and $VH_3$ and $VL_4$ forms a Fv, and the single chain diabody-type in which each pairs of $VH_1$ and $VL_4$, and $VH_2$ and $VL_3$ forms a Fv. Peak 1 and peak 2 were considered to have either one of the conformations; the bivalent scFv-type or the single chain diabody-type.

Protease-limited proteolysis was developed as an analysis method for identifying the two types of conformational isomers. Since the linker portion of sc(Fv)2 has a relatively free structure, it is considered to have low resistance to proteases, and peak 1, peak 2, and hVB22B u2-wz4 sc(Fv)2 (The ratio of peak 1:peak 2 is approximately 1:4) were reacted with subtilisin A, a type of protease, under the following condition:

20 mM sodium citrate 150 mM NaCl, pH7.5
hVB22B u2-wz4 sc(Fv)2 peak 1 or peak 2: 0.15 mg/mL
Subtilisin A: 10 µg/mL
37° C., 30 minutes After the reaction, reductive SDS-PAGE was performed using Phastgel Homogeneous 12.5%. As a result as shown in FIG. 15, hVB22B u2-wz4 sc(Fv)2 bulk, peak 1, and peak 2 all showed the same band patterns. The use of the above-mentioned reaction conditions was found to enable partial and limited digestion of the linker portions of hVB22B u2-wz4 sc(Fv)2, since specific bands for each of the fragments that appeared to be produced by the digestion of the three linker portions of hVB22B u2-wz4 sc(Fv)2 were obtained.

When one of the three linkers is cleaved in the bivalent scFv-type and single chain diabody-type conformations, as shown in FIG. 16, under native conditions, the apparent molecular weight will not change no matter which linker among the three is cleaved in the single chain diabody-type conformation due to non-covalent bonding between VH and VL. However, in the bivalent scFv-type when the central linker is cleaved, molecular species having half the molecular weight will be produced. Therefore, hVB22B u2-wz4 sc(Fv)2 bulk, peak 1, and peak 2 whose linkers were partially cleaved by the above-mentioned reaction conditions were analyzed by gel filtration chromatography using TSK Super SW2000 (TOSOH). Gel filtration chromatography was performed under the following conditions:

Mobile phase: DPBS(−) pH7.4
Flow rate: 0.2 mL/min

As a result, as shown in FIG. 17, minibody peaks was not observed at all in peak 2, whereas, minibody peaks (approximately half the molecular weight) were observed for peak 1. hVB22B u2-wz4 sc(Fv)2 bulk which is a mixture of peak 1 and peak 2 showed low-molecular weight peaks whose amount correspond to the abundance ratio of peak 1. Therefore, these results identified peak 1 as a bivalent scFv-type and peak 2 as a single chain diabody-type.

[Example 12] Preparation, Conformational Isomer Analysis, and Identification of VH/VL Interface-Modified sc(Fv)2

12-1. Preparation of VH/VL Interface-Modified sc(Fv)2

VH/VL interface-modified sc(Fv)2 was prepared by the following method to confirm whether the formation of conformational isomers of sc(Fv)2 could be regulated through regulation of the association by the VH/VL interface modification to sc(Fv)2, which is a minibody.

Gln at position 39 of VH (position 39 in the amino acid sequence of SEQ ID NO: 13; see SEQ ID NO: 289 of WO2005/56604), and Gln at position 38 of VL (position 43 in the amino acid sequence of SEQ ID NO: 14; see SEQ ID NO: 289 of WO2005/56604) which are amino acids that form the VH/VL interface of u2-wz4 were modified as follows. First, the hVB22B u2-wz4(v1) se(Fv)2 gene (hereinafter referred to as v1; the nucleotide sequence is shown in SEQ ID NO: 15, and the amino acid sequence encoded by the nucleotide sequence is shown in SEQ ID NO: 16), in which Gln at position 39 of VH1 (genetic codon: CAG) was modified to Glu (genetic codon: GAG), Gln at position 38 of VL2 (genetic codon: CAG) was modified to Glu (genetic codon: GAG), Gln at position 39 of VH3 (genetic codon: CAG) was modified to Lys (genetic codon: AAG), and Gln at position 38 of VL4 (genetic codon: CAG) was modified to Lys (genetic codon: AAG), was produced. Furthermore, the hVB22B u2-wz4(v3) sc(Fv)2 gene (hereinafter referred to as v3; the nucleotide sequence is shown in SEQ ID NO: 17, and the amino acid sequence encoded by the nucleotide sequence is shown in SEQ ID NO: 18), in which Gln at position 39 of VH1 (genetic codon: CAG) was modified to Glu (genetic codon: GAG), Gln at position 38 of VL2 (genetic codon: CAG) was modified to Lys (genetic codon: AAG), Gln at position 39 of VH3 (genetic codon: CAG) was modified to Lys (genetic codon: AAG), and Gln at position 38 of VL4 (genetic codon: CAG) was modified to Glu (genetic codon: GAG), was produced. Gene modification was carried out by introducing point mutations using QuikChange Site-Directed Mutagenesis Kit (STRATAGENE) according to the manufacturer's protocol. After confirming the nucleotide sequences of each genes, stable cell lines were prepared by constructing expression vectors by cloning DNA fragments into expression vector pCXND3, and introducing the gene into CHO-DG44 cells. The v1-producing CHO cell line and v3-producing CHO cell line were established according to the method shown in Example 11.

Monomeric molecules of variants v1 and v3 were purified according to the method of Example 11 using the MG10-GST fusion protein immobilized column. The results of gel filtration chromatography shown in FIG. 18 showed that for variants v1 and v3, the dimers and larger aggregates decreased in the culture supernatant and the proportion of monomers increased from 59% (u2-wz4 before modification) to 89% for v1 and 77% for v3. It seems that modification of amino acids at the VH/VL interface inhibits unfavorable associations by charge repulsion and promotes favorable association in variants v1 and v3. Accordingly, efficient expression of the monomeric molecules was successfully accomplished by this regulation of the association.

12-2. Conformational Isomer Analysis and Identification of VH/VL Interface-Modified sc(Fv)2

The ratios of conformational isomers present in the obtained VH/VL interface-modified v1 and v3, and in the unmodified u2-wz4 were analyzed by cation exchange chromatography and isoelectric focusing. The conformations were identified by the protease-limited proteolysis method.

Cation exchange chromatography was performed as follows:
Column: TSK-gel Bioassist S, 4.6 mmφ×50 mm (TOSOH)
Flow rate: 0.8 mL/min
Detection wavelength: 220 nm
Elution condition:
Eluent A: 20 mmol/L Phosphate buffer (pH 7.0)
Eluent B: 20 mmol/L Phosphate buffer/500 mmol/L NaCl (pH7.0)
Gradient:

| Time (minutes) | B % |
|---|---|
| 0 | 0 |
| 5 | 0 |
| 25 | 30 |
| 25.1 | 100 |
| 35 | 100 |
| 35.1 | 0 |

Isoelectric focusing was performed as follows. PhastGel Dry IEF gel (Amersham Biosciences) was swollen for 30 minutes in the gel swelling solution described below. First, the samples were applied to the swollen gel, and subjected to electrophoresis using the PhastSystem under the following conditions. After electrophoresis, the gel was soaked for 30 minutes in a 20% TCA solution, then subjected to a five-minute wash for three times or more in milliQ water, and then to Coomassie stained or silver stained depending on the protein concentration of the samples. In Coomassie staining, 0.02% CBB contaning 0.1% $CuSO_4$ (w/v) was used as the solution for staining, and 30% methanol containing 10% acetic acid was used for decolorization. In silver staining, Silver stain kit, Protein (Amersham Biosciences) was used and staining was performed according to the standard protocol attached to the kit.

| <gel swelling solution> | |
|---|---|
| Pharmalyte 8.5-10 | 80 µL |
| Biolyte 7-9 | 10 µL |
| Biolyte 3-9 | 10 µL |
| 20% Glycerol | 2.0 mL |

| <electrophoresis program> | |
|---|---|
| SAMPLE APPLICATION DOWN AT step 2 | 0 Vh |
| SAMPLE APPLICATION UP AT step 3 | 0 Vh |
| Step 1 2000 V 2.5 mA 3.5 W 15° C. | 75 Vh |
| Step 2 200 V 2.5 mA 3.5 W 15° C. | 15 Vh |
| Step 3 2000 V 2.5 mA 3.5 W 15° C. | 410 Vh |

Conformations were identified under the following conditions by the protease-limited proteolysis method. Peak 1 purified from u2-wz4, peak 2 purified from u2-wz4, and variant v1 and variant v3 were allowed to react using subtilisin A under the following conditions:
20 mM sodium citrate, 150 mM NaCl, pH7.5
hVB22B u2-wz4 sc(Fv)2 peak 1 or peak 2: 0.15 mg/mL
Subtilisin A: 10 µg/mL
37° C., 30 minutes The obtained reaction solution was analyzed by gel filtration chromatography under the following conditions:
Column: TSKgel Super2000sw (TOSOH)
Eluent: 50 mM sodium phosphate, 300 mM KCl, pH7.0
Flow rate: 0.2 mL/min
Detection: 220 nm From the results of conformational isomer analysis by cation exchange chromatography and isoelectric focusing shown in FIGS. 19 and 20, u2-wz4 was found to be expressed as a mixture of both conformational isomers in which 24% is the bivalent scFv-type and 76% is the single chain diabody-type, whereas 100% of variant v1 was expressed as the single chain diabody-type conformational isomer, and 100% of variant v3 was expressed as the bivalent scFv-type conformational isomer. Furthermore, as shown in FIG. 21, the results of protease-limited proteolysis showed that the minibody peaks are found in variant v3 as in peak 1 purified from u2-wz4 and that the minibody peaks are absent in variant v1 as in peak 2 purified from u2-wz4. This data confirms that variant v1 is expressed as a single chain diabody-type conformational isomer and variant v3 is expressed as a bivalent scFv-type conformational isomer.

[Example 13] Activity Assessment and Stability Assessment of VH/VL Interface-Modified sc(Fv)2

13-1. Assessment of Biological Activity of VH/VL Interface-Modified sc(Fv)2

It has been reported in literature (Blood 2005; 105:562-566) that anti-human MpI antibody VB22B sc(Fv)2 shows TPO-like agonist activity. Accordingly, the TPO-like agonist activity of the separated conformational isomers was assessed using BaF3-human MpI or BaF3-monkey MpI that indicates TPO-dependent growth.

Each cell was washed twice with RPMI1640 (Invitrogen) containing 1% Fetal Bovine Serum (Invitrogen), then suspended in RPMI1640 containing 10% Fetal Bovine Serum to $4 \times 10^5$ cells/mL, and then dispensed into a 96-well plate at 60 µL/well. 40 µL of rhTPO (R&D) or the conformational isomer sample was added to each well at various concentrations and, and the cells were cultured at 37° C. under 5% $CO_2$ for 24 hours. Immediately after adding WST-8 reagent (Cell Count Reagent SF, Nakalai Tesque) at 10 µL/well, the absorbance at 450 nm (control: 655 nm) was measured on Benchmark Plus, and the absorbance at 450 nm (control: 655 nm) was measured again after culturing for 2 hours. Since WST-8 reagent exhibits a chromogenic reaction at 450 nm depending on the number of viable cells, TPO-like agonist activity was assessed using the change in absorption during the 2 hours as an indicator.

The results of assessing TPO-like agonist activity in BaF3-human MpI and BaF3-monkey MpI using the purified VB22B sc(Fv)2 conformational isomer are shown individually in FIG. 22. Comparison of agonist activity of the conformational isomers of peak 1 and peak 2 indicated that peak 2 possessed a significantly higher activity. This suggested that in order for anti-MpI antibody sc(Fv)2 to exert TPO-like agonist activity, it has to form a single chain diabody conformation.

According to the method indicated in Example 1, agonist activity of VH/VL interface-modified v1 and v3 were evaluated. Agonist activity differs greatly between the conformational isomers, and as shown in FIG. 12, peak 2 having a single chain diabody conformation showed a very high agonist activity, whereas the activity of peak 1 having a bivalent scFv conformation was decreased significantly. As shown in FIG. 22, variant v1 showed the same activity as peak 2, and variant v3 showed nearly the same activity as peak 1. Accordingly, biological activities also confirmed that variant v1 formed a single chain diabody conformation, and variant v3 forms a bivalent scFv conformation.

13-2. Assessment of Stability of VH/VL Interface-Modified sc(Fv)2

To assess the stability of peak 1 purified from u2-wz4, peak 2 purified from u2-wz4, variant v1, and variant v3, the denaturation transition temperature (Tm value) was measured using differential scanning calorimetry under the following conditions.

DSC: N-DSCII (Applied Thermodynamics)
Elation conditions: 20 mM sodium citrate, 300 mM NaCl, pH7.0
Protein concentration: 0.1 mg/mL
Scanning speed: 1° C./minute The results of the respective DSC measurements are shown in FIG. 23. The Tm values for peak 2 purified from uw-wz4 and variant v1 had nearly the same Tm values as the unmodified form, and their stabilities were found to be the same. Between peak 1 purified from u2-wz4 and variant v3, variant v3 showed slightly lower stability. As an example of interface regulation performed according to methods that utilize the knob-into-hole technique, there is a report (Acta. Pharmacol. Sin. 2005 26(6): 649-58) that in the heterologous association of IgG CH3 domains, the Tm value for the unmodified CH3 domain is 80.4° C., whereas the Tm value for the modified CH3 domain is 69.4° C., and the Tm value decreases by a large amount and the stability decreases. In contrast, it was confirmed in the present invention that association can be regulated without decreasing the stability.

Next, stability assessment was performed by thermal acceleration tests under the following conditions on peak 1 purified from u2-wz4 and peak 2 purified from u2-wz4, and on VH/VL interface-modified variants v1 and v3.

<Thermal Acceleration Conditions>
Solution conditions: 20 mM sodium citrate, pH 6.0
Protein concentration: 0.25 mg/mL
Acceleration conditions: 40° C.-6 days, 12 days The accelerated samples were analyzed by gel filtration chromatography and cation exchange chromatography under the following conditions.

As shown in FIG. 24, the results of gel filtration chromatography analysis confirmed that the monomer recovery rate is nearly the same for peak 2 purified from u2-wz4 and variant v1, and the stability of association was nearly the same. The monomer recovery rate was also nearly the same for peak 1 purified from u2-wz4 and variant v3, and the stability of association was nearly the same in both conformational isomers.

As indicated in FIG. 25, as a result of cation exchange chromatography analysis, purified peak 1 in the unmodified form isomerized to peak 2 by an isomerization reaction, and purified peak 2 in the unmodified form isomerized to peak 1 by an isomerization reaction, whereas the VH/VL interface-modified v1 and v2 did not undergo an isomerization reaction even after the thermal acceleration. It was found out that applying modifications to the VH/VL interface allow one of the two types of conformational isomers alone to be expressed at 100%, and in addition, the respective conformational isomers obtained do not undergo an isomerization reaction and can be stably stored.

The present Example demonstrated that one of the two types of conformational isomers alone can be expressed at 100% by using the VH/VL interface modifications applied to v1 and v3. A known method for VH/VL-interface regulation for obtaining a single chain antibody having the conformation of interest is a method of regulating the conformations of bispecific diabodies using the knobs-into-holes technique (Protein Sci. 1997 April; 6(4):781-8, Remodeling domain interfaces to enhance heterodimer formation, Zhu Z, Presta L G, Zapata G, Carter P). It is reported that this method increases the percentage of formation of the heterodimer conformation of interest from 72% to 92% by modifying amino acids at a total of four positions per VH/VL interface. In contrast the present invention succeeded in obtaining the conformation of interest at 100% and without decreasing the thermal stability and the stability of the conformational isomer by modifying amino acids at four positions.

[Example 14] Humanization of Bispecific Antibody Carrying a Hybrid L Chain

The bispecific antibody (Japanese Patent Application No. 2005-112514) composed of a combination of anti-Factor IXa antibody A69-VH, anti-Factor X antibody B26-VH, and hybrid L chain (BBA), which was the most effective in shortening blood coagulation time, was subjected to humanization as follows.

14-1. Homology Search of Humanized Antibodies

Using database constructed by obtaining amino acid sequence data of human antibodies from publicly disclosed Kabat Database (ftp://ftp.ebi.ac.uk/pub/databases/kabat/) and IMGT Database (http://imgt.cines.fr/), homology search was carried out separately for the mouse A69-H chain variable region (amino acid sequence: SEQ ID NO: 57), mouse B26-H chain variable region (amino acid sequence: SEQ ID NO: 58), and mouse BBA-L chain variable region (amino acid sequence: SEQ ID NO: 59). The results confirmed that they have high homologies to the human antibody sequences shown below, and it was thus decided that they would be used as the framework region (hereinafter abbreviated as FR) of humanized antibodies.

(1) A69-H chain variable region: KABATID-000064 (Kabat Database)
(Kipps et al., J. Can. Invest. 1991-87:2087-2096)
(2) B26-H chain variable region: EMBL Accession No. AB063872(IMGT Database)
(Unpublished data)
(3) BBA-L chain variable region: KABATID-024300 (Kabat Database)
(Welschof et al., J. Immunol. Method 1995; 179:203-214)
Humanized antibodies in which complementarity determining regions (hereinafter abbreviated as CDR) of each mouse antibody were grafted into the FRs of human antibodies (1)-(3) were prepared.

Also, the web homology search site publicly disclosed by NCBI (http://www.ncbi.nlm.nih.gov/BLAST/) was used to search secretory signal sequences of human antibodies that are highly homologous to the human antibodies of (1)-(3). The following secretory signal sequences obtained by the search were used.

(1) A69-H chain variable region: GenBank Accession No. AF062257
(2) B26-H chain variable region: GenBank Accession No. AAC18248
(3) BBA-L chain variable region: GenBank Accession No. AAA59100

14-2. Construction of Humanized Antibody Gene Expression Vector

Twelve synthetic oligoDNAs of about 50 bases were prepared from a nucleotide sequence encoding the amino acid sequence from the secretory signal sequence to the antibody variable region, such that about 20 bases of their 3'-end anneal with each other. Furthermore, a primer annealing to the 5'-end of an antibody variable region gene and having the XhoI cleavage sequence, and a primer annealing to the 3'-end of an antibody variable region gene, having the SfiI cleavage sequence and also encoding the 5'-end sequence of the intron sequence were prepared.

1 μL each of the synthetic oligoDNAs prepared at 2.5 μM were mixed, and 1× TaKaRa Ex Taq Buffer, 0.4 mM dNTPs, and 0.5 units TaKaRa Ex Taq (all from Takara Shuzo) were added to prepare 48 μL of a reaction solution. After heating this at 94° C. for 5 minutes, 2 cycles of reacting at 94° C. for 2 minutes, 55° C. for 2 minutes, and 72° C. for 2 minutes were performed to assemble and elongate each of the synthetic oligoDNAs. Next, 1 μL (10 μM each) of primers annealing to the 5'-end and to the 3'-end of the antibody gene were added, and the antibody variable region genes were amplified by 35 cycles of reacting at 94° C. for 30 seconds, 55° C. for 30 seconds, and 72° C. for 1 min and then reacting at 75° C. for 5 minutes. After PCR, the whole amount of the reaction solution was subjected to 1% agarose gel electrophoresis. Amplified fragments having the size of interest (approximately 400 bp) were purified using the QIAquick Gel Extraction Kit (QIAGEN) according to the method described in the instruction manual, and were eluted with 30 μL of sterile water. These fragments were cloned using the pGEM-T Easy Vector System (Promega) according to the method described in the instruction manual. Nucleotide sequence of each of the DNA fragments was determined using the BigDye Terminator Cycle Sequencing Kit (Applied Biosystems) and ABI PRISM 3730xL DNA Sequencer (Applied Biosystems) according to the method described in the instruction manual.

The H-chain variable region fragment-inserted plasmid and the L-chain variable region fragment-inserted plasmid, each of which were confirmed to have the correct humanized antibody variable region gene sequence, were digested with XhoI and SfiI, and EcoRI respectively. Then, the reaction solution was subjected to 1% agarose gel electrophoresis. DNA fragments having the size of interest (approximately 400 bp) were purified using QIAquick Gel Extraction Kit (QIAGEN) according to the method described in the instruction manual, and eluted with 30 μL of sterile water. Then, expression vectors for animal cells were prepared as follows. To preferentially express IgG4 whose H chains are of a heterologous combination, a CH3 portion amino acid-substituted IgG4 was used by referring to the knobs-into-holes technique of IgG1 (Non-Patent Document 3). Furthermore, to promote H chain dimer formation, amino acid substitution (-ppcpScp-->-ppcpPcp-) was also introduced to the hinge. Humanized A69 H chain expression vector was prepared by inserting humanized A69 H chain variable region antibody gene fragment into an expression vector prepared by inserting Y349C and T366W-substituted constant region gene to pCAGGS comprising a chicken β-actin promoter (Niwa et al. 1991 Gene, 108: 193-199). Humanized B26 H chain expression vector was prepared by inserting humanized B26 H chain variable region antibody gene fragment into an expression vector prepared by inserting E356C, T366S, L368A, and Y407V-substituted constant region gene to pCAGGS. Plasmid (pCAG-gκDNA) prepared by inserting a wild type antibody L chain constant region to pCAGGS was digested with EcoRI to prepare expression vectors inserted with humanized BBA L chain variable region antibody gene fragment. Ligation reaction was performed using Rapid DNA Ligation Kit (Roche Diagnostics), and DH5α strain *E. coli* (TOYOBO) was transformed.

14-3. Preparation of Humanized Bispecific Antibodies

Humanized bispecific antibodies were expressed according to the method described in Example 4-2 or according to the following method. Human fetal renal carcinoma cell-derived HEK293H strain (Invitrogen) was suspended in a DMEM medium (Invitrogen) containing 10% FCS (Invitrogen), and 10 mL of this was seeded at a cell density of 5-6×10$^5$ cells/mL in each dish used for adhesive cells (10-cm diameter, CORNING) and cultured for one day and night in a $CO_2$ incubator (37° C., 5% $CO_2$). Then, the medium was removed by suction, and 6.9 mL of CHO-S-SFM-II (Invitrogen) medium was added. The plasmid DNA mixture solution prepared in 14-2 (total of 13.8 μg) was mixed with 20.7 μL of 1 μg/mL Polyethylenimine (Polysciences Inc.) and 690 μL of CHO-S-SFMII medium, left to stand at room temperature for 10 minutes, then the cells were seeded into each dish and incubated in a $CO_2$ incubator (37° C., 5% $CO_2$) for 4-5 hours. Thereafter, 6.9 mL of CHO-S-SFM-II medium was added and then the cells were incubated in a CO$_2$ incubator for 3 days. The culture supernatant was recovered, then cells were removed by centrifugation (at approximately 2000 g for 5 minutes at room temperature), and the solution was sterilized by passing it through a 0.22 μm filter MILLEX®-GV (Millipore). The sample was stored at 4° C. until use.

Next, antibodies were purified according to the method described in Example 4-4, and the antibody concentration was quantified according to the method described in Example 4-5 or according to the following method. Protein A was immobilized on Sensor Chip CM5 (BIACORE) using BIAcore3000 (BIACORE). More specifically, Protein A-immobilized sensor chip was prepared according to the manufacturer's protocol by reacting an activated sensor chip with a Protein A solution diluted to 50 μg/mL with 10 mM aqueous sodium acetate solution (pH 4.0, BIACORE) at 5 μL/min for 30 minutes, and then performing a blocking operation. This sensor chip was used to measure the concentration of the culture supernatant and the purified product using BIAcore Q. HBS-EP Buffer (BIACORE) was used for the immobilization of the sensor chip and for the measurements of concentration. As a standard for concentration measurements, human IgG4 (humanized anti-TF antibody, see WO 99/51743) diluted with HBS-EP Buffer in a two-fold dilution series up to six stages beginning at 2000 ng/mL was used.

14-4. Activity Assessment of Humanized Bispecific Antibodies and Modification of Antibody Sequence To assess the plasma coagulation abilities of the prepared humanized bispecific antibody and the chimeric bispecific antibody (A69/B26/BBA), the effects of the antibodies on APTT were examined using F. VIII-deficient plasma according to the method of Example 5. A humanized bispecific antibody whose blood coagulation ability had decreased was subjected to amino acid modifications in the human antibody FR in order to increase its activity. During expression and secretion 3 types of antibodies, humanized A69/humanized BBA antibody, humanized B26/humanized BBA antibody, and humanized A69/humanized B26/humanized BBA bispecific antibody were expressed, these 3 types of antibodies were separated, and amino acid modifications that decrease the isoelectric point of the humanized A69 H chain variable region and increase the isoelectric point of the humanized B26 H chain variable region were carried out in order to purify the bispecific antibody alone. Specifically, mutations were introduced to the humanized antibody variable region using a QuikChange Site-Directed Mutagenesis Kit (Stratagene) according to the method described in the instruction manual. The H-chain variable region fragment-inserted plasmid and L-chain variable region fragment-inserted plasmid were confirmed to have the humanized antibody variable region gene sequence of interest were digested with XhoI and SfiI, and EcoRI respectively. The reaction solution was subjected to 1% agarose gel electrophoresis. DNA fragments having the size of interest (approximately 400 bp) were purified using QIAquick Gel Extraction Kit (QIAGEN) according to the method described in the instruction manual, and eluted with 30 μL of sterile water. Then, expression vectors for animal cells were prepared according to the method described in Example 14-2. Humanized bispecific antibody was prepared according to the method described in Example 14-3, and blood coagulation activity was evaluated according to the method described in Example 5.

By repeated amino acid modifications of the FR sequence and assessment of blood coagulation ability, humanized bispecific antibody (humanized A69 (hA69-PFL)/humanized B26 (hB26-PF)/humanized BBA (hAL-AQ)) having the same level of activity as the chimeric bispecific antibody (A69/B26/BBA) was obtained (FIG. 26). Each of the antibody variable region sequences are indicated in the following SEQ ID NOs.

(1) humanized A69 antibody VH (hA69-PFL) SEQ ID NO: 19 (nucleotide sequence), SEQ ID NO: 20 (amino acid sequence)
(2) humanized B26 antibody VH (hB26-PF) SEQ ID NO: 21 (nucleotide sequence), SEQ ID NO: 22 (amino acid sequence)
(3) humanized BBA antibody VL (hAL-AQ) SEQ ID NO: 23 (nucleotide sequence), SEQ ID NO: 24 (amino acid sequence)

[Example 15] Selection of Amino Acid Modification Positions in the Constant Region to Improve the Formation Efficiency of a Bispecific Antibody Aiming for the increase in the formation efficiency of a bispecific antibody, a heterodimer, by using charge repulsion, examinations were carried out by modifying amino acids present at the constant region CH3 interface. First, from the crystal structure of the CH3 region (Protein Data bank, PDB code 1OQX), pairs of amino acids that interact electrostatically during CH3 homodimer formation were searched. As a result, at the interface during CH3 homodimer formation, 3 pairs, H-chain positions 356 and 439, positions 357 and 370, and positions 399 and 409 (the numbers are based on the EU numbering system Kabat E A et al. 1991. Sequences of Proteins of Immunological Interest. NIH)), were found to be interacting electrostatically where each of the amino acids carry a positive charge and a negative charge, and these were selected as the positions for modification. It was postulated that heterodimer formation would be promoted by a modification method that carries out a modification by switching the charge of pairs of positively and negatively charged amino acids. The principle of this regulation is described in FIG. 27. Experiments were also performed with modifications that simultaneously introduce disulfide bonds to the CH3 interface. The positions of the modified amino acids are summarized in Table 1.

[Example 16] Amino Acid Modifications at the Interface of Humanized Bispecific Antibody Constant Region CH3

To modify the amino acids at the H-chain constant region CH3 interface selected in Example 15, the following operation was performed. Each H-chain constant region was amplified by PCR using the human IgG1 and human IgG4 H-chain constant region genes as templates and using a 5'-end primer designed so that the nucleotide sequence encoding two amino acids (Ala-Ser) in the N-terminal side of the H-chain constant region will be an NheI recognition sequence (GCTAGC) and a primer that anneals to the 3'-end and that carries a NotI recognizing site. Then, pBCH (comprising an IgG1 constant region gene) and pBCH4 (IgG4 comprising a constant region gene) linked to a vector prepared by digesting pBluescriptKS+ vector (TOYOBO) with NheI and Not I (both from TaKaRa) were prepared. PCR was performed using a primer that is complementary to the 5'-end nucleotide sequence of the H-chain variable region of the humanized A69 antibody and humanized B26 antibody and that has a Kozak sequence (CCACC) and an EcoRI recognition sequence, and a primer on the 3'-end nucleotide sequence having an NheI recognition sequence, and the obtained PCR products were inserted into pBCH or pBCH4 digested with EcoRI and NheI (both from TaKaRa) and the variable regions and the constant regions were linked. Next, to modify amino acids present at the H-chain constant region CH3 interface, mutations were introduced to the H-chain constant regions using QuikChange Site-Directed Mutagenesis Kit (Stratagene) according to the method described in the instruction manual. The H-chain gene fragment-inserted plasmid was confirmed to have the H-chain constant region gene sequence of interest and then was digested with EcoRI and NotI (both from TaKaRa). The reaction solution was subjected to 1% agarose gel electrophoresis. H-chain gene fragments having the size of interest (approximately 1400 bp) were purified using QIAquick Gel Extraction Kit (QIAGEN) according to the method described in the instruction manual, and eluted with 30 μL of sterile water. Then, the fragments were inserted into pCAGGS digested with EcoRI and NotI to prepare expression plasmids. Preparation of humanized bispecific antibodies was performed following the method described in Example 14-3. The positions of modified amino acids are summarized in Table 1. The EU numbering system (Kabat E A et al. 1991. Sequences of Proteins of Immunological Interest. NIH) was employed for the numbers of the modified positions shown in Table 1. The alphabet in front of the number of the modified position is the one-letter code representation for the amino acid before modification, and the alphabet after the number indicates the one letter code representation of the amino acid after modification.

ized A69 antibody, BiAb, a heterodimer of humanized A69 antibody and humanized B26 antibody, and B-Homo, a homodimer of humanized B26 antibody were calculated.
Column: ProPac WCX-10, 4×250 nm, (Dionex)
Mobile phase:
  A: 10 mmol/L NaH$_2$PO$_4$/Na$_2$HPO$_4$, pH6.25
  B: 10 mmol/L NaH$_2$PO$_4$/Na$_2$PO$_4$, 500 mmol/L NaCl, pH6.25
Flow rate: 1.0 mL/min
Gradient: 10% B (5 min)→(40 min)→60% B→(5 min) →100% B (5 min)
Detection: 220 nm For Wild type, KiH, s2, s3, s1C, s2C, s3C, w3C, and w3C2, BiAbs were purified by collecting BiAb peak fractions from the IEX analyses described above. The BiAb fractions were concentrated using Amicon Ultra, MWCO 10000 (Millipore), then dialyzed overnight against 20 mM sodium acetate, 150 mM NaCl, pH6.0 while cooling, and then recovered. BiAb concentrations were made uniform at 0.1 mg/mL, initial samples and samples at 60° C. for one week (60° C.-1 week) were individually dispensed into vials in duplicates, and stability tests were performed on the 60° C.-1 week samples. Gel filtration chromatographic (SEC) analysis was performed, and the rate of recovery of the monomer peak was calculated (60° C.-1 week sample monomer peak area/initial sample monomer peak area×100). Conditions for the gel filtration chromatographic analyses were as follows:

TABLE 1

| | | Humanized A69 antibody H-chain constant region | | Humanized A26 antibody H-chain constant region | |
|---|---|---|---|---|---|
| | Name | Modified position | SEQ ID NO of the amino acid | Modified position | SEQ ID NO of the amino acid |
| IgG4 | wild type | — | 25 | — | 25 |
| | KiH | Y349C, T366W | 9 | E356C, T366S, L368A, Y407V | 11 |
| | s1 | R409D | 26 | D399K | 27 |
| | s2 | K370E | 28 | E357K | 29 |
| | s3 | K439E | 30 | E356K | 31 |
| | w1 | R409D, K370E | 32 | D399K, E357K | 33 |
| | w2 | R409D, K439E | 34 | D399K, E356K | 35 |
| | w3 | K370E, K439E | 36 | E357K, E356K | 37 |
| | s1C | R409D, Y349C | 38 | D399K, S354C | 39 |
| | s2C | K370E, Y349C | 40 | E357K, S354C | 41 |
| | s3C | K439E, Y349C | 42 | E356K, S354C | 43 |
| | w3C | K370E, K439E, Y349C | 44 | E357K, E356K, S354C | 45 |
| | w3C2 | K370E, K439E, S354C | 46 | E357K, E356K, Y349C | 47 |
| IgG1 | wild type | — | 48 | — | 48 |
| | KiH | Y349C, T366W | 49 | D356C, T366S, L368A, Y407V | 50 |
| | w1 | R409D, K370E | 51 | D399K, E357K | 52 |
| | w2 | R409D, K439E | 53 | D399K, E356K | 54 |
| | w3 | K370E, K439E | 55 | E357K, E356K | 56 |

In the Table shown above, KiH indicates the variant described in Non-Patent Document 3 prepared using the Knobs-into-holes technique.

[Example 17] Assessment of Formation Efficiency and Stability of the CH3 Interface-Modified Bispecific Antibodies (IgG4-Type)

IgG4-type wild type, KiH, s1, s2, s3, w1, w2, w3, s1C, s2C, s3C, w3C, and w3C2 were analyzed by cation exchange chromatography (IEX), and the formation efficiency of bispecific antibody (hereinafter referred to as BiAb) was evaluated. The conditions for the cation exchange chromatographic analysis were as follows, and the ratio of the peak areas of A-Homo, a homodimer of human- Column: Super3000 (TOSOH)
Mobile phase: 50 mM sodium phosphate, 300 mM KCl, pH7.0
Flow rate: 0.2 mL/min
Detection: 220 nm The IEX chromatograms of the IgG4-type wild type, s1, s2, s3, and w1 are shown in FIG. 28, and the percentages of formation of A-Homo, BiAb, and B-Homo by the wild type, KiH, s1, s2, s3, w1, w2, w3, s1C, s2C, s3C, w3C, and w3C2 are shown in FIG. 29. The monomer recovery rates after 60° C. for one week are shown in FIG. 30.

As shown in FIGS. 28 and 29, efficiency of the intended BiAb formation improved greatly as compared to the wild type for every one of the CH3 interface-modified variants found in the present Example. Since CH3 is in the constant region, when making modifications to the native amino acids, the modified positions are desirably kept to minimum from the viewpoint of antigenicity. For introduction of knobs and holes, in KiH, a total of four positions in the both H chains are modified and in addition two positions are modified for disulfide bond introduction, and a total of six positions are modified. Therefore, as shown in FIG. 29, the efficiency of BiAb formation is high. However, the results of stability tests shown in FIG. 30 shows that thermal stability is significantly lowered compared to the wild type even though a disulfide bond is introduced. To develop antibodies into medical pharmaceuticals, stable formulations are necessary and thus, a higher thermal stability is more desirable.

On the other hand, every one of the CH3 interface-modified variants found in the present Example was successful in greatly improving the efficiency of the intended BiAb formation as compared to the wild type. Among these variants, for example, high BiAb formation efficiency of 90% or more was achieved by modification of s2, s3, w1, w2, w3, and s1C at a total of two or four positions which is fewer compared to KiH (six modified positions), which the risk of antigenicity is considered to be low. Furthermore, the results of stability tests shown in FIG. 30 showed that among the variants, for example, s2, s3, w3, w3C, and w3C2 have high BiAb formation efficiency of 90% or more and also have higher thermal stability (higher percentage of monomer recovery) than KiH, and s3, s2c, s3C, w3C, and w3C2 have much higher thermal stability than the wild type, and they will be useful for developing stable pharmaceutical formulations.

The present Example demonstrated that by modifying the amino acids at H-chain positions 356, 357, 370, 399, 409, and 439 in the CH3 interface to introduce charge-induced molecular repulsion, efficiency of the intended BiAb formation could be greatly improved. It also showed that by introducing disulfide bonds and such modifications individually or in combination, BiAb formation efficiency could be greatly improved with fewer modifications than in KiH, and that BiAb formation efficiency could be greatly improved with higher stability than in KiH, and even more with a higher thermal stability than in the wild type.

[Example 18] Coagulation Activity Assessment of CH3 Interface-Modified Bispecific Antibodies Coagulation activity was assessed according to the method described in Example 5, using CH3 interface-modified IgG4-type bispecific antibodies (s1, s2, s3, w1, w2, and w3) purified in Example 16. As shown in FIG. 31, since coagulation activity did not change even when the amino acids at the constant region CH3 interface was modified, modification of CH3 interface amino acids were shown not to affect the structure of the variable regions involved in reacting with the antigens.

[Example 19] Assessment of the Formation Efficiency of CH3 Interface-Modified Bispecific Antibodies (IgG1-Type)

IgG1-type wild type, KiH, w1, w2, and w3 were analyzed by cation exchange chromatography (IEX), and BiAb formation efficiency was evaluated. The conditions of the cation exchange chromatographic analysis are as follows, and the ratio of the peak areas of A-Homo, a homodimer of humanized A69 antibody, BiAb, a heterodimer of humanized A69 antibody and humanized B26 antibody, and B-Homo, a homodimer of humanized B26 antibody were calculated.

Column: ProPac WCX-10, 4×250 nm, (Dionex)
Mobile phase:
  A: 10 mmol/L $NaH_2PO_4/Na_2HPO_4$, pH6.25
  B: 10 mmol/L $NaH_2PO_4/Na_2HPO_4$, 500 mmol/L NaCl, pH6.25
Flow rate: 1.0 mL/min
Gradient: 10% B (5 min)→(40 min)→60% B→(5 min)→100% B (5 min)
Detection: 220 nm The percentages of formation of A-Homo, BiAb, and B-Homo by the IgG1-type wild type, KiH, w1, w2, and w3 are shown in FIG. 32. Alike IgG4-type, the efficiency of the intended BiAb formation greatly improved in every one of them as compared to the wild type. As in the IgG4-types, high BiAb formation efficiency of 90% or more was achieved by modification at four positions, which is less than that of KiH, and the risk of antigenicity is considered to be small. The present Example showed that the method of modifying the amino acids at H-chain positions 356, 357, 370, 399, 409, and 439 in the CH3 interface can be applied not only to antibody constant region subclass IgG4, but also to the IgG1, and is applicable to IgG antibodies in general.

INDUSTRIAL APPLICABILITY

In that the present invention requires only a small number of amino acid substitutions, the methods of the present invention find exceptional utility in regulating association without changing the structure and function (activity) of the original polypeptides. Thus, there is little effect on antigenicity. Accordingly, bispecific antibodies that actually maintain activity can be obtained efficiently by following the methods of the present invention.

The invention claimed is:

1. A method for producing a desired multi-specific antibody, the method comprising
   (a) identifying a first polypeptide that forms part of a multi-specific antibody by associating directly with either (i) a second polypeptide different from the first polypeptide or (ii) a third polypeptide different from the first and second polypeptides, wherein the first polypeptide comprises an antibody heavy chain CH3 region and an antibody heavy chain variable domain, wherein the second and third polypeptides respectively comprise different antibody light chain variable domains, wherein the amino acid residue at position 39 (Kabat numbering) ("H39") of the heavy chain variable domain of the first polypeptide and the amino acid residue at position 38 (Kabat numbering) ("L38") of the light chain variable domain of the second or third polypeptide can form part or all of an interface in the multi-specific antibody, wherein the residues at H39 of the first polypeptide and L38 of the second polypeptide may be charged or uncharged, but if both are charged they do not have the same charge, and wherein the multi-specific antibody contains a fourth polypeptide comprising an antibody heavy chain CH3 region and an antibody heavy chain variable domain different from the heavy chain variable domain of the first polypeptide;
   (b) producing a nucleic acid encoding a modified first polypeptide in which the residue at H39 is substituted with a first substitute residue;
   (c) producing a nucleic acid encoding a modified second polypeptide in which the residue at L38 is substituted with a second substitute residue, wherein the first and second substitute residues are either both positively charged or both negatively charged, wherein the like charges of the first and second substitute residues inhibit direct association between the modified first polypeptide and the modified second polypeptide;
   (d) expressing the nucleic acids of (b) and (c), a nucleic acid encoding the third polypeptide, and a nucleic acid encoding the fourth polypeptide, thereby producing an expression product, wherein the residue at position 39 (Kabat numbering) of the heavy chain variable domain of the fourth polypeptide has either no charge or a charge that is opposite to that of the first substitute residue; and
   (e) collecting the expression product of (d), the expression product comprising the desired multi-specific antibody comprising (1) the modified first polypeptide associated directly with the third polypeptide, and (2) the modified second polypeptide associated directly with the fourth polypeptide,
   wherein any one or more of the following criteria (1) to (6) is true:
   (1) amino acid residues at EU numbering positions 356 and 439 in the CH3 region of the first polypeptide either both have a positive charge or both have a negative charge, and if either of the amino acid residues at EU numbering positions 356 and 439 in the CH3 region of the fourth polypeptide is charged, it has a charge opposite to the charge of the amino acid residues at EU numbering positions 356 and 439 in the CH3 region of the first polypeptide;
   (2) amino acid residues at EU numbering positions 357 and 370 in the CH3 region of the first polypeptide either both have a positive charge or both have a negative charge, and if either of the amino acid residues at EU numbering positions 357 and 370 in the CH3 region of the fourth polypeptide is charged, it has a charge opposite to the charge of the amino acid residues at EU numbering positions 357 and 370 in the CH3 region of the first polypeptide;
   (3) amino acid residues at EU numbering positions 399 and 409 in the CH3 region of the first polypeptide either both have a positive charge or both have a negative charge, and if either of the amino acid residues at EU numbering positions 399 and 409 in the CH3 region of the fourth polypeptide is charged, it has a charge opposite to the charge of the amino acid residues at EU numbering positions 399 and 409 in the CH3 region of the first polypeptide;
   (4) amino acid residues at EU numbering positions 356 and 439 in the CH3 region of the fourth polypeptide either both have a positive charge or both have a negative charge, and if either of the amino acid residues at EU numbering positions 356 and 439 in the CH3 region of the first polypeptide is charged, it has a charge opposite to the charge of the amino acid residues at EU numbering positions 356 and 439 in the CH3 region of the fourth polypeptide;
   (5) amino acid residues at EU numbering positions 357 and 370 in the CH3 region of the fourth polypeptide either both have a positive charge or both have a negative charge, and if either of the amino acid residues at EU numbering positions 357 and 370 in the CH3 region of the first polypeptide is charged, it has a charge opposite to the charge of the amino acid residues at EU numbering positions 357 and 370 in the CH3 region of the fourth polypeptide;
   (6) amino acid residues at EU numbering positions 399 and 409 in the CH3 region of the fourth polypeptide either both have a positive charge or both have a negative charge, and if either of the amino acid residues at EU numbering positions 399 and 409 in the CH3 region of the first polypeptide is charged, it has a charge opposite to the charge of the amino acid residues at EU numbering positions 399 and 409 in the CH3 region of the fourth polypeptide.

2. The method of claim 1, wherein each of the first and second substitute amino acid residues is glutamic acid (E).

3. The method of claim 1, wherein each of the first and second substitute amino acid residues is aspartic acid (D).

4. The method of claim 1, wherein each of the first and second substitute amino acid residues is lysine (K).

5. The method of claim 1, wherein each of the first and second substitute amino acid residues is arginine (R).

6. The method of claim 1, wherein each of the first and second substitute amino acid residues is histidine (H).

7. The method of claim 1, wherein the amino acid residue at position 38 (Kabat numbering) of the light chain variable domain of the third polypeptide has either no charge or a charge opposite to that of the first substitute residue.

8. The method of claim 1, wherein the multi-specific antibody of (e) is a bispecific antibody.

9. The method of claim 1, wherein criteria (1) and (4) are true.

10. The method of claim 1, wherein criteria (2) and (5) are true.

11. The method of claim 1, wherein criteria (3) and (6) are true.

12. A method for producing a desired multi-specific antibody, the method comprising
(a) identifying a first polypeptide that forms part of a multi-specific antibody by associating directly with either (i) a second polypeptide different from the first polypeptide or (ii) a third polypeptide different from the first and second polypeptides, wherein the first polypeptide comprises an antibody heavy chain CH3 region and an antibody heavy chain variable domain, wherein the second and third polypeptides respectively comprise different antibody light chain variable domains, wherein the amino acid residue at position 39 (Kabat numbering) ("H39") of the heavy chain variable domain of the first polypeptide and the amino acid residue at position 38 (Kabat numbering) ("L38") of the light chain variable domain of the second or third polypeptide can form part or all of an interface in the multi-specific antibody, wherein the residue at L38 of the second polypeptide is a charged residue and the residue at H39 of the first polypeptide is either uncharged or has a charge different from that of the residue at L38 of the second polypeptide, and wherein the multi-specific antibody contains a fourth polypeptide comprising an antibody heavy chain CH3 region and an antibody heavy chain variable domain different from the heavy chain variable domain of the first polypeptide;
(b) producing a nucleic acid encoding a modified first polypeptide in which the residue at H39 is substituted with a substitute residue of the same charge as the residue at L38 of the second polypeptide, wherein the like charges of the substitute residue and the residue at L38 of the second polypeptide inhibit direct association between the modified first polypeptide and the second polypeptide;
(c) expressing the nucleic acid of (b), a nucleic acid encoding the second polypeptide, a nucleic acid encoding the third polypeptide, and a nucleic acid encoding the fourth polypeptide, thereby producing an expression product, wherein the residue at position 39 (Kabat numbering) of the heavy chain variable domain of the fourth polypeptide has either no charge or a charge that is opposite to that of the substitute residue; and
(d) collecting the expression product of (c), the expression product comprising the desired multi-specific antibody comprising (1) the modified first polypeptide associated directly with the third polypeptide, and (2) the second polypeptide associated directly with the fourth polypeptide,
wherein any one or more of the following criteria (1) to (6) is true:
(1) amino acid residues at EU numbering positions 356 and 439 in the CH3 region of the first polypeptide either both have a positive charge or both have a negative charge, and if either of the amino acid residues at EU numbering positions 356 and 439 in the CH3 region of the fourth polypeptide is charged, it has a charge opposite to the charge of the amino acid residues at EU numbering positions 356 and 439 in the CH3 region of the first polypeptide;
(2) amino acid residues at EU numbering positions 357 and 370 in the CH3 region of the first polypeptide either both have a positive charge or both have a negative charge, and if either of the amino acid residues at EU numbering positions 357 and 370 in the CH3 region of the fourth polypeptide is charged, it has a charge opposite to the charge of the amino acid residues at EU numbering positions 357 and 370 in the CH3 region of the first polypeptide;
(3) amino acid residues at EU numbering positions 399 and 409 in the CH3 region of the first polypeptide either both have a positive charge or both have a negative charge, and if either of the amino acid residues at EU numbering positions 399 and 409 in the CH3 region of the fourth polypeptide is charged, it has a charge opposite to the charge of the amino acid residues at EU numbering positions 399 and 409 in the CH3 region of the first polypeptide;
(4) amino acid residues at EU numbering positions 356 and 439 in the CH3 region of the fourth polypeptide either both have a positive charge or both have a negative charge, and if either of the amino acid residues at EU numbering positions 356 and 439 in the CH3 region of the first polypeptide is charged, it has a charge opposite to the charge of the amino acid residues at EU numbering positions 356 and 439 in the CH3 region of the fourth polypeptide;
(5) amino acid residues at EU numbering positions 357 and 370 in the CH3 region of the fourth polypeptide either both have a positive charge or both have a negative charge, and if either of the amino acid residues at EU numbering positions 357 and 370 in the CH3 region of the first polypeptide is charged, it has a charge opposite to the charge of the amino acid residues at EU numbering positions 357 and 370 in the CH3 region of the fourth polypeptide;
(6) amino acid residues at EU numbering positions 399 and 409 in the CH3 region of the fourth polypeptide either both have a positive charge or both have a negative charge, and if either of the amino acid residues at EU numbering positions 399 and 409 in the CH3 region of the first polypeptide is charged, it has a charge opposite to the charge of the amino acid residues at EU numbering positions 399 and 409 in the CH3 region of the fourth polypeptide.

13. The method of claim 12, wherein the substitute amino acid residue and the amino acid residue at L38 of the second polypeptide are both glutamic acid (E).

14. The method of claim 12, wherein the substitute amino acid residue and the amino acid residue at L38 of the second polypeptide are both aspartic acid (D).

15. The method of claim 12, wherein the substitute amino acid residue and the amino acid residue at L38 of the second polypeptide are both lysine (K).

16. The method of claim 12, wherein the substitute amino acid residue and the amino acid residue at L38 of the second polypeptide are both arginine (R).

17. The method of claim 12, wherein the substitute amino acid residue and the amino acid residue at L38 of the second polypeptide are both histidine (H).

18. The method of claim 12, wherein the amino acid residue at position 38 (Kabat numbering) of the light chain variable domain of the third polypeptide has either no charge or a charge opposite to that of the substitute residue.

19. The method of claim 12, wherein the multi-specific antibody of (d) is a bispecific antibody.

20. The method of claim 12, wherein criteria (1) and (4) are true.

21. The method of claim 12, wherein criteria (2) and (5) are true.

22. The method of claim 12, wherein criteria (3) and (6) are true.

23. A method for producing a desired multi-specific antibody, the method comprising
  (a) identifying a first polypeptide that forms part of a multi-specific antibody by associating directly with either (i) a second polypeptide different from the first polypeptide or (ii) a third polypeptide different from the first and second polypeptides, wherein the first polypeptide comprises an antibody heavy chain CH3 region and an antibody heavy chain variable domain, wherein the second and third polypeptides respectively comprise different antibody light chain variable domains, wherein the amino acid residue at position 39 (Kabat numbering) ("H39") of the heavy chain variable domain of the first polypeptide and the amino acid residue at position 38 (Kabat numbering) ("L38") of the light chain variable domain of the second or third polypeptide can form part or all of an interface in the multi-specific antibody, wherein the residue at H39 of the first polypeptide is a charged residue and the residue at L38 of the second polypeptide is either uncharged or has a charge different from that of the residue at H39, and wherein the multi-specific antibody contains a fourth polypeptide comprising an antibody heavy chain CH3 region and an antibody heavy chain variable domain different from the heavy chain variable domain of the first polypeptide;
  (b) producing a nucleic acid encoding a modified second polypeptide in which the residue at L38 is substituted with a substitute residue of the same charge as the residue at H39 of the first polypeptide, wherein the like charges of the substitute residue and the residue at H39 inhibit direct association between the first polypeptide and the modified second polypeptide;
  (c) expressing the nucleic acid of (b), a nucleic acid encoding the first polypeptide, a nucleic acid encoding the third polypeptide, and a nucleic acid encoding the fourth polypeptide, thereby producing an expression product, wherein the residue at position 39 (Kabat numbering) of the heavy chain variable domain of the fourth polypeptide has either no charge or a charge that is opposite to the charge of the residue at H39 of the first polypeptide; and
  (d) collecting the expression product of (c), the expression product comprising the desired multi-specific antibody comprising (1) the first polypeptide associated directly with the third polypeptide, and (2) the modified second polypeptide associated directly with the fourth polypeptide, wherein any one or more of the following criteria (1) to (6) is true:
  (1) amino acid residues at EU numbering positions 356 and 439 in the CH3 region of the first polypeptide either both have a positive charge or both have a negative charge, and if either of the amino acid residues at EU numbering positions 356 and 439 in the CH3 region of the fourth polypeptide is charged, it has a charge opposite to the charge of the amino acid residues at EU numbering positions 356 and 439 in the CH3 region of the first polypeptide;
  (2) amino acid residues at EU numbering positions 357 and 370 in the CH3 region of the first polypeptide either both have a positive charge or both have a negative charge, and if either of the amino acid residues at EU numbering positions 357 and 370 in the CH3 region of the fourth polypeptide is charged, it has a charge opposite to the charge of the amino acid residues at EU numbering positions 357 and 370 in the CH3 region of the first polypeptide;
  (3) amino acid residues at EU numbering positions 399 and 409 in the CH3 region of the first polypeptide either both have a positive charge or both have a negative charge, and if either of the amino acid residues at EU numbering positions 399 and 409 in the CH3 region of the fourth polypeptide is charged, it has a charge opposite to the charge of the amino acid residues at EU numbering positions 399 and 409 in the CH3 region of the first polypeptide;
  (4) amino acid residues at EU numbering positions 356 and 439 in the CH3 region of the fourth polypeptide either both have a positive charge or both have a negative charge, and if either of the amino acid residues at EU numbering positions 356 and 439 in the CH3 region of the first polypeptide is charged, it has a charge opposite to the charge of the amino acid residues at EU numbering positions 356 and 439 in the CH3 region of the fourth polypeptide;
  (5) amino acid residues at EU numbering positions 357 and 370 in the CH3 region of the fourth polypeptide either both have a positive charge or both have a negative charge, and if either of the amino acid residues at EU numbering positions 357 and 370 in the CH3 region of the first polypeptide is charged, it has a charge opposite to the charge of the amino acid residues at EU numbering positions 357 and 370 in the CH3 region of the fourth polypeptide;
  (6) amino acid residues at EU numbering positions 399 and 409 in the CH3 region of the fourth polypeptide either both have a positive charge or both have a negative charge, and if either of the amino acid residues at EU numbering positions 399 and 409 in the CH3 region of the first polypeptide is charged, it has a charge opposite to the charge of the amino acid residues at EU numbering positions 399 and 409 in the CH3 region of the fourth polypeptide.

24. The method of claim 23, wherein the amino acid residue at H39 of the first polypeptide and the substitute amino acid residue are both glutamic acid (E).

25. The method of claim 23, wherein the amino acid residue at H39 of the first polypeptide and the substitute amino acid residue are both aspartic acid (D).

26. The method of claim 23, wherein the amino acid residue at H39 of the first polypeptide and the substitute amino acid residue are both lysine (K).

27. The method of claim 23, wherein the amino acid residue at H39 of the first polypeptide and the substitute amino acid residue are both arginine (R).

28. The method of claim 23, wherein the amino acid residue at H39 of the first polypeptide and the substitute amino acid residue are both histidine (H).

29. The method of claim 23, wherein the amino acid residue at position 38 (Kabat numbering) of the light chain variable domain of the third polypeptide has either no charge or a charge opposite to that of the residue at H39 of the first polypeptide.

30. The method of claim 23, wherein the multi-specific antibody of (d) is a bispecific antibody.

31. The method of claim 23, wherein criteria (1) and (4) are true.

32. The method of claim 23, wherein criteria (2) and (5) are true.

33. The method of claim 23, wherein criteria (3) and (6) are true.

34. A method for producing a desired multi-specific antibody, the method comprising
(a) identifying a first polypeptide that forms part of a multi-specific antibody by associating directly with either (i) a second polypeptide different from the first polypeptide or (ii) a third polypeptide different from the first and second polypeptides, wherein the first polypeptide comprises an antibody light chain variable domain, wherein the second polypeptide comprises an antibody heavy chain CH3 region and a heavy chain variable domain, and third polypeptide comprises an antibody heavy chain CH3 region and a heavy chain variable domain different from the heavy chain variable domain of the second polypeptide, wherein the amino acid residue at position 38 (Kabat numbering) ("L38") of the light chain variable domain of the first polypeptide and the amino acid residue at position 39 (Kabat numbering) ("H39") of the heavy chain variable domain of the second or third polypeptide can form part or all of an interface in the multi-specific antibody, wherein the residues at L38 of the first polypeptide and H39 of the second polypeptide may be charged or uncharged, but if both are charged they do not have the same charge, and wherein the multi-specific antibody contains a fourth polypeptide comprising an antibody light chain variable domain different from the light chain variable domain of the first polypeptide;
(b) producing a nucleic acid encoding a modified first polypeptide in which the residue at L38 is substituted with a first substitute residue;
(c) producing a nucleic acid encoding a modified second polypeptide in which the residue at H39 is substituted with a second substitute residue, wherein the first and second substitute residues are either both positively charged or both negatively charged, and wherein the like charges of the first and second substitute residues inhibit direct association between the modified first polypeptide and the modified second polypeptide;
(d) expressing the nucleic acids of (b) and (c), a nucleic acid encoding the third polypeptide, and a nucleic acid encoding the fourth polypeptide, thereby producing an expression product, wherein the residue at position 38 (Kabat numbering) of the light chain variable domain of the fourth polypeptide has either no charge or a charge that is opposite to that of the first substitute residue; and
(e) collecting the expression product of (d), the expression product comprising the desired multi-specific antibody comprising (1) the modified first polypeptide associated directly with the third polypeptide, and (2) the modified second polypeptide associated directly with the fourth polypeptide,
wherein any one or more of the following criteria (1) to (6) is true:
(1) amino acid residues at EU numbering positions 356 and 439 in the CH3 region of the second polypeptide either both have a positive charge or both have a negative charge, and if either of the amino acid residues at EU numbering positions 356 and 439 in the CH3 region of the third polypeptide is charged, it has a charge opposite to the charge of the amino acid residues at EU numbering positions 356 and 439 in the CH3 region of the second polypeptide;
(2) amino acid residues at EU numbering positions 357 and 370 in the CH3 region of the second polypeptide either both have a positive charge or both have a negative charge, and if either of the amino acid residues at EU numbering positions 357 and 370 in the CH3 region of the third polypeptide is charged, it has a charge opposite to the charge of the amino acid residues at EU numbering positions 357 and 370 in the CH3 region of the second polypeptide;
(3) amino acid residues at EU numbering positions 399 and 409 in the CH3 region of the second polypeptide either both have a positive charge or both have a negative charge, and if either of the amino acid residues at EU numbering positions 399 and 409 in the CH3 region of the third polypeptide is charged, it has a charge opposite to the charge of the amino acid residues at EU numbering positions 399 and 409 in the CH3 region of the second polypeptide;
(4) amino acid residues at EU numbering positions 356 and 439 in the CH3 region of the third polypeptide either both have a positive charge or both have a negative charge, and if either of the amino acid residues at EU numbering positions 356 and 439 in the CH3 region of the second polypeptide is charged, it has a charge opposite to the charge of the amino acid residues at EU numbering positions 356 and 439 in the CH3 region of the third polypeptide;
(5) amino acid residues at EU numbering positions 357 and 370 in the CH3 region of the third polypeptide either both have a positive charge or both have a negative charge, and if either of the amino acid residues at EU numbering positions 357 and 370 in the CH3 region of the second polypeptide is charged, it has a charge opposite to the charge of the amino acid residues at EU numbering positions 357 and 370 in the CH3 region of the third polypeptide;
(6) amino acid residues at EU numbering positions 399 and 409 in the CH3 region of the third polypeptide either both have a positive charge or both have a negative charge, and if either of the amino acid residues at EU numbering positions 399 and 409 in the CH3 region of the second polypeptide is charged, it has a charge opposite to the charge of the amino acid residues at EU numbering positions 399 and 409 in the CH3 region of the third polypeptide.

35. The method of claim 34, wherein the amino acid residue at position 39 (Kabat numbering) of the heavy chain variable domain of the third polypeptide has either no charge or a charge opposite to that of the first substitute residue.

36. The method of claim 34, wherein the multi-specific antibody of (e) is a bispecific antibody.

37. The method of claim 34, wherein each of the first and second substitute amino acid residues is glutamic acid (E).

38. The method of claim 34, wherein criteria (1) and (4) are true.

39. The method of claim 34, wherein criteria (2) and (5) are true.

40. The method of claim 34, wherein criteria (3) and (6) are true.

41. A method for producing a desired multi-specific antibody, the method comprising
  (a) identifying a first polypeptide that forms a multi-specific antibody by associating directly with either (i) a second polypeptide different from the first polypeptide or (ii) a third polypeptide different from the first and second polypeptides, wherein the first polypeptide comprises an antibody light chain variable domain, wherein the second polypeptide comprises an antibody heavy chain CH3 region and a heavy chain variable domain, and third polypeptide comprises an antibody heavy chain CH3 region and a heavy chain variable domain different from the heavy chain variable domain of the second polypeptide, wherein the amino acid residue at position 38 (Kabat numbering) ("L38") of the light chain variable domain of the first polypeptide and the amino acid residue at position 39 (Kabat numbering) ("H39") of the heavy chain variable domain of the second or third polypeptide can form part or all of an interface in the multi-specific antibody, wherein the residue at H39 of the second polypeptide is a charged residue, wherein the residue at L38 of the first polypeptide is either uncharged or has a charge different from that of the residue at H39 of the second polypeptide, and wherein the multi-specific antibody contains a fourth polypeptide comprising an antibody light chain variable domain different from the light chain variable domain of the first polypeptide;
  (b) producing a nucleic acid encoding a modified first polypeptide in which the residue at L38 is substituted with a substitute residue of the same charge as the residue at H39 of the second polypeptide, wherein the like charges of the substitute residue and the residue at H39 of the second polypeptide inhibit direct association between the modified first polypeptide and the second polypeptide;
  (c) expressing the nucleic acid of (b), a nucleic acid encoding the second polypeptide, a nucleic acid encoding the third polypeptide, and a nucleic acid encoding the fourth polypeptide, thereby producing an expression product, wherein the residue at position 38 (Kabat numbering) of the light chain variable domain of the fourth polypeptide has either no charge or a charge that is opposite to that of the substitute residue; and
  (d) collecting the expression product of (c), the expression product comprising the desired multi-specific antibody comprising (1) the modified first polypeptide associated directly with the third polypeptide, and (2) the second polypeptide associated directly with the fourth polypeptide,
  wherein any one or more of the following criteria (1) to (6) is true:
    (1) amino acid residues at EU numbering positions 356 and 439 in the CH3 region of the second polypeptide either both have a positive charge or both have a negative charge, and if either of the amino acid residues at EU numbering positions 356 and 439 in the CH3 region of the third polypeptide is charged, it has a charge opposite to the charge of the amino acid residues at EU numbering positions 356 and 439 in the CH3 region of the second polypeptide;
    (2) amino acid residues at EU numbering positions 357 and 370 in the CH3 region of the second polypeptide either both have a positive charge or both have a negative charge, and if either of the amino acid residues at EU numbering positions 357 and 370 in the CH3 region of the third polypeptide is charged, it has a charge opposite to the charge of the amino acid residues at EU numbering positions 357 and 370 in the CH3 region of the second polypeptide;
    (3) amino acid residues at EU numbering positions 399 and 409 in the CH3 region of the second polypeptide either both have a positive charge or both have a negative charge, and if either of the amino acid residues at EU numbering positions 399 and 409 in the CH3 region of the third polypeptide is charged, it has a charge opposite to the charge of the amino acid residues at EU numbering positions 399 and 409 in the CH3 region of the second polypeptide;
    (4) amino acid residues at EU numbering positions 356 and 439 in the CH3 region of the third polypeptide either both have a positive charge or both have a negative charge, and if either of the amino acid residues at EU numbering positions 356 and 439 in the CH3 region of the second polypeptide is charged, it has a charge opposite to the charge of the amino acid residues at EU numbering positions 356 and 439 in the CH3 region of the third polypeptide;
    (5) amino acid residues at EU numbering positions 357 and 370 in the CH3 region of the third polypeptide either both have a positive charge or both have a negative charge, and if either of the amino acid residues at EU numbering positions 357 and 370 in the CH3 region of the second polypeptide is charged, it has a charge opposite to the charge of the amino acid residues at EU numbering positions 357 and 370 in the CH3 region of the third polypeptide;
    (6) amino acid residues at EU numbering positions 399 and 409 in the CH3 region of the third polypeptide either both have a positive charge or both have a negative charge, and if either of the amino acid residues at EU numbering positions 399 and 409 in the CH3 region of the second polypeptide is charged, it has a charge opposite to the charge of the amino acid residues at EU numbering positions 399 and 409 in the CH3 region of the third polypeptide.

42. The method of claim 41, wherein the amino acid residue at position 39 (Kabat numbering) of the heavy chain variable domain of the third polypeptide has either no charge or a charge opposite to that of the substitute residue.

43. The method of claim 41, wherein the multi-specific antibody of (d) is a bispecific antibody.

44. The method of claim 41, wherein the substitute residue and the residue at H39 of the second polypeptide are both glutamic acid (E).

45. The method of claim 41, wherein criteria (1) and (4) are true.

46. The method of claim 41, wherein criteria (2) and (5) are true.

47. The method of claim 41, wherein criteria (3) and (6) are true.

48. A method for producing a desired multi-specific antibody, the method comprising
  (a) identifying a first polypeptide that forms part of a multi-specific antibody by associating directly with either (i) a second polypeptide different from the first polypeptide or (ii) a third polypeptide different from the first and second polypeptides, wherein the first polypeptide comprises an antibody light chain variable domain, wherein the second polypeptide comprises an antibody heavy chain CH3 region and a heavy chain variable domain, and the third polypeptide comprises an antibody heavy chain CH3 region and a heavy chain variable domain different from the heavy chain variable domain of the second polypeptide, wherein the amino acid residue at position 38 (Kabat numbering) ("L38") of the light chain variable domain of the first polypeptide and the amino acid residue at position 39 (Kabat numbering) ("H39") of the heavy chain variable domain of the second or third polypeptide can form part or all of an interface in the multi-specific antibody, wherein the residue at L38 of the first polypeptide is a charged residue, wherein the residue at H39 of the second polypeptide is either uncharged or has a charge different from that of the residue at L38 of the first polypeptide, and wherein the multi-specific antibody contains a fourth polypeptide comprising an antibody light chain variable domain different from the heavy chain variable domain of the first polypeptide;
(b) producing a nucleic acid encoding a modified second polypeptide in which the residue at H39 is substituted with a substitute residue of the same charge as the residue at L38 of the first polypeptide, wherein the like charges of the substitute residue and the residue at L38 of the first polypeptide inhibit direct association between the first polypeptide and the modified second polypeptide;
(c) expressing the nucleic acid of (b), a nucleic acid encoding the first polypeptide, a nucleic acid encoding the third polypeptide, and a nucleic acid encoding the fourth polypeptide, thereby producing an expression product, wherein the residue at position 38 (Kabat numbering) of the light chain variable domain of the fourth polypeptide has either no charge or a charge that is opposite to the charge of the residue at L38 of the light chain variable domain of the first polypeptide; and
(d) collecting the expression product of (c), the expression product comprising the desired multi-specific antibody comprising (1) the first polypeptide associated directly with the third polypeptide, and (2) the modified second polypeptide associated directly with the fourth polypeptide,
wherein any one or more of the following criteria (1) to (6) is true:
(1) amino acid residues at EU numbering positions 356 and 439 in the CH3 region of the second polypeptide either both have a positive charge or both have a negative charge, and if either of the amino acid residues at EU numbering positions 356 and 439 in the CH3 region of the third polypeptide is charged, it has a charge opposite to the charge of the amino acid residues at EU numbering positions 356 and 439 in the CH3 region of the second polypeptide;
(2) amino acid residues at EU numbering positions 357 and 370 in the CH3 region of the second polypeptide either both have a positive charge or both have a negative charge, and if either of the amino acid residues at EU numbering positions 357 and 370 in the CH3 region of the third polypeptide is charged, it has a charge opposite to the charge of the amino acid residues at EU numbering positions 357 and 370 in the CH3 region of the second polypeptide;
(3) amino acid residues at EU numbering positions 399 and 409 in the CH3 region of the second polypeptide either both have a positive charge or both have a negative charge, and if either of the amino acid residues at EU numbering positions 399 and 409 in the CH3 region of the third polypeptide is charged, it has a charge opposite to the charge of the amino acid residues at EU numbering positions 399 and 409 in the CH3 region of the second polypeptide;
(4) amino acid residues at EU numbering positions 356 and 439 in the CH3 region of the third polypeptide either both have a positive charge or both have a negative charge, and if either of the amino acid residues at EU numbering positions 356 and 439 in the CH3 region of the second polypeptide is charged, it has a charge opposite to the charge of the amino acid residues at EU numbering positions 356 and 439 in the CH3 region of the third polypeptide;
(5) amino acid residues at EU numbering positions 357 and 370 in the CH3 region of the third polypeptide either both have a positive charge or both have a negative charge, and if either of the amino acid residues at EU numbering positions 357 and 370 in the CH3 region of the second polypeptide is charged, it has a charge opposite to the charge of the amino acid residues at EU numbering positions 357 and 370 in the CH3 region of the third polypeptide;
(6) amino acid residues at EU numbering positions 399 and 409 in the CH3 region of the third polypeptide either both have a positive charge or both have a negative charge, and if either of the amino acid residues at EU numbering positions 399 and 409 in the CH3 region of the second polypeptide is charged, it has a charge opposite to the charge of the amino acid residues at EU numbering positions 399 and 409 in the CH3 region of the third polypeptide.

49. The method of claim 48, wherein the amino acid residue at position 39 (Kabat numbering) of the heavy chain variable domain of the third polypeptide has either no charge or a charge opposite to that of the residue at L38 of the first polypeptide.

50. The method of claim 48, wherein the multi-specific antibody of (d) is a bispecific antibody.

51. The method of claim 48, wherein the substitute residue and the residue at L38 of the first polypeptide are both glutamic acid (E).

52. The method of claim 48, wherein criteria (1) and (4) are true.

53. The method of claim 48, wherein criteria (2) and (5) are true.

54. The method of claim 48, wherein criteria (3) and (6) are true.

* * * * *

SEQUENCE LISTING

```
<160> NUMBER OF SEQ ID NOS: 60

<210> SEQ ID NO 1
<211> LENGTH: 423
<212> TYPE: DNA
<213> ORGANISM: Artificial Sequence
<220> FEATURE:
<223> OTHER INFORMATION: an artificially synthesized sequence

<400> SEQUENCE: 1
atgaaacacc tgtggttctt cctcctcctg gtggcagctc ccagatgggt cctgtctcag      60
gtgcagctgc agcagtcagg acctggcctc gtgaaacctt ctgagactct gtctctcacc     120
```

```
tgcactgtct ctggctactc catctccagt ggttattact ggacctggat ccggcagcct      180
ccaggaaagg gtctggaatg gattggctac atatccttcg acgtaccaa tgactacaac       240 ccatctctca aaaatcgagt caccatctct cgtgacacat ctaagaacaa ttttttccctg    300 aagttgaact ctgtaactgc tgcagacaca gctgtatatt actgtgcaag aggccccccc     360
gctacttact ggggccaagg gactctggtc actgtctctt caggtaagtc ggcctcgggg    420
gcc                                                                   423

<210> SEQ ID NO 2
<211> LENGTH: 115
<212> TYPE: PRT
<213> ORGANISM: Artificial Sequence
<220> FEATURE:
<223> OTHER INFORMATION: an artificially synthesized sequence

<400> SEQUENCE: 2

Gln Val Gln Leu Gln Gln Ser Gly Pro Gly Leu Val Lys Pro Ser Glu
1               5                   10                  15

Thr Leu Ser Leu Thr Cys Thr Val Ser Gly Tyr Ser Ile Ser Ser Gly
            20                  25                  30

Tyr Tyr Trp Thr Trp Ile Arg Gln Pro Pro Gly Lys Gly Leu Glu Trp
        35                  40                  45

Ile Gly Tyr Ile Ser Phe Asp Gly Thr Asn Asp Tyr Asn Pro Ser Leu
    50                  55                  60

Lys Asn Arg Val Thr Ile Ser Arg Asp Thr Ser Lys Asn Asn Phe Ser
65                  70                  75                  80

Leu Lys Leu Asn Ser Val Thr Ala Ala Asp Thr Ala Val Tyr Tyr Cys
                85                  90                  95

Ala Arg Gly Pro Pro Ala Thr Tyr Trp Gly Gln Gly Thr Leu Val Thr
            100                 105                 110

Val Ser Ser
        115

<210> SEQ ID NO 3
<211> LENGTH: 384
<212> TYPE: DNA
<213> ORGANISM: Artificial Sequence
<220> FEATURE:
<223> OTHER INFORMATION: an artificially synthesized sequence

<400> SEQUENCE: 3
atggacatga gggtgcccgc tcagctcctg gggctcctgc tactctggct ccgaggtgcc      60
agatgtgaaa ttgtgttgac gcagtctcca tcctccctgt ctgcatctgt aggagacaga    120
gtcaccatca cttgcagggc cacctcaagt gtaaattaca tttactggta tcagcagaaa    180
ccagggaaag cccctaagct cctgatctat tatacatcca acctggctcc tggggtccca    240
tcaaggttca gcggcagtgg atctgggaca gatttcactc tcaccatcaa cagcctgcag    300
cctgaagatt ttgcaactta ctattgccag cagttttcta gttccccatg gacgttcggc    360
ggagggacca agctggagat caaa                                            384

<210> SEQ ID NO 4
<211> LENGTH: 106
<212> TYPE: PRT
<213> ORGANISM: Artificial Sequence
<220> FEATURE:
<223> OTHER INFORMATION: an artificially synthesized sequence

<400> SEQUENCE: 4
```

Glu Ile Val Leu Thr Gln Ser Pro Ser Ser Leu Ser Ala Ser Val Gly
1               5                   10                  15

Asp Arg Val Thr Ile Thr Cys Arg Ala Thr Ser Ser Val Asn Tyr Ile
            20                  25                  30

Tyr Trp Tyr Gln Gln Lys Pro Gly Lys Ala Pro Lys Leu Leu Ile Tyr
        35                  40                  45

Tyr Thr Ser Asn Leu Ala Pro Gly Val Pro Ser Arg Phe Ser Gly Ser
    50                  55                  60

Gly Ser Gly Thr Asp Phe Thr Leu Thr Ile Asn Ser Leu Gln Pro Glu
65                  70                  75                  80

Asp Phe Ala Thr Tyr Tyr Cys Gln Gln Phe Ser Ser Pro Trp Thr
                85                  90                  95

Phe Gly Gly Gly Thr Lys Leu Glu Ile Lys
            100                 105

<210> SEQ ID NO 5
<211> LENGTH: 443
<212> TYPE: DNA
<213> ORGANISM: Artificial Sequence
<220> FEATURE:
<223> OTHER INFORMATION: an artificially synthesized sequence

<400> SEQUENCE: 5

```
atggactgga cctggagggt cttctgcttg ctggctgtag ctccaggtgc tcactcccag      60
gtgcagctgg tgcagtctgg ggctgaggtg aagaagcctg gggcctcagt gaaggtttcc     120
tgcaaggcat ctggatacac cttcacccac tttgttttgc actgggtgcg acaggcccct     180
ggacaagggc ttgagtggat gggatatatt attccttaca atgatggtac aagtacaat      240 gagaagttca aaggcagagt caccatgacc agtgacacgt ccacgagcac agtctacatg     300
gagctgagca tcctgaaatc tgaggacacg gccgtgtatt tctgtgcgag agggaatagg     360
tacgacgtag gttcctatgc tatggactac tggggccaag ggaccacggt caccgtctca     420
tcaggtaagt ggcctcgggg gcc                                             443
```

<210> SEQ ID NO 6
<211> LENGTH: 123
<212> TYPE: PRT
<213> ORGANISM: Artificial Sequence
<220> FEATURE:
<223> OTHER INFORMATION: an artificially synthesized sequence

<400> SEQUENCE: 6

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr His Phe
            20                  25                  30

Val Leu His Trp Val Arg Gln Ala Pro Gly Gln Gly Leu Glu Trp Met
        35                  40                  45

Gly Tyr Ile Ile Pro Tyr Asn Asp Gly Thr Lys Tyr Asn Glu Lys Phe
    50                  55                  60

Lys Gly Arg Val Thr Met Thr Ser Asp Thr Ser Thr Ser Thr Val Tyr
65                  70                  75                  80

Met Glu Leu Ser Ile Leu Arg Ser Glu Asp Thr Ala Val Tyr Phe Cys
                85                  90                  95

Ala Arg Gly Asn Arg Tyr Asp Val Gly Ser Tyr Ala Met Asp Tyr Trp
            100                 105                 110

Gly Gln Gly Thr Thr Val Thr Ser Val Ser Ser
            115                 120

<210> SEQ ID NO 7
<211> LENGTH: 399
<212> TYPE: DNA
<213> ORGANISM: Artificial Sequence
<220> FEATURE:
<223> OTHER INFORMATION: an artificially synthesized sequence

<400> SEQUENCE: 7

```
atggtgttgc agacccaggt cttcatttct ctgttgctct ggatctctgg tgcctacggg      60
gacatcgtga tgacccagtc tccagactcc ctggctgtgt ctctgggcga gagggccacc     120
atcaactgca gtccagtca gagccttta tatagtagca atcaaaagaa ctacttggcc      180
tggtaccagc agaaaccagg acagcctcct aagctgctca tttactgggc atccactagg     240
gaatctgggg tccctgaccg attcagtggc agcgggtctg ggacagattt cactctcaag     300
atcagccgcg tgcaggctga agatgtggga gtttattact gtcagcaata ttataggttt     360
ccgtacacgt tcggcggagg gaccaaggtg gagatcaaa                            399
```

<210> SEQ ID NO 8
<211> LENGTH: 113
<212> TYPE: PRT
<213> ORGANISM: Artificial Sequence
<220> FEATURE:
<223> OTHER INFORMATION: an artificially synthesized sequence

<400> SEQUENCE: 8

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Tyr Ser
            20                  25                  30

Ser Asn Gln Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Lys
65                  70                  75                  80

Ile Ser Arg Val Gln Ala Glu Asp Val Gly Val Tyr Tyr Cys Gln Gln
                85                  90                  95

Tyr Tyr Arg Phe Pro Tyr Thr Phe Gly Gly Gly Thr Lys Val Glu Ile
            100                 105                 110

Lys

<210> SEQ ID NO 9
<211> LENGTH: 327
<212> TYPE: PRT
<213> ORGANISM: Homo sapiens

<400> SEQUENCE: 9

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

```
Leu Ser Ser Val Val Thr Val Pro Ser Ser Leu Gly Thr Lys Thr
 65                  70                  75                  80

Tyr Thr Cys Asn Val Asp His Lys Pro Ser Asn Thr Lys Val Asp Lys
                 85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
210                 215                 220

Glu Pro Gln Val Cys Thr Leu Pro Pro Ser Gln Glu Glu Met Thr Lys
225                 230                 235                 240

Asn Gln Val Ser Leu Trp Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 10
<211> LENGTH: 107
<212> TYPE: PRT
<213> ORGANISM: Homo sapiens

<400> SEQUENCE: 10

Arg Thr Val Ala Ala Pro Ser Val Phe Ile Phe Pro Pro Ser Asp Glu
 1               5                  10                  15

Gln Leu Lys Ser Gly Thr Ala Ser Val Val Cys Leu Leu Asn Asn Phe
             20                  25                  30

Tyr Pro Arg Glu Ala Lys Val Gln Trp Lys Val Asp Asn Ala Leu Gln
         35                  40                  45

Ser Gly Asn Ser Gln Glu Ser Val Thr Glu Gln Asp Ser Lys Asp Ser
     50                  55                  60

Thr Tyr Ser Leu Ser Ser Thr Leu Thr Leu Ser Lys Ala Asp Tyr Glu
 65                  70                  75                  80

Lys His Lys Val Tyr Ala Cys Glu Val Thr His Gln Gly Leu Ser Ser
                 85                  90                  95

Pro Val Thr Lys Ser Phe Asn Arg Gly Glu Cys
            100                 105
```

```
                100             105

<210> SEQ ID NO 11
<211> LENGTH: 327
<212> TYPE: PRT
<213> ORGANISM: Homo sapiens

<400> SEQUENCE: 11

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Cys Glu Met Thr Lys
225                 230                 235                 240

Asn Gln Val Ser Leu Ser Cys Ala Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Val Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 12
<211> LENGTH: 1572
<212> TYPE: DNA
<213> ORGANISM: Homo sapiens
```

<400> SEQUENCE: 12

```
atggactgga cctggaggtt cctctttgtg gtggcagcag ctacaggtgt ccagtcccag    60
gtgcagctgg tgcagtctgg acctgaggtg aagaagcctg ggcctcagt gaaggtctcc   120
tgcaaggctt ctggatacac cttcaccaac tcctggatga actgggtgag cagaggcct   180
ggaaagggtc ttgagtggat tggacggatt tatcctggag atggagaaac tatctacaat   240
gggaaattca gggtcagagt cacgattacc gcggacgaat ccacgagcac agcctacatg   300
caactgagca gcctgagatc tgaggacacg gccgtgtatt actgtgcgag aggctatgat   360
gattactcgt ttgcttactg gggccaggga accacggtca ccgtctcttc aggtggtggt   420
ggatccggag gtggtggatc gggtggtgga ggatcggata ttgtgatgac tcagtctcca   480
ctctcccctgc ccgtcacccc tggagagccg gcctccatct cctgcaggtc tagtaagagt   540
ctcctgcata gtaatggcaa cacttacttg tattggttcc tgcagaagcc agggcagtct   600
ccacagctcc tgatctatcg gatgtccaac cttgcctcag gggtccctga caggttcagt   660
ggcagtggat caggcacaga ttttacactg aaaatcagca gagtggaggc tgaggatgtt   720
ggggtttatt actgcatgca acatatagaa tatcctttta cgttcggcca agggaccaaa   780
ctggaaatca aggaggtgg tggatcgggt ggtggtggtt cggaggcgg tggatcgcag   840
gtgcagctgg tgcagtctgg acctgaggtg aagaagcctg ggcctcagt gaaggtctcc   900
tgcaaggctt ctggatacac cttcaccaac tcctggatga actgggtgag cagaggcct   960
ggaaagggtc ttgagtggat tggacggatt tatcctggag atggagaaac tatctacaat  1020
gggaaattca gggtcagagt cacgattacc gcggacgaat ccacgagcac agcctacatg  1080
caactgagca gcctgagatc tgaggacacg gccgtgtatt actgtgcgag aggctatgat  1140
gattactcgt ttgcttactg gggccaggga accacggtca ccgtctcttc aggtggtggt  1200
ggatccggag gtggtggatc gggtggtgga ggatcggata ttgtgatgac tcagtctcca  1260
ctctcccctgc ccgtcacccc tggagagccg gcctccatct cctgcaggtc tagtaagagt  1320
ctcctgcata gtaatggcaa cacttacttg tattggttcc tgcagaagcc agggcagtct  1380
ccacagctcc tgatctatcg gatgtccaac cttgcctcag gggtccctga caggttcagt  1440
ggcagtggat caggcacaga ttttacactg aaaatcagca gagtggaggc tgaggatgtt  1500
ggggtttatt actgcatgca acatatagaa tatcctttta cgttcggcca agggaccaaa  1560
ctggaaatca aa                                                      1572
```

<210> SEQ ID NO 13
<211> LENGTH: 118
<212> TYPE: PRT
<213> ORGANISM: Homo sapiens

<400> SEQUENCE: 13

```
Gln Val Gln Leu Val Gln Ser Gly Pro Glu Val Lys Lys Pro Gly Ala
1               5                   10                  15

Ser Val Lys Val Ser Cys Lys Ala Ser Gly Tyr Thr Phe Thr Asn Ser
            20                  25                  30

Trp Met Asn Trp Val Arg Gln Arg Pro Gly Lys Gly Leu Glu Trp Ile
        35                  40                  45

Gly Arg Ile Tyr Pro Gly Asp Gly Glu Thr Ile Tyr Asn Gly Lys Phe
    50                  55                  60

Arg Val Arg Val Thr Ile Thr Ala Asp Glu Ser Thr Ser Thr Ala Tyr
65                  70                  75                  80
```

Met Gln Leu Ser Ser Leu Arg Ser Glu Asp Thr Ala Val Tyr Tyr Cys
            85                  90                  95

Ala Arg Gly Tyr Asp Asp Tyr Ser Phe Ala Tyr Trp Gly Gln Gly Thr
            100                 105                 110

Thr Val Thr Val Ser Ser
        115

<210> SEQ ID NO 14
<211> LENGTH: 112
<212> TYPE: PRT
<213> ORGANISM: Homo sapiens

<400> SEQUENCE: 14

Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Gly Asn Thr Tyr Leu Tyr Trp Phe Leu Gln Lys Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln His
                85                  90                  95

Ile Glu Tyr Pro Phe Thr Phe Gly Gln Gly Thr Lys Leu Glu Ile Lys
            100                 105                 110

<210> SEQ ID NO 15
<211> LENGTH: 1572
<212> TYPE: DNA
<213> ORGANISM: Artificial Sequence
<220> FEATURE:
<223> OTHER INFORMATION: an artificially synthesized sequence

<400> SEQUENCE: 15
atggactgga cctggaggtt cctctttgtg gtggcagcag ctacaggtgt ccagtcccag     60
gtgcagctgg tgcagtctgg acctgaggtg aagaagcctg ggcctcagt gaaggtctcc    120 tgcaaggctt ctggatacac cttcaccaac tcctggatga actgggtgag ggagaggcct    180
ggaaagggtc ttgagtggat tggacggatt tatcctggag atggagaaac tatctacaat    240
gggaaattca gggtcagagt cacgattacc gcggacgaat ccacgagcac agcctacatg    300
caactgagca gcctgagatc tgaggacacg gccgtgtatt actgtgcgag aggctatgat    360
gattactcgt ttgcttactg gggccaggga accacggtca ccgtctcttc aggtggtggt    420
ggatccggag gtggtggatc gggtggtgga ggatcggata ttgtgatgac tcagtctcca    480
ctctccctgc ccgtcacccc tggagagccg gcctccatct cctgcaggtc tagtaagagt    540
ctcctgcata gtaatggcaa cacttacttg tattggttcc tgcagaagcc agggcagtct    600
ccacagctcc tgatctatcg gatgtccaac cttgcctcag ggtccctga caggttcagt    660 ggcagtggat caggcacaga ttttacactg aaaatcagca gtggaggc tgaggatgtt    720 ggggtttatt actgcatgca acatatagaa tatccttta cgttcggcca agggaccaaa    780
ctggaaatca aaggaggtgg tggatcgggt ggtggtggtt cgggaggcgg tggatcgcag    840
gtgcagctgg tgcagtctgg acctgaggtg aagaagcctg ggcctcagt gaaggtctcc    900 tgcaaggctt ctggatacac cttcaccaac tcctggatga actgggtgag gaagaggcct    960

```
ggaaagggtc ttgagtggat tggacggatt tatcctggag atggagaaac tatctacaat    1020
gggaaattca gggtcagagt cacgattacc gcggacgaat ccacgagcac agcctacatg    1080
caactgagca gcctgagatc tgaggacacg gccgtgtatt actgtgcgag aggctatgat    1140
gattactcgt ttgcttactg gggccaggga accacggtca ccgtctcttc aggtggtggt    1200
ggatccggag gtggtggatc gggtggtgga ggatcggata ttgtgatgac tcagtctcca    1260
ctctcccctg ccgtcacccc tggagagccg gcctccatct cctgcaggtc tagtaagagt    1320
ctcctgcata gtaatggcaa cacttacttg tattggttcc tgaagaagcc agggcagtct    1380
ccacagctcc tgatctatcg gatgtccaac cttgcctcag ggtccctga caggttcagt    1440 ggcagtggat caggcacaga ttttacactg aaaatcagca gagtggaggc tgaggatgtt    1500
ggggtttatt actgcatgca acatatagaa tatcctttta cgttcggcca agggaccaaa    1560
ctggaaatca aa                                                        1572
```

<210> SEQ ID NO 16
<211> LENGTH: 524
<212> TYPE: PRT
<213> ORGANISM: Artificial Sequence
<220> FEATURE:
<223> OTHER INFORMATION: an artificially synthesized sequence

<400> SEQUENCE: 16

```
Met Asp Trp Thr Trp Arg Phe Leu Phe Val Val Ala Ala Ala Thr Gly
1               5                   10                  15

Val Gln Ser Gln Val Gln Leu Val Gln Ser Gly Pro Glu Val Lys Lys
            20                  25                  30

Pro Gly Ala Ser Val Lys Val Ser Cys Lys Ala Ser Gly Tyr Thr Phe
        35                  40                  45

Thr Asn Ser Trp Met Asn Trp Val Arg Glu Arg Pro Gly Lys Gly Leu
    50                  55                  60

Glu Trp Ile Gly Arg Ile Tyr Pro Gly Asp Gly Glu Thr Ile Tyr Asn
65                  70                  75                  80

Gly Lys Phe Arg Val Arg Val Thr Ile Thr Ala Asp Glu Ser Thr Ser
                85                  90                  95

Thr Ala Tyr Met Gln Leu Ser Ser Leu Arg Ser Glu Asp Thr Ala Val
            100                 105                 110

Tyr Tyr Cys Ala Arg Gly Tyr Asp Asp Tyr Ser Phe Ala Tyr Trp Gly
        115                 120                 125

Gln Gly Thr Thr Val Thr Val Ser Ser Gly Gly Gly Ser Gly Gly
    130                 135                 140

Gly Gly Ser Gly Gly Gly Gly Ser Asp Ile Val Met Thr Gln Ser Pro
145                 150                 155                 160

Leu Ser Leu Pro Val Thr Pro Gly Glu Pro Ala Ser Ile Ser Cys Arg
                165                 170                 175

Ser Ser Lys Ser Leu Leu His Ser Asn Gly Asn Thr Tyr Leu Tyr Trp
            180                 185                 190

Phe Leu Glu Lys Pro Gly Gln Ser Pro Gln Leu Leu Ile Tyr Arg Met
        195                 200                 205

Ser Asn Leu Ala Ser Gly Val Pro Asp Arg Phe Ser Gly Ser Gly Ser
    210                 215                 220

Gly Thr Asp Phe Thr Leu Lys Ile Ser Arg Val Glu Ala Glu Asp Val
225                 230                 235                 240

Gly Val Tyr Tyr Cys Met Gln His Ile Glu Tyr Pro Phe Thr Phe Gly
```

245                 250                 255
Gln Gly Thr Lys Leu Glu Ile Lys Gly Gly Gly Ser Gly Gly Gly
                260                 265                 270
Gly Ser Gly Gly Gly Ser Gln Val Gln Leu Val Gln Ser Gly Pro
            275                 280                 285
Glu Val Lys Lys Pro Gly Ala Ser Val Lys Val Ser Cys Lys Ala Ser
        290                 295                 300
Gly Tyr Thr Phe Thr Asn Ser Trp Met Asn Trp Val Arg Lys Arg Pro
305                 310                 315                 320
Gly Lys Gly Leu Glu Trp Ile Gly Arg Ile Tyr Pro Gly Asp Gly Glu
                325                 330                 335
Thr Ile Tyr Asn Gly Lys Phe Arg Val Arg Val Thr Ile Thr Ala Asp
                340                 345                 350
Glu Ser Thr Ser Thr Ala Tyr Met Gln Leu Ser Ser Leu Arg Ser Glu
            355                 360                 365
Asp Thr Ala Val Tyr Tyr Cys Ala Arg Gly Tyr Asp Asp Tyr Ser Phe
        370                 375                 380
Ala Tyr Trp Gly Gln Gly Thr Thr Val Thr Val Ser Ser Gly Gly Gly
385                 390                 395                 400
Gly Ser Gly Gly Gly Gly Ser Gly Gly Gly Gly Ser Asp Ile Val Met
                405                 410                 415
Thr Gln Ser Pro Leu Ser Leu Pro Val Thr Pro Gly Glu Pro Ala Ser
            420                 425                 430
Ile Ser Cys Arg Ser Ser Lys Ser Leu Leu His Ser Asn Gly Asn Thr
        435                 440                 445
Tyr Leu Tyr Trp Phe Leu Lys Lys Pro Gly Gln Ser Pro Gln Leu Leu
    450                 455                 460
Ile Tyr Arg Met Ser Asn Leu Ala Ser Gly Val Pro Asp Arg Phe Ser
465                 470                 475                 480
Gly Ser Gly Ser Gly Thr Asp Phe Thr Leu Lys Ile Ser Arg Val Glu
                485                 490                 495
Ala Glu Asp Val Gly Val Tyr Tyr Cys Met Gln His Ile Glu Tyr Pro
            500                 505                 510
Phe Thr Phe Gly Gln Gly Thr Lys Leu Glu Ile Lys
        515                 520

<210> SEQ ID NO 17
<211> LENGTH: 1572
<212> TYPE: DNA
<213> ORGANISM: Artificial Sequence
<220> FEATURE:
<223> OTHER INFORMATION: an artificially synthesized sequence

<400> SEQUENCE: 17
atggactgga cctggaggtt cctctttgtg gtggcagcag ctacaggtgt ccagtcccag     60
gtgcagctgg tgcagtctgg acctgaggtg aagaagcctg ggcctcagt gaaggtctcc    120 tgcaaggctt ctggatacac cttcaccaac tcctggatga actgggtgag ggagaggcct    180
ggaaagggtc ttgagtggat tggacggatt tatcctggag atggagaaac tatctacaat    240
gggaaattca gggtcagagt cacgattacc gcggacgaat ccacgagcac agcctacatg    300
caactgagca gcctgagatc tgaggacacg gccgtgtatt actgtgcgag aggctatgat    360
gattactcgt ttgcttactg gggccaggga accacggtca ccgtctcttc aggtggtggt    420
ggatccggag gtggtggatc gggtggtgga ggatcggata ttgtgatgac tcagtctcca    480

```
ctctccctgc cgtcacccc tggagagccg gcctccatct cctgcaggtc tagtaagagt      540
ctcctgcata gtaatggcaa cacttacttg tattggttcc tgaagaagcc agggcagtct      600
ccacagctcc tgatctatcg gatgtccaac cttgcctcag gggtccctga caggttcagt      660
ggcagtggat caggcacaga ttttacactg aaaatcagca gagtggaggc tgaggatgtt      720
ggggtttatt actgcatgca acatatagaa tatccttta cgttcggcca agggaccaaa      780
ctggaaatca aggaggtgg tggatcgggt ggtggtggtt cgggaggcgg tggatcgcag      840
gtgcagctgg tgcagtctgg acctgaggtg aagaagcctg ggcctcagt gaaggtctcc      900
tgcaaggctt ctggatacac cttcaccaac tcctggatga actgggtgag gaagaggcct      960
ggaaagggtc ttgagtggat tggacggatt tatcctggag atggagaaac tatctacaat     1020
gggaaattca gggtcagagt cacgattacc gcggacgaat ccacgagcac agcctacatg     1080
caactgagca gcctgagatc tgaggacacg gccgtgtatt actgtgcgag aggctatgat     1140
gattactcgt ttgcttactg gggccaggga accacggtca ccgtctcttc aggtggtggt     1200
ggatccggag gtggtggatc gggtggtgga ggatcggata ttgtgatgac tcagtctcca     1260
ctctccctgc cgtcacccc tggagagccg gcctccatct cctgcaggtc tagtaagagt     1320
ctcctgcata gtaatggcaa cacttacttg tattggttcc tgaagaagcc agggcagtct     1380
ccacagctcc tgatctatcg gatgtccaac cttgcctcag gggtccctga caggttcagt     1440
ggcagtggat caggcacaga ttttacactg aaaatcagca gagtggaggc tgaggatgtt     1500
ggggtttatt actgcatgca acatatagaa tatccttta cgttcggcca agggaccaaa     1560
ctggaaatca aa                                                          1572
```

<210> SEQ ID NO 18
<211> LENGTH: 524
<212> TYPE: PRT
<213> ORGANISM: Artificial Sequence
<220> FEATURE:
<223> OTHER INFORMATION: an artificially synthesized sequence

<400> SEQUENCE: 18

Met Asp Trp Thr Trp Arg Phe Leu Phe Val Val Ala Ala Ala Thr Gly
1               5                   10                  15

Val Gln Ser Gln Val Gln Leu Val Gln Ser Gly Pro Glu Val Lys Lys
            20                  25                  30

Pro Gly Ala Ser Val Lys Val Ser Cys Lys Ala Ser Gly Tyr Thr Phe
        35                  40                  45

Thr Asn Ser Trp Met Asn Trp Val Arg Glu Arg Pro Gly Lys Gly Leu
    50                  55                  60

Glu Trp Ile Gly Arg Ile Tyr Pro Gly Asp Gly Glu Thr Ile Tyr Asn
65                  70                  75                  80

Gly Lys Phe Arg Val Arg Val Thr Ile Thr Ala Asp Glu Ser Thr Ser
                85                  90                  95

Thr Ala Tyr Met Gln Leu Ser Ser Leu Arg Ser Glu Asp Thr Ala Val
            100                 105                 110

Tyr Tyr Cys Ala Arg Gly Tyr Asp Asp Tyr Ser Phe Ala Tyr Trp Gly
        115                 120                 125

Gln Gly Thr Thr Val Thr Val Ser Ser Gly Gly Gly Gly Ser Gly Gly
    130                 135                 140

Gly Gly Ser Gly Gly Gly Gly Ser Asp Ile Val Met Thr Gln Ser Pro
145                 150                 155                 160

Leu Ser Leu Pro Val Thr Pro Gly Glu Pro Ala Ser Ile Ser Cys Arg

| | | | | | 165 | | | | 170 | | | | 175 | | |
|---|---|---|---|---|---|---|---|---|---|---|---|---|---|---|---|
Ser Ser Lys Ser Leu Leu His Ser Asn Gly Asn Thr Tyr Leu Tyr Trp
        180                 185             190

Phe Leu Lys Lys Pro Gly Gln Ser Pro Gln Leu Leu Ile Tyr Arg Met
  195                 200             205

Ser Asn Leu Ala Ser Gly Val Pro Asp Arg Phe Ser Gly Ser Gly Ser
     210               215            220

Gly Thr Asp Phe Thr Leu Lys Ile Ser Arg Val Glu Ala Glu Asp Val
225               230             235            240

Gly Val Tyr Tyr Cys Met Gln His Ile Glu Tyr Pro Phe Thr Phe Gly
         245              250            255

Gln Gly Thr Lys Leu Glu Ile Lys Gly Gly Gly Ser Gly Gly Gly
           260            265            270

Gly Ser Gly Gly Gly Ser Gln Val Gln Leu Val Gln Ser Gly Pro
     275             280           285

Glu Val Lys Lys Pro Gly Ala Ser Val Lys Val Ser Cys Lys Ala Ser
  290                 295             300

Gly Tyr Thr Phe Thr Asn Ser Trp Met Asn Trp Val Arg Lys Arg Pro
305               310             315            320

Gly Lys Gly Leu Glu Trp Ile Gly Arg Ile Tyr Pro Gly Asp Gly Glu
         325              330            335

Thr Ile Tyr Asn Gly Lys Phe Arg Val Arg Val Thr Ile Thr Ala Asp
           340            345            350

Glu Ser Thr Ser Thr Ala Tyr Met Gln Leu Ser Ser Leu Arg Ser Glu
     355               360            365

Asp Thr Ala Val Tyr Tyr Cys Ala Arg Gly Tyr Asp Asp Tyr Ser Phe
  370                 375             380

Ala Tyr Trp Gly Gln Gly Thr Thr Val Thr Val Ser Ser Gly Gly Gly
385               390             395            400

Gly Ser Gly Gly Gly Ser Gly Gly Gly Ser Asp Ile Val Met
         405              410            415

Thr Gln Ser Pro Leu Ser Leu Pro Val Thr Pro Gly Glu Pro Ala Ser
           420            425            430

Ile Ser Cys Arg Ser Ser Lys Ser Leu Leu His Ser Asn Gly Asn Thr
     435             440            445

Tyr Leu Tyr Trp Phe Leu Glu Lys Pro Gly Gln Ser Pro Gln Leu Leu
  450                 455             460

Ile Tyr Arg Met Ser Asn Leu Ala Ser Gly Val Pro Asp Arg Phe Ser
465               470             475            480

Gly Ser Gly Ser Gly Thr Asp Phe Thr Leu Lys Ile Ser Arg Val Glu
         485              490            495

Ala Glu Asp Val Gly Val Tyr Tyr Cys Met Gln His Ile Glu Tyr Pro
           500            505            510

Phe Thr Phe Gly Gln Gly Thr Lys Leu Glu Ile Lys
     515               520

<210> SEQ ID NO 19
<211> LENGTH: 411
<212> TYPE: DNA
<213> ORGANISM: Homo sapiens

<400> SEQUENCE: 19
atggactgga cctggagaat cctcttttg gtggcagcag ccaaaggtgc ccactccgag   60
gtccagcttg tgcagtctgg ggctgaggtg gtgaagcctg gtcctcagt gaaggtttcc  120

```
tgcacggcct ctggatacac cttcagtgac tactatatgc actgggtgcg ccaggccccc      180
ggagaagggc ttgagtggat gggatacatt aatcctagca gtggttatac taagtacaat      240
cggaagttca gggacagagt caccattacc gcggacaaat ccacgagcac agcctacatg      300
gagctgagca gcctgagatc tgaagacacg gctgtgtatt actgtgcgag agggggtctc      360
ggttactacc ttgactactg gggcgagggc accacggtca ccgtctcctc a               411
```

<210> SEQ ID NO 20
<211> LENGTH: 137
<212> TYPE: PRT
<213> ORGANISM: Homo sapiens

<400> SEQUENCE: 20

```
Met Asp Trp Thr Trp Arg Ile Leu Phe Leu Val Ala Ala Ala Lys Gly
1               5                   10                  15

Ala His Ser Glu Val Gln Leu Val Gln Ser Gly Ala Glu Val Val Lys
            20                  25                  30

Pro Gly Ser Ser Val Lys Val Ser Cys Thr Ala Ser Gly Tyr Thr Phe
        35                  40                  45

Ser Asp Tyr Tyr Met His Trp Val Arg Gln Ala Pro Gly Glu Gly Leu
    50                  55                  60

Glu Trp Met Gly Tyr Ile Asn Pro Ser Ser Gly Tyr Thr Lys Tyr Asn
65                  70                  75                  80

Arg Lys Phe Arg Asp Arg Val Thr Ile Thr Ala Asp Lys Ser Thr Ser
                85                  90                  95

Thr Ala Tyr Met Glu Leu Ser Ser Leu Arg Ser Glu Asp Thr Ala Val
            100                 105                 110

Tyr Tyr Cys Ala Arg Gly Gly Leu Gly Tyr Tyr Leu Asp Tyr Trp Gly
        115                 120                 125

Glu Gly Thr Thr Val Thr Val Ser Ser
    130                 135
```

<210> SEQ ID NO 21
<211> LENGTH: 414
<212> TYPE: DNA
<213> ORGANISM: Homo sapiens

<400> SEQUENCE: 21

```
atggactgga cctggagcat cctttctctg gtggcagcag caacaggtgc ccactccgag      60
gtgcagctgg tgcagtctgg agctcaggtg aagaagccgg ggcctcagt gaaggtctcc      120 tgcaaggcct ctggctacac gttttccgac aacaacatgg actgggtgcg acaggccct      180 ggaaaagggc ttgagtggat gggagatatt aatactaaaa gtggtggttc tatctacaac      240
cagaagttca gggcagagt catcatgacc atagacaaat ccacgggcac agcctacatg      300
gaattgagga gcctgagatc agacgacacg gccatatatt actgtgcgag aggaggagc      360 tacggctact actttgacta ctgggggccgg ggaaccctgg tcaccgtctc ctca           414
```

<210> SEQ ID NO 22
<211> LENGTH: 138
<212> TYPE: PRT
<213> ORGANISM: Homo sapiens

<400> SEQUENCE: 22

```
Met Asp Trp Thr Trp Ser Ile Leu Phe Leu Val Ala Ala Ala Thr Gly
1               5                   10                  15
```

Ala His Ser Glu Val Gln Leu Val Gln Ser Gly Ala Gln Val Lys Lys
            20                  25                  30

Pro Gly Ala Ser Val Lys Val Ser Cys Lys Ala Ser Gly Tyr Thr Phe
        35                  40                  45

Ser Asp Asn Asn Met Asp Trp Val Arg Gln Ala Pro Gly Lys Gly Leu
50                  55                  60

Glu Trp Met Gly Asp Ile Asn Thr Lys Ser Gly Ser Ile Tyr Asn
65                  70                  75                  80

Gln Lys Phe Lys Gly Arg Val Ile Met Thr Ile Asp Lys Ser Thr Gly
                85                  90                  95

Thr Ala Tyr Met Glu Leu Arg Ser Leu Arg Ser Asp Asp Thr Ala Ile
            100                 105                 110

Tyr Tyr Cys Ala Arg Arg Ser Tyr Gly Tyr Tyr Phe Asp Tyr Trp
        115                 120                 125

Gly Arg Gly Thr Leu Val Thr Val Ser Ser
        130                 135

<210> SEQ ID NO 23
<211> LENGTH: 384
<212> TYPE: DNA
<213> ORGANISM: Homo sapiens

<400> SEQUENCE: 23
atggacatga gggtccccgc tcagctcctg gggctcctgc tactctggct ccgaggtgcc    60
agatgtgaca tcgtgatgac ccagtctcca tcctccctgt ctgcatctgt aggagacaga   120
gtcaccatca cttgcaaggc cagtcagaat gtgggactg ctgtagcctg gtatcagcag   180
aaaccaggga agcccctaa gctcctgatc tattcggcat cctaccgggc cagtggggtc   240
ccatcaaggt tcagtggcag tcgatatggg acagatttca ctctcaccat ctcaagcttg   300
caacctgaag atttagcaac ttactactgt cagcaatata gcaactatat cacgttcggc   360
caagggacca aggtggagat caaa                                          384

<210> SEQ ID NO 24
<211> LENGTH: 128
<212> TYPE: PRT
<213> ORGANISM: Homo sapiens

<400> SEQUENCE: 24

Met Asp Met Arg Val Pro Ala Gln Leu Leu Gly Leu Leu Leu Leu Trp
1               5                   10                  15

Leu Arg Gly Ala Arg Cys Asp Ile Val Met Thr Gln Ser Pro Ser Ser
            20                  25                  30

Leu Ser Ala Ser Val Gly Asp Arg Val Thr Ile Thr Cys Lys Ala Ser
        35                  40                  45

Gln Asn Val Gly Thr Ala Val Ala Trp Tyr Gln Gln Lys Pro Gly Lys
50                  55                  60

Ala Pro Lys Leu Leu Ile Tyr Ser Ala Ser Tyr Arg Ala Ser Gly Val
65                  70                  75                  80

Pro Ser Arg Phe Ser Gly Ser Arg Tyr Gly Thr Asp Phe Thr Leu Thr
                85                  90                  95

Ile Ser Ser Leu Gln Pro Glu Asp Leu Ala Thr Tyr Tyr Cys Gln Gln
            100                 105                 110

Tyr Ser Asn Tyr Ile Thr Phe Gly Gln Gly Thr Lys Val Glu Ile Lys
        115                 120                 125

<210> SEQ ID NO 25
<211> LENGTH: 327
<212> TYPE: PRT
<213> ORGANISM: Homo sapiens

<400> SEQUENCE: 25

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 26
<211> LENGTH: 327
<212> TYPE: PRT
<213> ORGANISM: Homo sapiens

<400> SEQUENCE: 26

Ala Ser Thr Lys Gly Pro Ser Val Phe Pro Leu Ala Pro Cys Ser Arg

```
                1               5                   10                  15
            Ser Thr Ser Glu Ser Thr Ala Ala Leu Gly Cys Leu Val Lys Asp Tyr
                            20                  25                  30

Phe Pro Glu Pro Val Thr Val Ser Trp Asn Ser Gly Ala Leu Thr Ser
                            35                  40                  45

Gly Val His Thr Phe Pro Ala Val Leu Gln Ser Ser Gly Leu Tyr Ser
                        50                  55                  60

Leu Ser Ser Val Val Thr Val Pro Ser Ser Leu Gly Thr Lys Thr
             65                 70                  75                  80

Tyr Thr Cys Asn Val Asp His Lys Pro Ser Asn Thr Lys Val Asp Lys
                            85                  90                  95

Arg Val Glu Ser Lys Tyr Gly Pro Pro Cys Pro Pro Cys Pro Ala Pro
                            100                 105                 110

Glu Phe Leu Gly Gly Pro Ser Val Phe Leu Phe Pro Pro Lys Pro Lys
                            115                 120                 125

Asp Thr Leu Met Ile Ser Arg Thr Pro Glu Val Thr Cys Val Val Val
                        130                 135                 140

Asp Val Ser Gln Glu Asp Pro Glu Val Gln Phe Asn Trp Tyr Val Asp
            145                 150                 155                 160

Gly Val Glu Val His Asn Ala Lys Thr Lys Pro Arg Glu Glu Gln Phe
                            165                 170                 175

Asn Ser Thr Tyr Arg Val Val Ser Val Leu Thr Val Leu His Gln Asp
                            180                 185                 190

Trp Leu Asn Gly Lys Glu Tyr Lys Cys Lys Val Ser Asn Lys Gly Leu
                            195                 200                 205

Pro Ser Ser Ile Glu Lys Thr Ile Ser Lys Ala Lys Gly Gln Pro Arg
                            210                 215                 220

Glu Pro Gln Val Tyr Thr Leu Pro Pro Ser Gln Glu Glu Met Thr Lys
            225                 230                 235                 240

Asn Gln Val Ser Leu Thr Cys Leu Val Lys Gly Phe Tyr Pro Ser Asp
                            245                 250                 255

Ile Ala Val Glu Trp Glu Ser Asn Gly Gln Pro Glu Asn Asn Tyr Lys
                            260                 265                 270

Thr Thr Pro Pro Val Leu Asp Ser Asp Gly Ser Phe Phe Leu Tyr Ser
                            275                 280                 285

Asp Leu Thr Val Asp Lys Ser Arg Trp Gln Glu Gly Asn Val Phe Ser
                            290                 295                 300

Cys Ser Val Met His Glu Ala Leu His Asn His Tyr Thr Gln Lys Ser
            305                 310                 315                 320

Leu Ser Leu Ser Leu Gly Lys
                            325

<210> SEQ ID NO 27
<211> LENGTH: 327
<212> TYPE: PRT
<213> ORGANISM: Homo sapiens

<400> SEQUENCE: 27

Ala Ser Thr Lys Gly Pro Ser Val Phe Pro Leu Ala Pro Cys Ser Arg
 1               5                   10                  15

Ser Thr Ser Glu Ser Thr Ala Ala Leu Gly Cys Leu Val Lys Asp Tyr
                 20                  25                  30

Phe Pro Glu Pro Val Thr Val Ser Trp Asn Ser Gly Ala Leu Thr Ser
             35                  40                  45
```

```
Gly Val His Thr Phe Pro Ala Val Leu Gln Ser Ser Gly Leu Tyr Ser
            50                  55                  60

Leu Ser Ser Val Val Thr Val Pro Ser Ser Leu Gly Thr Lys Thr
 65                  70                  75                  80

Tyr Thr Cys Asn Val Asp His Lys Pro Ser Asn Thr Lys Val Asp Lys
                    85                  90                  95

Arg Val Glu Ser Lys Tyr Gly Pro Pro Cys Pro Pro Cys Pro Ala Pro
                100                 105                 110

Glu Phe Leu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
                180                 185                 190

Trp Leu Asn Gly Lys Glu Tyr Lys Cys Lys Val Ser Asn Lys Gly Leu
            195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
                260                 265                 270

Thr Thr Pro Pro Val Leu Lys Ser Asp Gly Ser Phe Phe Leu Tyr Ser
            275                 280                 285

Arg Leu Thr Val Asp Lys Ser Arg Trp Gln Glu Gly Asn Val Phe Ser
290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 28
<211> LENGTH: 327
<212> TYPE: PRT
<213> ORGANISM: Homo sapiens

<400> SEQUENCE: 28

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95
```

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
            165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
            195                 200                 205

Pro Ser Ser Ile Glu Lys Thr Ile Ser Lys Ala Lys Gly Gln Pro Arg
            210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Glu Gly Phe Tyr Pro Ser Asp
            245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
            275                 280                 285

Arg Leu Thr Val Asp Lys Ser Arg Trp Gln Glu Gly Asn Val Phe Ser
            290                 295                 300

Cys Ser Val Met His Glu Ala Leu His Asn His Tyr Thr Gln Lys Ser
305                 310                 315                 320

Leu Ser Leu Ser Leu Gly Lys
            325

<210> SEQ ID NO 29
<211> LENGTH: 327
<212> TYPE: PRT
<213> ORGANISM: Homo sapiens

<400> SEQUENCE: 29

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
            50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
            85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val

```
                130               135               140
Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
                180                 185                 190

Trp Leu Asn Gly Lys Glu Tyr Lys Cys Lys Val Ser Asn Lys Gly Leu
                195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Lys Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
                260                 265                 270

Thr Thr Pro Pro Val Leu Asp Ser Asp Gly Ser Phe Phe Leu Tyr Ser
                275                 280                 285

Arg Leu Thr Val Asp Lys Ser Arg Trp Gln Glu Gly Asn Val Phe Ser
290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 30
<211> LENGTH: 327
<212> TYPE: PRT
<213> ORGANISM: Homo sapiens

<400> SEQUENCE: 30

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
                35                  40                  45

Gly Val His Thr Phe Pro Ala Val Leu Gln Ser Ser Gly Leu Tyr Ser
            50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
                100                 105                 110

Glu Phe Leu Gly Gly Pro Ser Val Phe Leu Phe Pro Pro Lys Pro Lys
                115                 120                 125

Asp Thr Leu Met Ile Ser Arg Thr Pro Glu Val Thr Cys Val Val Val
                130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175
```

-continued

```
Asn Ser Thr Tyr Arg Val Val Ser Val Leu Thr Val Leu His Gln Asp
                180                 185                 190

Trp Leu Asn Gly Lys Glu Tyr Lys Cys Lys Val Ser Asn Lys Gly Leu
            195                 200                 205

Pro Ser Ser Ile Glu Lys Thr Ile Ser Lys Ala Lys Gly Gln Pro Arg
        210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
        290                 295                 300

Cys Ser Val Met His Glu Ala Leu His Asn His Tyr Thr Gln Glu Ser
305                 310                 315                 320

Leu Ser Leu Ser Leu Gly Lys
                325

<210> SEQ ID NO 31
<211> LENGTH: 327
<212> TYPE: PRT
<213> ORGANISM: Homo sapiens

<400> SEQUENCE: 31

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
        130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
                180                 185                 190

Trp Leu Asn Gly Lys Glu Tyr Lys Cys Lys Val Ser Asn Lys Gly Leu
            195                 200                 205

Pro Ser Ser Ile Glu Lys Thr Ile Ser Lys Ala Lys Gly Gln Pro Arg
        210                 215                 220
```

```
Glu Pro Gln Val Tyr Thr Leu Pro Pro Ser Gln Lys Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 32
<211> LENGTH: 327
<212> TYPE: PRT
<213> ORGANISM: Homo sapiens

<400> SEQUENCE: 32

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Met Thr Lys
225                 230                 235                 240

Asn Gln Val Ser Leu Thr Cys Leu Val Glu Gly Phe Tyr Pro Ser Asp
                245                 250                 255

Ile Ala Val Glu Trp Glu Ser Asn Gly Gln Pro Glu Asn Asn Tyr Lys
```

```
                    260                 265                 270
Thr Thr Pro Pro Val Leu Asp Ser Asp Gly Ser Phe Phe Leu Tyr Ser
            275                 280                 285

Asp Leu Thr Val Asp Lys Ser Arg Trp Gln Glu Gly Asn Val Phe Ser
        290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 33
<211> LENGTH: 327
<212> TYPE: PRT
<213> ORGANISM: Homo sapiens

<400> SEQUENCE: 33

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Lys Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Lys Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300
```

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 34
<211> LENGTH: 327
<212> TYPE: PRT
<213> ORGANISM: Homo sapiens

<400> SEQUENCE: 34

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Asp Leu Thr Val Asp Lys Ser Arg Trp Gln Glu Gly Asn Val Phe Ser
    290                 295                 300

Cys Ser Val Met His Glu Ala Leu His Asn His Tyr Thr Gln Glu Ser
305                 310                 315                 320

Leu Ser Leu Ser Leu Gly Lys
                325

<210> SEQ ID NO 35

```
<211> LENGTH: 327
<212> TYPE: PRT
<213> ORGANISM: Homo sapiens

<400> SEQUENCE: 35

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Lys Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Lys Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 36
<211> LENGTH: 327
<212> TYPE: PRT
<213> ORGANISM: Homo sapiens

<400> SEQUENCE: 36

Ala Ser Thr Lys Gly Pro Ser Val Phe Pro Leu Ala Pro Cys Ser Arg
1               5                   10                  15
```

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Glu Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Glu Ser
305                 310                 315                 320

Leu Ser Leu Ser Leu Gly Lys
                325

<210> SEQ ID NO 37
<211> LENGTH: 327
<212> TYPE: PRT
<213> ORGANISM: Homo sapiens

<400> SEQUENCE: 37

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser

```
                50                  55                  60
Leu Ser Ser Val Val Thr Val Pro Ser Ser Leu Gly Thr Lys Thr
 65                  70                  75                  80

Tyr Thr Cys Asn Val Asp His Lys Pro Ser Asn Thr Lys Val Asp Lys
                     85                  90                  95

Arg Val Glu Ser Lys Tyr Gly Pro Pro Cys Pro Pro Cys Pro Ala Pro
                100                 105                 110

Glu Phe Leu Gly Gly Pro Ser Val Phe Leu Phe Pro Pro Lys Pro Lys
                115                 120                 125

Asp Thr Leu Met Ile Ser Arg Thr Pro Glu Val Thr Cys Val Val Val
                130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
                180                 185                 190

Trp Leu Asn Gly Lys Glu Tyr Lys Cys Lys Val Ser Asn Lys Gly Leu
                195                 200                 205

Pro Ser Ser Ile Glu Lys Thr Ile Ser Lys Ala Lys Gly Gln Pro Arg
                210                 215                 220

Glu Pro Gln Val Tyr Thr Leu Pro Pro Ser Gln Lys Lys Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
                260                 265                 270

Thr Thr Pro Pro Val Leu Asp Ser Asp Gly Ser Phe Phe Leu Tyr Ser
                275                 280                 285

Arg Leu Thr Val Asp Lys Ser Arg Trp Gln Glu Gly Asn Val Phe Ser
                290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 38
<211> LENGTH: 327
<212> TYPE: PRT
<213> ORGANISM: Homo sapiens

<400> SEQUENCE: 38

Ala Ser Thr Lys Gly Pro Ser Val Phe Pro Leu Ala Pro Cys Ser Arg
 1               5                  10                  15

Ser Thr Ser Glu Ser Thr Ala Ala Leu Gly Cys Leu Val Lys Asp Tyr
                 20                  25                  30

Phe Pro Glu Pro Val Thr Val Ser Trp Asn Ser Gly Ala Leu Thr Ser
                 35                  40                  45

Gly Val His Thr Phe Pro Ala Val Leu Gln Ser Ser Gly Leu Tyr Ser
                 50                  55                  60

Leu Ser Ser Val Val Thr Val Pro Ser Ser Leu Gly Thr Lys Thr
 65                  70                  75                  80

Tyr Thr Cys Asn Val Asp His Lys Pro Ser Asn Thr Lys Val Asp Lys
                     85                  90                  95
```

```
Arg Val Glu Ser Lys Tyr Gly Pro Pro Cys Pro Pro Cys Pro Ala Pro
                100                 105                 110

Glu Phe Leu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
        130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
210                 215                 220

Glu Pro Gln Val Cys Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Asp Leu Thr Val Asp Lys Ser Arg Trp Gln Gln Gly Asn Val Phe Ser
290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 39
<211> LENGTH: 327
<212> TYPE: PRT
<213> ORGANISM: Homo sapiens

<400> SEQUENCE: 39

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
                100                 105                 110

Glu Phe Leu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
        130                 135                 140
```

```
Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Cys Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Lys Ser Asp Gly Ser Phe Phe Leu Tyr Ser
        275                 280                 285

Arg Leu Thr Val Asp Lys Ser Arg Trp Gln Gly Asn Val Phe Ser
290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 40
<211> LENGTH: 327
<212> TYPE: PRT
<213> ORGANISM: Homo sapiens

<400> SEQUENCE: 40

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
```

```
                    180                 185                 190
Trp Leu Asn Gly Lys Glu Tyr Lys Cys Lys Val Ser Asn Lys Gly Leu
            195                 200                 205
Pro Ser Ser Ile Glu Lys Thr Ile Ser Lys Ala Lys Gly Gln Pro Arg
        210                 215                 220
Glu Pro Gln Val Cys Thr Leu Pro Pro Ser Gln Glu Met Thr Lys
225                 230                 235                 240
Asn Gln Val Ser Leu Thr Cys Leu Val Glu Gly Phe Tyr Pro Ser Asp
                245                 250                 255
Ile Ala Val Glu Trp Glu Ser Asn Gly Gln Pro Glu Asn Asn Tyr Lys
            260                 265                 270
Thr Thr Pro Pro Val Leu Asp Ser Asp Gly Ser Phe Phe Leu Tyr Ser
        275                 280                 285
Arg Leu Thr Val Asp Lys Ser Arg Trp Gln Gln Gly Asn Val Phe Ser
    290                 295                 300
Cys Ser Val Met His Glu Ala Leu His Asn His Tyr Thr Gln Lys Ser
305                 310                 315                 320
Leu Ser Leu Ser Leu Gly Lys
                325

<210> SEQ ID NO 41
<211> LENGTH: 327
<212> TYPE: PRT
<213> ORGANISM: Homo sapiens

<400> SEQUENCE: 41

Ala Ser Thr Lys Gly Pro Ser Val Phe Pro Leu Ala Pro Cys Ser Arg
1               5                   10                  15
Ser Thr Ser Glu Ser Thr Ala Ala Leu Gly Cys Leu Val Lys Asp Tyr
            20                  25                  30
Phe Pro Glu Pro Val Thr Val Ser Trp Asn Ser Gly Ala Leu Thr Ser
        35                  40                  45
Gly Val His Thr Phe Pro Ala Val Leu Gln Ser Ser Gly Leu Tyr Ser
    50                  55                  60
Leu Ser Ser Val Val Thr Val Pro Ser Ser Ser Leu Gly Thr Lys Thr
65                  70                  75                  80
Tyr Thr Cys Asn Val Asp His Lys Pro Ser Asn Thr Lys Val Asp Lys
                85                  90                  95
Arg Val Glu Ser Lys Tyr Gly Pro Pro Cys Pro Pro Cys Pro Ala Pro
            100                 105                 110
Glu Phe Leu Gly Gly Pro Ser Val Phe Leu Phe Pro Pro Lys Pro Lys
        115                 120                 125
Asp Thr Leu Met Ile Ser Arg Thr Pro Glu Val Thr Cys Val Val Val
    130                 135                 140
Asp Val Ser Gln Glu Asp Pro Glu Val Gln Phe Asn Trp Tyr Val Asp
145                 150                 155                 160
Gly Val Glu Val His Asn Ala Lys Thr Lys Pro Arg Glu Glu Gln Phe
                165                 170                 175
Asn Ser Thr Tyr Arg Val Val Ser Val Leu Thr Val Leu His Gln Asp
            180                 185                 190
Trp Leu Asn Gly Lys Glu Tyr Lys Cys Lys Val Ser Asn Lys Gly Leu
        195                 200                 205
Pro Ser Ser Ile Glu Lys Thr Ile Ser Lys Ala Lys Gly Gln Pro Arg
    210                 215                 220
```

```
Glu Pro Gln Val Tyr Thr Leu Pro Pro Cys Gln Glu Lys Met Thr Lys
225                 230                 235                 240

Asn Gln Val Ser Leu Thr Cys Leu Val Lys Gly Phe Tyr Pro Ser Asp
            245                 250                 255

Ile Ala Val Glu Trp Glu Ser Asn Gly Gln Pro Glu Asn Asn Tyr Lys
        260                 265                 270

Thr Thr Pro Pro Val Leu Asp Ser Asp Gly Ser Phe Phe Leu Tyr Ser
    275                 280                 285

Arg Leu Thr Val Asp Lys Ser Arg Trp Gln Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 42
<211> LENGTH: 327
<212> TYPE: PRT
<213> ORGANISM: Homo sapiens

<400> SEQUENCE: 42

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Cys Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
            245                 250                 255

Ile Ala Val Glu Trp Glu Ser Asn Gly Gln Pro Glu Asn Asn Tyr Lys
        260                 265                 270
```

```
Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Glu Ser
305                 310                 315                 320

Leu Ser Leu Ser Leu Gly Lys
                325

<210> SEQ ID NO 43
<211> LENGTH: 327
<212> TYPE: PRT
<213> ORGANISM: Homo sapiens

<400> SEQUENCE: 43

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Cys Gln Lys Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
```

```
305              310              315              320
Leu Ser Leu Ser Leu Gly Lys
                325

<210> SEQ ID NO 44
<211> LENGTH: 327
<212> TYPE: PRT
<213> ORGANISM: Homo sapiens

<400> SEQUENCE: 44

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Cys Thr Leu Pro Pro Ser Gln Glu Glu Met Thr Lys
225                 230                 235                 240

Asn Gln Val Ser Leu Thr Cys Leu Val Glu Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Glu Ser
305                 310                 315                 320

Leu Ser Leu Ser Leu Gly Lys
                325

<210> SEQ ID NO 45
<211> LENGTH: 327
```

```
<212> TYPE: PRT
<213> ORGANISM: Homo sapiens

<400> SEQUENCE: 45

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Cys Gln Lys Lys Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 46
<211> LENGTH: 327
<212> TYPE: PRT
<213> ORGANISM: Homo sapiens

<400> SEQUENCE: 46

Ala Ser Thr Lys Gly Pro Ser Val Phe Pro Leu Ala Pro Cys Ser Arg
1               5                   10                  15
```

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Cys Gln Glu Glu Met Thr Lys
225                 230                 235                 240

Asn Gln Val Ser Leu Thr Cys Leu Val Glu Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Glu Ser
305                 310                 315                 320

Leu Ser Leu Ser Leu Gly Lys
                325

<210> SEQ ID NO 47
<211> LENGTH: 327
<212> TYPE: PRT
<213> ORGANISM: Homo sapiens

<400> SEQUENCE: 47

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

```
Leu Ser Ser Val Val Thr Val Pro Ser Ser Leu Gly Thr Lys Thr
 65                  70                  75                  80

Tyr Thr Cys Asn Val Asp His Lys Pro Ser Asn Thr Lys Val Asp Lys
                     85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
210                 215                 220

Glu Pro Gln Val Cys Thr Leu Pro Pro Ser Gln Lys Lys Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 48
<211> LENGTH: 330
<212> TYPE: PRT
<213> ORGANISM: Homo sapiens

<400> SEQUENCE: 48

Ala Ser Thr Lys Gly Pro Ser Val Phe Pro Leu Ala Pro Ser Ser Lys
  1               5                  10                  15

Ser Thr Ser Gly Gly Thr Ala Ala Leu Gly Cys Leu Val Lys Asp Tyr
                 20                  25                  30

Phe Pro Glu Pro Val Thr Val Ser Trp Asn Ser Gly Ala Leu Thr Ser
             35                  40                  45

Gly Val His Thr Phe Pro Ala Val Leu Gln Ser Ser Gly Leu Tyr Ser
         50                  55                  60

Leu Ser Ser Val Val Thr Val Pro Ser Ser Leu Gly Thr Gln Thr
 65                  70                  75                  80

Tyr Ile Cys Asn Val Asn His Lys Pro Ser Asn Thr Lys Val Asp Lys
                     85                  90                  95

Lys Val Glu Pro Lys Ser Cys Asp Lys Thr His Thr Cys Pro Pro Cys
```

```
                    100                 105                 110
Pro Ala Pro Glu Leu Leu Gly Gly Pro Ser Val Phe Leu Phe Pro Pro
            115                 120                 125
Lys Pro Lys Asp Thr Leu Met Ile Ser Arg Thr Pro Glu Val Thr Cys
    130                 135                 140
Val Val Val Asp Val Ser His Glu Asp Pro Glu Val Lys Phe Asn Trp
145                 150                 155                 160
Tyr Val Asp Gly Val Glu Val His Asn Ala Lys Thr Lys Pro Arg Glu
                165                 170                 175
Glu Gln Tyr Asn Ser Thr Tyr Arg Val Val Ser Val Leu Thr Val Leu
            180                 185                 190
His Gln Asp Trp Leu Asn Gly Lys Glu Tyr Lys Cys Lys Val Ser Asn
        195                 200                 205
Lys Ala Leu Pro Ala Pro Ile Glu Lys Thr Ile Ser Lys Ala Lys Gly
    210                 215                 220
Gln Pro Arg Glu Pro Gln Val Tyr Thr Leu Pro Pro Ser Arg Asp Glu
225                 230                 235                 240
Leu Thr Lys Asn Gln Val Ser Leu Thr Cys Leu Val Lys Gly Phe Tyr
                245                 250                 255
Pro Ser Asp Ile Ala Val Glu Trp Glu Ser Asn Gly Gln Pro Glu Asn
            260                 265                 270
Asn Tyr Lys Thr Thr Pro Pro Val Leu Asp Ser Asp Gly Ser Phe Phe
        275                 280                 285
Leu Tyr Ser Lys Leu Thr Val Asp Lys Ser Arg Trp Gln Gln Gly Asn
    290                 295                 300
Val Phe Ser Cys Ser Val Met His Glu Ala Leu His Asn His Tyr Thr
305                 310                 315                 320
Gln Lys Ser Leu Ser Leu Ser Pro Gly Lys
                325                 330

<210> SEQ ID NO 49
<211> LENGTH: 330
<212> TYPE: PRT
<213> ORGANISM: Homo sapiens

<400> SEQUENCE: 49

Ala Ser Thr Lys Gly Pro Ser Val Phe Pro Leu Ala Pro Ser Ser Lys
1               5                   10                  15
Ser Thr Ser Gly Gly Thr Ala Ala Leu Gly Cys Leu Val Lys Asp Tyr
            20                  25                  30
Phe Pro Glu Pro Val Thr Val Ser Trp Asn Ser Gly Ala Leu Thr Ser
        35                  40                  45
Gly Val His Thr Phe Pro Ala Val Leu Gln Ser Ser Gly Leu Tyr Ser
    50                  55                  60
Leu Ser Ser Val Val Thr Val Pro Ser Ser Leu Gly Thr Gln Thr
65                  70                  75                  80
Tyr Ile Cys Asn Val Asn His Lys Pro Ser Asn Thr Lys Val Asp Lys
                85                  90                  95
Lys Val Glu Pro Lys Ser Cys Asp Lys Thr His Thr Cys Pro Pro Cys
            100                 105                 110
Pro Ala Pro Glu Leu Leu Gly Gly Pro Ser Val Phe Leu Phe Pro Pro
        115                 120                 125
Lys Pro Lys Asp Thr Leu Met Ile Ser Arg Thr Pro Glu Val Thr Cys
    130                 135                 140
```

```
Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
            165                 170                 175

Glu Gln Tyr Asn Ser Thr Tyr Arg Val Val Ser Val Leu Thr Val Leu
        180                 185                 190

His Gln Asp Trp Leu Asn Gly Lys Glu Tyr Lys Cys Lys Val Ser Asn
    195                 200                 205

Lys Ala Leu Pro Ala Pro Ile Glu Lys Thr Ile Ser Lys Ala Lys Gly
210                 215                 220

Gln Pro Arg Glu Pro Gln Val Cys Thr Leu Pro Pro Ser Arg Asp Glu
225                 230                 235                 240

Leu Thr Lys Asn Gln Val Ser Leu Trp Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 50
<211> LENGTH: 330
<212> TYPE: PRT
<213> ORGANISM: Homo sapiens

<400> SEQUENCE: 50

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190
```

His Gln Asp Trp Leu Asn Gly Lys Glu Tyr Lys Cys Lys Val Ser Asn
              195                 200                 205

Lys Ala Leu Pro Ala Pro Ile Glu Lys Thr Ile Ser Lys Ala Lys Gly
         210                 215                 220

Gln Pro Arg Glu Pro Gln Val Tyr Thr Leu Pro Pro Ser Arg Cys Glu
225                 230                 235                 240

Leu Thr Lys Asn Gln Val Ser Leu Ser Cys Ala Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Val Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 51
<211> LENGTH: 330
<212> TYPE: PRT
<213> ORGANISM: Homo sapiens

<400> SEQUENCE: 51

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu

Leu Thr Lys Asn Gln Val Ser Leu Thr Cys Leu Val Glu Gly Phe Tyr
            245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Asp Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 52
<211> LENGTH: 330
<212> TYPE: PRT
<213> ORGANISM: Homo sapiens

<400> SEQUENCE: 52

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Lys
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

```
Asn Tyr Lys Thr Thr Pro Pro Val Leu Lys Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 53
<211> LENGTH: 330
<212> TYPE: PRT
<213> ORGANISM: Homo sapiens

<400> SEQUENCE: 53

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Asp Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320
```

```
Gln Glu Ser Leu Ser Leu Ser Pro Gly Lys
            325                 330

<210> SEQ ID NO 54
<211> LENGTH: 330
<212> TYPE: PRT
<213> ORGANISM: Homo sapiens

<400> SEQUENCE: 54

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Lys Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Lys Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 55
<211> LENGTH: 330
<212> TYPE: PRT
```

<213> ORGANISM: Homo sapiens

<400> SEQUENCE: 55

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Glu Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Glu Ser Leu Ser Leu Ser Pro Gly Lys
                325                 330

<210> SEQ ID NO 56
<211> LENGTH: 330
<212> TYPE: PRT
<213> ORGANISM: Homo sapiens

<400> SEQUENCE: 56

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr

```
                    20                  25                  30
Phe Pro Glu Pro Val Thr Val Ser Trp Asn Ser Gly Ala Leu Thr Ser
                35                  40                  45

Gly Val His Thr Phe Pro Ala Val Leu Gln Ser Ser Gly Leu Tyr Ser
            50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Lys Lys
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 57
<211> LENGTH: 119
<212> TYPE: PRT
<213> ORGANISM: Mus musculus

<400> SEQUENCE: 57

Met Glu Val Gln Leu Gln Gln Ser Gly Ala Glu Leu Val Lys Pro Gly
1               5                   10                  15

Ala Ser Val Lys Leu Ser Cys Thr Ala Ser Gly Phe Asn Ile Lys Asp
                20                  25                  30

Tyr Tyr Met His Trp Ile Lys Gln Arg Pro Gly Gln Gly Leu Glu Trp
            35                  40                  45

Leu Gly Tyr Ile Asn Pro Ser Ser Gly Tyr Thr Lys Tyr Asn Arg Lys
        50                  55                  60
```

```
Phe Arg Asp Lys Ala Thr Leu Thr Ala Asp Lys Ser Ser Ser Thr Ala
 65                  70                  75                  80

Tyr Met Gln Leu Thr Ser Leu Thr Tyr Glu Asp Ser Ala Val Tyr Tyr
                 85                  90                  95

Cys Ala Arg Gly Gly Asn Gly Tyr Tyr Leu Asp Tyr Trp Gly Gln Gly
            100                 105                 110

Thr Thr Leu Thr Val Ser Ser
            115

<210> SEQ ID NO 58
<211> LENGTH: 120
<212> TYPE: PRT
<213> ORGANISM: Mus musculus

<400> SEQUENCE: 58

Met Gln Val Gln Leu Gln Gln Ser Gly Pro Glu Leu Val Lys Pro Gly
  1               5                  10                  15

Ala Ser Val Lys Ile Ser Cys Lys Ala Ser Gly Tyr Thr Phe Thr Asp
                 20                  25                  30

Asn Asn Met Asp Trp Val Lys Gln Ser His Gly Lys Gly Leu Glu Trp
             35                  40                  45

Ile Gly Asp Ile Asn Thr Lys Ser Gly Gly Ser Ile Tyr Asn Gln Lys
 50                  55                  60

Phe Lys Gly Lys Ala Thr Leu Thr Ile Asp Lys Ser Ser Ser Thr Ala
 65                  70                  75                  80

Tyr Met Glu Leu Arg Ser Leu Thr Ser Glu Asp Thr Ala Val Tyr Tyr
                 85                  90                  95

Cys Ala Arg Arg Arg Ser Tyr Gly Tyr Tyr Phe Asp Tyr Trp Gly Gln
            100                 105                 110

Gly Thr Thr Leu Thr Val Ser Ser
            115                 120

<210> SEQ ID NO 59
<211> LENGTH: 107
<212> TYPE: PRT
<213> ORGANISM: Homo sapiens

<400> SEQUENCE: 59

Asp Ile Val Met Thr Gln Ser His Lys Phe Met Ser Thr Ser Val Gly
  1               5                  10                  15

Asp Arg Val Ser Ile Thr Cys Lys Ala Ser Gln Asn Val Gly Thr Ala
                 20                  25                  30

Val Ala Trp Tyr Gln Gln Lys Pro Gly Gln Ser Pro Lys Leu Leu Ile
             35                  40                  45

Tyr Ser Ala Ser Tyr Arg Tyr Ser Gly Val Pro Asp Arg Phe Thr Gly
 50                  55                  60

Ser Arg Tyr Gly Thr Asp Phe Thr Leu Thr Ile Ser Asn Val Gln Ser
 65                  70                  75                  80

Glu Asp Leu Ala Asp Tyr Leu Cys Gln Gln Tyr Ser Asn Tyr Ile Thr
                 85                  90                  95

Phe Gly Gly Gly Thr Lys Leu Glu Leu Lys Arg
            100                 105

<210> SEQ ID NO 60
<211> LENGTH: 15
<212> TYPE: PRT
<213> ORGANISM: Artificial Sequence
<220> FEATURE:
```

-continued

```
<223> OTHER INFORMATION: synthetic

<400> SEQUENCE: 60

Gly Gly Gly Gly Ser Gly Gly Gly Gly Ser Gly Gly Gly Gly Ser
1               5                  10                  15
```